US012655130B2

(12) United States Patent
Heckrodt et al.

(10) Patent No.: US 12,655,130 B2
(45) Date of Patent: Jun. 16, 2026

(54) 5-MEMBERED HETEROARYL CARBOXAMIDE COMPOUNDS FOR TREATMENT OF HBV

(71) Applicant: ASSEMBLY BIOSCIENCES, INC., South San Francisco, CA (US)

(72) Inventors: Thilo Heckrodt, South San Francisco, CA (US); Michael Walker, South San Francisco, CA (US); Min Zhong, South San Francisco, CA (US)

(73) Assignee: ASSEMBLY BIOSCIENCES, INC., South San Francisco, CA (US)

( * ) Notice: Subject to any disclaimer, the term of this patent is extended or adjusted under 35 U.S.C. 154(b) by 897 days.

(21) Appl. No.: 17/920,544

(22) PCT Filed: Apr. 21, 2021

(86) PCT No.: PCT/US2021/028323

§ 371 (c)(1),
(2) Date: Oct. 21, 2022

(87) PCT Pub. No.: WO2021/216656

PCT Pub. Date: Oct. 28, 2021

(65) Prior Publication Data

US 2023/0183213 A1 Jun. 15, 2023

Related U.S. Application Data

(60) Provisional application No. 63/014,001, filed on Apr. 22, 2020.

(51) Int. Cl.

| | |
|---|---|
| ***C07D 403/08*** | (2006.01) |
| ***A61P 31/20*** | (2006.01) |
| ***C07D 233/90*** | (2006.01) |
| ***C07D 263/34*** | (2006.01) |
| ***C07D 277/56*** | (2006.01) |
| ***C07D 401/08*** | (2006.01) |
| ***C07D 471/04*** | (2006.01) |
| ***C07D 487/04*** | (2006.01) |
| ***C07D 498/04*** | (2006.01) |

(52) U.S. Cl.

CPC ............ *C07D 403/08* (2013.01); *A61P 31/20* (2018.01); *C07D 233/90* (2013.01); *C07D 263/34* (2013.01); *C07D 277/56* (2013.01); *C07D 401/08* (2013.01); *C07D 471/04* (2013.01); *C07D 487/04* (2013.01); *C07D 498/04* (2013.01); *C07B 2200/05* (2013.01)

(58) Field of Classification Search

CPC .. C07D 487/04; C07D 403/08; C07D 233/90; C07D 263/34; C07D 277/56; C07D 401/08; C07D 471/04; C07D 498/04; A61P 31/20; C07B 2200/05

See application file for complete search history.

(56) References Cited

U.S. PATENT DOCUMENTS

| | | | | |
|---|---|---|---|---|
| 9,895,349 | B2 * | 2/2018 | Vandyck | A61P 1/16 |
| 10,450,270 | B2 * | 10/2019 | VanDyck | A61K 31/454 |
| 11,548,868 | B2 * | 1/2023 | Zhang | A61P 35/00 |
| 2017/0015658 | A1 | 1/2017 | Turner, Jr. et al. | |

FOREIGN PATENT DOCUMENTS

| | | | |
|---|---|---|---|
| CN | 109937201 | A | 6/2019 |
| CN | 108347943 | B | 7/2020 |
| CN | 109069488 | B | 9/2021 |
| CN | 109843892 | B | 1/2022 |
| JP | 2016518437 | A | 6/2016 |
| JP | 2016525141 | A | 8/2016 |
| JP | 2022508953 | A | 1/2022 |
| WO | 2013006394 | A1 | 1/2013 |
| WO | 2013010069 | A1 | 1/2013 |
| WO | 2013102655 | A1 | 7/2013 |
| WO | 2014033167 | A1 | 3/2014 |
| WO | 2014033170 | A1 | 3/2014 |
| WO | 2014033176 | A1 | 3/2014 |
| WO | 2014037480 | A1 | 3/2014 |
| WO | 2014074906 | A1 | 5/2014 |
| WO | 2014089296 | A2 | 6/2014 |
| WO | 2014106019 | A2 | 7/2014 |
| WO | 2014131847 | A1 | 9/2014 |
| WO | 2014161888 | A1 | 10/2014 |
| WO | 2014184328 | A1 | 11/2014 |
| WO | 2014184350 | A1 | 11/2014 |
| WO | 2014184365 | A1 | 11/2014 |
| WO | 2015011281 | A1 | 1/2015 |
| WO | 2019076358 | A1 | 4/2019 |
| WO | 2021216660 | A1 | 10/2021 |

OTHER PUBLICATIONS

International Search Report, issued in PCT/US2021/028323, dated Jul. 19, 2021.

International Preliminary Report on Patentability, issued in PCT/US2021/028305, dated Oct. 25, 2022.

Lahlali et al., "Novel Potent Capsid Assembly Modulators Regulate Multiple Steps of the Hepatitis B Virus Life Cycle", Antimicrobial Agents and Chemotherapy, vol. 62, No. 10, Jul. 16, 2018, pp. 10-15.

* cited by examiner

*Primary Examiner* — James H Alstrum-Acevedo

*Assistant Examiner* — Carolyn L. Ladd

(74) *Attorney, Agent, or Firm* — Barnes & Thornburg LLP

(57) ABSTRACT

The present disclosure relates to 5-membered heteroaryl carboxamide compounds, which may disrupt Hepatitis B (HBV) core protein assembly. The present disclosure further relates to pharmaceutical compositions comprising 5-membered heteroaryl carboxamide compounds which may disrupt HBV core protein assembly. The present disclosure further relates to uses of 5-membered heteroaryl carboxamide compounds and pharmaceutical compositions thereof in methods of treating Hepatitis B (HBV) infection.

32 Claims, 2 Drawing Sheets

Specification includes a Sequence Listing.

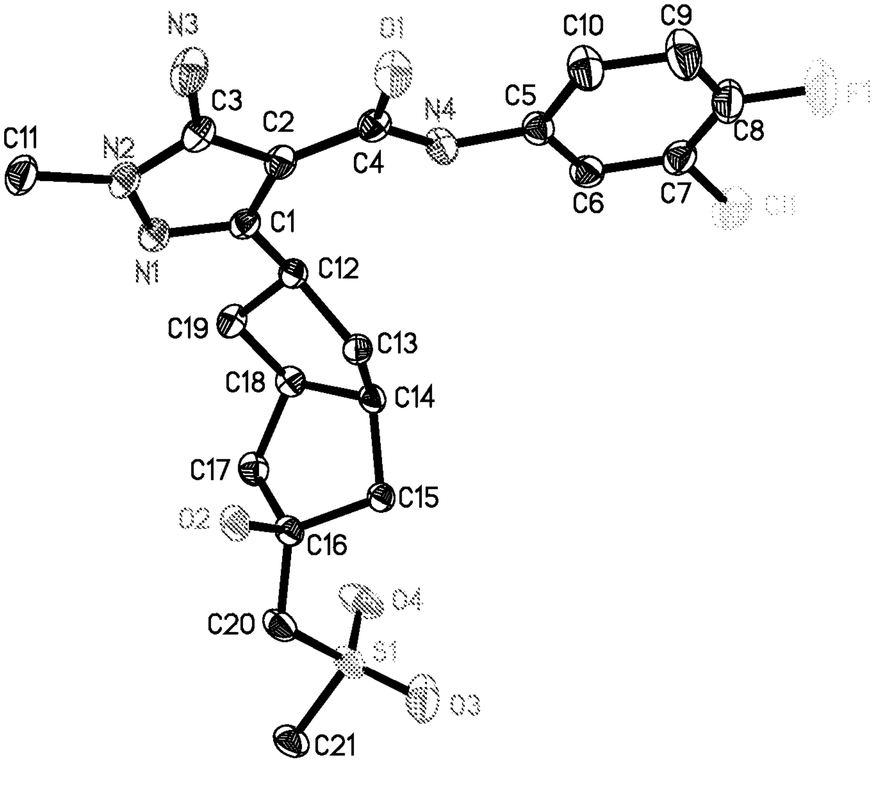
Fig. 1 The ORTEP plot for compound AIA-227-2

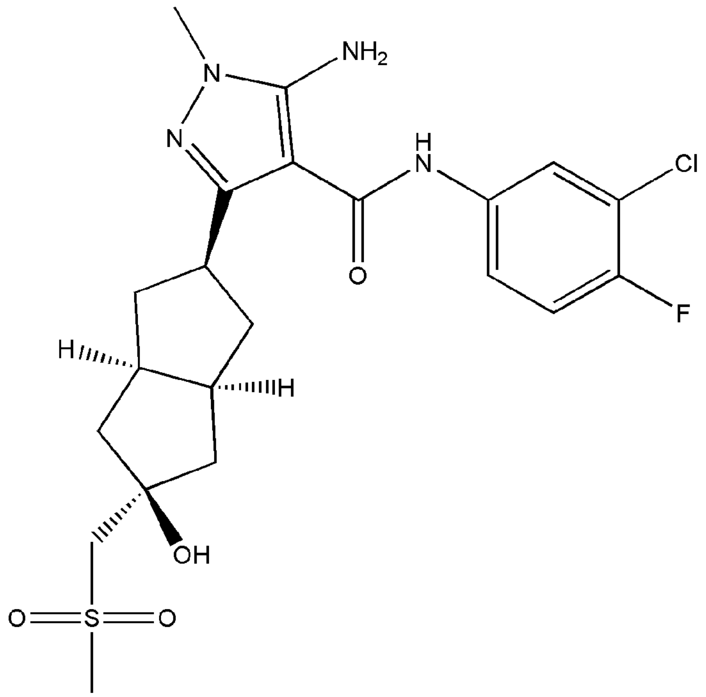
Fig. 2 The relative stereochemistry scheme of compound AIA-227-2.

SEQUENCE LISTING

```
<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: PCR primer

<400> SEQUENCE: 1

ctgtgccttg ggtggcttt                                                19


<210> SEQ ID NO 2
<211> LENGTH: 24
<212> TYPE: DNA
<213> ORGANISM: Artificial Sequence
<220> FEATURE:
<223> OTHER INFORMATION: PCR primer

<400> SEQUENCE: 2

aaggaaagaa gtcagaaggc aaaa                                          24


<210> SEQ ID NO 3
<211> LENGTH: 30
<212> TYPE: DNA
<213> ORGANISM: Artificial Sequence
<220> FEATURE:
<223> OTHER INFORMATION: Fluorescent probe
<220> FEATURE:
<221> NAME/KEY: misc_feature
<222> LOCATION: (1)..(1)
<223> OTHER INFORMATION: FAM
<220> FEATURE:
<221> NAME/KEY: misc_feature
<222> LOCATION: (9)..(9)
<223> OTHER INFORMATION: ZEN quencher
<220> FEATURE:
<221> NAME/KEY: misc_feature
<222> LOCATION: (30)..(30)
<223> OTHER INFORMATION: 3IABkFQ quencher

<400> SEQUENCE: 3

agctccaaat tctttataag ggtcgatgtc                                    30
```

5-MEMBERED HETEROARYL CARBOXAMIDE COMPOUNDS FOR TREATMENT OF HBV

CROSS-REFERENCE TO RELATED APPLICATIONS

This application is a National Stage application of International Application No. PCT/US2021/028323, filed Apr. 21, 2021, which claims the benefit of U.S. Provisional Application No. 63/014,001, filed Apr. 22, 2020.

REFERENCE TO SEQUENCE LISTING SUBMITTED VIA EFS-WEB

This application was filed electronically via EFS-Web and includes an electronically submitted sequence listing in .txt format. The file contains a sequence listing in the form of a ST.25 .txt file and does not go beyond the disclosure of the international application as filed. No new matter is presented. The sequence listing contained in this .txt file is part of the specification and is hereby incorporated by reference herein in its entirety.

BACKGROUND

Hepatitis B (HBV) causes viral hepatitis that can further lead to chronic liver disease and increase the risk of liver cirrhosis and liver cancer (hepatocellular carcinoma). Worldwide, about 2 billion people have been infected with HBV, around 360 million people are chronically infected, and every year HBV infection causes more than one half million deaths. HBV can be spread by body fluids: from mother to child, by sex, and via blood products. Children born to HBV-positive mothers may also be infected, unless vaccinated at birth.

The hepatitis virus particle is composed of a lipid envelope studded with surface protein (HBsAg) that surrounds the viral core. The core is composed of a protein shell, or capsid, built of 120 core protein (Cp) dimers, which in turn contains the relaxed circular DNA (rcDNA) viral genome as well as viral and host proteins. In an infected cell, the genome is found as a covalently closed circular DNA (cccDNA) in the host cell nucleus. The cccDNA is the template for viral RNAs and thus viral proteins. In the cytoplasm, Cp assembles around a complex of full-length viral RNA (the so-called pregenomic RNA or pgRNA and viral polymerase (P). After assembly, P reverse transcribes the pgRNA to rcDNA within the confines of the capsid to generate the DNA-filled viral core.

At present, chronic HBV is primarily treated with nucleos(t)ide analogs (e.g., entecavir) that suppress the virus while the patient remains on treatment, but do not eliminate the infection, even after many years of treatment. Once a patient starts taking nucleos(t)ide analogs, most must continue taking them or risk the possibility of a life-threatening immune response due to viral rebound. Further, nucleotide therapy may lead to the emergence of antiviral drug resistance.

The only FDA approved alternative to nucleos(t)ide analogs is treatment with interferon α or pegylated interferon α. Unfortunately, the adverse event incidence and profile of interferon α can result in poor tolerability, and many patients are unable to complete therapy. Moreover, only a small percentage of patients are considered appropriate for interferon therapy, as only a small subset of patients is likely to have a sustained clinical response to a course of interferon therapy. As a result, interferon-based therapies are used in only a small percentage of all diagnosed patients who elect treatment.

Thus, current HBV treatments can range from palliative to watchful waiting. Nucleotide analogs suppress virus production, treating the symptom, but leave the infection intact. Interferon α has severe side effects and less tolerability among patients and is successful as a finite treatment strategy in only a small minority of patients. There is a clear on-going need for more effective treatments for HBV infections.

SUMMARY

The present disclosure provides, in part, 5-membered heteroaryl carboxamide compounds and pharmaceutical compositions thereof, useful for disruption of HBV core protein assembly, and methods of treating HBV infections.

In one aspect, the disclosure provides a compound of Formula I:

Formula I

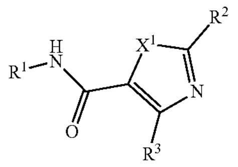

or a pharmaceutically acceptable salt thereof, where the variables are described in the detailed description.

In another aspect, the disclosure provides pharmaceutical compositions comprising a compound of Formula I, or a pharmaceutically acceptable salt thereof, and a pharmaceutically acceptable excipient.

In another aspect, the disclosure provides a method of treating an HBV infection in a subject in need thereof, comprising: administering to the subject a therapeutically effective amount of compound of Formula I, or a pharmaceutically acceptable salt thereof.

In another aspect, the disclosure provides a method of treating an HBV infection in a subject in need thereof, comprising: administering to the subject a pharmaceutical composition comprising a therapeutically effective amount of a compound of Formula I, or a pharmaceutically acceptable salt thereof, and a pharmaceutically acceptable excipient.

BRIEF DESCRIPTION OF DRAWINGS

FIG. 1 shows the ORTEP plot for compound CP-AIA-227-2.

FIG. 2 shows the relative stereochemistry scheme of compound CP-AIA-227-2.

DETAILED DESCRIPTION

The features and other details of the disclosure will now be more particularly described. Before further description of the present disclosure, certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

I. DEFINITIONS

The term "alkenyl" as used herein refers to an unsaturated straight or branched hydrocarbon having at least one carbon-carbon double bond. Exemplary alkenyl groups include, but are not limited to, a straight or branched group of 2-6 carbon atoms, referred to herein as $C_{2-6}$alkenyl. Exemplary alkenyl groups include, but are not limited to, vinyl, allyl, butenyl, and pentenyl, etc.

The term "alkoxy" as used herein refers to a straight or branched alkyl group attached to oxygen (i.e., alkyl-O—). Exemplary alkoxy groups include, but are not limited to, alkoxy groups of 1-6 or 1-4 carbon atoms, referred to herein as $C_{1-6}$alkoxy and $C_{1-4}$alkoxy, respectively. Exemplary alkoxy groups include, but are not limited to methoxy, ethoxy, and isopropoxy, etc.

The term "alkoxyalkyl" as used herein refers to an alkyl group substituted with an alkoxy group. Examples include, but are not limited to, $CH_3CH_2OCH_2$—, $CH_3OCH_2CH_2$— and $CH_3OCH_2$—, etc.

The term "alkyl" as used herein refers to a saturated straight or branched hydrocarbon. Exemplary alkyl groups include, but are not limited to, straight or branched hydrocarbons of 1-6 or 1-4 carbon atoms, referred to herein as $C_{1-6}$ alkyl and $C_{1-4}$ alkyl, respectively. Exemplary alkyl groups include, but are not limited to, methyl, ethyl, n-propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, t-butyl, n-pentyl, isopentyl, neopentyl, and n-hexyl, etc. The term "alkylene" as used herein refers to a biradical alkyl group.

The term "alkynyl" as used herein refers to an unsaturated straight or branched hydrocarbon having at least one carbon-carbon triple bond. Exemplary alkynyl groups include, but are not limited to, straight or branched groups of 2-6 carbon atoms, referred to herein as $C_{2-6}$alkynyl. Exemplary alkynyl groups include, but are not limited to, ethynyl, propynyl, butynyl, pentynyl, hexynyl, and methylpropynyl, etc.

The term "carbonyl" as used herein refers to the biradical —C(O)—.

The term "cyano" as used herein refers to the radical —CN.

The term "cycloalkyl" as used herein refers to a saturated monocyclic hydrocarbon group of, for example, 3-6 carbons, referred to herein as $C_{3-6}$ monocycloalkyl, or bicyclic hydrocarbon ring structure of, for example, 8-12 carbons, referred to herein as $C_{8-12}$bicycloalkyl. For bicyclic cycloalkyl groups, the two rings may be attached through the same or different carbons. Exemplary monocyclic cycloalkyl groups include, but are not limited to, cyclohexyl, cyclopentyl, cyclopentenyl, cyclobutyl and cyclopropyl. Exemplary bicyclic cycloalkyl groups include, but are not limited to, spiro[2.5]octanyl, spiro[3.5]nonanyl, bicyclo[2.2.2]octanyl, bicyclo[4.1.0]heptanyl, octahydropentalenyl, bicyclo[4.2.0]octanyl, bicyclo[1.1.1]pentanyl, bicyclo[2.2.1]heptanyl, and bicyclo[2.2.2]octanyl.

The term "cycloalkenyl" as used herein refers to a partially unsaturated monocyclic hydrocarbon group of, for example, 4-6 carbons, referred to herein as $C_{4-6}$monocycloalkenyl, or bicyclic hydrocarbon ring structure of, for example, 8-12 carbons, referred to herein as $C_{8-12}$bicycloalkenyl. For bicyclic cycloalkenyl groups: 1) either one or both rings may contain one or more double bonds and 2) the two rings may be attached through the same or different ring carbons. Exemplary monocyclic cycloalkenyl groups include, but are not limited to, cyclopropenyl, cyclobutenyl, cyclopentenyl, cyclohexenyl and cycloheptenyl. Exemplary bicyclic cycloalkenyl groups include, but are not limited to, spiro[2.5]oct-5-enyl, spiro[2.5]oct-4-enyl, spiro[3.5]non-5-enyl, spiro[3.5]non-6-enyl, bicyclo[4.1.0]hept-3-enyl, bicyclo[4.1.0]hept-2-enyl, and bicyclo[2.2.2]oct-2-enyl.

The term "carbocyclyl" as used herein refers to a bicyclic ring system formed by fusing a phenyl ring to a $C_{3-6}$monocycloalkyl or $C_{4-6}$monocycloalkenyl ring. Examples of carbocyclyls include, but are not limited to, 2,3-dihydro-1H-indenyl, 1,2,3,4-tetrahydronaphthalenyl and 1H-indenyl.

The terms "halo" or "halogen" as used herein refer to F, Cl, Br or I.

The term "haloalkyl" as used herein refers to an alkyl group substituted with one or more halogen atoms. For example, halo$C_{1-6}$alkyl refers to a straight or branched alkyl group of 1-6 carbon atoms substituted with one or more halogen atoms. Examples include, but are not limited to, $CH_2F$—, $CHCl_2$—, —$CHF_2$, $CF_3$—, $CF_3CH_2$—, $CH_3CF_2$, $CF_3CCl_2$— and $CF_3CF_2$—.

The term "haloalkoxy" as used herein refers to an alkoxy group substituted with one or more halogen atoms. Examples include, but are not limited to, $CCl_3O$—, $CF_3O$—, $CHF_2O$—$CF_3CH_2O$—, and $CF_3CF_2O$—.

The terms "heteroaryl" as used herein refers to a 5-6 membered monocyclic or 8-12 membered bicyclic aromatic ring system containing one to four independently selected heteroatoms, such as nitrogen, oxygen and sulfur. Where possible, the heteroaryl ring may be linked to the adjacent radical though carbon or nitrogen. Examples of 5-6 membered monocyclic heteroaryl groups include, but are not limited to, furanyl, thiophenyl (also referred to as thienyl), pyrrolyl, thiazolyl, oxazolyl, isothiazolyl, isoxazolyl, imidazolyl, pyrazolyl, 1H-1,2,3-triazolyl, 2H-1,2,3-triazolyl, 1,2,4-triazolyl, pyridinyl (also referred to as pyridyl), pyridazinyl, pyrimidinyl, pyrazinyl, 1,3,5-triazinyl, 1,2,4-triazinyl, 1,2,3-triazinyl, 1,2,4-oxadiazolyl, 1,3,4-oxadiazolyl, 1,2,5-oxadiazolyl, 1,2,4-thiadiazolyl, 1,3,4-thiadiazolyl, 1,2,5-thiadiazolyl and tetrazolyl. Examples of 8-12 membered bicyclic heteroaryl groups include, but are not limited to, benzofuranyl, isobenzofuranyl, benzo[b]thiophenyl, benzo[c]thiophenyl, indolyl, isoindolyl, benzo[d]isoxazolyl, benzo[c]isoxazolyl, benzo[d]oxazolyl, benzo[d]isothiazolyl, benzo[c]isothiazolyl, benzo[d]thiazolyl, indazolyl, benzo[d]imidazolyl, benzo[d]imidazolyl, and benzo[d][1,2,3]triazolyl.

The term "heterocycloalkyl" refers to a saturated 3-6 membered monocyclic or 8-12 membered bicyclic ring system, referred to herein as $C_{3-6}$monoheterocycloalkyl and $C_{8-12}$biheterocycloalkyl, containing one to four independently selected heteroatoms, such as nitrogen, oxygen, and sulfur (including its oxidation states: S(O) and $SO_2$). Where possible, heterocycloalkyl rings may be linked to the adjacent radical through carbon or nitrogen. Examples of $C_{3-6}$monoheterocycloalkyl groups include, but are not limited to, aziridinyl, oxiranyl, thiiranyl 1,1-dioxide, oxetanyl, azetidinyl, thietanyl 1,1-dioxide, pyrrolidinyl, tetrahydrofuranyl, piperidinyl, tetrahydro-2H-pyranyl, morpholinyl, thiomorpholinyl, and piperazinyl. Examples of $C_{8-12}$biheterocycloalkyl groups include, but are not limited to, 1,4-dioxaspiro[4.5]decanyl and 1,5-dioxaspiro[5.5]undecanyl.

The term "heterocycloalkenyl" refers to a partially unsaturated 3-6 membered monocyclic or 8-12 membered bicyclic ring system, referred to herein as $C_{3-6}$monoheterocycloalkenyl and $C_{8-12}$biheterocycloalkenyl, containing one to four independently selected heteroatoms, such as nitrogen, oxygen, and sulfur (including its oxidation states: S(O)

or $S(O)_2$). Where possible, heterocycloalkenyl rings may be linked to the adjacent radical through carbon or nitrogen. For bicyclic heterocycloalkenyl groups: 1) either one or both rings may contain one or more double bonds and 2) the two rings may be attached through the same or different ring atoms. Examples of $C_{3-6}$monoheterocycloalkenyl groups include, but are not limited to, 2,3-dihydro-1H-pyrrolyl, 2,5-dihydro-1H-pyrrolyl, 4,5-dihydro-1H-pyrazolyl, 2,3-dihydro-1H-pyrazolyl, 4,5-dihydro-1H-imidazolyl, 2,3-dihydro-1H-imidazolyl, 2,3-dihydrothiophenyl, 2,5-dihydrothiophenyl, 4,5-dihydrothiazolyl, 2,3-dihydrothiazolyl, 4,5-dihydroisothiazolyl, 2,3-dihydroisothiazolyl, 2,3-dihydrofuranyl, 2,5-dihydrofuranyl, 4,5-dihydrooxazolyl, 2,3-dihydrooxazolyl, 4,5-dihydroisoxazolyl, 2,3-dihydroisoxazolyl, 3,4-dihydropyridinyl, 2,3-dihydropyridinyl, 2,3,4,5-tetrahydropyridinyl, 1,6-dihydropyridazinyl, 4,5-dihydropyridazinyl, 3,4,5,6-tetrahydropyridazinyl, 4,5-dihydropyrimidinyl, 1,2,5,6-tetrahydropyrimidinyl, 1,2-dihydropyrimidinyl, 1,2-dihydropyrazinyl, 2,3-dihydropyrazinyl, 1,2,3,6-tetrahydropyrazinyl, 4H-1,4-oxazinyl, 3,4-dihydro-2H-1,4-oxazinyl, 4H-1,4-thiazinyl, and 3,4-dihydro-2H-1,4-thiazinyl. Examples of $C_{8-12}$biheterocycloalkenyl groups include, but are not limited to, 6,7-dihydroindolyl, 4,5-dihydroindolyl, 7,8-dihydroimidazo[1,2-a]pyridinyl, 5,6-dihydroimidazo[1,2-a]pyridinyl, 4,5-dihydrobenzo[d]imidazolyl, 6,7-dihydro-1H-indazolyl, 4,5-dihydro-1H-indazolyl, 4,5-dihydropyrazolo[1,5-a]pyridinyl, and 6,7-dihydropyrazolo[1,5-a]pyridinyl.

The term "heterocyclyl" as used herein refers to a bicyclic ring system formed by either (1) fusing a phenyl ring to a 3-6 membered monocyclic heterocycloalkyl or 4-7 membered monocyclic heterocycloalkenyl ring, or (2) fusing a 5-6 membered monocyclic heteroaryl ring to a $C_{3-6}$ cycloalkyl, $C_{4-7}$ cycloalkenyl, 3-6 membered monocyclic heterocycloalkyl or 4-6 membered monocyclic heterocycloalkenyl ring. Where possible, the rings may be linked to the adjacent radical though carbon or nitrogen. Examples of heterocyclyls include, but are not limited to isochromanyl, 2H-quinolinyl, 6,7,8,9-tetrahydro-5H-[1,2,4]triazolo[4,3-a]azepine, 5,6,8,9-tetrahydro-[1,2,4]triazolo[4,3-d][1,4]oxazepane, 6,7-dihydro-5H,9H-[1,2,4]triazolo[3,4-c][1,4]oxazepane, 5,6,8,9-tetrahydro-712-[1,2,4]triazolo[4,3-d][1,4]diazepine, 8,9-dihydro-5H-[1,2,4]triazolo[4,3-a]azepine, 6,9-dihydro-5H-[1,2,4]triazolo[4,3-a]azepine, 5,6,7,8-tetrahydro-[1,2,4]triazolo[4,3-a]pyridine, 5,6-dihydro-8H-[1,2,4]triazolo[3,4-c][1,4]oxazine, 5,6,7,8-tetrahydroimidazo[1,2-a]pyridine, and 5H,9H-[1,2,4]triazolo[3,4-c][1,4]oxazepine.

The terms "hydroxy" and "hydroxyl" as used herein refers to the radical —OH.

The term "hydroxyalkyl" as used herein refers to an alkyl group substituted with one or more hydroxy groups. Examples include, but are not limited to, $HOCH_2$—, $HOCH_2CH_2$—, $CH_3CH(OH)CH_2$— and $HOCH_2CH(OH)CH_2$—.

The term "hydroxyalkoxy" as used herein refers to an alkoxy group substituted with one or more hydroxy groups. Examples include but are not limited to $HOCH_2O$—, $HOCH_2CH_2O$—, $CH_3CH(OH)CH_2O$— and $HOCH_2CH(OH)CH_2O$—.

The term "$R^aR^bNC_{1-6}$ alkyl-," as used herein refers to an alkyl group substituted with a $R^aR^bN$— group, as defined herein. Examples include but are not limited to $NH_2CH_2$—, $NH(CH_3)CH_2$—, $N(CH_3)_2CH_2CH_2$— and $CH_3CH(NH_2)CH_2$—.

The term "$R^aR^bNC_{1-6}$alkoxy," as used herein refers to an alkoxy group substituted with a $R^aR^bN$— groups, as defined herein. Examples include but are not limited to $NH_2CH_2$—, $NH(CH_3)CH_2O$—, $N(CH_3)_2CH_2CH_2O$—, and $CH_3CH(NH_2)CH_2O$—.

The term "oxo" as used herein refers to the radical =O.

As used herein, when a bicyclic ring is shown with a floating point of attachment and/or floating substituents, for example as in

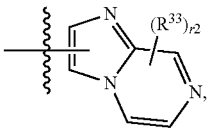

it signifies that the bicyclic ring can be attached via a carbon atom on either ring, and that the substituents (e.g., the $R^{33}$ group(s)) can be independently attached to either or both rings.

The terms "Individual," "patient," or "subject" are used interchangeably and include any animal, including mammals, preferably mice, rats, other rodents, rabbits, dogs, cats, swine, cattle, sheep, horses, or primates, and most preferably humans. The compounds or pharmaceutical compositions of the disclosure can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, dogs, primates, and the like). The mammal treated in the methods of the disclosure is desirably a mammal in which treatment of HBV infection is desired.

The term "modulation" includes antagonism (e.g., inhibition), agonism, partial antagonism and/or partial agonism.

The term "Pharmaceutically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, fillers, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable excipients.

The term "pharmaceutically acceptable salt(s)" as used herein refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The term "therapeutically effective amount" or "effective amount" as used herein refers to the amount of the subject compound that will elicit the biological or medical response of a tissue, system or animal, (e.g., mammal or human) that is being sought by the researcher, veterinarian, medical doctor or other clinician. The compounds or pharmaceutical compositions of the disclosure are administered in therapeutically effective amounts to treat a disease. Alternatively, a therapeutically effective amount of a compound is the quantity required to achieve a desired therapeutic and/or prophylactic effect.

The term "treating" includes any effect, e.g., lessening, reducing, modulating, or eliminating, via disruption of HBV core protein assembly, that results in the improvement of the disease. "Disruption" includes inhibition of HBV viral assembly and infection.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present disclosure encompasses various stereoisomers of these compounds and mixtures thereof. Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond. The symbol ⎓ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds of the disclosure may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic ring may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diastereomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well-known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantiomeric and diastereoselective transformations and may involve the use of chiral auxiliaries. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like, and it is intended that the disclosure embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The disclosure also embraces isotopically labeled compounds of the disclosure which are identical to those recited herein, except that one or more atoms are replaced by an atom having an atomic mass or mass number different from the atomic mass or mass number usually found in nature. Examples of isotopes that can be incorporated into compounds of the disclosure include isotopes of hydrogen, carbon, nitrogen, oxygen, phosphorus, sulfur, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound of the disclosure may have one or more H atom replaced with deuterium.

Certain isotopically-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of the disclosure can generally be prepared by following procedures analogous to those disclosed in the examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al., Nature Reviews Drug Discovery 2008, 7, 255).

II. 5-MEMBERED HETEROARYL CARBOXAMIDE COMPOUNDS

In one aspect, the present disclosure provides a compound of Formula I

Formula I

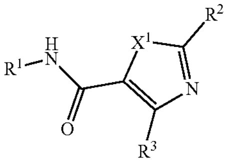

or a pharmaceutically acceptable salt thereof, wherein:

L is $C_{1-4}$alkylene or halo$C_{1-4}$alkylene;

$L^1$ and $L^2$ are independently a bond, $C_{1-6}$alkylene, O, $NR^c$, C(O), C(O)O, C(O)$NR^c$, $S(O)_t$, or $S(O)_tNR^c$;

$X^1$ is $NR^{x1}$, O or S;

$X^2$ is O, $NR^{13}$, $CR^{13}R^8$, C(O), or $S(O)_t$;

$X^3$ is O, $NR^4$, $CR^4R^8$, C(O), or $S(O)_t$;

$X^4$ and $X^6$ are independently O or S;

$X^5$ is O, S or $NR^0$;

$R^a$, $R^b$ and $R^c$ are independently selected for each occurrence from the group consisting of hydrogen, $C_{1-6}$ alkyl, halo$C_{1-6}$ alkyl and $C_{3-6}$ monocycloalkyl;

$R^d$ is hydrogen, OH, $C_{1-6}$ alkyl or $C_{1-6}$ alkoxy;

$R^{x1}$ is hydrogen, $C_{1-4}$ alkyl, $C_{1-4}$ alkenyl, $C_{1-4}$ alkynyl, halo$C_{1-4}$ alkyl, or $C_{3-6}$ monocycloalkyl; or $R^{x1}$ and $R^2$ together form a $—CH_2CH_2CH_2—$, $—CH_2CH_2CH_2CH_2—$, $—CH_2CH_2O—$, $—CH_2OCH_2—$, $—CH_2CH_2CH_2O—$ $—CH_2CH_2OCH_2—$, $—CH_2CH_2—NH—$ $—CH_2NHCH_2—$, $—CH_2CH_2CH_2NH—$ or $—CH_2CH_2NHCH_2—$ group;

$R^{0a}$ is independently selected for each occurrence from the group consisting of hydrogen, halogen, OH, CN, $NO_2$, $R^aR^bN—$, $C_{1-4}$alkyl and halo$C_{1-4}$alkyl;

$R^{4a}$ and $R^{6a}$ are independently hydrogen or $C_{1-4}$ alkyl;

$R^0$, $R^6$ and $R^{11}$ are independently selected for each occurrence from the group consisting of hydrogen, halogen, OH, CN, $NO_2$, oxo, $R^dN=$, hydrazino, formyl, azido, silyl, siloxy, HOC(O)—, $R^aR^bN—$, $R^aR^bNS(O)_t—$, $C_{1-6}$alkyl, $C_{2-6}$alkenyl, $C_{2-6}$alkynyl, halo$C_{1-6}$alkyl, hydroxy$C_{1-6}$alkyl-, $R^aR^bNC_{1-6}$alkyl-, HOC(O)$C_{1-6}$alkyl-, $R^aR^bNC_{1-6}$alkyl$NR^c—$, $C_{1-6}$alkyl$NR^aC_{1-6}$alkyl$NR^c—$, $C_{1-6}$alkoxy, halo$C_{1-6}$alkoxy, hydroxy$C_{1-6}$alkoxy-, $R^aR^bNC_{1-6}$alkoxy-, $C_{1-6}$alkoxy$C_{1-6}$alkyl-, halo$C_{1-6}$alkoxy$C_{1-6}$alkyl-, $R^aR^bNC(O)—$, $C_{1-6}$alkylC(O)—, $C_{1-6}$alkoxyC(O)—, $C_{1-6}$alkylC(O)O—, $C_{1-6}$alkyl$S(O)_q—$, $C_{1-6}$alkyl$S(O)_tNR^c—$, $C_{1-6}$alkyl $S(O)_tC_{1-6}$alkyl-, $C_{1-6}$alkyl$S(O)_tNR^aC_{1-6}$alkyl-, $C_{3-6}$cycloalkyl$S(O)_tC_{1-6}$alkyl-, $C_{1-6}$alkylC(O)$C_{1-6}$alkyl-, and $C_{1-6}$alkylC(O)O$C_{1-6}$alkyl-;

$R^1$ is a phenyl or 5-6 membered monocyclic heteroaryl, wherein the phenyl or 5-6 membered monocyclic heteroaryl is optionally substituted with one, two, or three independently selected $R^{11}$ groups;

$R^2$ and $R^8$ are independently selected from the group consisting of hydrogen, halo, CN, OH, $R^aR^bN$, $C_{1-4}$alkyl, halo$C_{1-4}$alkyl, $C_{3-5}$monocycloalkyl, $C_{1-4}$alkoxy, and halo$C_{1-4}$alkoxy;

$R^3$ is

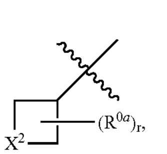

,

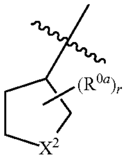

,

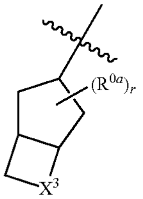

,

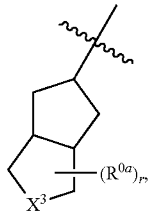

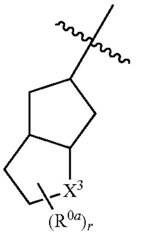

or

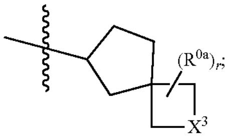

$R^4$ is $R^5$-$L^1$-, $R^6$ or $R^9$; or $R^4$ and $R^8$ together with the carbon atom to which they are attached form a

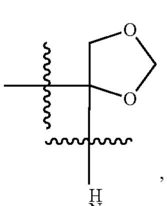

,

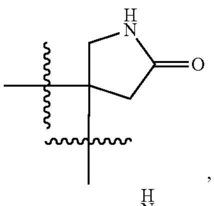

,

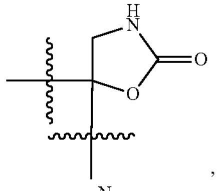

,

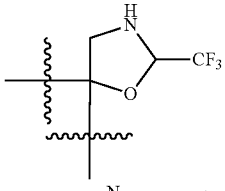

,

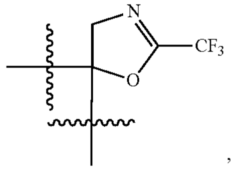

,

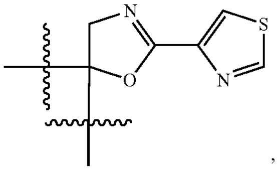

,

-continued
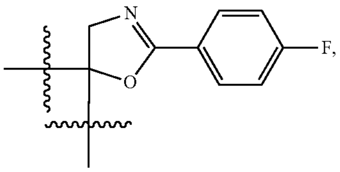
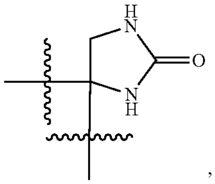
,
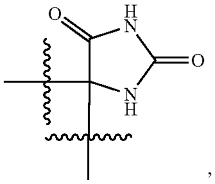
, or
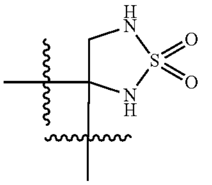
group;
$R^5$ is
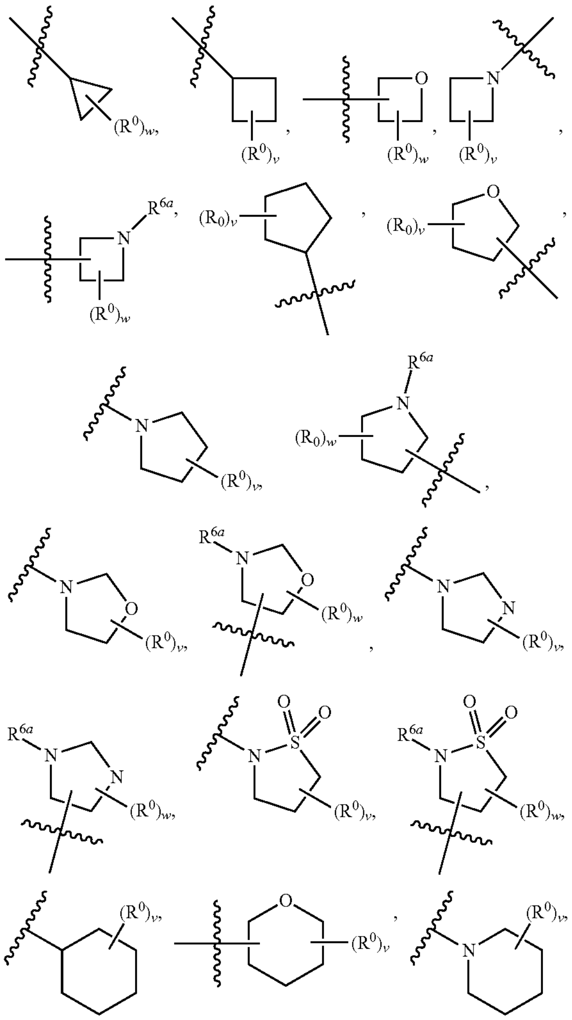
-continued
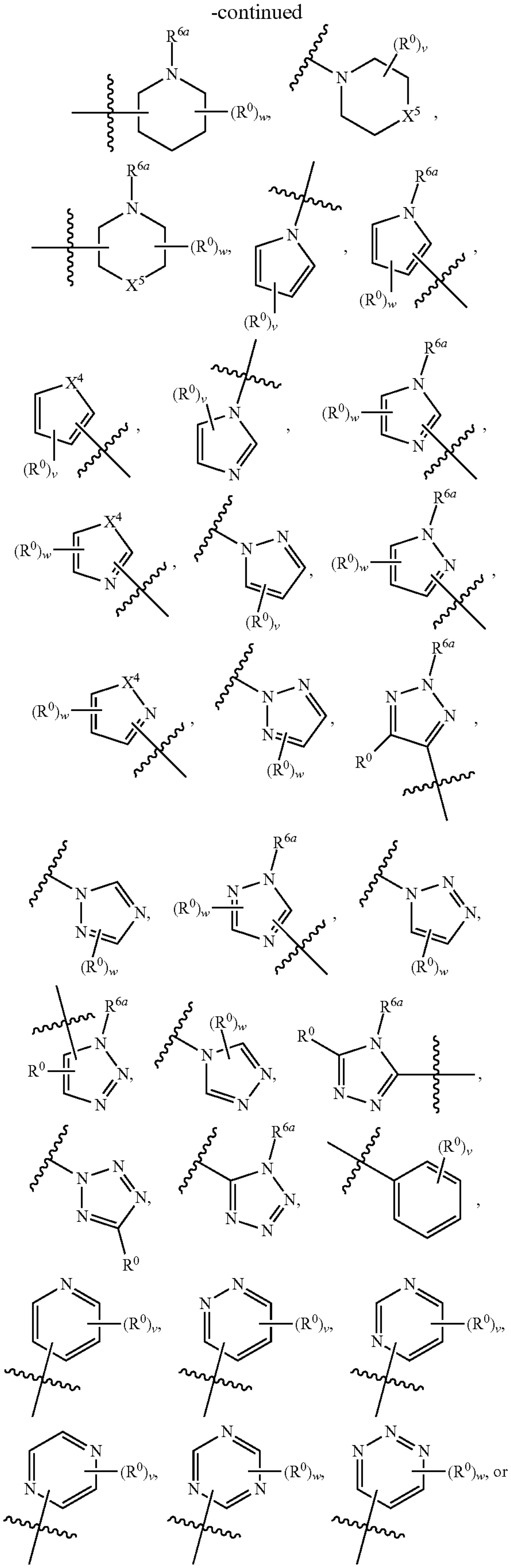
or -continued

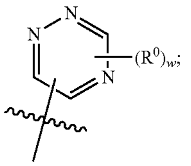

$R^9$ is $R^{14}S(O)_q$-L-, $R^{14}S(O)_q$NH-L-, or $R^{14}C(O)$NH-L-;

$R^{10}$ is

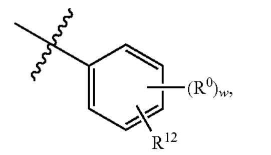

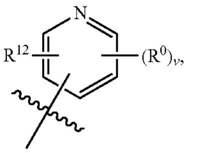

or

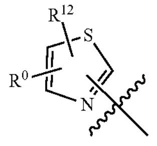

;

$R^{12}$ is

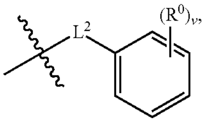

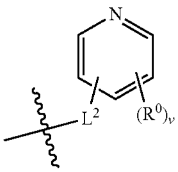

,

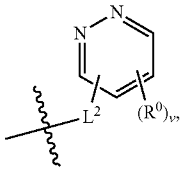

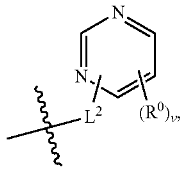

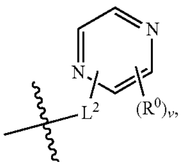

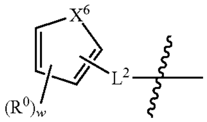

,

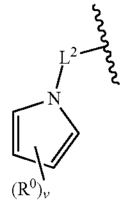

,

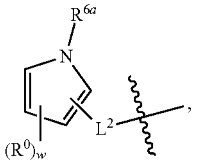

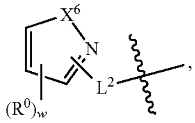

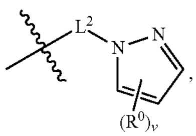

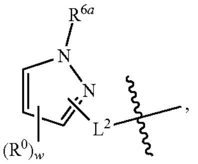

-continued

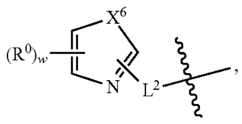

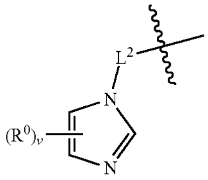

, and

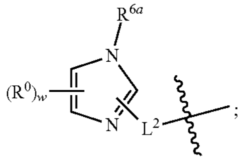

$R^{13}$ is $R^5$-$L^1$-, $R^{10}$-$L^1$-, $R^6$ or $R^9$;

$R^{14}$ is $R^aR^bN$—, $C_{1-6}$alkyl, $C_{2-6}$alkenyl, $C_{2-6}$alkynyl, $C_{1-6}$haloalkyl, $C_{1-6}$alkoxy, $C_{1-6}$haloalkyl, $C_{1-6}$haloalkoxy, or $R^5$-$L^1$-;

q, r, t, and w are independently selected for each occurrence from 0, 1 and 2; and v is independently selected for each occurrence from 0, 1, 2 and 3.

The following embodiments further describe a compound of Formula I, or a pharmaceutically acceptable salt thereof. It will be appreciated that all chemically allowable combinations of the embodiments described herein are envisioned as further embodiments of the invention.

In certain embodiments, $X^1$ is S.

In certain embodiments, $X^1$ is $NR^{x1}$.

In certain embodiments, $X^1$ is $NR^{x1}$ and $R^{x1}$ is hydrogen of methyl.

In certain embodiments, $X^1$ is $NR^{x1}$ and $R^{x1}$ is methyl.

In certain embodiments, $X^2$ is $CR^{13}R^8$;

In certain embodiments, $X^3$ is $CR^4R^8$.

In certain embodiments, $L^1$ is a bond.

In certain embodiments, $L^1$ is a $C_{1-6}$alkylene.

In certain embodiments, r is 0.

In certain embodiments, $R^1$ is

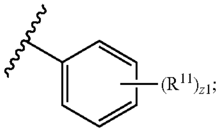

$R^{11}$ is independently selected for each occurrence from the group consisting of halogen, CN, $C_{1-6}$alkyl and halo$C_{1-6}$alkyl; and z1 is 0, 1, 2 or 3.

In certain embodiments, $R^{11}$ is independently selected for each occurrence from the group consisting of halogen and CN.

In certain embodiments, $R^{11}$ is independently selected for each occurrence from the group consisting of F, Cl, Br and I.

In certain embodiments, $R^1$ is selected from the group consisting of:

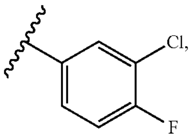

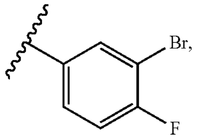

-continued

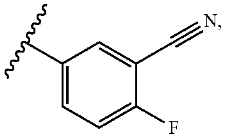

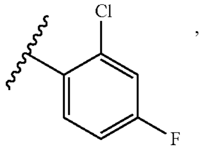

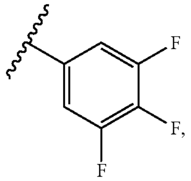

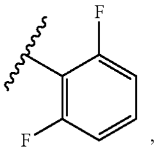

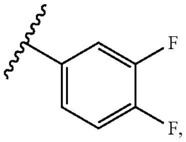

and

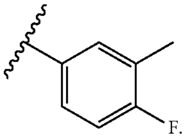

In certain embodiments, $R^1$ is

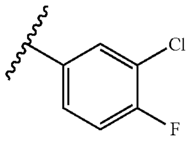

or

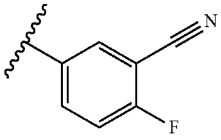

.

In certain embodiments, $R^1$ is

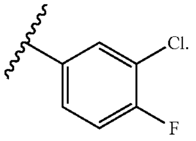 [SMILES: *c1ccc(F)c(Cl)c1]

In certain embodiments, $X^1$ is $NR^{x1}$, $R^{x1}$ is hydrogen or methyl, and $R^1$ is

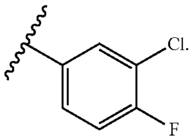 [SMILES: *c1ccc(F)c(Cl)c1]

In certain embodiments, $R^1$ is a 5-6 membered monocyclic heteroaryl optionally substituted with one, two, or three substituents independently selected from the group consisting of halogen, CN, $C_{1-6}$alkyl, and halo$C_{1-6}$alkyl.

In certain embodiments, $R^1$ is

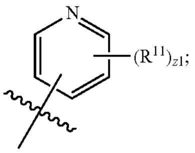

$R^{11}$ is independently selected for each occurrence from the group consisting of halogen, CN, $C_{1-6}$alkyl and halo$C_{1-6}$alkyl; and z1 is 0, 1, 2 or 3.

In certain embodiments, $R^2$ is hydrogen.

In certain embodiments, $R^2$ is $R^aR^bN$;

In certain embodiments, $R^2$ is $R^aR^bN$, and $R^a$ and $R^b$ are independently selected the group consisting of hydrogen and $C_{1-6}$alkyl.

In certain embodiments, $R^2$ is $NH_2$.

In certain embodiments, $X^1$ is $NR^{x1}$, $R^{x1}$ is hydrogen or methyl, $R^1$ is

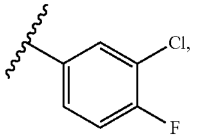 [SMILES: *c1ccc(F)c(Cl)c1]

and $R^2$ is hydrogen.

In certain embodiments, $X^1$ is $NR^{x1}$, $R^{x1}$ is hydrogen or methyl, $R^1$ is

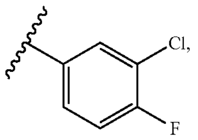 [SMILES: *c1ccc(F)c(Cl)c1]

and $R^2$ is $NH_2$.

In certain embodiments, $R^3$ is

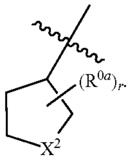

In certain embodiments, $R^3$ is

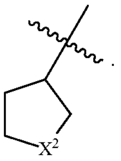

In certain embodiments, $R^3$ is

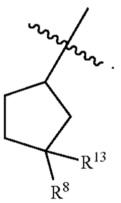

In certain embodiments, $R^3$ is

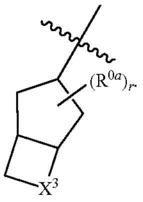

In certain embodiments, $R^3$ is

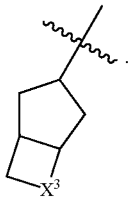

In certain embodiments, $R^3$ is

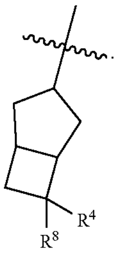

In certain embodiments, $R_3$ is

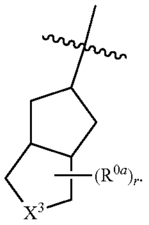

In certain embodiments, $R^3$ is

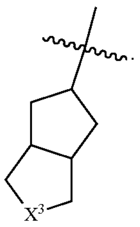

In certain embodiments, $R^3$ is

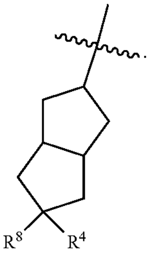

In certain embodiments, $R^3$ is

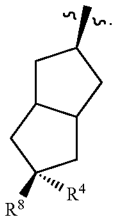

In certain embodiments, $R^3$ is

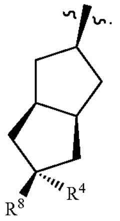

In certain embodiments, $R^4$ is $R^5$-$L^1$-.

In certain embodiments, $R^4$ is $R^5$.

In certain embodiments, $R^4$ is $R^6$.

In certain embodiments, $R^4$ is $R^9$.

In certain embodiments, or $R^4$ and $R^8$ together with the carbon atom to which they are attached form a

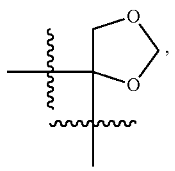

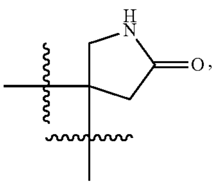

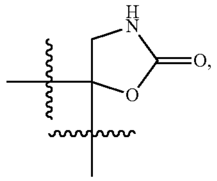

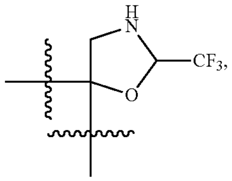

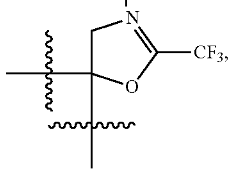

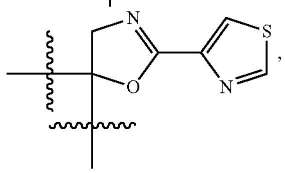

-continued
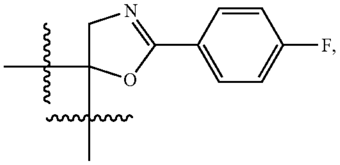
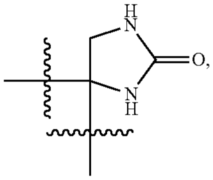
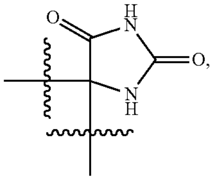
or
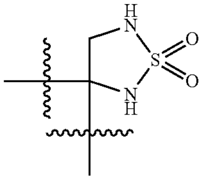
group.
In certain embodiments, $R^5$ is
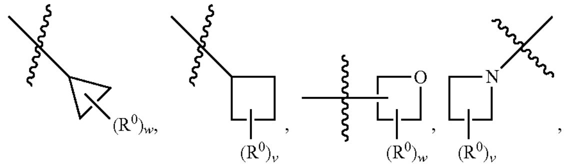
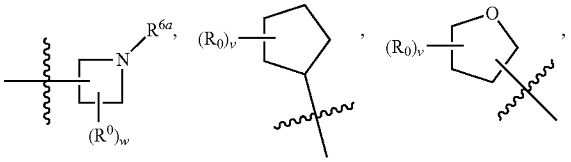
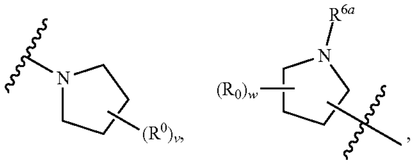
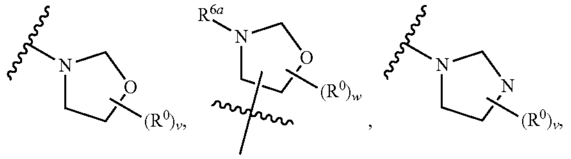
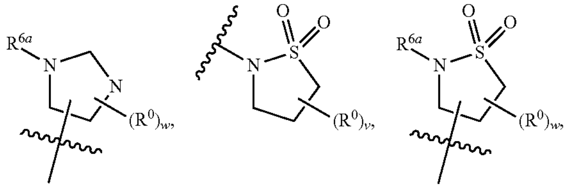
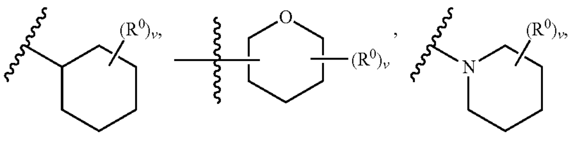
-continued
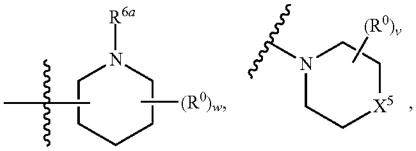
or
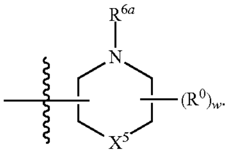
In certain embodiments, $R^5$ is
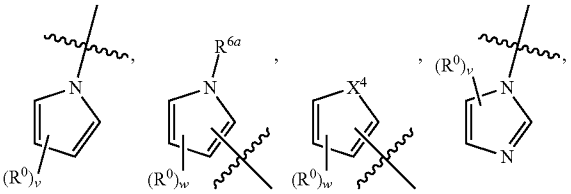
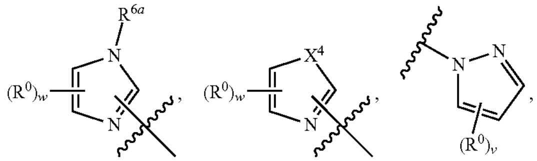
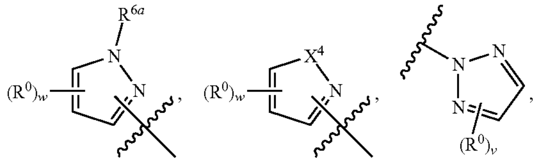
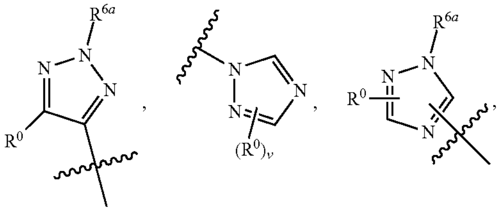
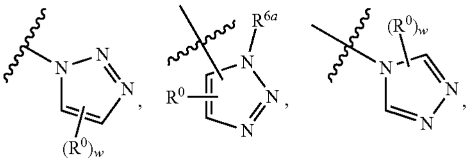
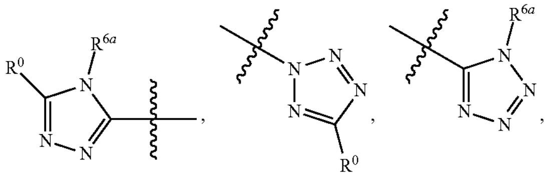
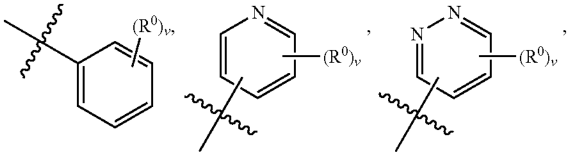

-continued

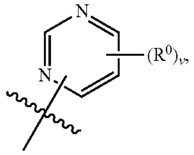

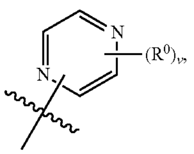

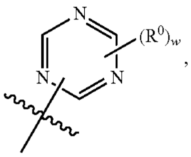

,

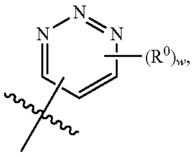

and

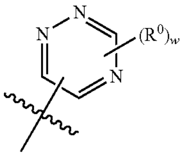

.

In certain embodiments, $R^5$ is

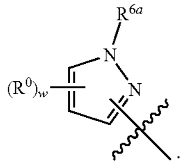

.

In certain embodiments, $R^6$ is $C_{1-6}$alkylS(O)$_t$$C_{1-6}$alkyl- or $C_{1-6}$alkylS(O)$_t$NR$^a$$C_{1-6}$alkyl-.

In certain embodiments, $R^8$ is hydrogen, OH or $C_{1-6}$alkoxy.

In certain embodiments, $R^8$ is OH.

In certain embodiments, $R^{14}$ is $R^aR^bN$—, $C_{1-6}$alkyl, $C_{2-6}$alkenyl, $C_{2-6}$alkynyl, $C_{1-6}$haloalkyl, $C_{1-6}$alkoxy, $C_{1-6}$haloalkyl, or $C_{1-6}$haloalkoxy.

In certain embodiments, $R^{14}$ is $R^5$-$L^1$-.

In certain embodiments, $R^{14}$ is $R^5$.

In certain embodiments, $X^1$ is $NR^{x1}$; $R^{x1}$ is hydrogen or methyl; $R^1$ is

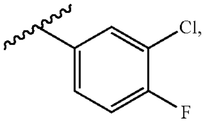 [SMILES: *c1ccc(F)c(Cl)c1]

$R^2$ is H; $R^3$ is

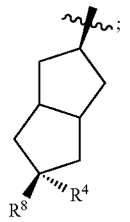

and $R^8$ is hydrogen, OH or $C_{1-6}$alkoxy.

In certain embodiments, $X^1$ is $NR^{x1}$; $R^{x1}$ is hydrogen or methyl; $R^1$ is

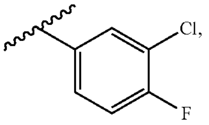 [SMILES: *c1ccc(F)c(Cl)c1]

$R^2$ is H; $R^3$ is

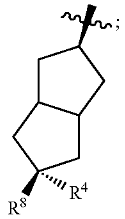

and $R^8$ is OH.

In certain embodiments, $X^1$ is $NR^{x1}$; $R^{x1}$ is hydrogen or methyl; $R^1$ is

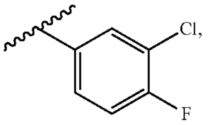 [SMILES: *c1ccc(F)c(Cl)c1]

$R^2$ is H; $R^3$ is

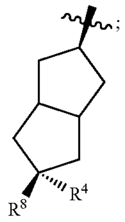

$R^5$ is

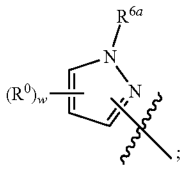

and $R^8$ is hydrogen, OH or $C_{1-6}$alkoxy.

In certain embodiments, $X^1$ is $NR^{x1}$; $R^{x1}$ is hydrogen or methyl; $R^1$ is

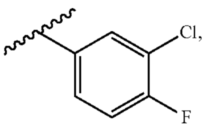 [SMILES: *c1ccc(F)c(Cl)c1]

$R^2$ is H; $R^3$ is

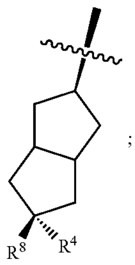

;

$R^5$ is

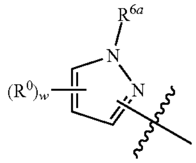

;

and $R^8$ is OH.

In certain embodiments, $X^1$ is $NR^{x1}$; $R^{x1}$ is hydrogen or methyl; $R^1$ is

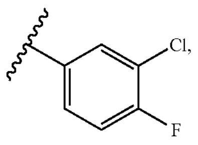

$R^2$ is $NH_2$; $R^3$ is

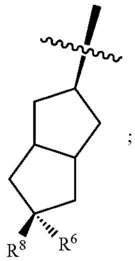

;

$R^6$ is $C_{1-6}$alkylS(O)$_t$C$_{1-6}$alkyl- or $C_{1-6}$alkylS(O)$_t$NR$^a$C$_{1-6}$alkyl-; and $R^8$ is hydrogen, OH or $C_{1-6}$alkoxy.

In certain embodiments, $X^1$ is $NR^{x1}$; $R^{x1}$ is hydrogen or methyl; $R^1$ is

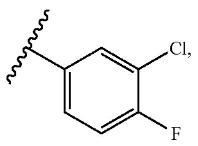

$R^2$ is $NH_2$; $R^3$ is

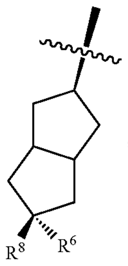

;

$R^6$ is $C_{1-6}$alkylS(O)$_t$C$_{1-6}$alkyl- or $C_{1-6}$alkylS(O)$_t$NR$^a$C$_{1-6}$alkyl-; and $R^8$ is OH.

III. PHARMACEUTICAL COMPOSITIONS AND KITS

In another aspect, the disclosure provides pharmaceutical compositions comprising a compound of Formula I, or a pharmaceutically acceptable salt thereof, and a pharmaceutically acceptable excipient. In particular, the present disclosure provides pharmaceutical compositions comprising compounds as disclosed herein formulated together with one or more pharmaceutically acceptable carriers. These formulations include those suitable for oral, rectal, topical, buccal, parenteral (e.g., subcutaneous, intramuscular, intradermal, or intravenous), rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

In another aspect, the disclosure provides a pharmaceutical composition comprises a compound according to any combination of the Examples described herein, or a pharmaceutically acceptable salt and/or stereoisomer thereof.

Exemplary pharmaceutical compositions of this disclosure may be used in the form of a pharmaceutical preparation, for example, in solid, semisolid or liquid form, which contains one or more compounds of the disclosure, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the disclosure, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present disclosure may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this disclosure suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants.

In another aspect, the disclosure provides enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that would meet the objectives of the present disclosure.

Advantageously, the disclosure also provides kits for use by e.g., a consumer in need of HBV infection treatment. Such kits include a suitable dosage form such as those described above and instructions describing the method of using such dosage form to mediate, reduce or prevent HBV infection. The instructions would direct the consumer or medical personnel to administer the dosage form according to administration modes known to those skilled in the art. Such kits could advantageously be packaged and sold in single or multiple kit units. An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . ." etc. Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

IV. METHODS

In a further aspect, a method for treating a hepatitis B infection in a patient in need thereof is provided, comprising administering to a subject or patient an effective amount of a disclosed compound, and/or administering a first disclosed compound and optionally, an additional, different disclosed compound(s). In another embodiment, a method for treating a hepatitis B infection in a patient in need thereof is provided, comprising administering to a subject or patient a therapeutically effective amount of a disclosed pharmaceutical composition or a pharmaceutical composition comprising a disclosed compound, or two or more disclosed compounds, and a pharmaceutically acceptable excipient.

For use in accordance with this aspect, the appropriate dosage is expected to vary depending on, for example, the particular compound employed, the mode of administration, and the nature and severity of the infection to be treated as well as the specific infection to be treated and is within the purview of the treating physician. Usually, an indicated administration dose may be in the range between about 0.1 to about 1000 μg/kg body weight. In some cases, the administration dose of the compound may be less than 400 μg/kg body weight. In other cases, the administration dose may be less than 200 μg/kg body weight. In yet other cases, the administration dose may be in the range between about 0.1 to about 100 μg/kg body weight. The dose may be conveniently administered once daily, or in divided doses up to, for example, four times a day or in sustained release form.

A compound of the present disclosure may be administered by any conventional route, in particular: enterally, topically, orally, nasally, e.g., in the form of tablets or capsules, via suppositories, or parenterally, e.g., in the form of injectable solutions or suspensions, for intravenous, intramuscular, sub-cutaneous, or intra-peritoneal injection. Suitable formulations and pharmaceutical compositions will include those formulated in a conventional manner using one or more physiologically acceptable carriers or excipients, and any of those known and commercially available and currently employed in the clinical setting. Thus, the compounds may be formulated for oral, buccal, topical, parenteral, rectal or transdermal administration or in a form suitable for administration by inhalation or insufflation (either orally or nasally).

For oral administration, pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g. lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). Tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). Preparations may also contain buffer salts, flavoring, coloring and sweetening agents as appropriate.

Preparations for oral administration may also be suitably formulated to give controlled-release or sustained release of the active compound(s) over an extended period. For buccal administration the compositions may take the form of tablets or lozenges formulated in a conventional manner known to the skilled artisan.

A disclosed compound may also be formulated for parenteral administration by injection e.g., by bolus injection or continuous infusion. Formulations for injection may be presented in unit dosage form e.g., in ampoules or in multi-dose containers, with an added preservative. The compositions may take such forms as suspensions, solutions or emulsions in oily or aqueous vehicles, and may contain additives such as suspending, stabilizing and/or dispersing agents. Alternatively, the compound may be in powder form for constitution with a suitable vehicle, e.g., sterile pyrogen-free water, before use. Compounds may also be formulated for rectal administration as suppositories or retention enemas, e.g., containing conventional suppository bases such as cocoa butter or other glycerides.

Also contemplated herein are methods and compositions that include a second active agent or administering a second active agent. For example, in addition to being infected with HBV, a subject or patient can further have HBV infection-related co-morbidities, i.e., diseases and other adverse health conditions associated with, exacerbated by, or precipitated by being infected with HBV. Contemplated herein are disclosed compounds in combination with at least one other agent that has previously been shown to treat these HBV-infection-related conditions.

In some cases, a disclosed compound may be administered as part of a combination therapy in conjunction with one or more antivirals. Example antivirals include nucleoside analogs, interferon α, and other assembly effectors, for instance heteroaryldihydropyrimidines (HAPs) such as methyl 4-(2-chloro-4-fluorophenyl)-6-methyl-2-(pyridin-2-yl)-1,4-dihydropyrimidine-5-carboxylate (HAP-1). For example, provided herein is a method of treating a patient suffering from hepatitis B infection comprising administering to the patient a first amount of a disclosed compound and a second amount of an antiviral, or other anti HBV agent, for example a second amount of a second compound selected from the group consisting of: an HBV capsid assembly promoter (for example, GLS4, BAY 41-4109, AT-130, DVR-23 (e.g., as depicted below),

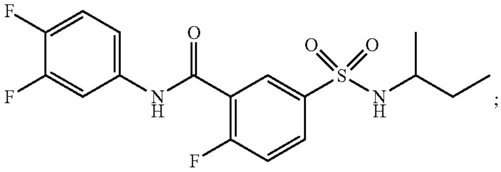
;

DVR-23

NVR 3-778, NVR1221 (by code); and N890 (as depicted below):

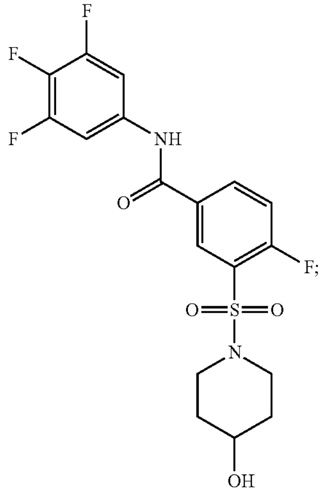 [SMILES: O=C(Nc1cc(F)c(F)c(F)c1)c1ccc(F)c(S(=O)(=O)N2CCC(O)CC2)c1]
;

other capsid inhibitors such as those disclosed in the following patent applications hereby incorporated by reference: WO2014037480, WO2014184328, WO2013006394, WO2014089296, WO2014106019, WO2013102655, WO2014184350, WO2014184365, WO2014161888, WO2014131847, WO2014033176, WO2014033167, and WO2014033170; Nucleos(t)ide analogs interfering with viral polymerase, such as entecavir (Baraclude), Lamivudine, (Epivir-HBV), Telbivudine (Tyzeka, Sebivo), Adefovir dipivoxil (Hepsera), Tenofovir (Viread), Tenofovir alafenamide fumarate (TAF), prodrugs of tenofavir (e.g. AGX-1009), L-FMAU (Clevudine), LB80380 (Besifovir) and:

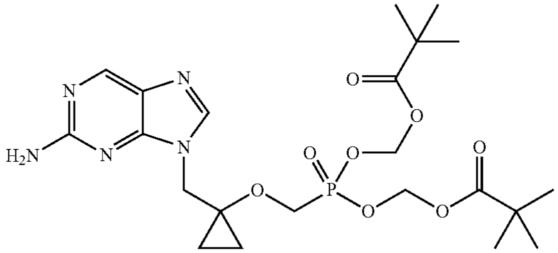
;

viral entry inhibitors such as Myrcludex B and related lipopeptide derivatives; HBsAg secretion inhibitors such as REP 9AC' and related nucleic acid-based amphipathic polymers, HBF-0529 (PBHBV-001), PBHBV-2-15 as depicted below:

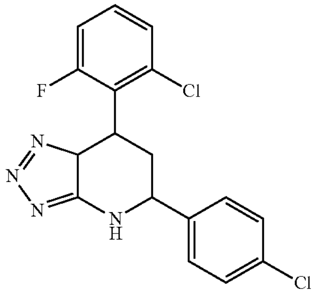

22: HBF-0529

-continued

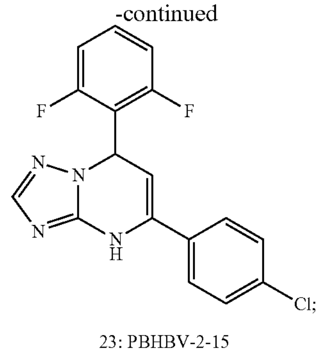

23: PBHBV-2-15 and BM601 as depicted below:

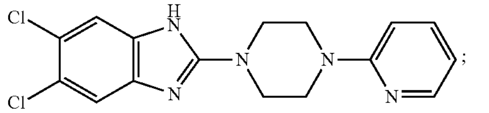 [SMILES: Clc1cc2nc(N3CCN(c4ccccn4)CC3)[nH]c2cc1Cl]

disruptors of nucleocapsid formation or integrity such as NZ-4/W28F:

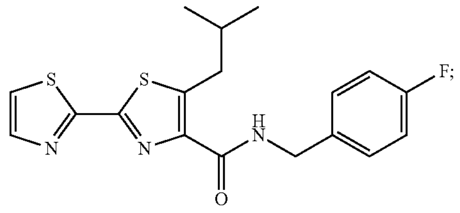

NZ-4 cccDNA formation inhibitors such as BSBI-25, CCC-0346, CCC-0975 as depicted below):

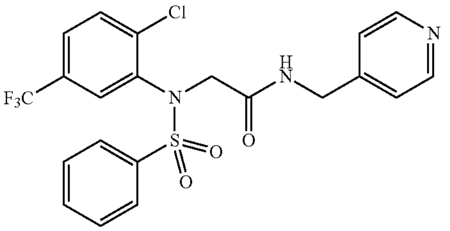

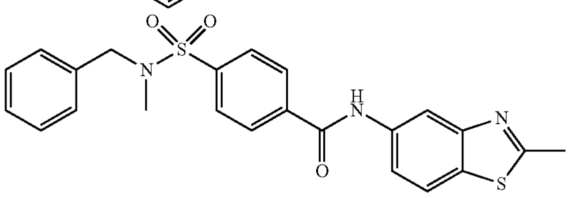

HBc directed transbodies such as those described in Wang Y, et al, Transbody against hepatitis B virus core protein inhibits hepatitis B virus replication in vitro, Int. Immunopharmacol (2014), located at //dx.doi.org/10.1016/j.intimp.2015.01.028; antiviral core protein mutant (such as Cp183-V124W and related mutations as described in WO/2013/010069, WO2014/074906, each incorporated by reference); inhibitors of HBx-interactions such as RNAi, antisense and nucleic acid based polymers targeting HBV RNA; e.g., RNAi (for example ALN-HBV, ARC-520, TKM-HBV, ddRNAi), antisense (ISIS-HBV), or nucleic acid based polymer: (REP 2139-Ca); immunostimulants such as Interferon alpha 2a (Roferon), Intron A (interferon alpha 2b), Pegasys (peginterferon alpha 2a), Pegylated IFN 2b, IFN lambda 1a and PEG IFN lambda 1a, Wellferon, Roferon, Infergen, lymphotoxin beta agonists such as CBE11 and BS1); Non-Interferon Immune enhancers such as Thymosin alpha-1 (Zadaxin) and Interleukin-7 (CYT107); TLR-7/9 agonists such as GS-9620, CYT003, Resiquimod; Cyclophilin inhibitors such as NVP018; OCB-030; SCY-635; Alisporivir; NIM811 and related cyclosporine analogs; vaccines such as GS-4774, TG1050, Core antigen vaccine; SMAC mimetics such as birinapant and other IAP-antagonists; Epigenetic modulators such as KMT inhibitors (EZH1/2, G9a, SETD7, Suv39 inhibitors), PRMT inhibitors, HDAC inhibitors, SIRT agonists, HAT inhibitors, WD antagonists (e.g. OICR-9429), PARP inhibitors, APE inhibitors, DNMT inhibitors, LSD1 inhibitors, JMJD HDM inhibitors, and Bromodomain antagonists; kinase inhibitors such as TKB1 antagonists, PLK1 inhibitors, SRPK inhibitors, CDK2 inhibitors, ATM & ATR kinase inhibitors; STING Agonists; Ribavirin; N-acetyl cysteine; NOV-205 (BAM205); Nitazoxanide (Alinia), Tizoxanide; SB 9200 Small Molecule Nucleic Acid Hybrid (SMNH); DV-601; Arbidol; FXR agonists (such as GW 4064 and Fexaramin); antibodies, therapeutic proteins, gene therapy, and biologics directed against viral components or interacting host proteins.

In some embodiments, the disclosure provides a method of treating a hepatitis B infection in a patient in need thereof, comprising administering a first compound selected from any one of the disclosed compounds, and one or more other HBV agents each selected from the group consisting of HBV capsid assembly promoters, HBF viral polymerase interfering nucleosides, viral entry inhibitors, HBsAg secretion inhibitors, disruptors of nucleocapsid formation, cccDNA formation inhibitors, antiviral core protein mutant, HBc directed transbodies, RNAi targeting HBV RNA, immunostimulants, TLR-7/9 agonists, cyclophilin inhibitors, HBV vaccines, SMAC mimetics, epigenetic modulators, kinase inhibitors, and STING agonists. In some embodiments, the disclosure provides a method of treating a hepatitis B infection in a patient in need thereof, comprising administering an amount of a disclosed compound, and administering another HBV capsid assembly promoter.

In some embodiments, the first and second amounts together comprise a pharmaceutically effective amount. The first amount, the second amount, or both may be the same, more, or less than effective amounts of each compound administered as monotherapies. Therapeutically effective amounts of a disclosed compound and antiviral may be co-administered to the subject, i.e., administered to the subject simultaneously or separately, in any given order and by the same or different routes of administration. In some instances, it may be advantageous to initiate administration of a disclosed compound first, for example one or more days or weeks prior to initiation of administration of the antiviral. Moreover, additional drugs may be given in conjunction with the above combination therapy.

In another embodiment, a disclosed compound may be conjugated (e.g., covalently bound directly or through molecular linker to a free carbon, nitrogen (e.g., an amino group), or oxygen (e.g., an active ester) of a disclosed compound), with a detection moiety, for e.g., a fluorophore moiety (such a moiety may for example re-emit a certain light frequency upon binding to a virus and/or upon photon excitation). Contemplated fluorophores include AlexaFluor® 488 (Invitrogen) and BODIPY FL (Invitrogen), as well as fluorescein, rhodamine, cyanine, indocarbocyanine, anthraquinones, fluorescent proteins, aminocoumarin, methoxycoumarin, hydroxycoumarin, Cy2, Cy3, and the like. Such disclosed compounds conjugated to a detection moiety may be used in e.g., a method for detecting HBV or biological pathways of HBV infection, e.g., in vitro or in vivo; and/or methods of assessing new compounds for biological activity.

V. EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

At least some of the compounds identified as "intermediates" herein are contemplated as compounds of the disclosure.

Abbreviations

- AcOH Acetic acid
- ACN Acetonitrile
- $Boc_2O$ Di-tert-butyl dicarbonate
- nBuLi n-Butyllithium
- DCM Dichloromethane
- DIAD Diisopropyl azodicarboxylate
- DIEA Diisopropyl ethylamine
- DMF N,N-Dimethylformamide
- DMSO Dimethyl sulfoxide
- DPPF 1,1'-Bis(diphenylphosphino)ferrocene
- EA, EtOAc Ethyl acetate
- $Et_3N$ Triethylamine
- HATU Hexafluorophosphate Azabenzotriazole Tetramethyl Uronium
- h, hr Hour(s)
- HPLC High performance liquid chromatography
- LCMS Liquid chromatography-mass spectrometry
- MeOH Methanol
- NMO N-Methylmorpholine-N-Oxide
- NBS N-Bromosuccinimide
- PE Petroleum ether
- iPrOH Isopropanol
- rt, r.t. Room temperature
- SFC Supercritical Fluid Chromatography
- TEA Triethylamine
- TFA Trifluoroacetic acid
- THF Tetrahydrofuran
- TLC Thin-layer chromatography
- XPhos 2-Dicyclohexylphosphino-2',4',6'-triisopropylbiphenyl Scheme I

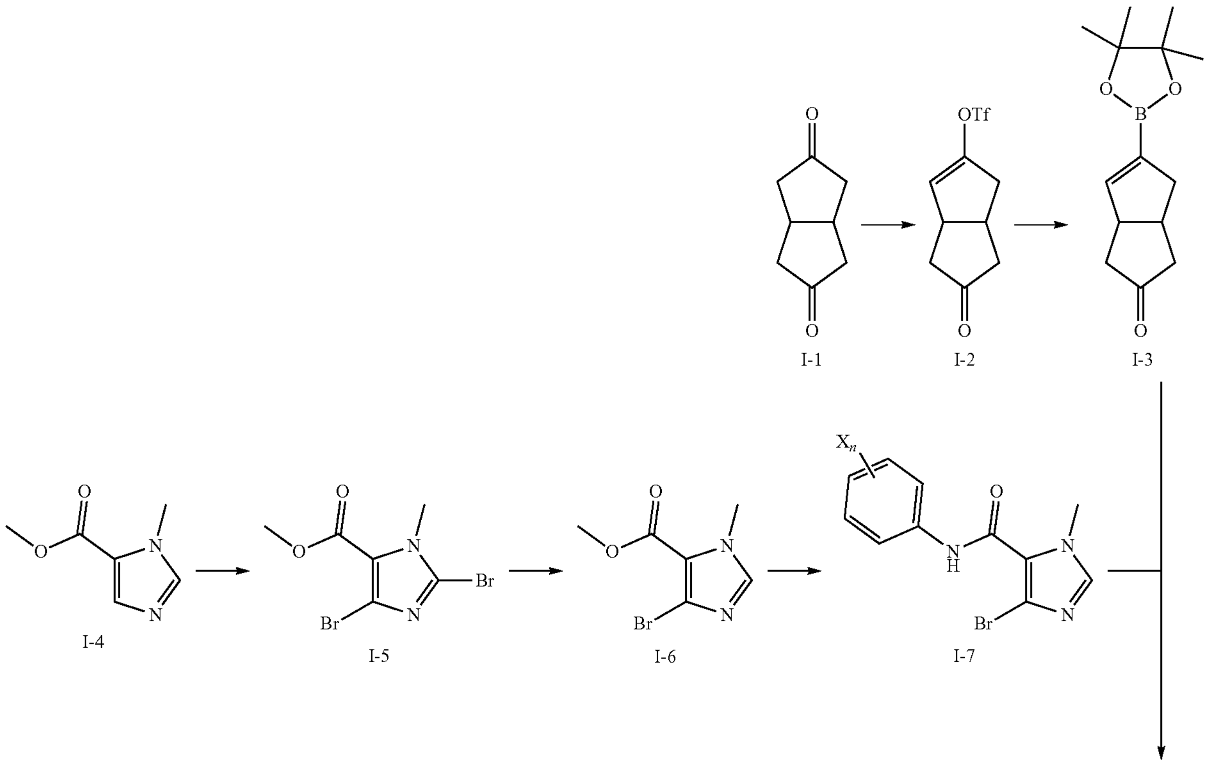

I-1 I-2 I-3

I-4 I-5 I-6 I-7

-continued
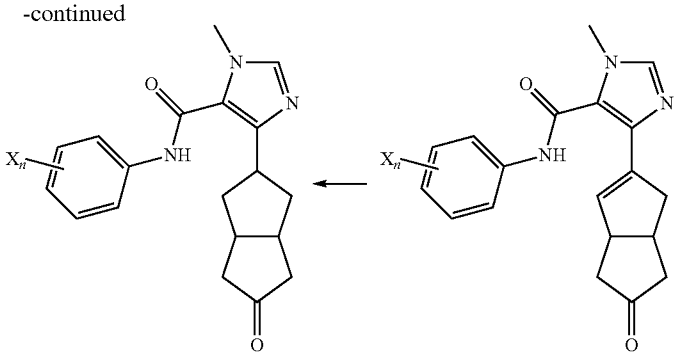
I-9 I-8
Scheme II
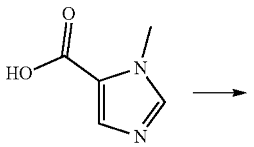
II-1
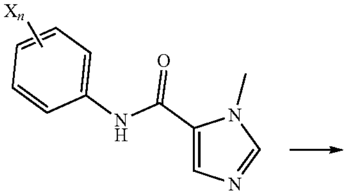
II-2
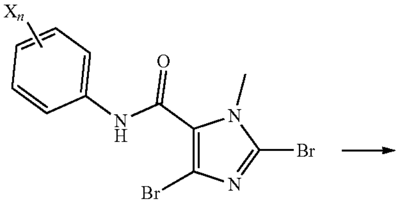
II-3
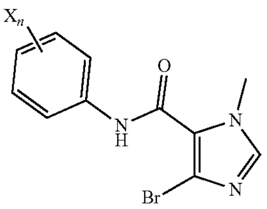
II-7
Scheme III
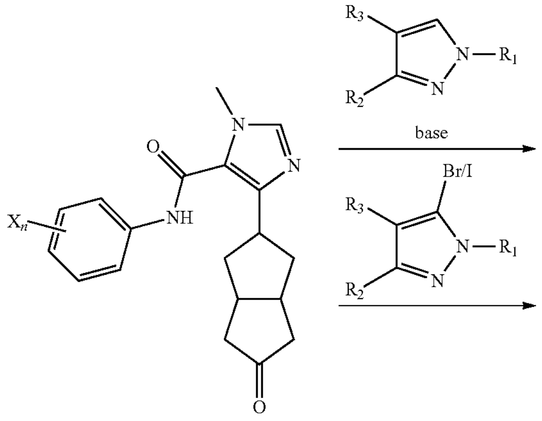
I-9
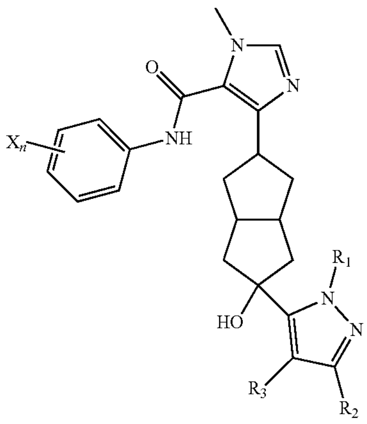

Scheme IV
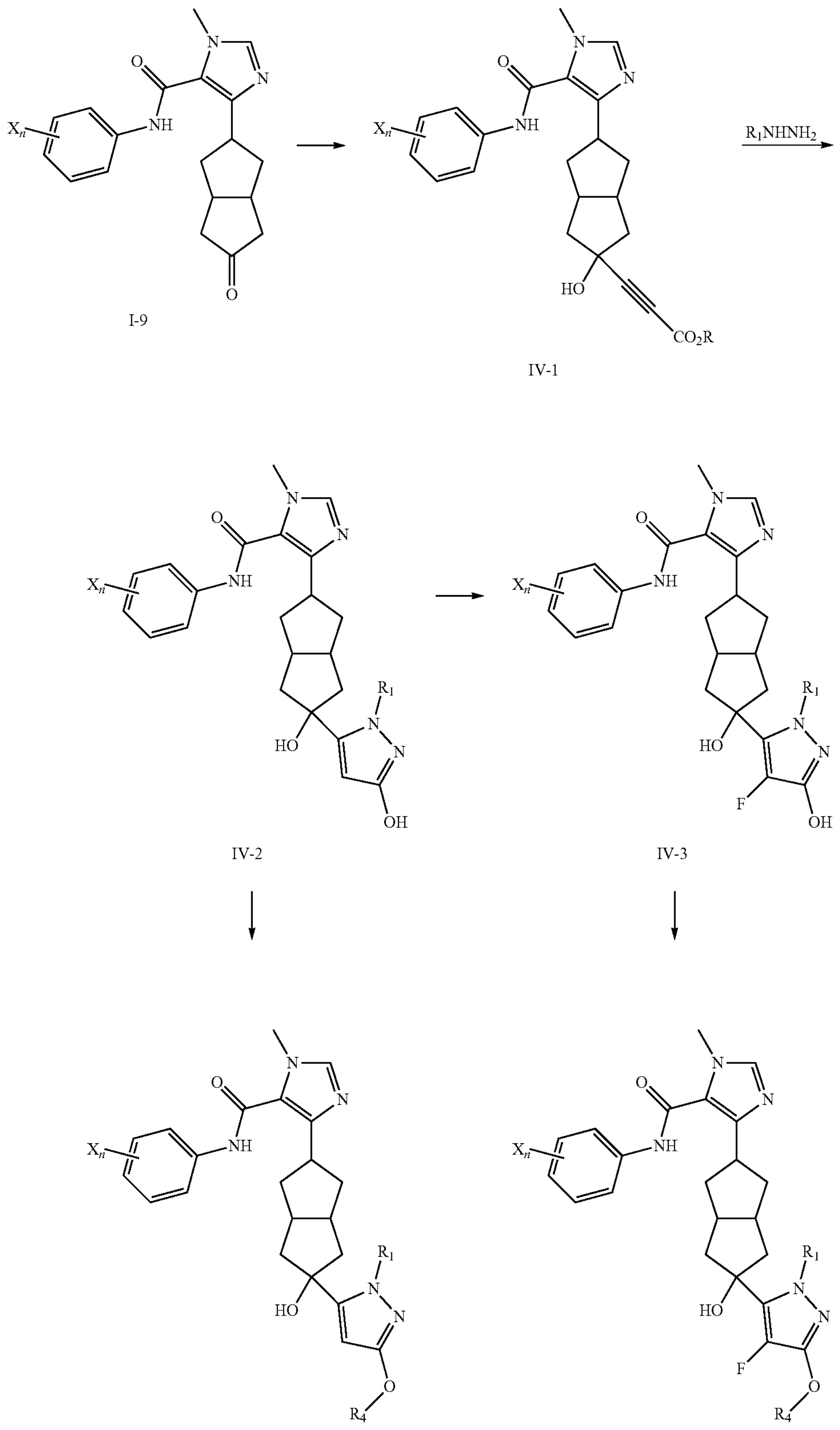
I-9
IV-1
IV-2
IV-3

Scheme V
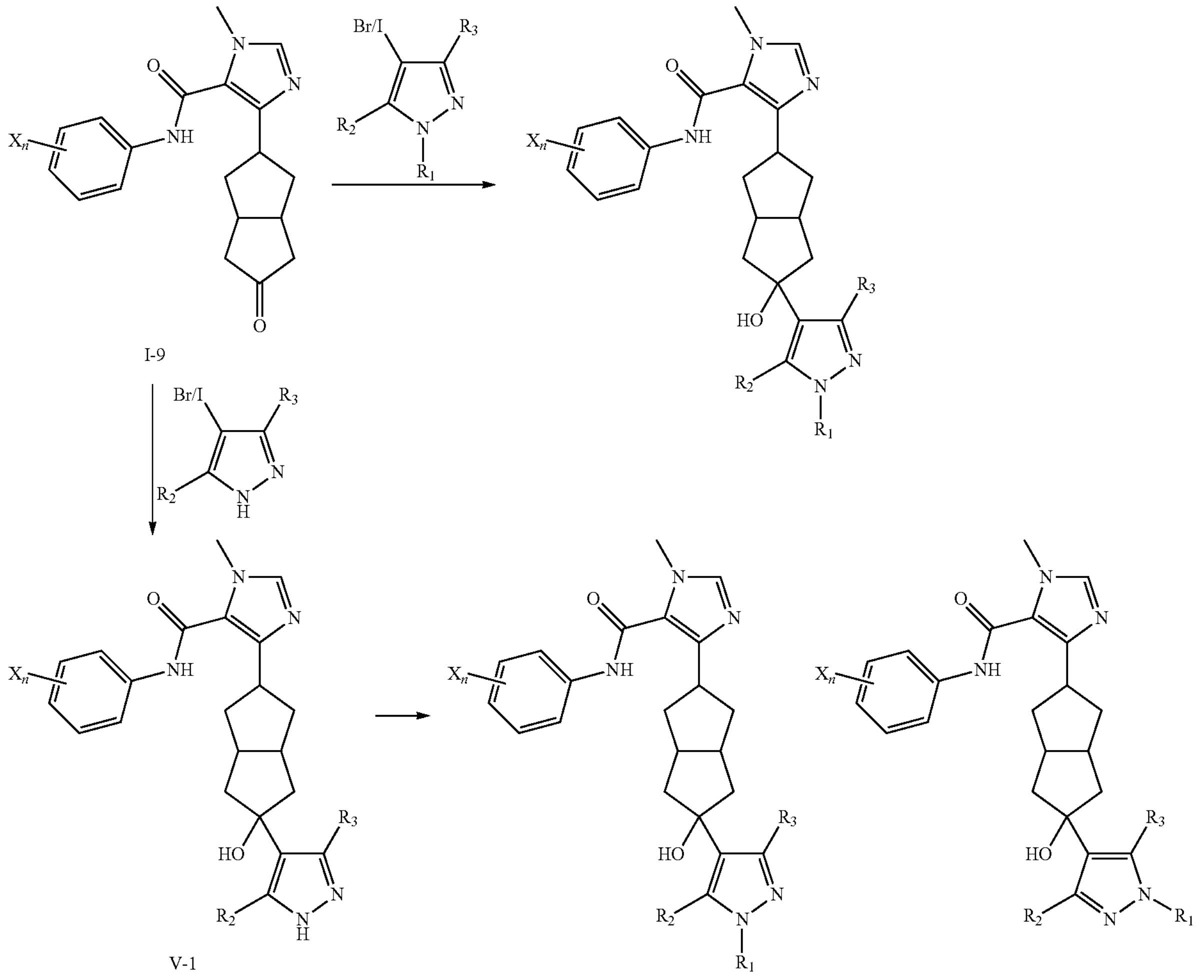
I-9
V-1
Scheme VI
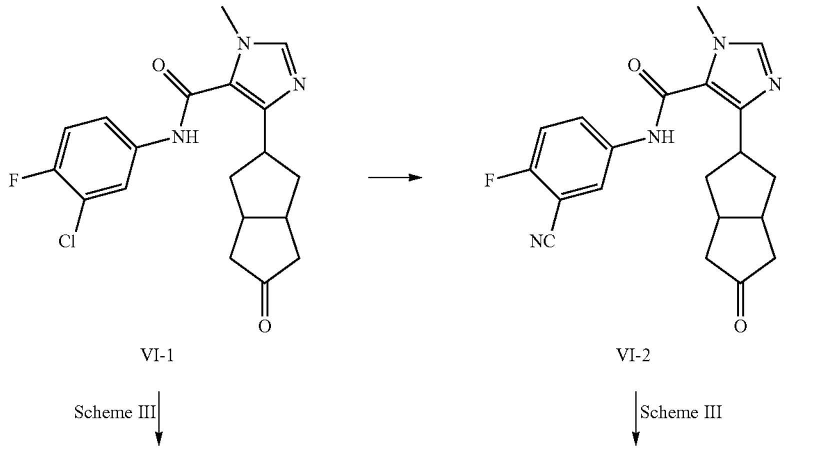
VI-1
VI-2

-continued

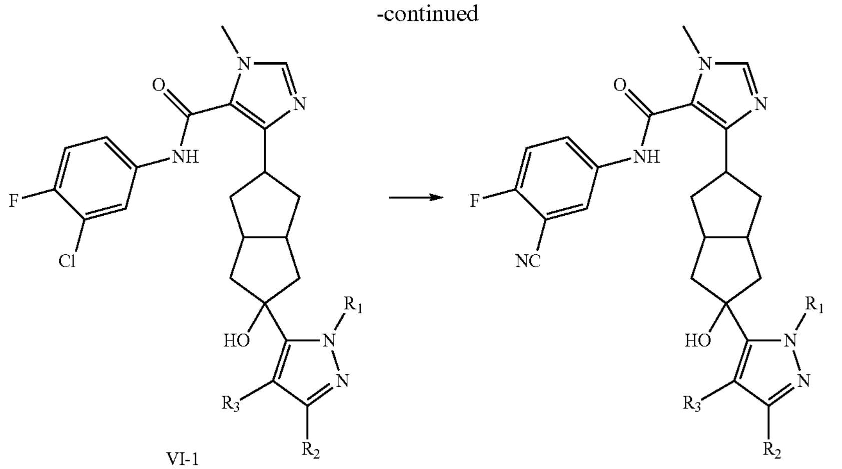

VI-1

Scheme VII

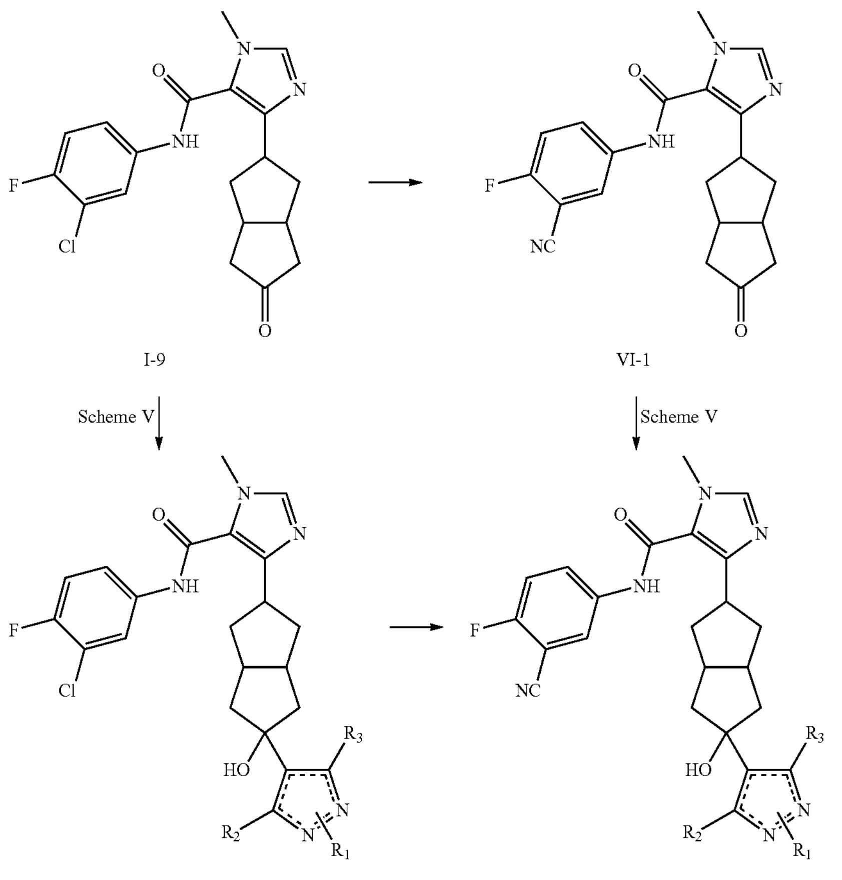

LCMS Method have been Used for the Analysis of Final Compounds:

Method A: X-Bridge BEH C-18 (3×50 mm×2.5 μm); Mobile phase: A; 0.025% formic acid in $H_2O$; B; $CH_3CN$; Injection volume: 2 μL; Flow rate: 1.2 mL/min, column temperature: 50° C.; Gradient program: 2% B to 98% B in 2.2 min, hold until 3 min, at 3.2 min B conc. is 2% till up to 4 min.

Method B: X-select CSH 18 (3×50 mm×2.5 μm); Mobile phase: A; 0.025% formic acid in $H_2O$; B; $CH_3CN$; Injection volume: 2 μL; Flow rate: 1.2 mL/min, column temperature: 50° C.; Gradient program: 0% B to 98% B in 2 min, hold until 3 min, at 3.2 min B conc. is 0% till up to 4 min.

Method C: X-select CSH 18 (3×50 mm×2.5 μm); Mobile phase: A; 0.05% formic acid in $H_2O$:$CH_3CN$ (95:5); B; 0.05% formic acid in $CH_3CN$; Injection volume: 2 μL; Flow rate: 1.2 mL/min, column temperature: 50° C.; Gradient program: 0% B to 98% B in 2 min, hold until 3 min, at 3.2 min B conc. is 0% till up to 4 min.

Method D: X-select CSH C18 (3×50 mm×2.5 μm); Mobile phase: A; 2 mM in Ammonium Bicarbonate; B; $CH_3CN$; Injection volume: 2 μL; Flow rate: 1.2 mL/min, column temperature: 50° C.; Gradient program: 0% B to 98% B in 2 min, hold till 3 min, at 3.2 min B conc. is 0% until up to 4 min.

Method E: X-select CSH 18 (3×50 mm×2.5 μm); Mobile phase: A; 0.05% formic acid in $H_2O$; B; $CH_3CN$; Injection volume: 2 μL; Flow rate: 1.5 mL/min, column temperature: 50° C.; Gradient program: 0% B to 100% B in 1.5 min, hold till 2.2 min, at 2.6 min B conc. is 0% until up to 3 min.

General Procedure for Amidation:

Method A (amide coupling using EDC·HCl): To a stirred solution of carboxylic acid (1 eq.) in 1,4-dioxane (5.84 mL/mmol) were added EDC·HCl (1.1 eq.), HOBt (1.1 eq.) and corresponding amine (1 eq.) at 0° C. and stirred for 5 min. To this solution, DIPEA (3 eq.) was added and the resulting reaction mixture was stirred at 90° C. for overnight. After completion, the reaction mixture was diluted with ice water and extracted with ethyl acetate. The organic layer was washed with sat. $NaHCO_3$ solution, water, dried over sodium sulfate, filtered and concentrated in vacuo to afford crude compound which was purified by silica gel column chromatography/prep. HPLC to afford the desired compound.

Method B (amide coupling using HATU): To a stirred solution of acid compound (1.1-1.2 eq.) in DMF/DCM (1.01 mL/mmol) at 0° C., DIPEA (2-3 eq.) and HATU (1.5-2.5 eq.) were added and stirred for 5 min. To this solution, corresponding amine (1 eq.) was added. The resulting reaction mixture was stirred at room temperature for 12-16 hr. After completion, the reaction mixture was diluted with ice cold water and extracted with ethyl acetate. The organic layer was collected; washed with brine; dried over anhydrous sodium sulphate and concentrated under reduced pressure to afford a crude compound. The crude compound was purified by either prep-HPLC or CombiFlash® column chromatography to afford the desired compound.

Method C ($AlMe_3$ mediated amidation): To a stirred solution of corresponding anilines (1.1 eq.) in DCM/Toluene (3 mL/mmol) at 0° C. under Argon atmosphere, $AlMe_3$ (2M in toluene, 2.5 eq.) was added and the reaction mixture was stirred at 0° C. for 10 min and continued stirring at room temperature for 1 h. To this solution, corresponding ester compound (1 eq.) was added at 0° C. under Argon atmosphere and the resulting reaction mixture was refluxed at 100° C. for 16 hr. After completion, the reaction mixture was cooled to 0° C.; quenched with aqueous 1N HCl solution slowly and extracted with ethyl acetate. The combined organic layers were collected, dried over anhydrous sodium sulphate and concentrated in vacuo. The crude compound was purified by washing with methanol to afford the desired compound.

Method D (amide coupling using acid chloride/derivatives): To a stirred solution of amine compound (1 eq.) in DCM (1.01 mL/mmol) was added TEA (1.5-3 eq.) at 0° C. and stirred for 5 min. To this solution, corresponding acid chloride/carbamic chloride/chloroformate (1.1-1.5 eq.) was added slowly at 0° C. and the reaction mixture was allowed to stir at room temperature until completion. After completion, the reaction mixture was diluted with ice cold water and extracted with ethyl acetate/DCM. The organic layer was collected; washed with brine; dried over anhydrous sodium sulphate and concentrated under reduced pressure to afford a crude compound. The crude compound was purified by either prep-HPLC or CombiFlash® column chromatography to afford the desired compound.

General Procedure for Grignard Reaction:

Method A (at lower temperature): To a stirred solution of keto compound (1 eq.) in dry THF (0.2 mL/mmol) in an inert atmosphere was added Grignard reagent (10 eq.) slowly via glass syringe at −78° C. and the reaction mixture stirred for 4 hr at same temperature then at room temperature for 2 h. After completion, the reaction mixture was diluted with sat. aq. solution of ammonium chloride and extracted with ethyl acetate/DCM. The organic layer was collected; washed with brine; dried over anhydrous sodium sulphate and concentrated on rotavapor to afford a crude compound. The crude compound was purified by either by CombiFlash® column chromatography or prep-HPLC to afford the desired compound.

General Method for Suzuki Coupling:

Method A: To a mixture of halo compound (1 eq.) and corresponding boronic acid/boronate ester (1.2-1.5 eq.) in 1,4-dioxane:water (4:1) (2.17 mL/mmol), $Na_2CO_3$ (2-3 eq.) was added and purged with Argon for 15 min. To this solution, $PdCl_2$ (dppf) (0.1 eq.) was added and purging with Argon continued for another 10 min. The resulting reaction mixture was stirred at 100° C. for 12-16 hr. After completion of the reaction, the reaction mixture was filtered through Celite®545 and evaporated to dryness. The residue was taken in ethyl acetate, washed with water, followed by brine, dried over anhydrous sodium sulphate and evaporated under reduced pressure. The crude product was purified by either CombiFlash® column chromatography or prep-HPLC to afford the desired compound.

General Procedure for Hydrogenation:

Method A: To a stirred solution of olefinic compound (1 eq.) in EtOAc (2.67 mL/mmol) under nitrogen atmosphere, 20% Pd/C (20% by w/w of olefinic compound) was added. The reaction mixture was stirred under hydrogen atmosphere (100 psi) at 40-50° C. for 4-7 h. After completion, the reaction mixture was filtered through a pad of Celite®545 and washed with EtOAc/methanol. The filtrate was concentrated under reduced pressure to compound which was purified by silica gel column chromatography or prep-HPLC to give the desired compound.

General Procedure for Keto-Reduction:

Method A: To a stirred solution of keto compound (1 eq.) in EtOH/MeOH (5 vol) (4.7 mL/mmol), at 0° C. under Argon atmosphere, $NaBH_4$ (1-2 eq.) was added and stirred at room temperature for 2-6 hr. After completion, the reaction mixture was concentrated in vacuo, the residue obtained was diluted with water and extracted using ethyl acetate. The combined organic layers were collected, dried over anhydrous sodium sulphate, filtered, concentrated in vacuo and purified by silica gel column chromatography/prep. HPLC to give the desired compound. Note: THF was also (1 vol) added as a co-solvent for substrates which are having poor solubility in alcoholic solvents.

Intermediate 1

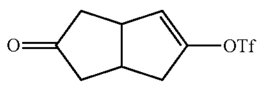 [SMILES: O=C1CC2C=C(OS(=O)(=O)C(F)(F)F)CC2C1]

5-Oxo-1,3a,4,5,6,6a-hexahydropentalen-2-yl trifluoromethanesulfonate. To a solution of 1,3,3a,4,6,6a-hexahydropentalene-2,5-dione (40.0 g, 289.5 mmol) and pyridine (24.0 g, 304.0 mmol) in DCM (600 ml) was added $Tf_2O$ (89.8 g, 318.5 mmol) dropwise at room temperature. The mixture was stirred at room temperature for 3 h. Brine (300 mL) was added, and the aqueous layer extracted with DCM (200 mL×3). The organic layer was separated, dried over $Na_2SO_4$ and concentrated to give the crude product which was purified by silica gel column chromatography using 8:1 (v/v) petroleum ether/ethyl acetate to afford 5-oxo-1,3a,4,5,6,6a-hexahydropentalen-2-yl trifluoromethanesulfonate as a yellow oil. $^1H$ NMR (400 MHz, $CDCl_3$): δ 5.63 (q, J=1.92 Hz, 1H), 3.57-3.50 (m, 1H), 3.14-3.00 (m, 2H), 2.67-2.58 (m, 1H), 2.56-2.40 (m, 2H), 2.34-2.26 (m, 1H), 2.17 (ddd, J=19.14, 7.34, 1.63 Hz, 1H) ppm.

Intermediate 2

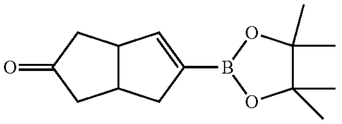 [SMILES: CC1(C)OB(C2=CC3CC(=O)CC3C2)OC1(C)C]

5-(4,4,5,5-Tetramethyl-1,3,2-dioxaborolan-2-yl)-3,3a,6,6a-tetrahydropentalen-2(1H)-one. A mixture of 5-oxo-1,3a,4,5,6,6a-hexahydropentalen-2-yl trifluoromethanesulfonate (110.0 g, 407.0 mmol), 4,4,5,5-tetramethyl-2-(4, 4,5,5-tetramethyl-1,3,2-dioxaborolan-2-yl)-1,3,2-dioxaborolane (108.5 g, 427.4 mmol), $Pd(dppf)Cl_2$ (8.9 g, 12.2 mmol) and potassium acetate (119.7 g, 1221.0 mmol) in dioxane (1000 ml) was stirred at 80° C. under an $N_2$ atmosphere for 2 h. The reaction mixture was filtered through a pad of Celite® and the filter cake was washed with EtOAc (250 mL×3). The filtrate was concentrated under vacuo and the residue was purified by silica gel column chromatography using 8:1 petroleum ether/ethyl acetate to afford 5-(4,4,5,5-tetramethyl-1,3,2-dioxaborolan-2-yl)-3,3a,6,6a-tetrahydropentalen-2(1H)-one as a yellow oil. $^1H$ NMR (400 MHz, $CDCl_3$): δ 6.37 (q, J=2.08 Hz, 1H), 3.54-3.41 (m, 1H), 3.05-2.93 (m, 1H), 2.79 (ddt, J=16.48, 7.58, 2.64, 2.64 Hz, 1H), 2.55-2.24 (m, 4H), 2.07-1.95 (m, 1H), 1.28 (s, 13H) ppm.

Intermediate 3

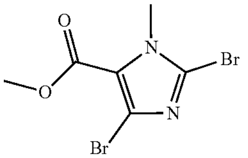

Methyl 2,4-dibromo-1-methyl-1H-Imidazole-5-carboxylate. To a solution of methyl 1-methyl-1H-imidazole-5-carboxylate (16.6 g, 118.5 mmol) in $CHCl_3$ (200 mL) was added NBS (78.3 g, 414.8 mmol) and AIBN (1.95 g, 11.9 mmol). The reaction mixture was stirred at 60° C. for 24 h. The mixture was concentrated and purified by column chromatography ($R_f$=0.4, PE:EA=5:1) to give methyl 2,4-dibromo-1-methyl-1H-imidazole-5-carboxylate (22.2 g, 63% yield) as a yellow solid.

Intermediate 4

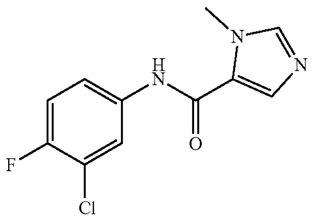 [SMILES: Cn1cncc1C(=O)Nc1ccc(F)c(Cl)c1]

N-(3-Chloro-4-fluorophenyl)-1-methyl-1H-Imidazole-5-carboxamide. To a solution of 1-methyl-1H-imidazole-5-carboxylic acid (10 g, 83 mmol), 3-chloro-4-fluoroaniline (18 g, 124 mmol) and $Et_3N$ (16 g, 160 mmol) in DMF (100 mL) was added HATU (63 g, 160 mmol) at room temperature. The reaction mixture was stirred at 25° C. overnight then poured into water (200 mL). Yellow solids were formed from the solution which was filtered and dried to provide N-(3-chloro-4-fluorophenyl)-1-methyl-1H-imidazole-5-carboxamide as a pale white solid. TLC; (50% ethyl acetate/petroleum ether) (Rf: 0.3). MS calcd. for $C_{11}H_9ClFN_3O$: 253.0; Found: 254.1 $[M+1]^+$.

Intermediate 5

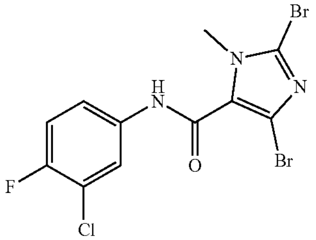 [SMILES: Cn1c(Br)nc(Br)c1C(=O)Nc1ccc(F)c(Cl)c1]

2,4-Dibromo-N-(3-chloro-4-fluorophenyl)-1-methyl-1H-imidazole-5-carboxamide. To a solution of N-(3-chloro-4-fluorophenyl)-1-methyl-1H-imidazole-5-carboxamide (4 g, 15 mmol) in $CHCl_3$ (100 mL) was added NBS (10 g, 60 mmol) and AIBN (0.25 g, 1.5 mmol) at room temperature. The reaction mixture was stirred at 50° C. for 18 h. The mixture was evaporated under vacuo to give a yellow residue. The residue was purified by silica gel chromatography to give 2,4-dibromo-N-(3-chloro-4-fluorophenyl)-1-methyl-1H-imidazole-5-carboxamide as yellow solid. TLC; 40% ethyl acetate/petroleum ether ($R_f$; 0.3). MS calcd. for $C_{11}H_7Br_2ClFN_3O$: 408.9; Found; 411.2 $[M+2]^+$.

Alternative synthesis of 2,4-Dibromo-N-(3-chloro-4-fluorophenyl)-1-methyl-1H-imidazole-5-carboxamide. To a solution of 2,4-dibromo-1-methyl-1H-imidazole-5-carboxylic acid (9.94 g, 35.0 mmol) in DMF (50 mL) was added HATU (13.3 g, 35.0 mmol) and DIPEA (9.69 g, 175 mmol) at 0° C., the reaction mixture was stirred at 0° C. for 1 h. Then 3-chloro-4-fluoroaniline (6.1 g, 42.0 mmol) was added and the reaction mixture stirred at room temperature overnight. The mixture was added dropwise to water (600 mL) and the resulting precipitate filtered to provide 2,4-dibromo- N-(3-chloro-4-fluorophenyl)-1-methyl-1H-imidazole-5-carboxamide (12.5 g, 87% yield) as a yellow solid.

Intermediate 6

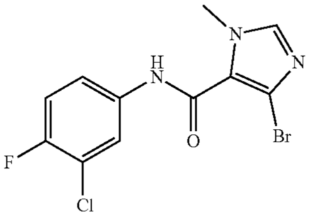 [SMILES: Cn1cnc(Br)c1C(=O)Nc1ccc(F)c(Cl)c1]

4-Bromo-N-(3-chloro-4-fluorophenyl)-1-methyl-1H-imidazole-5-carboxamide. To a solution of 2,4-dibromo-N-(3-chloro-4-fluorophenyl)-1-methyl-1H-imidazole-5-carboxamide (1.1 g, 2.0 mmol) in THF (50 mL) was added $CH_3MgI$ (2 mL, 4.0 mmol) slowly at room temperature. The reaction mixture was stirred at 50° C. for 4 h then poured into water (50 ml) and extracted with ethyl acetate (20 mL×3). The organic layer was dried and concentrated. The residue was purified by silica gel chromatography to give 4-bromo-N-(3-chloro-4-fluorophenyl)-1-methyl-1H-imidazole-5-carboxamide as a yellow solid. TLC; 50% ethyl acetate/petroleum ether (Rf: 0.3). MS calcd. for $C_{11}H_8BrClFN_3O$: 331.0; Found: 332.1 $[M+1]^+$.

Alternative procedure for the synthesis of 4-bromo-N-(3-chloro-4-fluorophenyl)-1-methyl-1H-imidazole-5-carboxamide. The titled compound was synthesized following the general procedure described above for amidation (Method C) to afford 4-bromo-N-(3-chloro-4-fluorophenyl)-1-methyl-1H-imidazole-5-carboxamide as a brown solid. TLC; 30% EtOAc/hexanes ($R_f$: 0.45); $^1H$ NMR (DMSO-$d_6$, 400 MHz): δ 10.41 (s, 1H), 7.96 (dd, J=6.8, 2.4 Hz, 1H), 7.85 (s, 1H), 7.63-7.60 (m, 1H), 7.43 (t, J=9.6 Hz, 1H), 3.75 (s, 3H); LCMS calcd. for $C_{11}H_8BrClFN_3O$: 331.0; Found: 332.1 $[M+1]^+$.

Intermediate 7

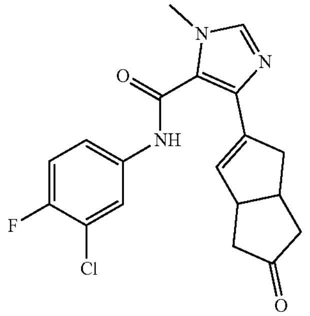 [SMILES: Cn1cnc(C2=CC3CC(=O)CC3C2)c1C(=O)Nc1ccc(F)c(Cl)c1]

N-(3-Chloro-4-fluorophenyl)-1-methyl-4-(5-oxo-1,3a,4,5,6,6a-hexahydropentalen-2-yl)-1H-imidazole-5-carboxamide. A mixture of 4-bromo-N-(3-chloro-4-fluorophenyl)-1-methyl-1H-imidazole-5-carboxamide (600 mg, 1.8 mmol), 5-(4,4,5,5-tetramethyl-1,3,2-dioxaborolan-2-yl)-3,3a,6,6a-tetrahydropentalen-2(1H)-one (448 mg, 1.8 mmol), $Pd(dppf)Cl_2$ (62 mg, 0.077 mmol) and $K_3PO_4$ (814 mg, 3.6 mmol) in dioxane (20 mL) and water (4 mL) was stirred at 100° C. for 4 h under $N_2$. EtOAc (20 mL) was then added to the mixture. The mixture was filtered, and the filtrate washed with $H_2O$ (35 mL×3). The organic layer was separated, dried over $Na_2SO_4$ and evaporated in vacuo to give a yellow residue. The residue was purified by silica gel column chromatography using 20-50% petroleum ether/ethyl acetate to give N-(3-chloro-4-fluorophenyl)-1-methyl-4-(5-oxo-1,3a,4,5,6,6a-hexahydropentalen-2-yl)-1H-imidazole-5-carboxamide as a brown solid. TLC; 5% MeOH/DCM ($R_f$: 0.2). MS calcd. for $C_{19}H_{17}ClFN_3O_2$: 373.13. Found; 374.1 $[M+1]^+$.

Alternative synthesis of N-(3-Chloro-4-fluorophenyl)-1-methyl-4-(5-oxo-1,3a,4,5,6,6a-hexahydropentalen-2-yl)-1H-imidazole-5-carboxamide. To a solution of 4-bromo-N-(3-chloro-4-fluorophenyl)-1-methyl-1H-imidazole-5-carboxamide (13.3 g, 40.0 mmol) in 1,4-dioxane/$H_2O$ (v/v=7:1, 120 mL) were added 5-(4,4,5,5-tetramethyl-1,3,2-dioxaborolan-2-yl)-3,3a,6,6a-tetrahydropentalen-2(1H)-one (12.2 g, 48.0 mmol), $Pd(dppf)Cl_2$ (2.9 g, 4.0 mmol) and $Na_2CO_3$ (10.6 g, 100.0 mmol), respectively, and the mixture was stirred at 100° C. overnight. The reaction mixture was cooled to room temperature, filtered through a pad of celite. The solid was washed with EA and the filtrate was concentrated to give the crude product, which was purified by column chromatography on silica gel with 5% of methanol in DCM (120 g silica gel column, 60 mL/min) to afford N-(3-chloro-4-fluorophenyl)-1-methyl-4-(5-oxo-1,3a,4,5,6,6a-hexahydropentalen-2-yl)-1H-imidazole-5-carboxamide (12.8 g, 85.6%) as a brown solid. TLC: 7% methanol/DCM ($R_f$: 0.5); MS calcd. for $C_{19}H_{17}ClFN_3O_2$: 373.1; Found: 374.3 $[M+1]^+$.

Example 1

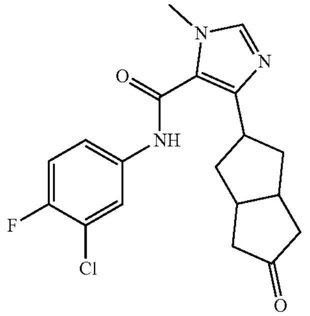 [SMILES: Cn1cnc(C2CC3CC(=O)CC3C2)c1C(=O)Nc1ccc(F)c(Cl)c1]

N-(3-Chloro-4-fluorophenyl)-1-methyl-4-(5-oxooctahydropentalen-2-yl)-1H-imidazole-5-carboxamide. To a solution of N-(3-chloro-4-fluorophenyl)-1-methyl-4-(5-oxo-1,3a,4,5,6,6a-hexahydropentalen-2-yl)-1H-imidazole-5-carboxamide (300 mg, 0.8 mmol) in THF (20 ml) was added Pd/C (30 mg, 10% Pd). The mixture was stirred at 30° C. for 5 h under $H_2$. The mixture was filtered, and the filtrate was evaporated in vacuo to give a yellow residue. The residue was purified by silica gel chromatography to give N-(3-chloro-4-fluorophenyl)-1-methyl-4-(5-oxooctahydropentalen-2-yl)-1H-imidazole-5-carboxamide a brown solid, as a single diastereomer. TLC; 50% ethyl acetate/petroleum ether ($R_f$: 0.3). MS calcd. for $C_{19}H_{19}ClFN_3O_2$: 375.2; Found; 376.2 $[M+1]^+$.

Alternative Synthesis of N-(3-Chloro-4-fluorophenyl)-1-methyl-4-(5-oxooctahydropentalen-2-yl)-1H-imidazole-5-carboxamide To a solution of N-(3-chloro-4-fluorophenyl)-1-methyl-4-(5-oxo-1,3a,4,5,6,6a-hexahydropentalen-2-yl)-1H-imidazole-5-carboxamide (12.8 g, 34.2 mmol) in THF (200 mL) was added Pd/C (6.4 g, 10%) under $H_2$ and the mixture stirred at room temperature for 4 hours. The mixture was filtered through a pad of celite and washed with methanol. The filtrate was concentrated in vacuo to give the crude product, which was purified by column chromatography on silica gel with 5% of methanol in DCM (80 g silica gel column, 50 mL/min) to afford N-(3-Chloro-4-fluorophenyl)-1-methyl-4-(5-oxooctahydropentalen-2-yl)-1H-imidazole-5-carboxamide, a gray solid, as a single diastereomer (12.0 g, 93.3%). TLC: 7% methanol/DCM ($R_f$: 0.5); MS calcd. for $C_{19}H_{19}ClFN_3O_2$: 375.2; MS Found: 376.3 $[M+1]^+$.

Example 2

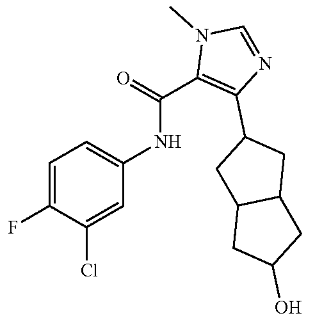 [SMILES: Cn1cnc(C2CC3CC(O)CC3C2)c1C(=O)Nc1ccc(F)c(Cl)c1]

N-(3-Chloro-4-fluorophenyl)-4-(5-hydroxyoctahydropentalen-2-yl)-1-methyl-1H-imidazole-5-carboxamide. To a solution of N-(3-chloro-4-fluorophenyl)-1-methyl-4-(5-oxooctahydropentalen-2-yl)-1H-imidazole-5-carboxamide (20 mg, 0.053 mmol) in MeOH (2 ml) was added $NaBH_4$ (36 mg, 0.95 mmol). The mixture was stirred at room temperature for 8 h. The mixture was evaporated in vacuo to give a yellow residue. The residue was purified by prep-HPLC to give N-(3-chloro-4-fluorophenyl)-4-(5-hydroxyoctahydropentalen-2-yl)-1-methyl-1H-imidazole-5-carboxamide, a white solid, as a single diastereomer. TLC; 50% ethyl acetate/petroleum ether ($R_f$: 0.3). MS calcd. for $C_{19}H_{21}ClFN_3O_2$: 377.1. Found; 378.2 $[M+1]^+$. $^1H$ NMR (DMSO-d6, 400 MHz): δ 10.22 (s, 1H), 7.96 (dd, J=6.8, 2.4 Hz, 1H), 7.64 (s, 1H), 7.58-7.54 (m, 1H), 7.40 (t, J=8.8 Hz, 1H), 4.50 (d, J=4.4 Hz, 1H), 4.03 (dd, J=6.8, 2.4 Hz, 1H), 3.66 (s, 3H), 3.26-3.20 (m, 1H), 2.32-2.28 (m, 2H), 2.11-2.05 (m, 2H), 1.95-1.89 (m, 2H), 1.70-1.62 (m, 2H), 1.30-1.23 (m, 2H) ppm.

Example 3

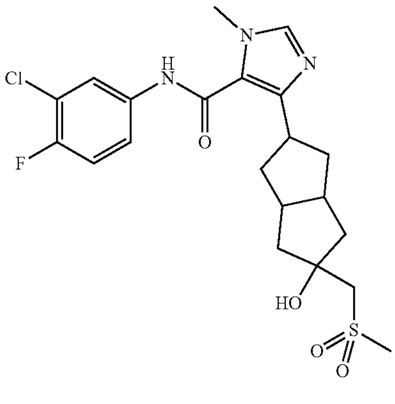 [SMILES: Cn1cnc(C2CC3CC(O)(CS(C)(=O)=O)CC3C2)c1C(=O)Nc1ccc(F)c(Cl)c1]

N-(3-Chloro-4-fluorophenyl)-4-(5-hydroxy-5-((methylsulfonyl)methyl)octahydropentalen-2-yl)-1-methyl-1H-imidazole-5-carboxamide. To a solution of methylsulfonylmethane (24 mg, 0.26 mmol) in THF (5 mL) was added n-BuLi (0.2 mL, 0.5 mmol) at −78° C. The solution was stirred at −78° C. for 30 min. N-(3-chloro-4-fluorophenyl)-4-(5-hydroxyoctahydropentalen-2-yl)-1-methyl-1H-imidazole-5-carboxamide (50 mg, 0.13 mmol) was then added and the reaction warmed slowly to rt and stirred for 5 h. The reaction mixture was quenched with $H_2O$ (20 mL) and extracted with ethyl acetate. The organic layer was concentrated in vacuo and the residue purified by prep-HPLC to give N-(3-chloro-4-fluorophenyl)-4-(5-hydroxy-5-((methylsulfonyl)methyl)octahydropentalen-2-yl)-1-methyl-1H-imidazole-5-carboxamide, a white solid, as a single diastereomer. TLC; 20% ethyl acetate/petroleum ether ($R_f$: 0.4). MS calcd. for $C_{21}H_{25}ClFN_3O_4S$: 469.1; Found; 470.2 $[M+1]^+$; $^1H$ NMR (DMSO-d6, 400 MHz): δ 10.22 (s, 1H), 7.96 (dd, J=6.8, 2.4 Hz, 1H), 7.64 (s, 1H), 7.59-7.55 (m, 1H), 7.41 (t, J=9.2 Hz, 1H), 4.94 (s, 1H), 3.66 (s, 3H), 3.24-3.19 (m, 3H), 2.97 (s, 3H), 2.49-2.44 (m, 2H), 2.08-2.01 (m, 4H), 1.78-1.75 (m, 2H), 1.61 (dd, J=13.2, 4.0 Hz, 2H) ppm.

Example 4

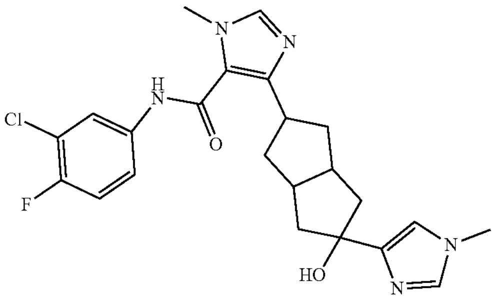 [SMILES: Cn1cnc(C2(O)CC3CC(c4ncn(C)c4C(=O)Nc4ccc(F)c(Cl)c4)CC3C2)c1]

N-(3-Chloro-4-fluorophenyl)-4-(5-hydroxy-5-(1-methyl-1H-imidazol-4-yl)octahydropentalen-2-yl)-1-methyl-1H-imidazole-5-carboxamide. To a solution of 4-iodo-1-methyl-1H-imidazole (208 mg, 1.0 mmol) in THF (5 mL) was added a solution of i-PrMgCl in THF (2.0 M, 0.5 mL, 1.0 mmol). The mixture was stirred at room temperature for 2 hours. To this solution was added a solution of N-(3-chloro-4-fluorophenyl)-1-methyl-4-(5-oxooctahydropentalen-2-yl)-1H-imidazole-5-carboxamide (46 mg, 0.08 mmol) in THF (2.0 mL). The final mixture was stirred at room temperature overnight. The reaction mixture was quenched with methanol (2.0 mL) and concentrated in vacuo. The residue was purified by prep-HPLC to provide N-(3-chloro-4-fluorophenyl)-4-(5-hydroxy-5-(1-methyl-1H-imidazol-4-yl)octahydropentalen-2-yl)-1-methyl-1H-imidazole-5-carboxamide a white solid, as a single diastereomer. MS calcd. for $C_{23}H_{25}ClFN_5O_2$: 457.2; Found; 458.3 $[M+1]^+$. $^1H$ NMR (DMSO-$d_6$, 400 MHz): 10.20 (s, 1H), 7.95 (dd, J=6.8, 2.4 Hz, 1H), 7.64 (s, 1H), 7.54-7.58 (m, 1H), 7.38-7.42 (m, 2H), 6.87 (s, 1H), 4.53 (s, 1H), 3.67 (s, 3H), 3.57 (s, 3H), 3.16-3.24 (m, 1H), 2.40-2.49 (m, 2H), 2.17-2.22 (m, 2H), 2.02-2.08 (m, 2H), 1.85-1.93 (m, 2H), 1.59-1.63 (m, 2H) ppm.

Example 5

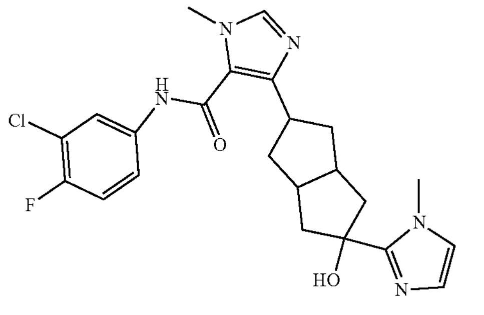 [SMILES: Cn1ccnc1C1(O)CC2CC(c3ncn(C)c3C(=O)Nc3ccc(F)c(Cl)c3)CC2C1]

N-(3-Chloro-4-fluorophenyl)-4-(5-hydroxy-5-(1-methyl-1H-imidazol-2-yl)octahydropentalen-2-yl)-1-methyl-1H-imidazole-5-carboxamide. To a solution of 1-methyl-1H-imidazole (82 mg, 1.0 mmol) in THF (2 mL) was added a solution of n-BuLi in hexane (2.5 M, 0.4 mL, 1.0 mmol). The mixture was stirred at room temperature for 2 hours. To this mixture was then added a solution of N-(3-chloro-4-fluorophenyl)-1-methyl-4-(5-oxooctahydropentalen-2-yl)-1H-imidazole-5-carboxamide (46 mg, 0.08 mmol) in THF (2.0 mL). The final mixture was stirred at room temperature overnight. The reaction mixture was quenched with methanol (2.0 mL) and concentrated in vacuo. The residue was purified by pre-HPLC to provide N-(3-chloro-4-fluorophenyl)-4-(5-hydroxy-5-(1-methyl-1H-imidazol-2-yl)octahydropentalen-2-yl)-1-methyl-1H-imidazole-5-carboxamides white solid, as a single diastereomer. MS calcd. for $C_{23}H_{25}ClFN_5O_2$: 457.2; Found: 458.3 $[M+1]^+$; $^1H$ NMR ($CD_3OD$, 400 MHz): 7.87 (dd, J=6.4, 2.4 Hz, 1H), 7.65 (s, 1H), 7.52-7.48 (m, 1H), 7.23 (t, J=8.8 Hz, 1H), 6.98 (d, J=1.2 Hz, 1H), 6.76 (d, J=1.2 Hz, 1H), 3.83 (s, 3H), 3.75 (s, 3H), 3.30-3.35 (m, 1H), 2.56-2.58 (m, 4H), 2.22-2.25 (m, 2H), 1.83-1.93 (m, 4H) ppm.

Synthesis of Examples 6-15. Examples 6-15 in Table 1 were synthesized according to the procedures provided above using the corresponding starting materials.

TABLE 1

| Examples 6-15 | |
|---|---|
| Example | Structure and Analysis |
| Example 6 | 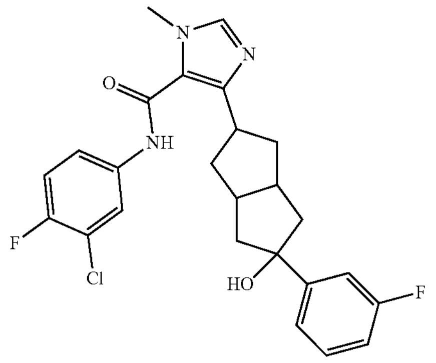 [SMILES: Cn1cnc(C2CC3CC(O)(c4cccc(F)c4)CC3C2)c1C(=O)Nc1ccc(F)c(Cl)c1] N-(3-Chloro-4-fluorophenyl)-4-(5-(3-fluorophenyl)-5-hydroxyoctahydropentalen-2-yl)-1-methyl-1H-imidazole-5-carboxamide MS calcd. for $C_{25}H_{24}ClF_2N_3O_2$; 471.2; Found: 472.0 $[M + 1]^+$. $^1H$ NMR (400 MHz, DMSO-$d_6$): δ 10.22 (s, 1H), 7.97-7.95 (m, 1H), 7.61 (m, 1H), 7.59-7.56 (m, 1H), 7.40 (t, J = 9.2 Hz, 1H), 7.32-7.29 (m, 1H), 7.26-7.21 (m, 2H), 7.01-6.97 (m, 1H), 4.96 (s, 1H), 3.67 (s, 3H), 3.24-3.19 (m, 2H), 2.58 (br.s, 2H), 2.07-2.02 (m, 5H), 1.83-1.80 (m, 2H) ppm. |
| Example 7 | 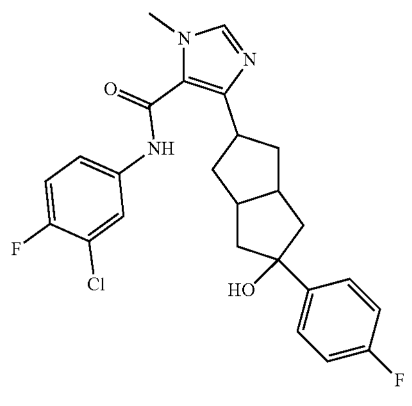 [SMILES: Cn1cnc(C2CC3CC(O)(c4ccc(F)cc4)CC3C2)c1C(=O)Nc1ccc(F)c(Cl)c1] N-(3-Chloro-4-fluorophenyl)-4-(5-(4-fluorophenyl)-5-hydroxyoctahydropentalen-2-yl)-1-methyl-1H-imidazole-5-carboxamide MS calcd. for $C_{25}H_{24}ClF_2N_3O_2$; 471.2; Found: 454.00 $[M - H_2O + 1]^+$. $^1H$ NMR |

TABLE 1-continued

| Example | Structure and Analysis |
|---|---|
| | Examples 6-15 |
| | (400 MHz, DMSO-$d_6$): δ 10.22 (s, 1H), 7.96 (dd, J = 6.8, 2.4 Hz 1H), 7.64 (s, 1H), 7.59-7.55 (m, 1H), 7.47-7.38 (m, 3H), 7.08 (t, J = 8.8 Hz, 2H), 4.89 (s, 1H), 3.67 (s, 3H), 3.32-3.17 (m, 1H), 2.59 (br.s, 2H), 2.08-1.97 (m, 5H), 1.83-1.79 (m, 2H), 1.46-1.44 (m, 1H) ppm. |
| Example 8 | 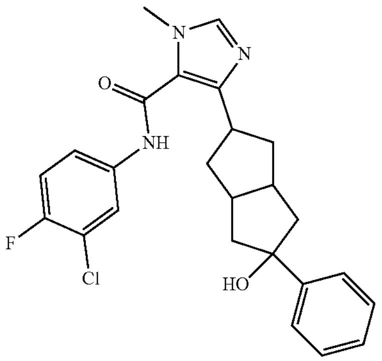 [SMILES: Cn1cnc(C2CC3CC(O)(c4ccccc4)CC3C2)c1C(=O)Nc1ccc(F)c(Cl)c1] N-(3-Chloro-4-fluorophenyl)-4-(5-hydroxy-5-phenyloctahydropentalen-2-yl)-1-methyl-1H-imidazole-5-carboxamide MS calcd. for $C_{25}H_{25}ClFN_3O_2$: 453.2; Found: 454.2 $[M + 1]^+$. $^1H$ NMR (400 MHz, DMSO-$d_6$): δ 10.22 (s, 1H), 7.96 (dd, J = 6.8, 2.4 Hz 1H), 7.65 (s, 1H), 7.58-7.55 (m, 1H), 7.44-7.38 (m, 3H), 7.27 (t, J = 7.2 Hz, 2H), 7.16 (t, J = 7.6 Hz, 1H), 4.82 (s, 1H), 3.67 (s, 3H), 3.25-3.19 (m, 1H), 2.55 (br.s, 2H), 2.10-2.01 (m, 6H), 1.83-1.80 (m, 2H) ppm. |
| Example 9 | 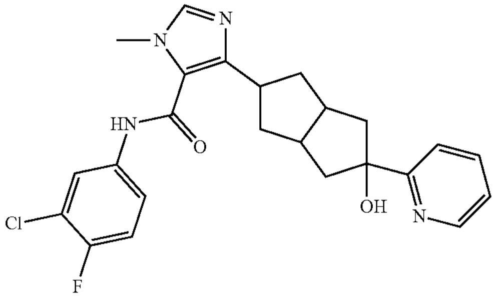 [SMILES: Cn1cnc(C2CC3CC(O)(c4ccccn4)CC3C2)c1C(=O)Nc1ccc(F)c(Cl)c1] N-(3-Chloro-4-fluorophenyl)-4-(5-hydroxy-5-(pyridin-2-yl) octahydropentalen-2-yl)-1-methyl-1H-imidazole-5-carboxamide MS calcd. for $C_{24}H_{24}ClFN_4O_2$; 454.2; Found: 455.0 $[M + 1]^+$. $^1H$ NMR (400 MHz, DMSO-$d_6$): δ 10.23 (s, 1H), 8.45 (d, J = 4.0 Hz, 1H), 7.97 (dd, J = 6.8 Hz, 2.0 Hz, 1H), 7.73 (t, J = 7.6 Hz, 1H), 7.67-7.60 (m, 2H), 7.59-7.54 (m, 1H), 7.40 (t, 7= 8.8 Hz, 1H), 7.18 (t, J = 6.8 Hz, 1H), 5.08 (s, 1H), 3.68 (s, 3H), 3.26-3.14 (m, 1H), 2.69-2.58 (m, 2H), 2.37-2.26 (m, 2H), 2.12-1.99 (m, 4H), 1.75-1.68 (m, 2H) ppm. |
| Example 10 | 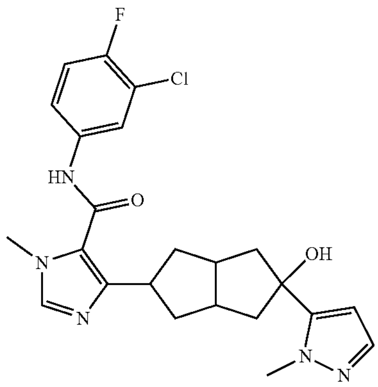 [SMILES: Cn1cnc(C2CC3CC(O)(c4ccnn4C)CC3C2)c1C(=O)Nc1ccc(F)c(Cl)c1] |

TABLE 1-continued

| Examples 6-15 | |
|---|---|
| Example | Structure and Analysis |
| | N-(3-chloro-4-fluorophenyl)-4-(5-hydroxy-5-(1-methyl-1H-pyrazol-5-yl) octahydropentalen-2-yl)-1-methyl-1H-imidazole-5-carboxamide MS calcd. for $C_{23}H_{25}ClFN_5O_2$: 457.2; Found: 458.2 $[M + 1]^+$; $^1H$ NMR (DMSO-d6, 400 MHz): δ 10.22 (s, 1H), 7.95 (dd, J = 6.8, 2.8 Hz, 1H), 7.65 (s, 1H), 7.59-7.55 (m, 1H), 7.40 (t, J = 9.2 Hz, 1H), 7.21 (d, J = 2 Hz, 1H), 6.08 (d, J = 1.6 Hz, 1H), 5.23 (s, 1H), 3.90 (s, 3H), 3.67 (s, 3H), 3.30-3.22 (m, 1H), 2.45-2.44 (m, 2H), 2.23-2.18 (m, 2H), 2.13-2.07 (m, 2H), 1.89-1.82 (m, 2H) ppm. |
| Example 11 | 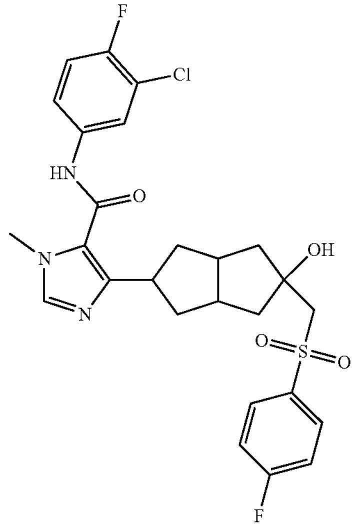 [SMILES: Cn1cnc(C2CC3CC(O)(CS(=O)(=O)c4ccc(F)cc4)CC3C2)c1C(=O)Nc1ccc(F)c(Cl)c1] N-(3-Chloro-4-fluorophenyl)-4-(5-(((4-fluorophenyl)sulfonyl)methyl)-5-hydroxyoctahydropentalen-2-yl)-1-methyl-1H-imidazole-5-carboxamide MS calcd. for $C_{26}H_{26}ClF_2N_3O_4S$: 549.1; Found: 550.2 $[M + 1]^+$; $^1H$ NMR (DMSO-d6, 400 MHz): δ 10.21 (s, 1H), 7.96-7.92 (m, 3H), 7.62 (s, 1H), 7.58-7.54 (m, 1H), 7.46-7.38 (m, 3H), 4.99 (s, 1H), 3.66 (s, 3H), 3.50 (s, 2H), 3.19-3.16 (m, 1H), 2.49-2.43 (m, 2H), 2.05-1.94 (m, 4H), 1.78-1.70 (m, 2H), 1.56-1.55 (m, 2H) ppm. |
| Example 12 | 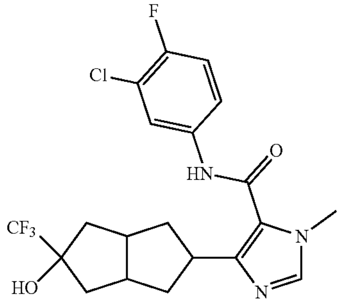 [SMILES: Cn1cnc(C2CC3CC(O)(C(F)(F)F)CC3C2)c1C(=O)Nc1ccc(F)c(Cl)c1] N-(3-Chloro-4-fluorophenyl)-4-(5-hydroxy-5-(trifluoromethyl)octahydropentalen-2-yl)-1-methyl-1H-imidazole-5-carboxamide. MS calcd for $C_{20}H_{20}ClF_4N_3O_2$: 445.1; Found: 446.1 $[M + 1]^+$; $^1H$ NMR (DMSO-d6, 400 MHz): δ 10.22 (s, 1H), 7.96 (dd, J = 6.8, 2.4 Hz, 1H), 7.65 (s, 1H), 7.59-7.55 (m, 1H), 7.40 (t, J = 8.8 Hz, 1H), 5.76 (s, 1H), 3.67 (s, 3H), 3.22-3.16 (m, 1H), 2.60-2.58 (m, 2H), 2.09-2.06 (m, 2H), 2.02-1.87 (m, 4H), 1.780 (m, 2H) ppm |

TABLE 1-continued

| Examples 6-15 | |
|---|---|
| Example | Structure and Analysis |
| Example 13 | 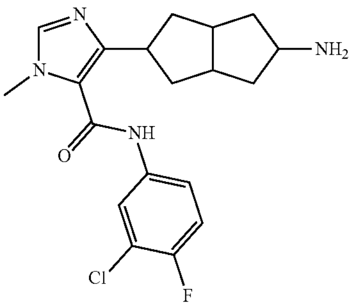 [SMILES: Cn1cnc(C2CC3CC(N)CC3C2)c1C(=O)Nc1ccc(F)c(Cl)c1]<br>4-(5-Aminooctahydropentalen-2-yl)-N-(3-chloro-4-fluorophenyl)-1-methyl-1H-imidazole-5-carboxamide<br>MS calcd for C19H22C1FN4O: 376.1; Found: 377.1 $[M + 1]^+$; $^1H$ NMR (DMSO-d6, 400 MHz): δ 10.23 (br, 1H), 7.94 (dd, J = 7.2, 2.8 Hz, 1H), 7.65 (s, 1H), 7.58-7.54 (m, 1H), 7.40 (t, J = 8.8 Hz, 1H), 3.67 (s, 3H), 3.28-3.11 (m, 1H), 3.10-3.07 (m, 1H), 2.45-2.32 (m, 2H), 2.09-1.96 (m, 4H), 1.60-1.57 (m, 2H), 1.55-0.98 (m, 2H) ppm. |
| Example 14 | 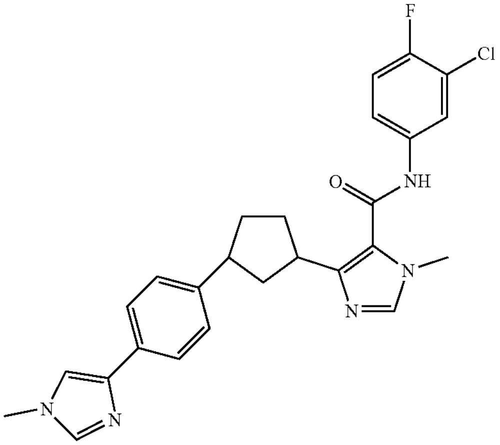 [SMILES: Cn1cnc(-c2ccc(C3CCC(c4ncn(C)c4C(=O)Nc4ccc(F)c(Cl)c4)C3)cc2)c1]<br>N-(3-Chloro-4-fluorophenyl)-1-methyl-4-(3-(4-(1-methyl-1H-imidazol-4-yl)phenyl)cyclopentyl)-1H-imidazole-5-carboxamide<br>MS calcd. for $C_{26}H_{25}ClFN_5O$: 477.2. Found: 478.2 $[M + 1]^+$; $^1H$ NMR (400 MHz, DMSO-$d_6$): δ 10.28 (s, 1H), 7.98 (dd, J = 6.8, 2.4 Hz, 1H), 7.70 (s, 1H), 7.64-7.58 (m, 4H), 7.51 (s, 1H), 7.41 (t, J = 9.2 Hz, 1H), 7.23 (d, J = 8.4 Hz, 2H), 3.69 (s, 3H), 3.66 (s, 3H), 3.1-3.47 (m, 1H), 3.10-3.09 (m, 1H), 2.29-2.26 (m, 1H), 2.05-2.01 (m, 2H), 1.99-1.89 (m, 2H), 1.75-1.73 (m, 1H) ppm. |
| Example 15 | 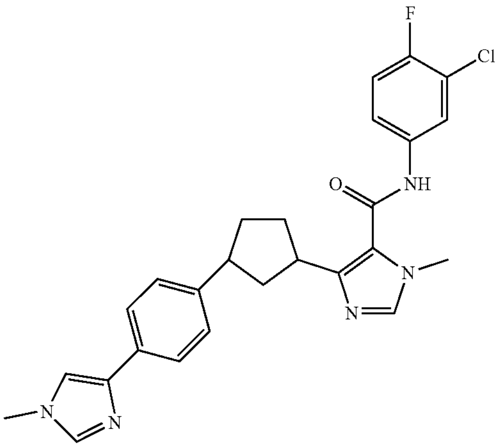 [SMILES: Cn1cnc(-c2ccc(C3CCC(c4ncn(C)c4C(=O)Nc4ccc(F)c(Cl)c4)C3)cc2)c1] |

TABLE 1-continued

| Examples 6-15 | |
|---|---|
| Example | Structure and Analysis |
| | N-(3-Chloro-4-fluorophenyl)-1-methyl-4-(3-(4-(1-methyl-1H-imidazol-4-yl)phenyl)cyclopentyl)-1H-imidazole-5-carboxamide MS calcd. for $C_{26}H_{25}ClFN_5O$: 477.2; Found; 478.2 $[M + 1]^+$; $^1H$ NMR (400 MHz, DMSO-$d_6$): δ 10.26 (s, 1H), 7.97 (dd, J = 6.8, 2.4 Hz, 1H), 7.70 (s, 1H), 7.62-7.56 (m, 4H), 7.50 (s, 1H), 7.40 (t, J = 9.2 Hz, 1H), 7.20 (d, J = 8 Hz, 2H), 3.69 (s, 3H), 3.66 (s, 3H), 3.65-3.63 (m, 1H), 3.26-3.24 (m, 1H), 2.19-2.08 (m, 3H), 1.98-1.86 (m, 2H), 1.66-1.62 (m, 1H) ppm. |

Intermediate 8

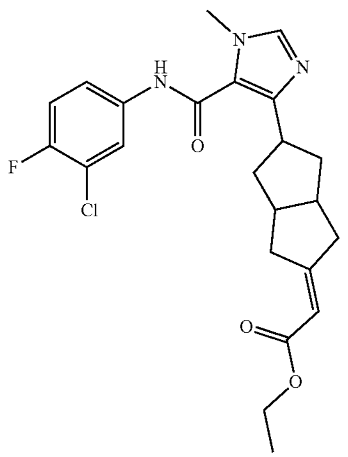 [SMILES: CCOC(=O)C=C1CC2CC(c3ncn(C)c3C(=O)Nc3ccc(F)c(Cl)c3)CC2C1]

Ethyl 2-(5-(5-((3-chloro-4-fluorophenyl)carbamoyl)-1-methyl-1H-imidazol-4-yl)hexahydropentalen-2(1H)-ylidene)acetate. To a solution of ethyl 2-(diethoxyphosphoryl)acetate (448 mg, 2 mmol) in dry THF (25 mL), was added NaH (48 mg, 2 mmol) slowly then stirred at 0° C. for 0.5 h. N-(3-Chloro-4-fluorophenyl)-1-methyl-4-(5-oxooctahydropentalen-2-yl)-1H-imidazole-5-carboxamide (375 mg, 1 mmol) in THF (5 mL) was added and stirring continued at rt for 3 h. Water was added and the pH adjusted value to 6-7 with $NH_4Cl$. The mixture was extracted with AcOEt and the organic phase dried and concentrated in vacuo. The residue was purified by column chromatography using 25-60% ethyl acetate/petroleum ether to afford ethyl 2-(5-(5-((3-chloro-4-fluorophenyl)carbamoyl)-1-methyl-1H-imidazol-4-yl)hexahydropentalen-2(1H)-ylidene)acetate as a pale yellow solid. TLC; 60% ethyl acetate/petroleum ether ($R_f$: 0.2). MS calcd. for $C_{23}H_{25}ClFN_3O_3$: 445.2; Found: 446.3 $[M+1]^+$.

Example 16

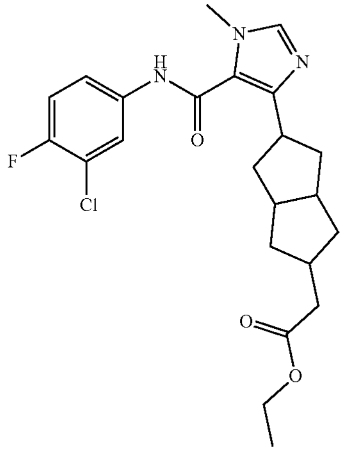 [SMILES: CCOC(=O)CC1CC2CC(c3ncn(C)c3C(=O)Nc3ccc(F)c(Cl)c3)CC2C1]

Ethyl 2-(5-(5-((3-chloro-4-fluorophenyl)carbamoyl)-1-methyl-1H-imidazol-4-yl)octahydropentalen-2-yl)acetate. To a solution of -(5-(5-((3-chloro-4-fluorophenyl)carbamoyl)-1-methyl-1H-imidazol-4-yl)hexahydropentalen-2(1H)-ylidene)acetate (223 mg, 0.5 mmol) in THF (15 mL) was added Pd/C (50 mg). The flask was then evacuated and backfilled with $H_2$. The solution was stirred at rt overnight. The mixture was filtered and concentrated. The residue was purified by prep-HPLC to afford ethyl 2-(5-(5-((3-chloro-4-fluorophenyl)carbamoyl)-1-methyl-1H-imidazol-4-yl)octahydropentalen-2-yl)acetate as a white solid. TLC; 60% ethyl acetate/petroleum ether ($R_f$: 0.2). MS calcd. for $C_{23}H_{27}ClFN_3O_3$: 447.2. Found; 448.3 $[M+1]^+$.

Intermediate 9

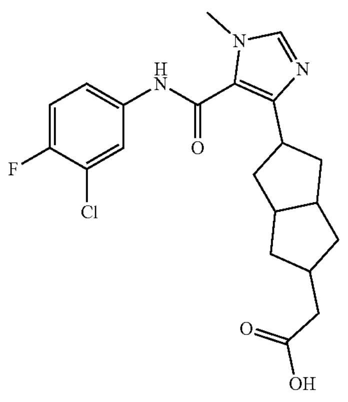 [SMILES: Cn1cnc(C2CC3CC(CC(=O)O)CC3C2)c1C(=O)Nc1ccc(F)c(Cl)c1]

2-(5-(5-((3-Chloro-4-fluorophenyl)carbamoyl)-1-methyl-1H-imidazol-4-yl)octahydropentalen-2-yl)acetic acid. To a solution of ethyl 2-(5-(5-((3-chloro-4-fluorophenyl)carbamoyl)-1-methyl-1H-imidazol-4-yl)octahydropentalen-2-yl) acetate (45 mg, 0.1 mmol) in $CH_3OH/H_2O$ (5 mL/1 mL) was added LiOH (42 mg, 1 mmol). The solution was stirred at rt for 4 h. Water was added, and the reaction mixture was adjusted to pH 5-6 with HCl (2M). The reaction was extracted with ethyl acetate (10 mL×3), the organic layer was washed with brine and dried over anhydrous sodium sulfate and concentrated in vacuo to afford crude 2-(5-(5-((3-chloro-4-fluorophenyl)carbamoyl)-1-methyl-1H-imidazol-4-yl)octahydropentalen-2-yl)acetic acid as a pale yellow solid. TLC; 100% ethyl acetate/petroleum ether ($R_f$: 0.1). MS calcd. for $C_{21}H_{23}ClFN_3O_3$: 419.1; Found: 420.2 $[M+1]^+$.

Example 17

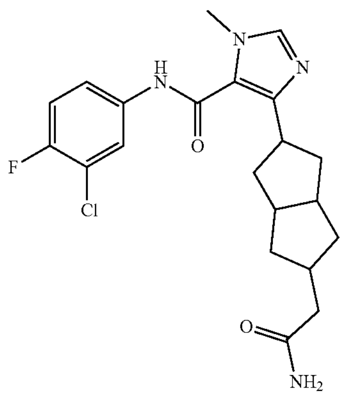 [SMILES: Cn1cnc(C2CC3CC(CC(N)=O)CC3C2)c1C(=O)Nc1ccc(F)c(Cl)c1]

4-(5-(2-Amino-2-oxoethyl)octahydropentalen-2-yl)-N-(3-chloro-4-fluorophenyl)-1-methyl-1H-imidazole-5-carboxamide. To a solution of 2-(5-(5-((3-chloro-4-fluorophenyl)carbamoyl)-1-methyl-1H-imidazol-4-yl) octahydropentalen-2-yl)acetic acid (43 mg, 0.1 mmol) in anhydrous DCM (10 mL), was added $NH_4Cl$ (54 mg, 1 mmol), HATU (38 mg, 0.1 mmol) and $Et_3N$ (101 mg, 1 mmol) and the mixture stirred at rt for 1 h. The solvent was removed, and the crude product was purified by prep-HPLC to afford 4-(5-(2-amino-2-oxoethyl)octahydropentalen-2-yl)-N-(3-chloro-4-fluorophenyl)-1-methyl-1H-imidazole-5-carboxamide as a white solid. TLC: 80% ethyl acetate/petroleum ether ($R_f$: 0.3). MS calcd. for $C_{21}H_{24}ClFN_4O_2$: 418.2; Found: 419.3 $[M+1]^+$. $^1H$ NMR (DMSO-$d_6$, 400 MHz): δ 10.21 (s, 1H), 7.95 (dd, J=7.2, 2.4 Hz, 1H), 7.65 (s, 1H), 7.58-7.55 (m, 1H), 7.40 (t, J=9.2 Hz, 1H), 7.19 (s, 1H), 6.65 (s, 1H), 3.66 (s, 3H), 3.34-3.32 (m, 1H), 2.43-2.36 (m, 2H), 2.21-2.18 (m, 1H), 2.10-2.06 (m, 4H), 1.99-1.92 (m, 2H), 1.50-1.47 (m, 2H), 0.93-0.90 (m, 2H) ppm.

Example 18

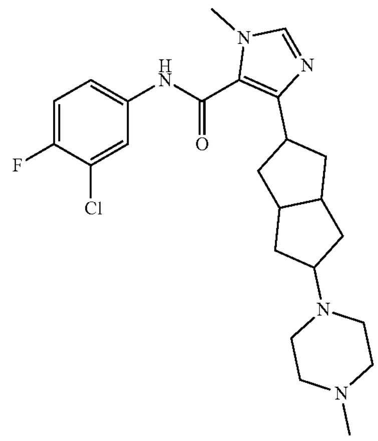 [SMILES: CN1CCN(C2CC3CC(c4ncn(C)c4C(=O)Nc4ccc(F)c(Cl)c4)CC3C2)CC1]

N-(3-Chloro-4-fluorophenyl)-1-methyl-4-(5-(4-methylpiperazin-1-yl)octahydropentalen-2-yl)-1H-imidazole-5-carboxamide. To a solution of N-(3-chloro-4-fluorophenyl)-1-methyl-4-(5-oxooctahydropentalen-2-yl)-1H-imidazole-5-carboxamide (50 mg, 0.13 mmol) in THF (3 ml) was added 1-methylpiperazine (110 mg, 1.1 mmol) and $NaBH_3CN$ (40 mg, 0.65 mmol). The mixture was stirred at 55° C. overnight. The solvent was removed in vacuo to give a yellow residue. This was purified by column chromatography and prep-HPLC to give N-(3-chloro-4-fluorophenyl)-1-methyl-4-(5-(4-methylpiperazin-1-yl)octahydropentalen-2-yl)-1H-imidazole-5-carboxamide as a white solid. TLC: 10% DCM/MeOH ($R_f$: 0.3). MS calcd. for $C_{24}H_{31}ClFN_5O$: 459.2; Found: 460.3 $[M+1]^+$; $^1H$ NMR (DMSO-$d_6$, 400 MHz): δ 10.23 (s, 1H), 7.95 (dd, J=6.8, 2.4 Hz, 1H), δ 7.66 (s, 1H), 7.59-7.55 (m, 1H), 7.41 (t, J=9.2 Hz, 1H), 3.67 (s, 3H), 3.25 (s, 1H), 2.49 (s, 1H), 3.36-3.30 (m, 9H), 2.18-2.00 (m, 8H), 1.58-1.50 (m, 2H), 1.17-1.09 (m, 2H) ppm.

Intermediate 10

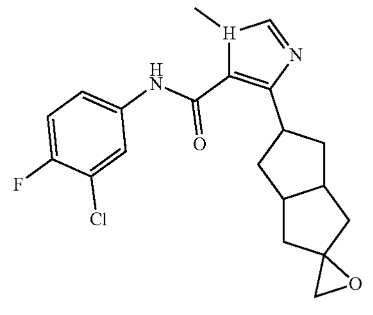

N-(3-Chloro-4-fluorophenyl)-4-(hexahydro-1'H-spiro[oxirane-2,2'-pentalen]-5'-yl)-1-methyl-1H-imidazole-5-carboxamide. To a solution of t-BuOK (0.75 g, 6.7 mmol) in THF (20 mL) was added trimethysulfonium iodide (1.47 g, 6.7 mmol). The mixture was stirred at rt for 1 h. N-(3-chloro-4-fluorophenyl)-1-methyl-4-(5-oxooctahydropentalen-2-yl)-1H-imidazole-5-carboxamide (0.5 g, 1.3 mmol) was added and the mixture heated to 60° C. for 2 h. The reaction was quenched with water and extracted by ethyl acetate (20 mL×3). The combined organic phase was concentrating in vacuo. The residue was purified by silica gel column chromatography using ethyl acetate/petroleum ether (2:1) to afford N-(3-chloro-4-fluorophenyl)-4-(hexahydro-1'H-spiro[oxirane-2,2'-pentalen]-5'-yl)-1-methyl-1H-imidazole-5-carboxamide as a white solid. TLC; 50% ethyl acetate/petroleum ether ($R_f$: 0.2). MS calcd. for $C_{20}H_{21}ClFN_3O_2$: 389.1; Found: 390.2 $[M+1]^+$.

Example 19

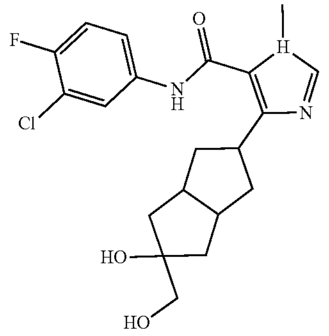

N-(3-Chloro-4-fluorophenyl)-4-(5-hydroxy-5-(hydroxymethyl)octahydro-pentalen-2-yl)-1-methyl-1H-imidazole-5-carboxamide Isomer I. To a solution of N-(3-chloro-4-fluorophenyl)-4-(hexahydro-1'H-spiro[oxirane-2,2'-pentalen]-5'-yl)-1-methyl-1H-imidazole-5-carboxamide (100 mg, 0.26 mmol) in THF/$H_2O$ (6:1, 5 mL) was added $H_2SO_4$ (0.1 mL), and the mixture was stirred at room temperature overnight. The reaction was basified by $NaHCO_3$ (aq) and then extracted with ethyl acetate. The combined organic layer was dried over $Na_2SO_4$ and concentrated in vacuo. The crude product was purified by prep-HPLC to afford N-(3-chloro-4-fluorophenyl)-4-(5-hydroxy-5-(hydroxymethyl)octahydro-pentalen-2-yl)-1-methyl-1H-imidazole-5-carboxamide Isomer I as a white solid. TLC; 5% MeOH/DCM ($R_f$: 0.4). MS calcd. for $C_{20}H_{23}ClFN_3O_3$: 407.1; Found: 408.2 $[M+1]^+$; $^1H$ NMR (DMSO-$d_6$, 400 MHz): δ 10.21 (s, 1H), 7.96 (dd, J=7.2, 2.8 Hz, 1H), 7.65 (s, 1H), 7.59-7.55 (m, 1H), 7.41 (t, J=8.8 Hz, 1H), 4.54 (t, J=5.6 Hz, 1H), 4.02 (s, 1H), 3.67 (s, 3H), 3.30 (s, 1H), 3.25 (d, J=5.6 Hz, 2H), 2.65-2.58 (m, 2H), 2.10-2.03 (m, 2H), 1.65-1.60 (m, 2H), 1.52-1.42 (m, 4H) ppm.

Example 20

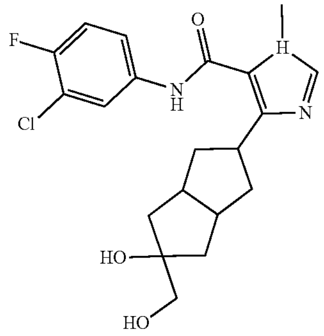

N-(3-Chloro-4-fluorophenyl)-4-(5-hydroxy-5-(hydroxymethyl)octahydro-pentalen-2-yl)-1-methyl-1H-imidazole-5-carboxamide Isomer II. To s solution of N-(3-chloro-4-fluorophenyl)-4-(hexahydro-1H-spiro[oxirane-2,2'-pentalen]-5'-yl)-1-methyl-1H-imidazole-5-carboxamide (100 mg, 0.26 mmol) in dioxane (2 mL) and water (0.5 mL) was added NaOH (80 mg, 2.0 mmol) and the mixture stirred at 100° C. for 24 h. After cooling, the pH was adjusted to 8 with 1N HCl, extracted with ethyl acetate. The combined organic layers were dried over $Na_2SO_4$ and concentrated in vacuo. The crude product was purified by prep-HPLC to afford N-(3-chloro-4-fluorophenyl)-4-(5-hydroxy-5-(hydroxymethyl)octahydro-pentalen-2-yl)-1-methyl-1H-imidazole-5-carboxamide Isomer II as a pale yellow solid. TLC; 5% MeOH/DCM ($R_f$: 0.4). MS calcd. for $C_{20}H_{23}ClFN_3O_3$: 407.1; Found: 408.2 $[M+1]^+$; $^1H$ NMR (DMSO-$d_6$, 400 MHz): δ 10.21 (s, 1H), 7.96 (dd, J=7.2, 2.8 Hz, 1H), 7.64 (s, 1H), 7.58-7.55 (m, 1H), 7.41 (t, J=8.8 Hz, 1H), 4.45 (t, J=5.6 Hz, 1H), 4.14 (s, 1H), 3.67 (s, 3H), 3.23-3.19 (m, 3H), 2.36-2.33 (m, 2H), 2.07-2.04 (m, 2H), 1.89-1.84 (m, 2H), 1.81-1.74 (m, 2H), 1.33 (dd, J=13.2, 4.4 Hz, 2H) ppm.

Example 21

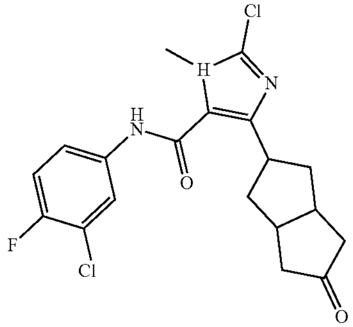

2-Chloro-N-(3-chloro-4-fluorophenyl)-1-methyl-4-(5-oxooctahydropentalen-2-yl)-1H-imidazole-5-carboxamide. To a solution of N-(3-chloro-4-fluorophenyl)-1-methyl-4-(5-oxooctahydropentalen-2-yl)-1H-imidazole-5-carboxamide. (200 mg, 0.53 mmol) in DMF (5 mL) was added NCS (700 mg, 5.3 mmol) and AIBN (0.25 g, 1.5 mmol) at room temperature. The reaction mixture was stirred at 35° C. overnight. The mixture was evaporated under vacuo to give a yellow residue. The residue was purified by silica gel chromatography to give 2-chloro-N-(3-chloro-4-fluorophenyl)-1-methyl-4-(5-oxooctahydropentalen-2-yl)-1H-imidazole-5-carboxamide as a yellow solid. TLC: 40% ethyl acetate/petroleum ether ($R_f$: 0.3). MS calcd. for $C_{19}H_{18}Cl_2FN_3O_2$: 409.1, Found: 410.2 $[M+1]^+$.

Example 22

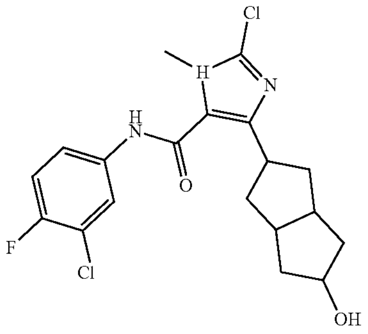

2-Chloro-N-(3-chloro-4-fluorophenyl)-4-(5-hydroxyoctahydropentalen-2-yl)-1-methyl-1H-imidazole-5-carboxamide. To a solution of 2-chloro-N-(3-chloro-4-fluorophenyl)-1-methyl-4-(5-oxooctahydropentalen-2-yl)-1H-imidazole-5-carboxamide (20 mg, 0.05 mmol) in MeOH (2 ml) was added $NaBH_4$ (36 mg, 0.95 mmol). The mixture was stirred at room temperature for 8 h. The solvent was evaporated in vacuo to give a yellow residue. The residue was purified by prep-HPLC to give 2-chloro-N-(3-chloro-4-fluorophenyl)-4-(5-hydroxyoctahydropentalen-2-yl)-1-methyl-1H-imidazole-5-carboxamide as a white solid. TLC; 50% ethyl acetate/petroleum ether ($R_f$: 0.3). MS calcd. for $C_{19}H_{20}Cl_2FN_3O_2$: 411.1; Found: 412.2 $[M+1]^+$; $^1H$ NMR (DMSO-d6, 400 MHz): δ 10.39 (s, 1H), 7.95 (dd, J=6.8, 4.8 Hz, 1H), 7.57-7.54 (m, 1H), 7.42 (t, J=9.2 Hz, 1H), 4.51 (d, J=4.0 Hz, 1H), 4.05 (dd, J=11.2, 6.8 Hz, 1H), 3.61 (s, 3H), 3.22-3.16 (m, 1H), 2.36-2.20 (m, 2H), 2.10-2.04 (m, 2H), 1.93-1.86 (m, 2H), 1.69-1.61 (m, 2H), 1.33-1.26 (m, 2H) ppm.

Intermediate 11

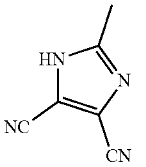

2-Methyl-1H-imidazole-4,5-dicarbonitrile. A solution of 2,3-diaminomaleonitrile (54 g, 0.5 mol) and $CH_3C(OEt)_3$ (9.6 g, 0.8 mmol) in xylene (200 mL) was stirred for 6 hours at 130° C. After cooling to room temperature it was filtered to afford 2-methyl-1H-imidazole-4,5-dicarbonitrile as a brown solid. TLC; 30% ethyl acetate/petroleum ether ($R_f$: 0.4). MS calcd. for $C_6H_4N_4$: 132.0. Found: 133.0 $[M+1]^+$.

Intermediate 12

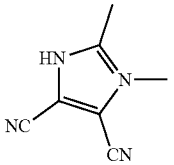

1,2-Dimethyl-1H-Imidazole-4,5-dicarbonitrile. To a suspension of -methyl-1H-imidazole-4,5-dicarbonitrile (50 g, 0.38 mol) and $NaHCO_3$ (160 g, 1.51 mol) in $H_2O$ (300 mL) was added dimethyl sulfate (62 g, 0.49 mol) drop wise at 55° C. and the reaction stirred for 6 hours at the same temperature. Ice water was added and extracted with ethyl acetate (300 mL×3). The organic layer was dried over anhydrous $Na_2SO_4$, filtered and concentrated to give 1,2-dimethyl-1H-imidazole-4,5-dicarbonitrile which was used in the next step without further purification. TLC; 30% ethyl acetate/petroleum ether ($R_f$: 0.5). MS calcd. for $C_7H_7N_4$:146.0; Found: 147.0 $[M+1]^+$.

Intermediate 13

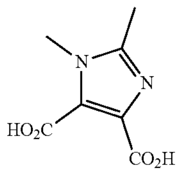

1,2-Dimethyl-1H-Imidazole-4,5-dicarboxylic add. A solution of 1,2-dimethyl-1H-imidazole-4,5-dicarbonitrile (41 g, 0.28 mol) in 2M NaOH aq. (45 g, 1.12 mol, 560 mL) was stirred for 6 hours at 100° C. After cooling to rt, the solution was acidified (pH=1) with 6N HCl aq. After filtration, the solid was dried in an oven for 16 hours at 100° C. to afford 1,2-dimethyl-1H-imidazole-4,5-dicarboxylic acid as a white solid. MS calcd. for $C_7H_8N_2O_4$; 184.0. Found; 185.1 $[M+1]^+$.

Intermediate 14

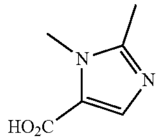

1,2-Dimethyl-1H-Imidazole-5-carboxylic acid. A suspension of 1,2-dimethyl-1H-imidazole-4,5-dicarboxylic acid (5 g, 27 mmol) in $Ac_2O$ (150 mL) was stirred for 16 hours at 100° C. The reaction was concentrated to give the crude product which was crystallized from acetone (100 mL) to afford 1,2-dimethyl-1H-imidazole-5-carboxylic acid as a brown solid. MS calcd. for $C_6H_8N_2O_2$: 140.1; Found: 141.1 $[M+1]^+$.

Intermediate 15

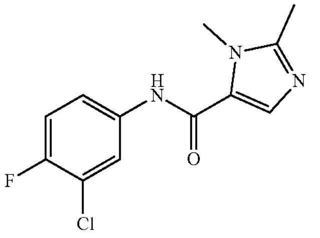 [SMILES: Cc1ncc(C(=O)Nc2ccc(F)c(Cl)c2)n1C]

N-(3-Chloro-4-fluorophenyl)-1,2-dimethyl-1H-imidazole-5-carboxamide. To a solution of 2-dimethyl-1H-imidazole-5-carboxylic acid (560 mg, 4 mmol), 3-chloro-4-fluoroaniline (870 mg, 6 mmol) and DIEA (1.03 g, 8 mmol) in THF/DMF (15 ml/3 mL) was added HATU (2.28 g, 6 mmol) and the reaction was stirred for 16 hours at room temperature. Ice water was added and extracted with ethyl acetate (30 mL×3). The organic layer was dried over anhydrous $Na_2SO_4$, concentrated to give the crude product which was purified by silica gel column chromatography using ethyl acetate/MeOH=10:1 to afford N-(3-chloro-4-fluorophenyl)-1,2-dimethyl-1H-imidazole-5-carboxamide as a white solid. TLC: 10% ethyl acetate/MeOH ($R_f$: 0.4). MS calcd. for C12H11ClFN3O: 267.1; Found; 268.1 $[M+1]^+$.

Intermediate 16

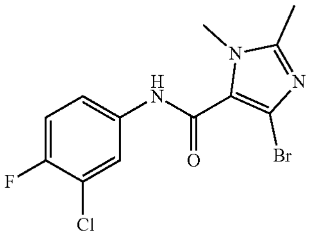 [SMILES: Cc1nc(Br)c(C(=O)Nc2ccc(F)c(Cl)c2)n1C]

4-Bromo-N-(3-chloro-4-fluorophenyl)-1,2-dimethyl-1H-imidazole-5-carboxamide. To a suspension of N-(3-chloro-4-fluorophenyl)-1,2-dimethyl-1H-imidazole-5-carboxamide (510 mg, 1.91 mmol) and NaOAc (1.57 g, 19.1 mmol) in EtOH (40 mL) was added $Br_2$ (1.5 g, 9.6 mmol) drop wise at 15° C. Then the reaction mixture was stirred for 11 hrs at room temperature. The reaction was quenched with 0.5% $NaHSO_3$ (aq.) and extracted with ethyl acetate (30 mL×2). The combined organic layers were washed with brine, dried over anhydrous $Na_2SO_4$, concentrated to give the residue which was purified through silica gel column chromatography using ethyl acetate/MeOH=10:1 to afford 4-bromo-N-(3-chloro-4-fluorophenyl)-1,2-dimethyl-1H-imidazole-5-carboxamide as a white solid. TLC: 10% ethyl acetate/MeOH ($R_f$: 0.6). MS calcd. for $C_{12}H_{10}BrClFN_3O$: 345.0; Found: 346.2 $[M+1]^+$.

Intermediate 17

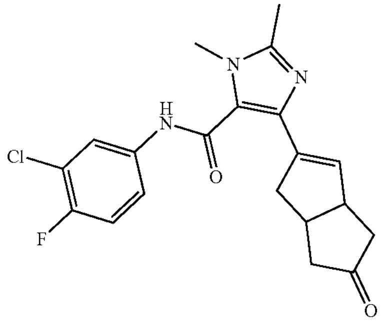 [SMILES: Cc1nc(C2=CC3CC(=O)CC3C2)c(C(=O)Nc2ccc(F)c(Cl)c2)n1C]

N-(3-chloro-4-fluorophenyl)-1,2-dimethyl-4-(5-oxo-1,3a,4,5,6,6a-hexahydropentalen-2-yl)-1H-imidazole-5-carboxamide. To a solution of 4-bromo-N-(3-chloro-4-fluorophenyl)-1,2-dimethyl-1H-imidazole-5-carboxamide (400 mg, 1.16 mmol), 5-(4,4,5,5-tetramethyl-1,3,2-dioxaborolan-2-yl)-3,3a,6,6a-tetrahydropentalen-2(1H)-one (431 mg, 1.74 mmol) and $Na_2CO_3$ (246 mg, 2.32 mmol) in a mixture of dioxane (20 mL) and $H_2O$ (5 mL) was added Pd(dppf)$Cl_2$ (50 mg) under a nitrogen atmosphere and the reaction stirred at 80° C. for 6 h. After cooling to rt, the mixture was filtered through a pad of Celite®. The filtrate was diluted with water and extracted with ethyl acetate (40 mL×2). The combined organic layers were concentrated to give a residue which was purified by silica gel column chromatography using ethyl acetate/MeOH=10:1 to afford N-(3-chloro-4-fluorophenyl)-1,2-dimethyl-4-(5-oxo-1,3a,4,5,6,6a-hexahydropentalen-2-yl)-1H-imidazole-5-carboxamide as a white solid. TLC: 10% ethyl acetate/MeOH ($R_f$: 0.3). MS calcd. for $C_{20}H_{19}ClFN_3O_2$: 387.1. Found: 388.2 $[M+1]^+$.

Example 23

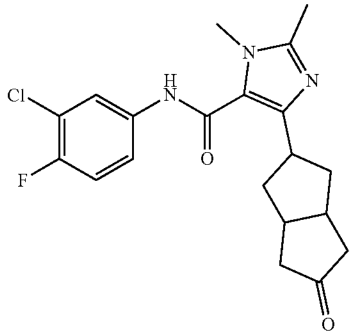 [SMILES: Cc1nc(C2CC3CC(=O)CC3C2)c(C(=O)Nc2ccc(F)c(Cl)c2)n1C]

N-(3-Chloro-4-fluorophenyl)-1,2-dimethyl-4-(5-oxooctahydropentalen-2-yl)-1H-imidazole-5-carboxamide. A mixture of N-(3-chloro-4-fluorophenyl)-1,2-dimethyl-4-(5-oxo-1,3a,4,5,6,6a-hexahydropentalen-2-yl)-1H-imidazole-5-carboxamide (300 mg, 0.77 mmol) and Pd/C (300 mg) in ethyl acetate (300 ml) was stirred at 30° C. for 6 hrs under $H_2$. The reaction mixture was cooled to room temperature and filtered through a pad of Celite®545, washed with ethyl acetate and concentrated to give the crude product which was purified by prep-HPLC to afford N-(3-chloro-4-fluorophenyl)-1,2-dimethyl-4-(5-oxooctahydropentalen-2-yl)-1H- imidazole-5-carboxamide as a white solid. TLC: 10% ethyl acetate/$CH_3OH$ ($R_f$: 0.5). MS calcd. for $C_{20}H_{21}ClFN_3O_2$: 589.2; Found: 390.2 $[M+1]^+$.

Example 24

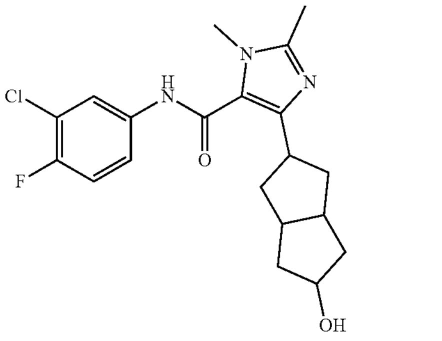 [SMILES: Cc1nc(C2CC3CC(O)CC3C2)c(C(=O)Nc2ccc(F)c(Cl)c2)n1C]

N-(3-Chloro-4-fluorophenyl)-4-(5-hydroxyoctahydropentalen-2-yl)-1,2-dimethyl-1H-imidazole-5-carboxamide. To a solution of N-(3-chloro-4-fluorophenyl)-1,2-dimethyl-4-(5-oxooctahydropentalen-2-yl)-1H-imidazole-5-carboxamide (35 mg, 0.09 mmol) in MeOH (2 mL) cooled to 0° C. was added $NaBH_4$ (11 mg, 0.27 mmol). The reaction was stirred at room temperature for 1 h. The mixture was poured into ice-water and extracted with ethyl acetate. The organic layer was concentrated to give the crude compound which was purified by prep-HPLC to afford N-(3-chloro-4-fluorophenyl)-4-(5-hydroxyoctahydropentalen-2-yl)-1,2-dimethyl-1H-imidazole-5-carboxamide as a white solid. TLC: 10% ethyl acetate/$CH_3OH$ ($R_f$: 0.4). MS calcd. for $C_{20}H_{23}ClFN_3O_2$: 391.1; Found: 392.1 $[M+1]^+$; $^1H$ NMR ($CD_3OD$, 400 MHz): δ 7.86 (dd, J=2.4 Hz, 6.4 Hz, 1H), 7.52-7.46 (m, 1H), 7.23 (t, J=8.8 Hz, 1H), 4.17-4.10 (m, 1H), 3.63 (s, 3H), 3.32-3.20 (m, 1H), 2.40-2.38 (m, 5H), 2.24-2.01 (m, 4H), 1.75-1.62 (m, 2H), 1.41-1.37 (m, 2H) ppm.

Synthesis of Examples 25-26. Examples 25-26 in Table 2 were synthesized according to the procedures provided above using the corresponding starting materials.

TABLE 2

Examples 25-26

| Example | Structure and analysis |
| --- | --- |
| Example 25 | 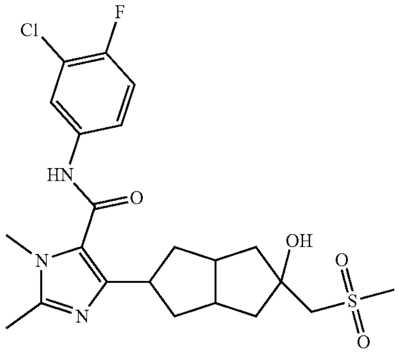 N-(3-Chloro-4-fluorophenyl)-4-(5-hydroxy-5-((methylsulfonyl)methyl)octahydropentalen-2-yl)-1,2-dimethyl-1H-imidazole-5-carboxamide MS calcd. for $C_{22}H_{27}ClFN_3O_4S$: 483.1; Found: 484.2 [M + 1]+; $^1H$ NMR (DMSO-$d_6$, 400 MHz): δ 10.10 (s, 1H), 7.95 (dd, J = 6.8, 2.8 Hz, 1H), 7.57-7.53 (m, 1H), 7.39 (t, J = 9.2 Hz, 1H), 4.97 (s, 1H), 3.55 (s, 3H), 3.24 (s, 2H), 3.18 (m, 1H), 2.98 (s, 3H), 2.43-2.41 (m, 2H), 2.30 (s, 3H), 2.07-2.02 (m, 4H), 1.78-1.76 (m, 2H), 1.63-1.69 (m, 2) ppm. |
| Example 26 | 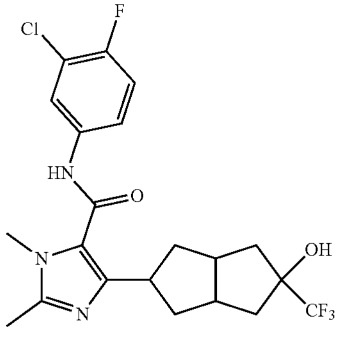 [SMILES: Cc1nc(C2CC3CC(O)(C(F)(F)F)CC3C2)c(C(=O)Nc2ccc(F)c(Cl)c2)n1C] N-(3-Chloro-4-fluorophenyl)-4-(5-hydroxy-5-(trifluoromethyl)octahydropentalen-2-yl)-1,2-dimethyl-1H-imidazole-5-carboxamide MS calcd. for Chemical Formula: $C_{21}H_{22}ClF_4N_3O_2$: 459.1; Found: 460.1 $[M + 1]^+$; |

TABLE 2-continued

| Examples 25-26 | |
|---|---|
| Example | Structure and analysis |
| | $^1$H NMR (DMSO-d6, 400 MHz): δ 10.14 (s, 1H), 7.95 (dd, J = 6.8, 2.4 Hz, 1H), 7.58-7.54 (m, 1H), 7.40 (t, J = 9.2 Hz, 1H), 5.78 (s, 1H), 3.55 (s, 3H), 3.17-3.14 (m, 1H), 2.59-2.57 (m, 2H), 2.30 (s, 3H), 2.06-1.89 (m, 6H), 1.89-1.71 (m, 2H) ppm. |

Example 27

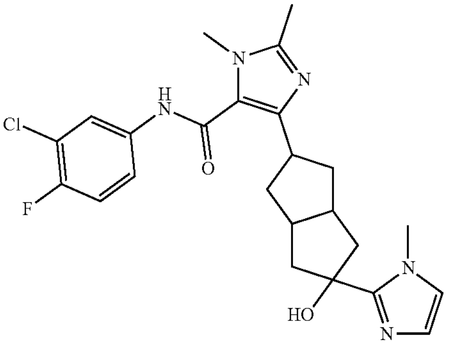 [SMILES: Cc1nc(C2CC3CC(O)(c4nccn4C)CC3C2)c(C(=O)Nc2ccc(F)c(Cl)c2)n1C]

N-(3-Chloro-4-fluorophenyl)-4-(5-hydroxy-5-(1-methyl-1H-imidazol-2-yl)octahydropentalen-2-yl)-1,2-dimethyl-1H-imidazole-5-carboxamide. To a solution of 1-methyl-1H-imidazole (101 mg, 1.23 mmol) in THF (2 mL) was added a n-BuLi in hexane (2.5 M, 0.5 mL, 1.25 mmol) at −78° C. The reaction was stirred at −78° C. for 1 hour. To this solution was added N N-(3-chloro-4-fluorophenyl)-1,2-dimethyl-4-(5-oxooctahydropentalen-2-yl)-1H-imidazole-5-carboxamide (60 mg, 0.154 mmol) in one portion. The reaction was stirred at −78° C. for 1 h then allowed to warm to rt overnight. The mixture was quenched with methanol (2.0 mL) and concentrated in vacuo. The residue was purified by prep-HPLC to provide N-(3-chloro-4-fluorophenyl)-4-(5-hydroxy-5-(1-methyl-1H-imidazol-2-yl)octahydropentalen-2-yl)-1,2-dimethyl-1H-imidazole-5-carboxamides white solid, as a single diastereomer. MS calcd. for $C_{24}H_{27}ClFN_5O_2$: 471.1; Found: 472.3 $[M+1]^+$; $^1$H NMR (DMSO-$d_6$, 400 MHz): δ 10.10 (s, 1H), 7.95 (dd, J=6.8, 2.8 Hz, 1H), 7.57-7.53 (m, 1H), 7.39 (t, J=9.2 Hz, 1H), 7.00 (s, 1H), 6.65 (s, 1H), 5.23 (s, 1H), 3.73 (s, 3H), 3.55 (s, 3H), 3.21-3.18 (m, 1H), 2.43-2.41 (m, 4H), 2.31 (s, 1H), 2.06-2.03 (m, 2H), 1.82-1.77 (m, 4H) ppm.

Synthesis of Examples 28-30. Examples 28-30 in Table 3 were synthesized according to the procedures provided above using the corresponding starting materials.

TABLE 3

| Examples 28-30 | |
|---|---|
| Example | Structure and analysis |
| Example 28 | 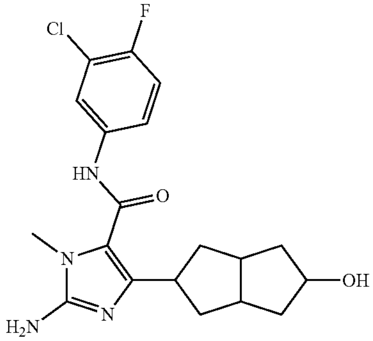 [SMILES: Cn1c(N)nc(C2CC3CC(O)CC3C2)c1C(=O)Nc1ccc(F)c(Cl)c1] 2-Amino-N-(3-chloro-4-fluorophenyl)-4-(5-hydroxyoctahydropentalen-2-yl)-1-methyl-1H-imidazole-5-carboxamide MS calcd. for $C_{19}H_{22}ClFN_4O_2$: 392.1; Found: 393.2 $[M + 1]^+$; $^1$H NMR ($CD_3OD$, 400 MHz): δ 7.80 (dd, J = 6.8, 2.4 Hz, 1H), 7.46-7.42 (m, 1H), 7.20 (t, J = 9.2 Hz, 1H), 4.16-4.12 (m, 1H), 3.43 (s, 3H), 3.34-3.25 (m, 1H), 2.44-2.39 (m, 2H), 2.18-2.03 (m, 4H), 1.72-1.64 (m, 2H), 1.42-1.35 (m, 2H) ppm. |

TABLE 3-continued

| Examples 28-30 | |
|---|---|
| Example | Structure and analysis |
| Example 29 | 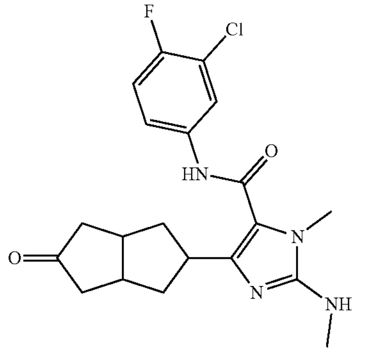 [SMILES: CNc1nc(C2CC3CC(=O)CC3C2)c(C(=O)Nc2ccc(F)c(Cl)c2)n1C] N-(3-Chloro-4-fluorophenyl)-1-methyl-2-(methylamino)-4-(5-oxooctahydropentalen-2-yl)-1H-imidazole-5-carboxamide MS calcd. for $C_{20}H_{22}ClFN_4O_2$: 404.1; Found: 405.2 [M + 1]$^+$; $^1$H NMR (DMSO-d6, 400 MHz): δ 9.75 (s, 1H), 7.91 (dd, J = 7.2, 2.8 Hz, 1 H), 7.55-7.51 (m, 1H), 7.36 (t, J = 8.8 Hz, 1H), 6.10 (d, J = 4.8 Hz, 1H), 3.43 (m, 1H), 3.11 (s, 3H), 2.79 (d, J = 4.8 Hz, 3H), 2.67-2.66 (m, 2H), 2.46-2.39 (m, 2H), 2.20-2.10 (m, 4H), 1.64-1.56 (m, 2H) ppm. |
| Example 30 | 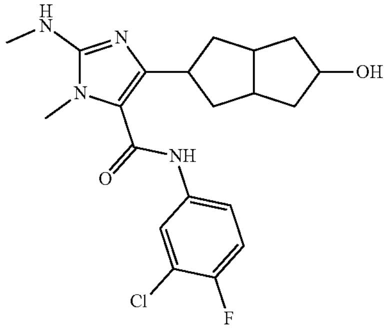 [SMILES: CNc1nc(C2CC3CC(O)CC3C2)c(C(=O)Nc2ccc(F)c(Cl)c2)n1C] N-(3-Chloro-4-fluorophenyl)-4-(5-hydroxyoctahydropentalen-2-yl)-1-methyl-2-(methylamino)-1H-imidazole-5-carboxamide MS calcd. for $C_{20}H_{24}ClFN_4O_2$: 406.2; Found: 407.2 [M + 1]$^+$; $^1$H NMR (DMSO-d6, 400 MHz): δ 9.69 (s, 1H), 7.90 (dd, J = 6.8, 2.4 Hz, 1H), 7.53-7.49 (m, 1H), 7.35 (t, J = 9.2 Hz, 1H), 6.05 (dd, J = 9.2, 4.4 Hz, 1H), 4.53 (d, J = 4.8 Hz, 1H), 4.02 (m, 1H), 3.31 (s, 3H), 3.26-3.21 (m, 1H), 2.81 (d, J = 4.8 Hz, 1H), 2.29-2.25 (m, 2H), 2.04-1.91 (m, 4H), 1.71-1.61 (m, 2H), 1.29-1.24 (m, 2H) ppm. |

Intermediate 18

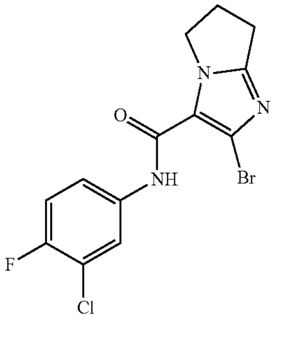 [SMILES: O=C(Nc1ccc(F)c(Cl)c1)c1c(Br)nc2n1CCC2]

2-Bromo-N-(3-chloro-4-fluorophenyl)-6,7-dihydro-5H-pyrrolo[1,2-a]imidazole-3-carboxamide. A solution of 2-bromo-6,7-dihydro-5H-pyrrolo[1,2-a]imidazole-3-carboxylic acid (500 mg, 2.2 mmol) in $SOCl_2$ (6 mL) was stirred at 80° C. for 4 hours. The reaction was concentrated to remove volatiles. The residue was dissolved in anhydrous DCM (5 mL). To this was added 3-chloro-4-fluoroaniline (473 mg, 3.3 mmol) and $Et_3N$ (440 mg, 4.4 mmol). The reaction was stirred at room temperature for 1 hour then concentrated to remove solvent. The residue was diluted with ethyl acetate and washed with brine. The ethyl acetate solution was dried over $Na_2SO_4$, filtered and concentrated. The residue was purified by silica gel column chromatography (40 g silica-gel column, eluted with petroleum ether/ethyl acetate) to give 2-bromo-N-(3-chloro-4-fluorophenyl)-6,7-dihydro-5H-pyrrolo[1,2-a]imidazole-3-carboxamide as a brown solid. TLC; 50%, ethyl acetate/petroleum ether ($R_f$: 0.3). MS calcd. for $C_{13}H_{10}BrClFN_3O$: 357.0; Found: 357.9 [M+1]$^+$.

Intermediate 19

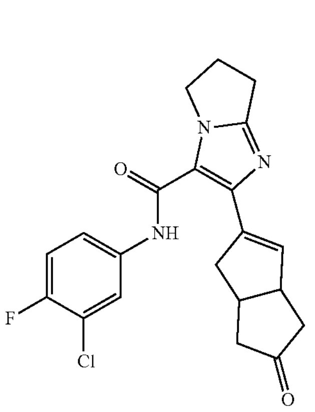 [SMILES: O=C1CC2C=C(c3nc4n(c3C(=O)Nc3ccc(F)c(Cl)c3)CCC4)CC2C1]

N-(3-Chloro-4-fluorophenyl)-2-(5-oxo-1,3a,4,5,6,6a-hexahydropentalen-2-yl)-6,7-dihydro-5H-pyrrolo[1,2-a]imidazole-3-carboxamide. To a solution of 2-bromo-N-(3-chloro-4-fluorophenyl)-6,7-dihydro-5H-pyrrolo[1,2-a]imidazole-3-carboxamide (660 mg, 1.9 mmol), 5-(4,4,5,5-tetramethyl-1,3,2-dioxaborolan-2-yl)-3,3a,6,6a-tetrahydropentalen-2(1H)-one (4.0 g 15% pure, 2.4 mmol) and $K_3PO_4$ (785 mg, 3.7 mmol) in dioxane (15 mL) and $H_2O$ (3 mL) was added Pd(dppf)$Cl_2$ (95 mg, 0.13 mmol), the reaction was stirred under nitrogen atmosphere at 80° C. overnight. The volatiles were removed in vacuo and the residue purified by silica gel column chromatography (40 g silica-gel column, eluted with petroleum ether/ethyl acetate) to give N-(3-chloro-4-fluorophenyl)-2-(5-oxo-1,3a,4,5,6,6a-hexahydropentalen-2-yl)-6,7-dihydro-5H-pyrrolo[1,2-a]imidazole-3-carboxamide as a white solid. TLC: 70% ethyl acetate/petroleum ether ($R_f$ 0.2). MS calcd. for $C_{21}H_{19}ClFN_3O_2$: 399.1; Found: 400.3 $[M+1]^+$.

Example 31

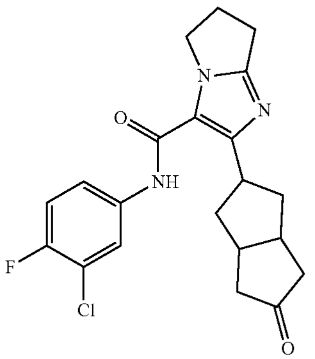 [SMILES: O=C1CC2CC(c3nc4n(c3C(=O)Nc3ccc(F)c(Cl)c3)CCC4)CC2C1]

N-(3-Chloro-4-fluorophenyl)-2-(5-oxooctahydropentalen-2-yl)-6,7-dihydro-5H-pyrrolo[1,2-a]imidazole-3-carboxamide. To a solution of N-(3-chloro-4-fluorophenyl)-2-(5-oxo-1,3a,4,5,6,6a-hexahydropentalen-2-yl)-6,7-dihydro-5H-pyrrolo[1,2-a]imidazole-3-carboxamide (100 mg, 0.3 mmol) in ethyl acetate (25 mL) was added Pd/C (100 mg, 100% w/w), the reaction solution was stirred under a hydrogen atmosphere at room temperature overnight. The reaction was then filtered, and the filtrate concentrated to give the crude product which was purified by prep-HPLC to give N-(3-chloro-4-fluorophenyl)-2-(5-oxooctahydropentalen-2-yl)-6,7-dihydro-5H-pyrrolo[1,2-a]imidazole-3-carboxamide as a white solid. TLC: 10% MeOH/DCM (Rf: 0.6). MS calcd. for $C_{21}H_{21}ClFN_3O_2$: 401.1; Found: 402.2 $[M+1]^+$. $^1H$ NMR ($CD_3OD$, 400 MHz): δ 7.83 (dd, J=6.8, 2.8 Hz, 1H), 7.51-7.47 (m, 1H), 7.23 (t, J=9.2 Hz, 1H), 4.16 (t, J=7.2 Hz, 2H), 3.64-3.55 (m, 1H), 2.88-2.78 (m, 3H), 2.66-2.58 (m, 2H), 2.56-2.49 (m, 2H), 2.39-2.32 (m, 2H), 2.25-2.19 (m, 2H), 1.75-1.67 (m, 4H) ppm.

Example 32

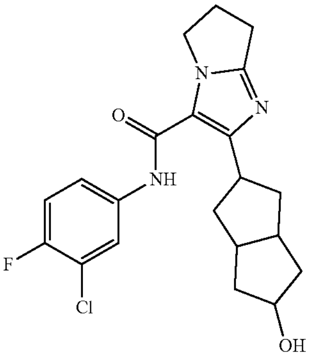 [SMILES: O=C(Nc1ccc(F)c(Cl)c1)c1c(C2CC3CC(O)CC3C2)nc2n1CCC2]

N-(3-Chloro-4-fluorophenyl)-2-(5-hydroxyoctahydropentalen-2-yl)-6,7-dihydro-5H-pyrrolo[1,2-a]imidazole-3-carboxamide Isomer I and Isomer II. To a solution of N-(3-chloro-4-fluorophenyl)-2-(5-oxooctahydropentalen-2-yl)-6,7-dihydro-5H-pyrrolo[1,2-a]imidazole-3-carboxamide (60 mg, 0.2 mmol) in MeOH (5 mL) was added $NaBH_4$ (11 mg, 0.3 mmol) and the solution stirred at room temperature for 3 hours. After the starting material was consumed, the volatiles were removed in vacuo, and the residue purified by prep-HPLC to afford N-(3-chloro-4-fluorophenyl)-2-(5-hydroxyoctahydropentalen-2-yl)-6,7-dihydro-5H-pyrrolo[1,2-a]imidazole-3-carboxamide Isomer I and Isomer II.

N-(3-Chloro-4-fluorophenyl)-2-(5-hydroxyoctahydropentalen-2-yl)-6,7-dihydro-5H-pyrrolo[1,2-a]imidazole-3-carboxamide Isomer I. MS calcd. for $C_{21}H_{23}ClFN_3O_2$: 403.1; Found: 404.2 $[M+1]^+$; $^1H$ NMR ($CD_3OD$, 400 MHz): δ 7.82 (dd, J=6.8, 2.8 Hz, 1H), 7.49-7.45 (m, 1H), 7.22 (t, J=9.2 Hz, 1H), 4.45-4.42 (m, 1H), 4.15 (t, J=7.2 Hz, 2H), 3.38-3.31 (m, 1H), 2.87-2.84 (m, 2H), 2.66-2.58 (m, 4H), 2.23-2.16 (m, 2H), 1.71-1.68 (m, 4H), 1.56-1.48 (m, 2H) ppm.

Example 33

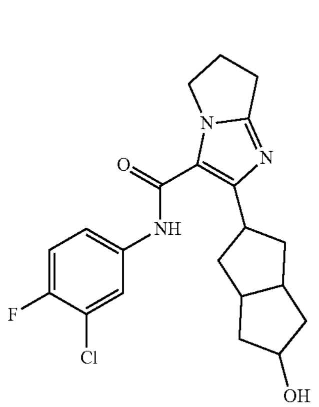 [SMILES: O=C(Nc1ccc(F)c(Cl)c1)c1c(C2CC3CC(O)CC3C2)nc2n1CCC2]

N-(3-Chloro-4-fluorophenyl)-2-(5-hydroxyoctahydropentalen-2-yl)-6,7-dihydro-5H-pyrrolo[1,2-a]imidazole-3-carboxamide Isomer II. MS calcd. for $C_{21}H_{23}ClFN_3O_2$: 403.1; Found: 404.2 $[M+1]^+$; $^1H$ NMR ($CD_3OD$, 400 MHz): δ 7.82 (dd, J=6.8, 2.8 Hz, 1H), 7.49-7.45 (m, 1H), 7.22 (t, J=8.8 Hz, 1H), 4.18-4.14 (m, 3H), 3.48-3.42 (m, 1H), 2.88-2.84 (m, 2H), 2.66-2.60 (m, 2H), 2.48-2.46 (m, 2H), 2.26-2.19 (m, 2H), 2.15-2.09 (m, 2H), 1.77-1.69 (m, 2H), 1.45-1.38 (m, 2H) ppm.

Example 34

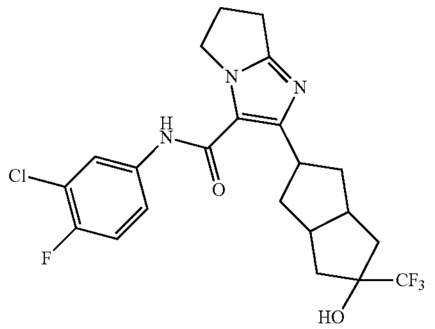 [SMILES: O=C(Nc1ccc(F)c(Cl)c1)c1c(C2CC3CC(O)(C(F)(F)F)CC3C2)nc2n1CCC2]

N-(3-Chloro-4-fluorophenyl)-2-(5-hydroxy-5-(trifluoromethyl)octahydropentalen-2-yl)-6,7-dihydro-5H-pyrrolo[1,2-a]imidazole-3-carboxamide. To a solution of N-(3-chloro-4-fluorophenyl)-2-(5-oxooctahydropentalen-2-yl)-6,7-dihydro-5H-pyrrolo[1,2-a]imidazole-3-carboxamide (100 mg, 0.25 mmol) in THF (2 mL) was added TBAF (0.75 mL (1M), 0.75 mmol) and $TMSCF_3$ (213 mg, 1.5 mmol) and the mixture stirred at 60° C. overnight. After cooling to room temperature, another batch of $TMSCF_3$ (213 mg, 1.5 mmol) was added and stirring continued at 60° C. for 6 h. After cooling to room temperature, another batch of $TMSCF_3$ (213 mg, 1.5 mmol) was added and the reaction was continued at 60° C. overnight. After the starting material was consumed completely, the reaction was concentrated. The residue was diluted with ethyl acetate and the organic phase was washed with brine, dried over anhydrous $Na_2SO_4$, filtered and concentrated to give crude compound which was purified by prep-HPLC to give N-(3-chloro-4-fluorophenyl)-2-(5-hydroxy-5-(trifluoromethyl)octahydropentalen-2-yl)-6,7-dihydro-5H-pyrrolo[1,2-a]imidazole-3-carboxamides white solid, as a single diastereomer. TLC: 5% MeOH/DCM ($R_f$: 0.4). MS calcd. for $C_{22}H_{22}ClF_4N_3O_2$: 471.1; Found: 472.2 $[M+1]^+$; $^1H$ NMR ($CD_3OD$, 400 MHz): δ 7.83 (dd, J=6.8, 2.8 Hz, 1H), 7.49-7.45 (m, 1H), 7.22 (t, J=9.2 Hz, 1H), 4.16 (t, J=7.2 Hz, 2H), 3.43-3.38 (m, 1H), 2.86 (t, J=7.2 Hz, 2H), 2.74-2.72 (m, 2H), 2.66-2.60 (m, 2H), 2.26-2.14 (m, 4H), 1.98-1.90 (m, 2H), 1.79 (d, J=13.6 Hz, 2H) ppm.

Example 35

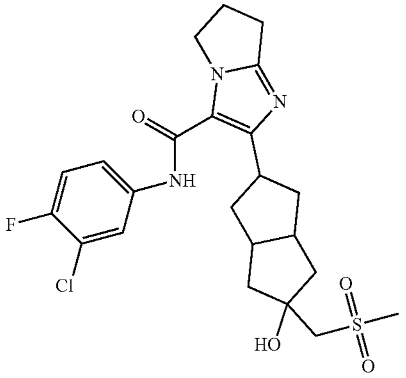 [SMILES: CS(=O)(=O)CC1(O)CC2CC(c3nc4n(c3C(=O)Nc3ccc(F)c(Cl)c3)CCC4)CC2C1]

N-(3-Chloro-4-fluorophenyl)-2-(5-hydroxy-5-((methylsulfonyl)methyl)octahydropentalen-2-yl)-6,7-dihydro-5H-pyrrolo[1,2-a]imidazole-3-carboxamide. To a solution of dimethylsulfone (75 mg, 0.8 mmol) in THF (1 mL) was added n-BuLi (0.32 mL, 0.8 mmol) at −78° C. under nitrogen atmosphere and the reaction was stirred at −78° C. for 1 h. N-(3-chloro-4-fluorophenyl)-2-(5-oxooctahydropentalen-2-yl)-6,7-dihydro-5H-pyrrolo[1,2-a]imidazole-3-carboxamide (40 mg, 0.1 mmol) in THF (1 mL) was added at −78° C. and the reaction stirred at −78° C. for 30 min. The reaction was then warmed to room temperature and stirred for 2 h. The reaction was quenched with water and concentrated. The residue was purified by prep-HPLC to give N-(3-chloro-4-fluorophenyl)-2-(5-hydroxy-5-((methylsulfonyl)methyl)octahydropentalen-2-yl)-6,7-dihydro-5H-pyrrolo[1,2-a]imidazole-3-carboxamides white solid, as a single diastereomer. TLC: 5% MeOH/DCM ($R_f$: 0.4). MS calcd. for Chemical Formula: $C_{23}H_{27}ClFN_3O_4S$: 495.1; Found: 496.2 $[M+1]^+$; $^1H$ NMR (DMSO-$d_6$, 400 MHz): δ 9.74 (s, 1H), 7.91 (dd, J=6.8, 2.4 Hz, 1H), 7.57-7.53 (m, 1H), 7.39 (t, J=8.8 Hz, 1H), 4.96 (s, 1H), 4.08 (t, J=7.2 Hz, 2H), 3.39-3.33 (m, 1H), 3.26 (s, 2H), 2.99 (s, 3H), 2.75 (t, J=7.2 Hz, 2H), 2.54-2.47 (m, 4H), 2.08-2.03 (m, 4H), 1.86-1.78 (m, 2H), 1.65-1.61 (m, 2H) ppm.

Synthesis of Examples 36-49. Examples 36-49 in Table 4 were synthesized according to the procedures provided above using the corresponding starting materials.

TABLE 4

| Examples 36-49 | |
|---|---|
| Example | Structure and analysis |
| Example 36 | 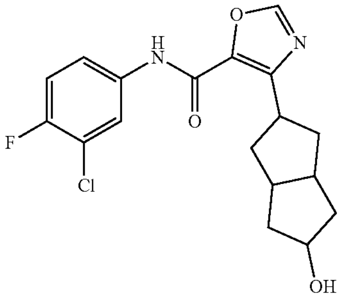 [SMILES: O=C(Nc1ccc(F)c(Cl)c1)c1ocnc1C1CC2CC(O)CC2C1] N-(3-Chloro-4-fluorophenyl)-4-(5-hydroxyoctahydropentalen-2-yl)oxazole-5-carboxamide MS calcd. for $C_{18}H_{18}ClFN_2O_3$: 364.1. Found: 365.0 $[M + 1]^+$; $^1H$ NMR (400 MHz, DMSO-d6): δ 10.46 (s, 1H), 8.53 (s, 1H), 8.05 (d, J = 4.8 Hz, 1H), 7.71-7.69 (m, 1H), 7.40 (t, J = 9.2 Hz, 1H), 4.52 (d, J = 4.0 Hz, 1H), 4.09 (s, 1H), 3.79-3.77 (m, 1H), 2.49-2.43 (m, 2H), 2.06-2.05 (m, 2H), 1.95-1.92 (m, 2H), 1.74-1.72 (m, 2H), 1.36-1.33 (m, 2H) ppm. |
| Example 37 | 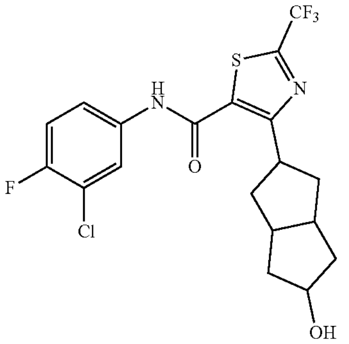 [SMILES: O=C(Nc1ccc(F)c(Cl)c1)c1sc(C(F)(F)F)nc1C1CC2CC(O)CC2C1] N-(3-chloro-4-fluorophenyl)-4-(5-hydroxyoctahydropentalen-2-yl)-2-(trifluoromethyl)thiazole-5-carboxamide MS calcd. for C19H17ClF4N2O2S: 448.1; Found: 449.2 $[M + 1]^+$; $^1H$ NMR (400 MHz, DMSO-$d_6$): δ 10.80-10.70 (m, 1H), 7.95 (dd, J = 7.2, 2.8 Hz, 1H), 7.59-7.56 (m, 1H), 7.44 (t, J = 8.8 Hz, 1H), 4.53 (d, J = 4.0 Hz, 1H), 4.15-4.05 (m, 1H), 3.62-3.58 (m, 1H), 2.45-2.40 (m, 2H), 2.22-2.16 (m, 2H), 1.96-1.78 (m, 4H), 1.40-1.34 (m, 2H) ppm. |
| Example 38 | 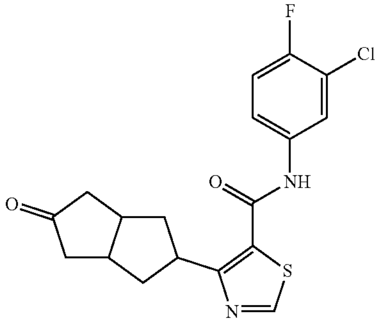 [SMILES: O=C1CC2CC(c3ncsc3C(=O)Nc3ccc(F)c(Cl)c3)CC2C1] N-(3-Chloro-4-fluorophenyl)-4-(5-oxooctahydropentalen-2-yl)thiazole-5-carboxamide MS calcd. for $C_{18}H_{16}ClFN_2O_2S$: 378.1; Found: 378.9 $[M + 1]^+$; $^1H$ NMR (400 MHz, DMSO-$d_6$): δ 10.48 (s, 1H), 9.15 (s, 1H), 8.00-7.94 (m, 1H), 7.65-7.58 (m, 1H), 7.41 (t, J = 8.8 Hz, 1H), 3.96-3.34 (m, 1H), 2.81-2.71 (m, 2H), 2.48-2.42 (m, 2H, merged), 2.36-2.25 (m, 2H), 2.16-2.05 (m, 2H), 1.73-1.61 (m, 2H) ppm. |

TABLE 4-continued

| Example | Structure and analysis |
|---|---|
| | Examples 36-49 |
| Example 39 | 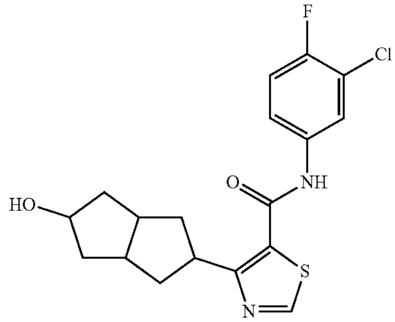 [SMILES: O=C(Nc1ccc(F)c(Cl)c1)c1scnc1C1CC2CC(O)CC2C1]<br>N-(3-Chloro-4-fluorophenyl)-4-(5-hydroxyoctahydropentalen-2-yl)thiazole-5-carboxamide<br>MS calcd. for $C_{18}H_{18}ClFN_2O_2S$: 380.1; Found: 380.9 $[M + 1]^+$; $^1H$ NMR (400 MHz, DMSO-$d_6$): δ 10.44 (s, 1H), 9.11 (s, 1H), 7.96 (dd, J = 6.8, 2.0 Hz, 1H), 7.62-7.56 (m, 1H), 7.40 (t, J = 9.2 Hz, 1H), 4.53 (d, J = 4.4 Hz, 1H), 4.11-4.03 (m, 1H), 3.72-3.62 (m, 1H), 2.48-2.32 (m, 2H), 2.20-2.09 (m, 2H), 1.98-1.90 (m, 2H), 1.88-1.74 (m, 2H), 1.40-1.28 (m, 2H) ppm. |
| Example 40 | 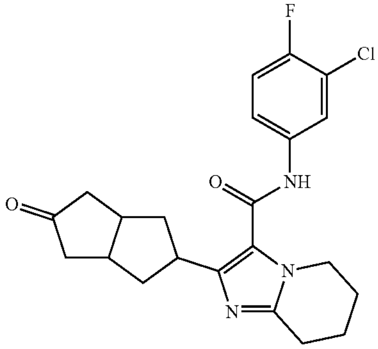 [SMILES: O=C1CC2CC(c3nc4n(c3C(=O)Nc3ccc(F)c(Cl)c3)CCCC4)CC2C1]<br>2-[-5-Oxo-2,3,3a,4,6,6a-hexahydro-1H-pentalen-2-yl]-N-(3-chloro-4-fluorophenyl)-5,6,7,8-tetrahydroimidazo[1,2-a]pyridine-3-carboxamide<br>$^1H$ NMR (600 MHz, DMSO-d6): δ 10.06 (s, 1H), 7.91 (dd, J = 6.9, 2.6 Hz, 1H), 7.54 (d, J = 8.8 Hz, 1H), 7.37 (t, J = 9.1 Hz, 1H), 3.95 (t, J = 5.9 Hz, 2H), 3.38 (td, J = 10.4, 5.2 Hz, 1H), 2.75-2.69 (m, 2H), 2.66 (d, J = 8.1 Hz, 2H), 2.44-2.38 (m, 2H), 2.23-2.15 (m, 2H), 2.04 (dd, J = 18.9, 3.9 Hz, 2H), 1.87-1.82 (m, 2H), 1.81-1.74 (m, 2H), 1.59-1.51 (m, 2H) ppm; MS calcd. for $C_{22}H_{23}ClFN_3O_2$: 415.1; Found: 416.2 $[M + 1]^+$. |
| Example 41 | 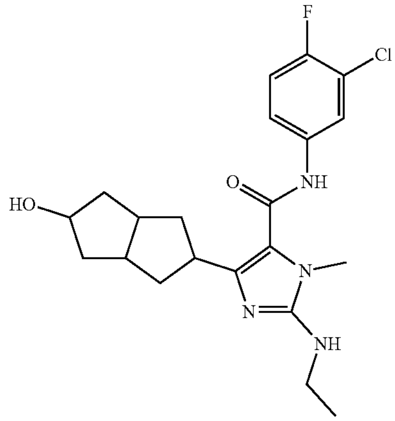 [SMILES: CCNc1nc(C2CC3CC(O)CC3C2)c(C(=O)Nc2ccc(F)c(Cl)c2)n1C]<br>5-[-5-Hydroxy-1,2,3,3a,4,5,6,6a-octahydropentalen-2-yl]-N-(3-chloro-4-fluorophenyl)-2-(ethylamino)-3-methyl-4-imidazolecarboxamide<br>MS calcd. for $C_{21}H_{26}ClFN_4O_2$: 420.2; Found: 421.3. |

TABLE 4-continued

| Examples 36-49 | |
|---|---|
| Example | Structure and analysis |
| Example 42 | 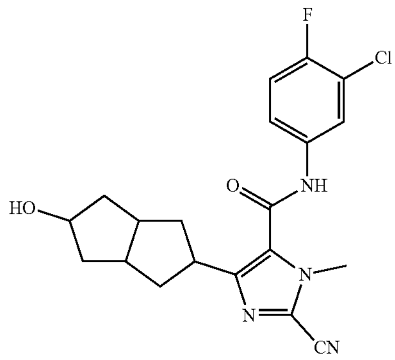 [SMILES: Cn1c(C#N)nc(C2CC3CC(O)CC3C2)c1C(=O)Nc1ccc(F)c(Cl)c1] 5-[-5-Hydroxy-1,2,3,3a,4,5,6,6a-octahydropentalen-2-yl]-N-(3-chloro-4-fluorophenyl)-2-cyano-3-methyl-4-imidazolecarboxamide MS calcd. for $C_{20}H_{20}ClFN_4O_2$: 402.1; Found: 403.2. |
| Example 43 | 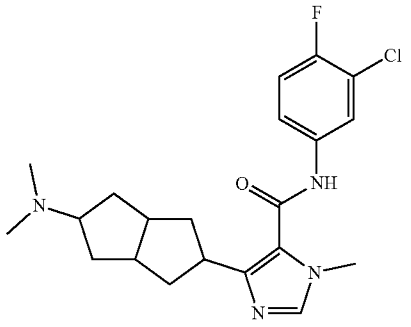 [SMILES: CN(C)C1CC2CC(c3ncn(C)c3C(=O)Nc3ccc(F)c(Cl)c3)CC2C1] 5-[5-(Dimethylamino)-1,2,3,3a,4,5,6,6a-octahydropentalen-2-yl]-N-(3-chloro-4-fluorophenyl)-3-methyl-4-imidazolecarboxamide MS calcd. for $C_{21}H_{26}ClFN_4O$: 404.2; Found: 405.3. |
| Example 44 | 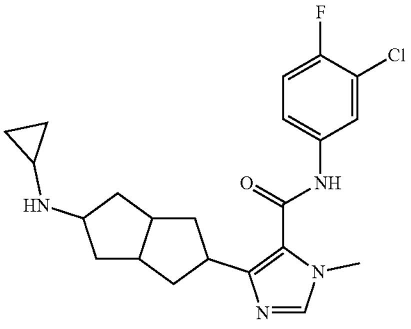 [SMILES: Cn1cnc(C2CC3CC(NC4CC4)CC3C2)c1C(=O)Nc1ccc(F)c(Cl)c1] 5-[-5-(Cyclopropylamino)-1,2,3,3a,4,5,6,6a-octahydropentalen-2-yl]-N-(3-chloro-4-fluorophenyl)-3-methyl-4-imidazolecarboxamide. Isomer I MS calcd. for $C_{22}H_{26}ClFN_4O$: 416.2; Found: 417.2. |

TABLE 4-continued

| Examples 36-49 | |
|---|---|
| Example | Structure and analysis |
| Example 45 | 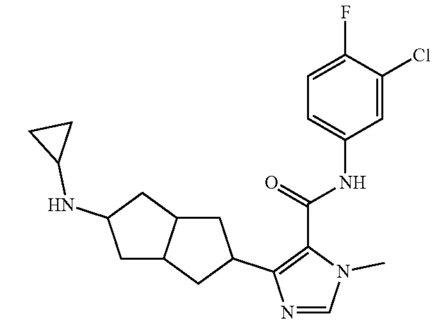 [SMILES: Cn1cnc(C2CC3CC(NC4CC4)CC3C2)c1C(=O)Nc1ccc(F)c(Cl)c1] 5-[-5-(Cyclopropylamino)-1,2,3,3a,4,5,6,6a-octahydropentalen-2-yl]-N-(3-chloro-4-fluorophenyl)-3-methyl-4-imidazolecarboxamide. Isomer II MS calcd. for $C_{22}H_{26}ClFN_4O$: 416.2; Found: 417.3. |
| Example 46 | 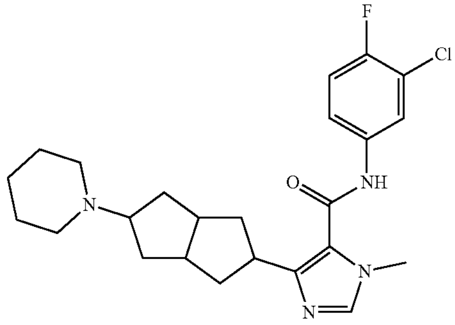 [SMILES: Cn1cnc(C2CC3CC(N4CCCCC4)CC3C2)c1C(=O)Nc1ccc(F)c(Cl)c1] 5-[-5-(1-Piperidinyl)-1,2,3,3a,4,5,6,6a-octahydropentalen-2-yl]-N-(3-chloro-4-fluorophenyl)-3-methyl-4-imidazolecarboxamide MS calcd. for $C_{24}H_{30}ClFN_4O$: 444.2; Found: 445.2. |
| Example 47 | 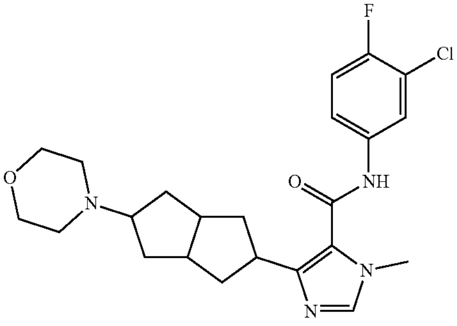 [SMILES: Cn1cnc(C2CC3CC(N4CCOCC4)CC3C2)c1C(=O)Nc1ccc(F)c(Cl)c1] 5-[-5-(4-Morpholinyl)-1,2,3,3a,4,5,6,6a-octahydropentalen-2-yl]-N-(3-chloro-4-fluorophenyl)-3-methyl-4-imidazolecarboxamide MS calcd. for $C_{23}H_{28}ClFN_4O_2$: 446.2; Found: 447.3. |

TABLE 4-continued

Examples 36-49

| Example | Structure and analysis |
| --- | --- |
| Example 48 | 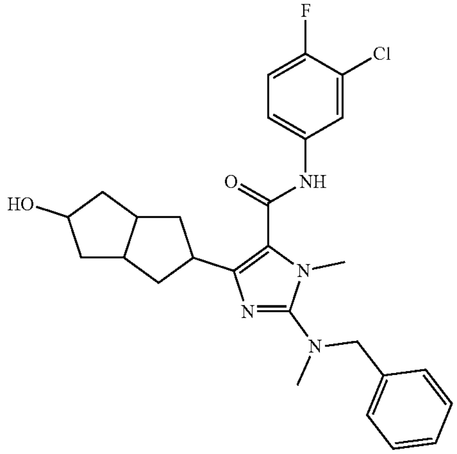 [SMILES: CN(Cc1ccccc1)c1nc(C2CC3CC(O)CC3C2)c(C(=O)Nc2ccc(F)c(Cl)c2)n1C] 2-(benzyl(methyl)amino)-N-(3-chloro-4-fluorophenyl)-4-(5-hydroxyoctahydropentalen-2-yl)-1-methyl-1H-imidazole-5-carboxamide MS calcd. for $C_{27}H_{30}ClFN_4O_2$: 496.2; Found: 497.3. |
| Example 49 | 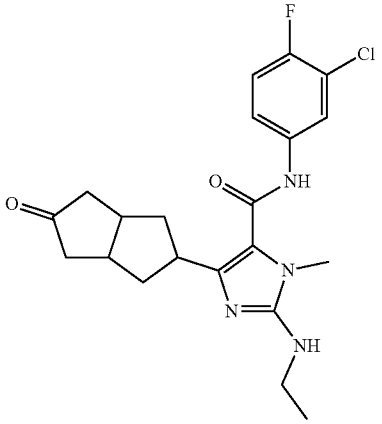 [SMILES: CCNc1nc(C2CC3CC(=O)CC3C2)c(C(=O)Nc2ccc(F)c(Cl)c2)n1C] N-(3-chloro-4-fluorophenyl)-2-(ethylamino)-1-methyl-4-(5-oxooctahydropentalen-2-yl)-1H-imidazole-5-carboxamide MS calcd. for $C_{21}H_{24}ClFN_4O_2$: 418.2; Found: 419.2. |

General Procedure for Alkylation, Method A

To a stirred solution of Ar—OH (1 eq.) and a halo compound (2 eq.) in acetonitrile/DMF (4 mL/mmol) was added $K_2CO_3$ (2 eq.) and KI (0.5 eq.). The reaction mixture was stirred at 60° C.-80° C. for 1216 h. The reaction progress was monitored by TLC. After completion, the reaction mixture was diluted with water and extracted with ethyl acetate. The combined organic layers were collected, dried over anhydrous sodium sulphate, and concentrated under reduced pressure to obtain crude compound which was purified by silica gel column chromatography or prep-HPLC to afford the desired compound.

General Procedure for Alkylation, Method B

To a stirred solution of Ar—OH (1 eq.) and a halo compound (2 eq) in DMF/ACN (6 mL/mmol) was added $Cs_2CO_3$ (2.5 eq.). The reaction mixture was stirred at RT/60° C. for 2-4 h. The reaction progress was monitored by TLC. After completion, the reaction mixture was diluted with water and extracted with ethyl acetate. The combined organic layers were collected, dried over anhydrous sodium sulphate, and concentrated under reduced pressure to obtain crude compound which was purified by silica gel column chromatography or prep-HPLC to afford the desired compound.

Intermediate 20

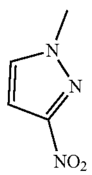

1-Methyl-3-nitro-1H-pyrazole. NaOtBu (19.11 g, 199.1 mmol) was added to a stirred solution of 3-nitro-1H-pyrazole (15 g, 132.7 mmol) in DMF (150 mL) at 0° C., and the reaction was stirred for 20 minutes. MeI (9.91 mL 159.24 mmol) was then added dropwise. The resulting mixture was stirred at RT for 16 h. The progress of the reaction was monitored by TLC. After completion, the reaction mixture was quenched with water and extracted with ethyl acetate. The organic layer was collected; washed with brine; dried over anhydrous sodium sulphate and concentrated under reduced pressure. The crude compound was purified by silica gel column chromatography to afford 1-methyl-3-nitro-1H-pyrazole (10 g, 59%) as an off white solid. TLC: 20% EtOAc/hexane ($R_f$: 0.2). $^1$H NMR (400 MHz, DMSO-$d_6$): δ 7.98 (s, 1H), 7.03 (d, J=2.0 Hz, 1H), 3.97 (s, 3H) ppm.

Example 50

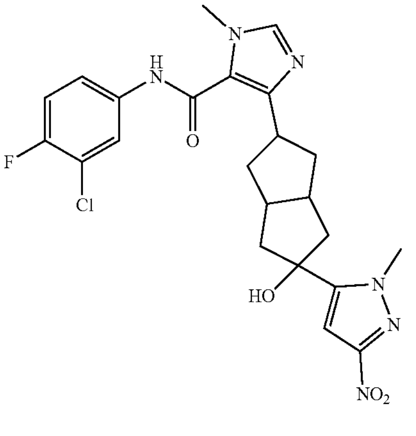 [SMILES: Cn1cnc(C2CC3CC(O)(c4cc([N+](=O)[O-])nn4C)CC3C2)c1C(=O)Nc1ccc(F)c(Cl)c1]

N-(3-Chloro-4-fluorophenyl)-4-(5-hydroxy-5-(1-methyl-3-nitro-1H-pyrazol-5-yl)octahydropentalen-2-yl)-1-methyl-1H-imidazole-5-carboxamide. LDA (2M in THF, 60 mL, 120 mmol) was added dropwise to a stirred solution of methyl-3-nitro-1H-pyrazole (10.16 g, 80 mmol) in dry THF (100 mL) at −78° C. under an inert atmosphere and the reaction mixture stirred for 2 h. To this was added a solution of N-(3-chloro-4-fluorophenyl)-1-methyl-4-(5-oxooctahydropentalen-2-yl)-1H-imidazole-5-carboxamide (3 g, 8 mmol) in THF at −78° C. The resulting reaction mixture was stirred at −78° C. for 1 h. The progress of the reaction was monitored by TLC and LCMS. After completion, the reaction was quenched with a saturated $NH_4Cl$ solution and extracted with ethyl acetate. The organic layer was collected; washed with brine; dried over anhydrous sodium sulphate and concentrated under reduced pressure. The crude compound was purified by silica gel column chromatography to afford N-(3-chloro-4-fluorophenyl)-4-5-hydroxy-5-(1-methyl-3-nitro-1H-pyrazol-5-yl)octahydropentalen-2-yl)-1-methyl-1H-imidazole-5-carboxamide as a single diastereomer (2 g, 50%) as an off white solid. TLC: 5% MeOH/DCM ($R_f$: 0.3). $^1$H-NMR (DMSO-d6, 400 MHz): δ 10.23 (s, 1H), 7.96 (dd, J=6.8 Hz, 2.4 Hz, 1H), 7.66 (s, 1H), 7.59-7.55 (m, 1H), 7.40 (t, J=9.2 Hz, 1H), 6.93 (s, 1H), 5.60 (s, 1H), 4.05 (s, 3H), 3.68 (s, 3H), 3.29-3.24 (m, 1H), 2.51-2.49 (m, 2H), 2.30-2.24 (m, 2H), 2.13-2.07 (m, 2H), 1.94-1.85 (m, 4H) ppm; MS calcd. for $C_{23}H_{24}ClFN_6O_4$: 502.2; Found: 503.3 $[M+1]^+$.

Example 51

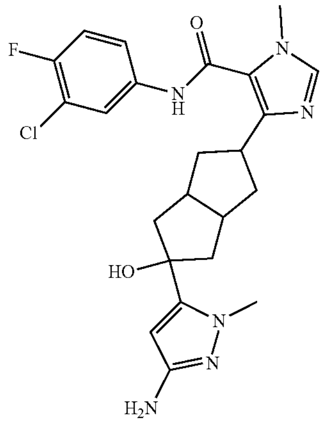 [SMILES: Cn1cnc(C2CC3CC(O)(c4cc(N)nn4C)CC3C2)c1C(=O)Nc1ccc(F)c(Cl)c1]

4-(5-(3-Amino-1-methyl-1H-pyrazol-5-yl)-5-hydroxyoctahydropentalen-2-yl)-N-(3-chloro-4-fluorophenyl)-1-methyl-1H-imidazole-5-carboxamide. 10% Pd/C (0.5 g) and $NaBH_4$ (1.06 g, 27.88 mmol) were added to a stirred solution of N-(3-chloro-4-fluorophenyl)-4-5-hydroxy-5-(1-methyl-3-nitro-1H-pyrazol-5-yl)octahydropentalen-2-yl)-1-methyl-1H-imidazole-5-carboxamide (2 g, 3.98 mmol) in MeOH (20 mL) under a nitrogen atmosphere. The reaction mixture was stirred at 0° C. for 30 minutes. The progress of the reaction was monitored by TLC and LCMS. After completion, the reaction mixture was filtered through a pad of Celite and washed with methanol. The filtrate was concentrated under reduced pressure. The residue was diluted with water and extracted with ethyl acetate. The organic layer was collected; washed with brine; dried over anhydrous sodium sulphate and concentrated under reduced pressure. The crude compound was purified by silica gel column chromatography to afford 4-5-(3-amino-1-methyl-1H-pyrazol-5-yl)-5-hydroxyoctahydropentalen-2-yl)-N-(3-chloro-4-fluorophenyl)-1-methyl-1H-imidazole-5-carboxamide (1.5 g, 80%) as an off white solid. TLC: 10% MeOH/DCM ($R_f$: 0.1). $^1$H NMR (400 MHz, DMSO-$d_6$): δ 10.25 (s, 1H), 7.95 (d, J=4.4 Hz, 1H), 7.76 (s, 1H), 7.58-7.54 (m, 1H), 7.41 (t, J=9.2 Hz, 1H), 6.62-5.57 (br s, 2H), 5.39 (s, 1H), 5.17 (s, 1H), 3.69 (s, 6H), 3.32-3.31 (m, 1H, merged), 2.50-2.32 (m, 2H, merged), 2.29-2.11 (m, 4H), 1.85-1.83 (m, 4H) ppm; MS calcd. for $C_{23}H_{26}ClFN_6O_2$; 472.2; Found: 471.2 $[M-1]^-$.

Example 52

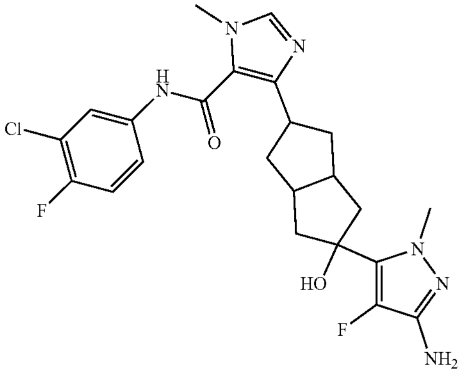 [SMILES: Cn1cnc(C2CC3CC(O)(c4c(F)c(N)nn4C)CC3C2)c1C(=O)Nc1ccc(F)c(Cl)c1]

4-(5-(3-Amino-4-fluoro-1-methyl-1H-pyrazol-5-yl)-5-hydroxyoctahydropentalen-2-yl)-N-(3-chloro-4-fluorophenyl)-1-methyl-1H-imidazole-5-carboxamide. Selectfluor (0.149 g, 0.42 mmol) and DIPEA (0.147 mL, 0.84 mmol) were added to a stirred solution of 4-(5-(3-amino-1-methyl-1H-pyrazol-5-yl)-5-hydroxyoctahydropentalen-2-yl)-N-(3-chloro-4-fluorophenyl)-1-methyl-1H-imidazole-5-carboxamide (0.2 g, 0.42 mmol) in ACN (5 mL). The reaction mixture was stirred at 100° C. for 16 h. The progress of the reaction was monitored by TLC and LCMS. After completion, the reaction mixture was concentrated under reduced pressure. The crude compound was purified by silica gel column chromatography to afford 4-(5-(3-amino-4-fluoro-1-methyl-1H-pyrazol-5-yl)-5-hydroxyoctahydropentalen-2-yl)-N-(3-chloro-4-fluorophenyl)-1-methyl-1H-imidazole-5-carboxamide (0.02 g, 10%) as an off white solid. TLC: 10% MeOH in DCM ($R_f$: 0.3). $^1$H NMR (400 MHz, DMSO-$d_6$): δ 10.19 (s, 1H), 7.95 (dd, J=6.8, 2.4 Hz, 1H), 7.63 (s, 1H), 7.57-7.53 (m, 1H), 7.39 (t, J=9.6 Hz, 1H), 5.21 (s, 1H), 4.47 (s, 2H), 3.66 (s, 3H), 3.60 (s, 3H), 3.30-3.14 (m, 1H), 2.50-2.40 (m, 2H, merged), 2.23-2.16 (m, 2H), 2.07-2.04 (m, 2H), 1.96-1.83 (m, 4H). MS calcd. for $C_{23}H_{25}ClF_2N_6O_2$: 490.2; Found: 473.1 $[M-H_2O+1]^+$.

Intermediate 21

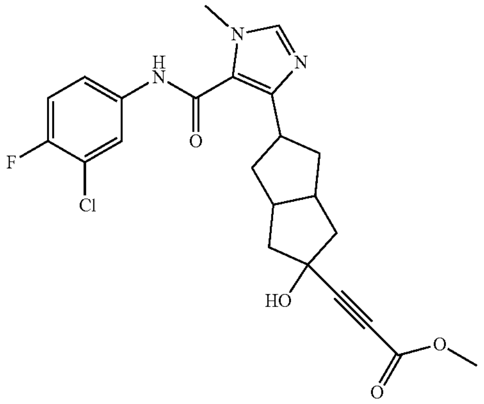 [SMILES: COC(=O)C#CC1(O)CC2CC(c3ncn(C)c3C(=O)Nc3ccc(F)c(Cl)c3)CC2C1]

Methyl 3-(5-(5-((3-chloro-4-fluorophenyl)carbamoyl)-1-methyl-1H-imidazol-4-yl)-2-hydroxyoctahydropentalen-2-yl)propiolate. n-BuLi (1.19 g, 18.6 mmol) was added to a stirred solution of methyl propiolate (1.56 g, 18.6 mmol) in dry THF (40 mL) at −78° C. in an inert atmosphere and the reaction mixture was stirred for 30 minutes. To this a solution of N-(3-chloro-4-fluorophenyl)-1-methyl-4-(5-oxooctahydropentalen-2-yl)-1H-imidazole-5-carboxamide (1 g, 2.66 mmol) in THF was added at −78° C. The resulting reaction mixture was stirred at −78° C. for 2 h. The progress of the reaction was monitored by TLC and LCMS. After completion, the reaction mixture was quenched with saturated $NH_4Cl$ solution and extracted with ethyl acetate. The organic layer was collected; washed with brine; dried over anhydrous sodium sulphate and concentrated under reduced pressure. The crude compound was purified by silica gel column chromatography to afford methyl 3-(5-(5-((3-chloro-4-fluorophenyl)carbamoyl)-1-methyl-1H-imidazol-4-yl)-2-hydroxyoctahydropentalen-2-yl)propiolate, an off white solid, as a single diastereomer. TLC: 5% MeOH/DCM ($R_f$: 0.3); $^1$H NMR (400 MHz, DMSO-$d_6$): δ 10.23 (s, 1H), 7.95 (d, J=6.4 Hz, 1H), 7.74-7.68 (m, 1H), 7.59-7.55 (m, 1H), 7.40 (t, J=8.8 Hz, 1H), 5.79 (s, 1H), 3.69 (s, 3H), 3.63 (s, 3H), 3.28-3.23 (m, 1H), 2.58-2.54 (m, 2H), 2.09-2.06 (m, 4H), 1.80-1.76 (m, 4H) ppm. MS calcd. for $C_{23}H_{23}ClFN_3O_4$: 459.1; Found: 460.2 $[M+1]^+$.

Example 53

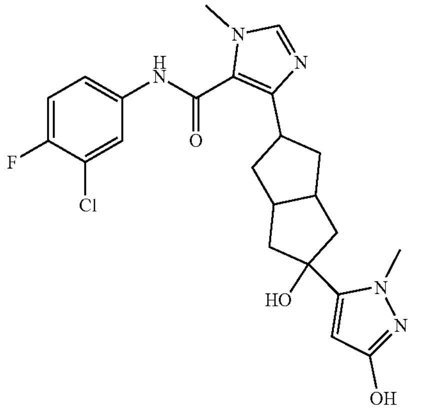 [SMILES: Cn1cnc(C2CC3CC(O)(c4cc(O)nn4C)CC3C2)c1C(=O)Nc1ccc(F)c(Cl)c1]

N-(3-Chloro-4-fluorophenyl)-4-(5-hydroxy-5-(3-hydroxy-1-methyl-1H-pyrazol-5-yl)octahydropentalen-2-yl)-1-methyl-1H-imidazole-5-carboxamide. TEA (2 g, 19.82 mmol) and 3-(5-(5-((3-Chloro-4-fluorophenyl)carbamoyl)-1-methyl-1H-imidazol-4-yl)-2-hydroxyoctahydropentalen-2-yl)propiolate (1.3 g, 2.83 mmol) were added to a stirred solution of methyl hydrazine sulphate (2.85 g, 19.82 mmol) in EtOH (20 mL). The reaction mixture was stirred at 50° C. for 24 h. The progress of the reaction was monitored by TLC and LCMS. After completion, the reaction mixture was concentrated under reduced pressure. The residue was diluted with water and extracted with ethyl acetate. The organic layer was collected; washed with brine; dried over anhydrous sodium sulphate and concentrated under reduced pressure to afford N-(3-chloro-4-fluorophenyl)-4-(5-hydroxy-5-(3-hydroxy-1-methyl-1H-pyrazol-5-yl)octahydropentalen-2-yl)-1-methyl-1H-imidazole-5-carboxamide (0.65 g, 49%) as a white solid. TLC: 8% MeOH/DCM ($R_f$: 0.2); $^1$H NMR (400 MHz, DMSO-$d_6$): δ 10.18 (s, 1H), 9.27 (s, 1H), 7.95 (d, J=4.4 Hz, 1H), 7.64 (s, 1H), 7.61-7.55 (m, 1H), 7.39 (t, J=8.8 Hz, 1H), 5.28 (s, 1H), 5.13 (s, 1H), 3.66 (s, 6H), 3.38-3.18 (m, 1H, merged), 2.60-2.38 (m, 2H, merged), 2.20-2.01 (m, 4H), 1.91-1.75 (m, 4H) ppm. MS calcd. for $C_{23}H_{25}ClFN_5O_3$: 473.2; Found: 473.9 $[M+1]^+$.

Example 54

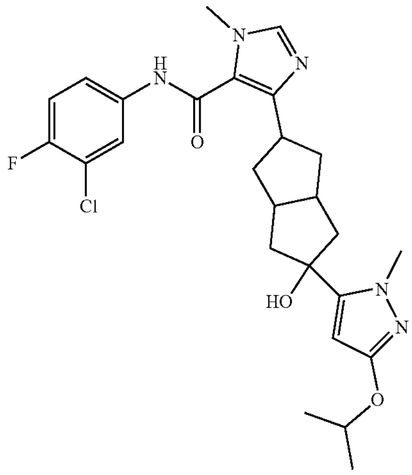 [SMILES: CC(C)Oc1cc(C2(O)CC3CC(c4ncn(C)c4C(=O)Nc4ccc(F)c(Cl)c4)CC3C2)n(C)n1]

N-(3-Chloro-4-fluorophenyl)-4-(5-hydroxy-5-(3-isopropoxy-1-methyl-1H-pyrazol-5-yl)octahydropentalen-2-yl)-1-methyl-1H-imidazole-5-carboxamide. The title compound was synthesized by alkylation of N-(3-chloro-4-fluorophenyl)-4-(5-hydroxy-5-(3-hydroxy-1-methyl-1H-pyrazol-5-yl)octahydropentalen-2-yl)-1-methyl-1H-imidazole-5-carboxamide using method A. $^{1}H$ NMR (400 MHz, DMSO-$d_6$): δ 10.21 (s, 1H), 7.99-7.94 (m, 1H), 7.64 (s, 1H), 7.60-7.54 (m, 1H), 7.40 (t, J=9.2 Hz, 1H), 5.47 (s, 1H), 5.20 (s, 1H), 4.61-4.54 (m, 1H), 3.71 (s, 3H), 3.67 (s, 3H), 3.29-3.18 (m, 1H), 2.48-2.39 (m, 2H), 2.20-2.04 (m, 4H), 1.90-1.78 (m, 4H), 1.21 (d, J=6.4 Hz, 6H) ppm; TLC: 10% MeOH/DCM ($R_f$: 0.3); MS calcd. for $C_{26}H_{31}ClFN_5O_3$: 515.2; Found: 516.1 $[M+1]^+$.

Example 55

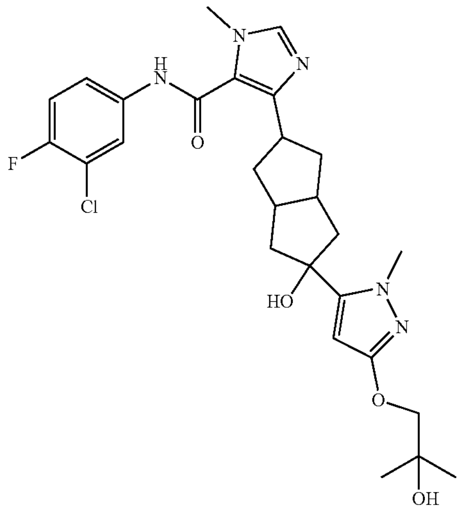 [SMILES: Cn1cnc(C2CC3CC(O)(c4cc(OCC(C)(C)O)nn4C)CC3C2)c1C(=O)Nc1ccc(F)c(Cl)c1]

N-(3-Chloro-4-fluorophenyl)-4-(5-hydroxy-5-(3-(2-hydroxy-2-methylpropoxy)-1-methyl-1H-pyrazol-5-yl)octahydropentalen-2-yl)-1-methyl-1H-imidazole-5-carboxamide. MeMgBr (3M in DEE, 0.59 mL, 1.78 mmol) was added slowly to a stirred solution of ethyl 2-((5-(5-(5-((3-chloro-4-fluorophenyl)carbamoyl)-1-methyl-1H-imidazol-4-yl)-2-hydroxyoctahydropentalen-2-yl)-1-methyl-1H-pyrazol-3-yl)oxy)acetate (0.5 g, 0.89 mmol) in dry THF (5 mL) at 0° C. in an inert atmosphere. The reaction mixture was stirred at RT for 2 h. The progress of the reaction was monitored by TLC. After completion, the reaction mixture was quenched with ice cold water and extracted with ethyl acetate. The organic layer was collected; washed with brine; dried over anhydrous sodium sulphate and concentrated under reduced pressure. The crude compound was purified by Combi-Flash® column chromatography followed by prep. HPLC to N-(3-chloro-4-fluorophenyl)-4-(5-hydroxy-5-(3-(2-hydroxy-2-methylpropoxy)-1-methyl-1H-pyrazol-5-yl)octahydropentalen-2-yl)-1-methyl-1H-imidazole-5-carboxamide (0.501 g, 61%) as an off white solid. TLC: 5% MeOH in DCM ($R_f$: 0.4); $^{1}H$ NMR (400 MHz, DMSO-$d_6$): δ 10.22 (s, 1H), 7.96 (dd, J=6.8 Hz, 2.4 Hz, 1H), 7.65 (s, 1H), 7.59-7.52 (m, 1H), 7.40 (t, J=9.6 Hz, 1H), 5.52 (s, 1H), 5.23 (s, 1H), 4.53 (s, 1H), 3.75-3.70 (m, 5H), 3.67 (s, 3H), 3.26-3.20 (m, 1H), 2.50-2.44 (m, 2H), 2.20-2.06 (m, 4H), 1.90-1.80 (m, 4H), 1.13 (s, 6H) ppm. MS calcd. for $C_{27}H_{33}ClFN_5O_4$: 545.2; Found: 546.3 $[M+1]^+$.

Intermediate 22

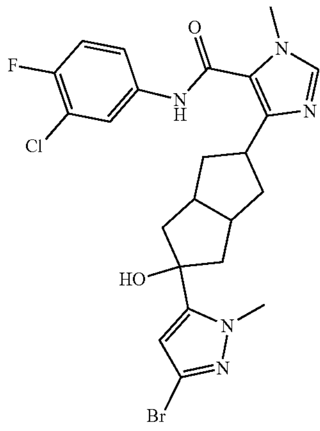 [SMILES: Cn1cnc(C2CC3CC(O)(c4cc(Br)nn4C)CC3C2)c1C(=O)Nc1ccc(F)c(Cl)c1]

4-(5-(3-Bromo-1-methyl-1H-pyrazol-5-yl)-5-hydroxyoctahydropentalen-2-yl)-N-(3-chloro-4-fluorophenyl)-1-methyl-1H-imidazole-5-carboxamide. n-BuLi (2 M in THF, 7.8 mL, 15.96 mmol) was added dropwise at −78° C. to a stirred solution of 3,5-dibromo-1-methyl-1H-pyrazole (3.8 g, 15.96 mmol) in dry THF (50 mL) in an inert atmosphere and the reaction mixture was stirred at same temperature for 35 minutes. To this was slowly added a solution of N-(3-chloro-4-fluorophenyl)-1-methyl-4-(5-oxooctahydropentalen-2-yl)-1H-imidazole-5-carboxamide (1 g, 2.65 mmol) in THF at −78° C. The reaction mixture was stirred at room temperature for 16 h. The progress of the reaction was monitored by TLC and LCMS. After completion, the reaction mixture was diluted with a sat. aq. solution of ammonium chloride and extracted with ethyl acetate. The organic layer was collected; washed with brine; dried over anhydrous sodium sulphate and concentrated under reduced pressure to afford the crude compound. The crude compound was purified by silica gel column chromatography to afford 4-(5-(3-bromo-1-methyl-1H-pyrazol-5-yl)-5-hydroxyoctahydropentalen-2-yl)-N-(3-chloro-4-fluorophenyl)-1- methyl-1H-imidazole-5-carboxamide as a single diastereomer (0.46 g, 32.39%). TLC: 5% MeOH/DCM ($R_f$: 0.3) $^1$H NMR (400 MHz, DMSO-$d_6$): δ 10.21 (s, 1H), 7.95 (dd, J=6.8, 2.4 Hz, 1H), 7.65 (s, 1H), 7.58-7.55 (m, 1H), 7.40 (t, J=9.2 Hz, 1H), 6.23 (s, 1H), 5.37 (s, 1H), 3.87 (s, 3H), 3.67 (s, 3H), 3.29-3.23 (m, 1H), 2.50-2.46 (m, 2H, merged), 2.22-2.07 (m, 4H), 1.87-1.83 (m, 4H) ppm; MS calcd. for $C_{23}H_{24}BrClFN_5O_2$: 535.1; Found: 536.1 $[M+1]^+$.

Example 56

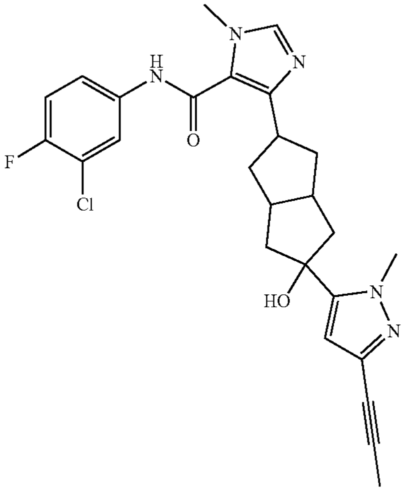 [SMILES: CC#Cc1cc(C2(O)CC3CC(c4ncn(C)c4C(=O)Nc4ccc(F)c(Cl)c4)CC3C2)n(C)n1]

N-(3-Chloro-4-fluorophenyl)-4-(5-hydroxy-5-(1-methyl-3-(prop-1-yn-1-yl)-1H-pyrazol-5-yl)octahydropentalen-2-yl)-1-methyl-1H-imidazole-5-carboxamide. Tributyl(1-propynyl)tin (153.7 mg, 0.46 mmol) was added to a stirred solution of 4-(5-(3-bromo-1-methyl-1H-pyrazol-5-yl)-5-hydroxyoctahydropentalen-2-yl)-N-(3-chloro-4-fluorophenyl)-1-methyl-1H-imidazole-5-carboxamide (50 mg, 0.09 mmol) in 1,4 dioxane (3 mL), and the mixture purged with Argon for 15 min. $Pd(PPh_3)_4$ (10.39 mg, 0.009 mmol) was then added and purging with Argon continued for another 10 min. The reaction mixture was stirred in a microwave at 140° C. for 45 minutes. The progress of the reaction was monitored by TLC and LCMS. After completion, the reaction mixture was diluted with water and extracted with ethyl acetate. The organic layer was collected; washed with brine; dried over anhydrous sodium sulphate and concentrated under reduced pressure. The crude compound was purified by CombiFlash® column chromatography to afford N-(3-chloro-4-fluorophenyl)-4-(5-hydroxy-5-(1-methyl-3-(prop-1-yn-1-yl)-1H-pyrazol-5-yl)octahydropentalen-2-yl)-1-methyl-1H-imidazole-5-carboxamide (6 mg, 12%) as an off white solid. TLC: 5% MeOH/DCM ($R_f$: 0.4); $^1$H NMR (400 MHz, $CD_3OD$): δ 7.92-7.87 (m, 1H), 7.66 (s, 1H), 7.55-7.48 (m, 1H), 7.24 (t, J=8.8 Hz, 1H), 6.21 (s, 1H), 3.94 (s, 3H), 3.77 (s, 3H), 3.38-3.26 (m, 1H, merged), 2.62-2.52 (m, 2H), 2.43-2.34 (m, 2H), 2.32-2.22 (m, 2H), 1.99 (s, 3H), 1.97-1.82 (m, 4H) ppm (amide and OH protons not observed); MS calcd. for $C_{26}H_{27}ClFN_5O_2$: 495.2; Found: 496.0.

Example 57

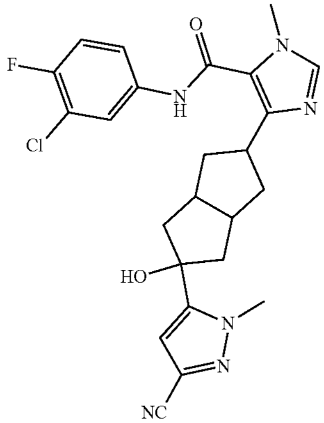 [SMILES: Cn1cnc(C2CC3CC(O)(c4cc(C#N)nn4C)CC3C2)c1C(=O)Nc1ccc(F)c(Cl)c1]

N-(3-Chloro-4-fluorophenyl)-4-(5-(3-cyano-1-methyl-1H-pyrazol-5-yl)-5-hydroxyoctahydropentalen-2-yl)-1-methyl-1H-imidazole-5-carboxamide. Zn $(CN)_2$ (49.4 mg, 0.42 mmol) and Zn dust (4.5 mg, 0.07 mmol) were added to a stirred solution of 4-(5-(3-bromo-1-methyl-1H-pyrazol-5-yl)-5-hydroxyoctahydropentalen-2-yl)-N-(3-chloro-4-fluorophenyl)-1-methyl-1H-imidazole-5-carboxamide (150 mg, 0.28 mmol) in DMA (3 mL) and the mixture purged with Argon for 10 min. To this solution, $Pd_2(dba)_3$ (12.8 mg, 0.014 mmol) and dppf (15.5 mg, 0.028 mmol) were added and purging with Argon continued for another 10 min. The resulting mixture was stirred at 130° C. for 12 h. The progress of the reaction was monitored by TLC. After completion, the mixture was filtered through a pad of Celite and washed with ethyl acetate. The filtrate was concentrated under reduced pressure. The residue was diluted with water and extracted with ethyl acetate. The organic layer was collected; washed with brine; dried over anhydrous sodium sulphate and concentrated under reduced pressure. The crude compound was purified by silica gel column chromatography to afford N-(3-chloro-4-fluorophenyl)-4-(5-(3-cyano-1-methyl-1H-pyrazol-5-yl)-5-hydroxy-octahydropentalen-2-yl)-1-methyl-1H-imidazole-5-carboxamide as an off white solid TLC: 5% MeOH in DCM ($R_f$: 0.4); $^1$H NMR (400 MHz, DMSO-$d_6$): δ10.20 (s, 1H), 7.98-7.91 (m, 1H), 7.64 (s, 1H), 7.59-7.52 (m, 1H), 7.38 (t, J=8.8 Hz, 1H), 6.85 (s, 1H), 5.50 (s, 1H), 3.99 (s, 3H), 3.66 (s, 3H), 3.42-3.16 (m, 1H, merged), 2.59-2.34 (m, 2H, merged), 2.28-2.02 (m, 4H), 1.95-1.76 (m, 4H) ppm; MS calcd. for $C_{24}H_{24}ClFN_6O_2$: 482.2; Found: 483.1 $[M+1]^+$.

Example 58

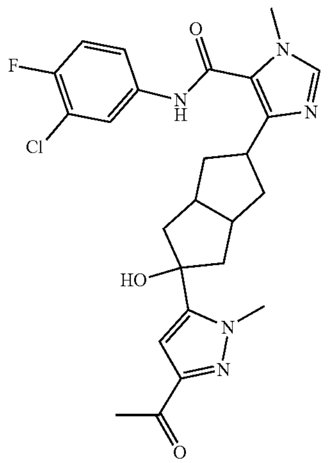 [SMILES: CC(=O)c1cc(C2(O)CC3CC(c4ncn(C)c4C(=O)Nc4ccc(F)c(Cl)c4)CC3C2)n(C)n1]

4-(5-(3-Acetyl-1-methyl-1H-pyrazol-5-yl)-5-hydroxyoctahydropentalen-2-yl)-N-(3-chloro-4-fluorophenyl)-1-methyl-1H-imidazole-5-carboxamide. MeMgI (3M in DEE, 0.13 mL, 0.419 mmol) was added slowly to a stirred solution of N-(3-chloro-4-fluorophenyl)-4-(5-(3-cyano-1-methyl-1H-pyrazol-5-yl)-5-hydroxyoctahydropentalen-2-yl)-1-methyl-1H-imidazole-5-carboxamide (50 mg, 0.103 mmol) in dry THF (5 mL) at 0° C. in an inert atmosphere, The reaction mixture was stirred at RT for 4 h. The progress of the reaction was monitored by TLC. After completion, the reaction mixture was diluted with a sat. aq. solution of ammonium chloride and extracted with ethyl acetate. The organic layer was collected; washed with brine; dried over anhydrous sodium sulphate and concentrated under reduced pressure. The crude compound was purified by prep. HPLC to afford 4-(5-(3-acetyl-1-methyl-1H-pyrazol-5-yl)-5-hydroxyoctahydropentalen-2-yl)-N-(3-chloro-4-fluorophenyl)-1-methyl-1H-imidazole-5-carboxamide (40 mg, 77.2%) as an off white solid. TLC: 5% MeOH in DCM ($R_f$: 0.4); $^1$H NMR (400 MHz, DMSO-$d_6$): δ10.20 (s, 1H), 7.98-7.92 (m, 1H), 7.65 (s, 1H), 7.60-7.54 (m, 1H), 7.40 (t, J=8.0 Hz, 1H), 6.53 (s, 1H), 5.39 (s, 1H), 4.00 (s, 3H), 3.68 (s, 3H), 3.40-3.20 (m, 1H, merged), 2.55-2.20 (m, 2H, merged), 2.42 (s, 3H), 2.28-2.20 (m, 2H), 2.15-2.05 (m, 2H), 1.94-1.85 (m, 4H) ppm. MS calcd. for $C_{25}H_{27}ClFN_5O_3$: 499.2; Found: 482.1 $[M-H_2O+1]^+$.

Example 59

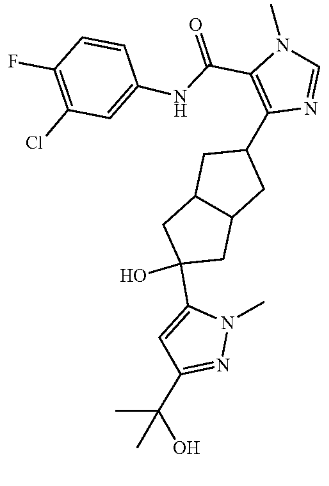 [SMILES: Cn1cnc(C2CC3CC(O)(c4cc(C(C)(C)O)nn4C)CC3C2)c1C(=O)Nc1ccc(F)c(Cl)c1]

N-(3-Chloro-4-fluorophenyl)-4-(5-hydroxy-5-(3-(2-hydroxypropan-2-yl)-1-methyl-1H-pyrazol-5-yl)octahydropentalen-2-yl)-1-methyl-1H-imidazole-5-carboxamide. MeMgI (3M in DEE, 0.66 mL, 2 mmol) was added slowly to a stirred solution of 4-(5-(3-acetyl-1-methyl-1H-pyrazol-5-yl)-5-hydroxyoctahydropentalen-2-yl)-N-(3-chloro-4-fluorophenyl)-1-methyl-1H-imidazole-5-carboxamide (100 mg, 0.2 mmol) in dry THF (5 mL) at 0° C. in an inert atmosphere. The reaction mixture was stirred at RT for 4 h. The progress of the reaction was monitored by TLC. After completion, the reaction mixture was diluted with sat. aq. solution of ammonium chloride and extracted with ethyl acetate. The organic layer was collected; washed with brine; dried over anhydrous sodium sulphate and concentrated under reduced pressure. The crude compound was purified by prep. HPLC to afford N-(3-chloro-4-fluorophenyl)-4-(5-hydroxy-5-(3-(2-hydroxypropan-2-yl)-1-methyl-1H-pyrazol-5-yl)octahydropentalen-2-yl)-1-methyl-1H-imidazole-5-carboxamide (40 mg, 39%) as an off white solid. TLC: 5% MeOH in DCM ($R_f$: 0.2); $^1$H NMR (400 MHz, DMSO-$d_6$): δ 10.20 (s, 1H), 7.96 (d, J=5.2 Hz, 1H), 7.65 (s, 1H), 7.60-7.54 (m, 1H), 7.40 (t, J=9.2 Hz, 1H), 6.01 (s, 1H), 5.18 (s, 1H), 4.67 (s, 1H), 3.83 (s, 3H), 3.68 (s, 3H), 3.28-3.20 (m, 1H), 2.55-2.40 (m, 2H, merged), 2.22-2.16 (m, 2H), 2.10-2.08 (m, 2H), 1.90-1.84 (m, 4H), 1.36 (s, 6H) ppm; MS calcd. for $C_{26}H_{31}ClFN_5O_3$: 515.2; Found: 516.2 $[M+1]^+$.

Example 60

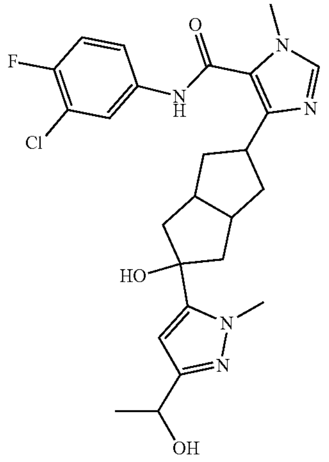 [SMILES: CC(O)c1cc(C2(O)CC3CC(c4ncn(C)c4C(=O)Nc4ccc(F)c(Cl)c4)CC3C2)n(C)n1]

N-(3-Chloro-4-fluorophenyl)-4-(5-hydroxy-5-(3-(1-hydroxyethyl)-1-methyl-1H-pyrazol-5-yl)octahydropentalen-2-yl)-1-methyl-1H-imidazole-5-carboxamide. $NaBH_4$ (3 mg, 0.08 mmol) was added to a stirred solution of 4-(5-(3-acetyl-1-methyl-1H-pyrazol-5-yl)-5-hydroxyoctahydropentalen-2-yl)-N-(3-chloro-4-fluorophenyl)-1-methyl-1H-imidazole-5-carboxamide (20 mg, 0.04 mmol) in MeOH (1 mL) at 0° C. The reaction mixture was stirred at RT for 16 h. The progress of the reaction was monitored by TLC. After completion, the reaction mixture was concentrated under reduced pressure. The residue was diluted with water and extracted with ethyl acetate. The organic layer was collected; washed with brine; dried over anhydrous sodium sulphate and concentrated under reduced pressure. The crude compound was purified by silica gel column chromatography followed by prep. HPLC to afford N-(3-chloro-4-fluorophenyl)-4-(5-hydroxy-5-(3-(1-hydroxyethyl)-1- methyl-1H-pyrazol-5-yl)octahydropentalen-2-yl)-1-methyl-1H-imidazole-5-carboxamide (5 mg, 25%). TLC: 10% MeOH/DCM ($R_f$: 0.4); $^1$H NMR (400 MHz, DMSO-$d_6$): δ 10.21 (s, 1H), 7.96 (d, J=4.0 Hz, 1H), 7.65 (s, 1H), 7.60-7.54 (m, 1H), 7.40 (t, J=9.2 Hz, 1H), 6.00 (s, 1H), 5.19 (s, 1H), 4.84 (d, J=4.8 Hz, 1H), 4.57 (t, J=5.6 Hz, 1H), 3.83 (s, 3H), 3.67 (s, 3H), 3.30-3.20 (m, 1H, merged), 2.55-2.40 (m, 2H, merged), 2.20-2.05 (m, 4H), 1.88-1.82 (m, 4H), 1.29 (d, J=6.4 Hz, 3H) ppm; MS calcd. for $C_{25}H_{29}ClFN_5O_3$: 501.2; Found: 502.1 $[M+1]^+$.

Example 61

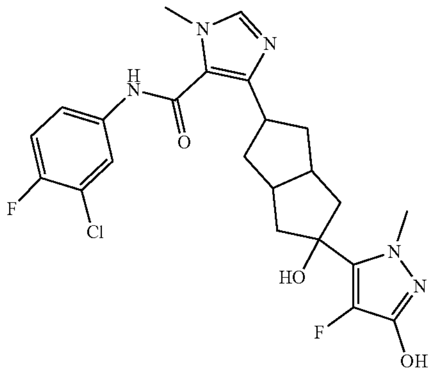 [SMILES: Cn1cnc(C2CC3CC(O)(c4c(F)c(O)nn4C)CC3C2)c1C(=O)Nc1ccc(F)c(Cl)c1]

N-(3-Chloro-4-fluorophenyl)-4-(5-(4-fluoro-3-hydroxy-1-methyl-1H-pyrazol-5-yl)-5-hydroxyoctahydropentalen-2-yl)-1-methyl-1H-imidazole-5-carboxamide. Selectfluor (2.99 g, 8.45 mmol) was added to a stirred solution of N-(3-chloro-4-fluorophenyl)-4-(5-hydroxy-5-(3-hydroxy-1-methyl-1H-pyrazol-5-yl)octahydropentalen-2-yl)-1-methyl-1H-imidazole-5-carboxamide (2 g, 4.22 mmol) in DMF (40 mL), The reaction mixture was stirred at RT for 16 h. The progress of the reaction was monitored by TLC and LCMS. After completion, the reaction mixture was diluted with water and extracted with 10% MeOH/DCM. The organic layer was collected; washed with brine; dried over anhydrous sodium sulphate and concentrated under reduced pressure to afford a crude compound. The crude compound was purified by CombiFlash® column chromatography to afford N-(3-chloro-4-fluorophenyl)-4-(5-(4-fluoro-3-hydroxy-1-methyl-1H-pyrazol-5-yl)-5-hydroxyoctahydropentalen-2-yl)-1-methyl-1H-imidazole-5-carboxamide (0.55 g, 38%) as a white solid. TLC: 10% MeOH in DCM ($R_f$: 0.2); $^1$H NMR (400 MHz, DMSO-$d_6$): δ 10.21 (s, 1H), 10.00-9.80 (m, 1H), 7.96 (d, J=5.2 Hz, 1H), 7.64 (s, 1H), 7.58-7.54 (m, 1H), 7.40 (t, J=8.0 Hz, 1H), 5.30 (s, 1H), 3.67 (s, 3H), 3.65 (s, 3H), 3.25-3.20 (m, 1H, merged), 2.60-2.45 (m, 2H, merged), 2.25-2.18 (m, 2H), 2.09-2.06 (m, 2H), 1.96-1.87 (m, 4H) ppm; MS calcd. for $C_{23}H_{24}ClF_2N_5O_3$: 491.2; Found: 492.1 $[M+1]^+$.

Example 62

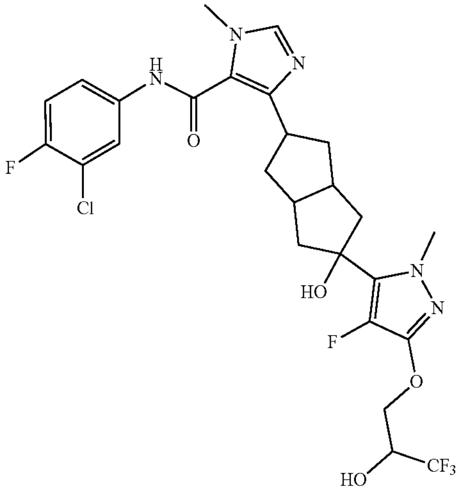 [SMILES: Cn1cnc(C2CC3CC(O)(c4c(F)c(OCC(O)C(F)(F)F)nn4C)CC3C2)c1C(=O)Nc1ccc(F)c(Cl)c1]

N-(3-Chloro-4-fluorophenyl)-4-(5-(4-fluoro-1-methyl-3-(3,3,3-trifluoro-2-hydroxypropoxy)-1H-pyrazol-5-yl)-5-hydroxyoctahydropentalen-2-yl)-1-methyl-1H-imidazole-5-carboxamide. The titled compound was synthesized by following the general procedure described above for alkylation (Method B) TLC: 10% MeOH/DCM ($R_f$: 0.3); $^1$H NMR (400 MHz, DMSO-$d_6$): δ 10.20 (s, 1H), 7.96 (d, J=6.0 Hz, 1H), 7.64 (s, 1H), 7.60-7.54 (m, 1H), 7.40 (t, J=9.2 Hz, 1H), 6.62 (d, J=6.8 Hz, 1H), 5.39 (s, 1H), 4.45-4.35 (m, 1H), 4.30-4.24 (m, 1H), 4.18-4.12 (m, 1H), 3.73 (s, 3H), 3.67 (s, 3H), 3.26-3.18 (m, 1H), 2.60-2.50 (m, 2H, merged). 2.25-2.20 (m, 2H), 2.10-2.06 (m, 2H), 1.94-1.88 (m, 4H) ppm; MS calcd. for $C_{26}H_{27}ClF_5N_5O_4$: 603.2; Found: 586.2 $[M-H_2O+1]^+$.

Intermediate 23

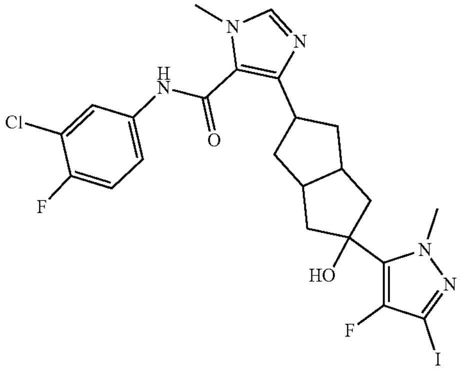 [SMILES: Cn1cnc(C2CC3CC(O)(c4c(F)c(I)nn4C)CC3C2)c1C(=O)Nc1ccc(F)c(Cl)c1]

N-(3-Chloro-4-fluorophenyl)-4-(5-(4-fluoro-3-iodo-1-methyl-1H-pyrazol-5-yl)-5-hydroxyoctahydropentalen-2-yl)-1-methyl-1H-imidazole-5-carboxamide. To a stirred solution of 4-fluoro-3-iodo-1-methyl-1H-pyrazole (2.42 g, 10.66 mmol) in dry THF (30 mL) at −78° C., LDA (5.33 mL, 10.66 mmol) was added dropwise, and the reaction mixture was stirred same temperature for 2 h. To this, a solution of N-(3-chloro-4-fluorophenyl)-1-methyl-4-(5-oxooctahydropentalen-2-yl)-1H-imidazole-5-carboxamide (0.4 g, 1.06 mmol) in THF was added at −78° C. The reaction mixture was stirred at same temperature & then at room temperature for 3 h. The progress of the reaction was monitored by TLC and LCMS. After completion, the reaction was quenched with saturated $NH_4Cl$ solution and extracted with ethyl acetate. The organic layer was collected; washed with brine; dried over anhydrous sodium sulphate and concentrated under reduced pressure. The crude compound was purified by silica gel column chromatography to afford N-(3-chloro-4-fluorophenyl)-4-(5-(4-fluoro-3-iodo-1-methyl-1H-pyrazol-5-yl)-5-hydroxyoctahydropentalen-2-yl)-1-methyl-1H-imidazole-5-carboxamide (0.250 g, 40.62%) an off white solid, as a single diastereomer. TLC: 5% MeOH/DCM ($R_f$: 0.3). $^1H$ NMR (400 MHz, DMSO-$d_6$): δ10.20 (s, 1H), 7.98-7.94 (m, 1H), 7.65 (s, 1H), 7.60-7.54 (m, 1H), 7.40 (t, J=9.2 Hz, 1H), 5.44 (s, 1H), 3.89 (s, 3H), 3.67 (s, 3H), 3.28-3.18 (m, 1H), 2.55-2.40 (m, 2H, merged), 2.24-2.18 (m, 2H), 2.10-2.06 (m, 2H), 1.98-1.90 (m, 4H) ppm. MS calcd. for $C_{23}H_{23}ClF_2IN_5O_2$: 601.1; Observed: 602.1 $[M+1]^+$.

Example 63

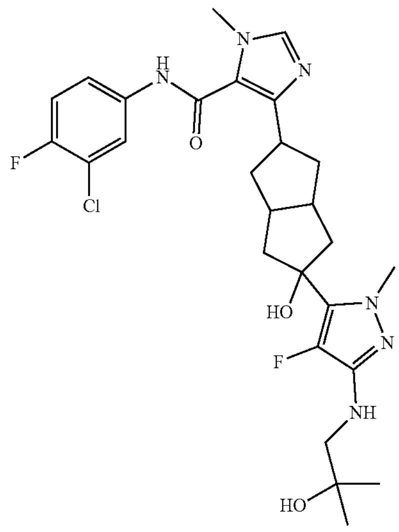 [SMILES: Cn1cnc(C2CC3CC(O)(c4c(F)c(NCC(C)(C)O)nn4C)CC3C2)c1C(=O)Nc1ccc(F)c(Cl)c1]

N-(3-Chloro-4-fluorophenyl)-4-(5-(4-fluoro-3-((2-hydroxy-2-methylpropyl)amino)-1-methyl-1H-pyrazol-5-yl)-5-hydroxyoctahydropentalen-2-yl)-1-methyl-1H-imidazole-5-carboxamide. $K_2CO_3$ (99 mg, 0.415 mmol) and L-proline (7.6 mg, 0.066 mmol) were added to a mixture of N-(3-chloro-4-fluorophenyl)-4-(5-(4-fluoro-3-iodo-1-methyl-1H-pyrazol-5-yl)-5-hydroxyoctahydropentalen-2-yl)-1-methyl-1H-imidazole-5-carboxamide (100 mg, 0.166 mmol) and 1-amino-2-methylpropan-2-ol (29.6 mg, 0.33 mmol) in DMSO (3 mL) and the solution purged with Argon for 10 min. To this solution, was added CuI (6.3 mg, 0.033 mmol) and purging with Argon continued for another 10 min. The resulting reaction mixture was stirred at 90° C. for 16 h. The progress of the reaction was monitored by TLC. After completion, the reaction mixture was diluted with water and extracted with 10% MeOH/DCM. The organic layer was collected; washed with brine; dried over anhydrous sodium sulphate and concentrated under reduced pressure. The crude compound was purified by prep. HPLC to afford N-(3-chloro-4-fluorophenyl)-4-(5-(4-fluoro-3-((2-hydroxy-2-methylpropyl)amino)-1-methyl-1H-pyrazol-5-yl)-5-hydroxyoctahydropentalen-2-yl)-1-methyl-1H-imidazole-5-carboxamide (20 mg, 21%). TLC: 10% MeOH/DCM ($R_f$: 0.2). $^1H$ NMR (400 MHz, DMSO-$d_6$) δ 10.21 (s, 1H), 7.95 (d, J=6.8 Hz, 1H), 7.64 (s, 1H), 7.58-7.54 (m, 1H), 7.40 (t, J=9.2 Hz, 1H), 5.25 (s, 1H), 4.53 (t, J=6.4 Hz, 1H), 4.45 (s, 1H), 3.67 (s, 3H), 3.64 (s, 3H), 3.26-3.22 (m, 1H), 2.94 (d, J=6.0 Hz, 2H), 2.55-2.40 (m, 2H, merged), 2.25-2.20 (m, 2H), 2.12-2.06 (m, 2H), 1.98-1.85 (m, 4H), 1.10 (s, 6H) ppm. MS calcd. for $C_{27}H_{33}ClF_2N_6O_3$: 562.2; Found: 563.2 $[M+1]^+$.

Example 64

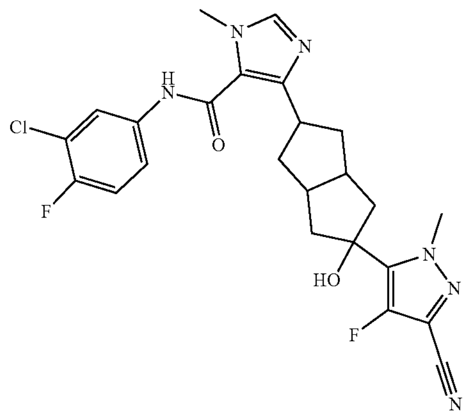 [SMILES: Cn1cnc(C2CC3CC(O)(c4c(F)c(C#N)nn4C)CC3C2)c1C(=O)Nc1ccc(F)c(Cl)c1]

N-(3-Chloro-4-fluorophenyl)-4-(5-(3-cyano-4-fluoro-1-methyl-1H-pyrazol-5-yl)-5-hydroxyoctahydropentalen-2-yl)-1-methyl-1H-Imidazole-5-carboxamide. $Zn(CN)_2$ (0.073 g, 0.623 mmol) and Zn dust (0.0054 g, 0.083 mmol) were added to a stirred solution of N-(3-chloro-4-fluorophenyl)-4-(5-(4-fluoro-3-iodo-1-methyl-1H-pyrazol-5-yl)-5-hydroxyoctahydropentalen-2-yl)-1-methyl-1H-imidazole-5-carboxamide (0.25 g, 0.415 mmol) in DMA (5 mL) which was purged with Argon for 10 min. To this solution, $Pd_2(dba)_3$ (0.038 g, 0.0415 mmol) and dppf (0.023 g, 0.0415 mmol) were added and purging with Argon continued for another 10 min. The resulting reaction mixture was stirred at 120° C. for 16 h. The progress of the reaction was monitored by TLC. After completion, the reaction mixture was concentrated under reduced pressure. The crude product was purified by silica gel column chromatography to afford N-(3-chloro-4-fluorophenyl)-4-(5-(3-cyano-4-fluoro-1-methyl-1H-pyrazol-5-yl)-5-hydroxyoctahydropentalen-2-yl)-1-methyl-1H-imidazole-5-carboxamide (0.160 g, 77%) as an off white solid. TLC: 5% MeOH in DCM ($R_f$: 0.4). MS calcd. for $C_{24}H_{23}ClF_2N_6O_2$: 500.2; Found: 501.1 $[M+1]^+$.

Example 65

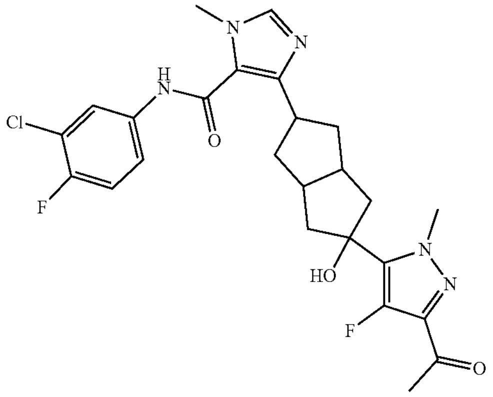 [SMILES: CC(=O)c1nn(C)c(C2(O)CC3CC(c4ncn(C)c4C(=O)Nc4ccc(F)c(Cl)c4)CC3C2)c1F]

4-(5-(3-Acetyl-4-fluoro-1-methyl-1H-pyrazol-5-yl)-5-hydroxyoctahydropentalen-2-yl)-N-(3-chloro-4-fluorophenyl)-1-methyl-1H-imidazole-5-carboxamide. MeMgI (3M in diethoxy ethane, 0.5 mL, 1.5 mmol) was added slowly to a stirred solution of N-(3-chloro-4-fluorophenyl)-4-(5-(3-cyano-4-fluoro-1-methyl-1H-pyrazol-5-yl)-5-hydroxyoctahydropentalen-2-yl)-1-methyl-1H-imidazole-5-carboxamide (0.15 g, 0.3 mmol) in dry THF (5 mL) at 0° C. under an inert atmosphere. The reaction mixture was stirred at 50° C. for 3 h. The progress of the reaction was monitored by TLC. After completion, the reaction mixture was diluted with sat. aq. ammonium chloride and extracted with ethyl acetate. The organic layer was collected; washed with brine; dried over anhydrous sodium sulphate and concentrated under reduced pressure. The crude compound was purified by silica gel column chromatography to afford 4-(5-(3-acetyl-4-fluoro-1-methyl-1H-pyrazol-5-yl)-5-hydroxyoctahydropentalen-2-yl)-N-(3-chloro-4-fluorophenyl)-1-methyl-1H-imidazole-5-carboxamide (0.105 g, 67%) as an off white solid. TLC: 5% MeOH in DCM ($R_f$: 0.2). $^1$H NMR (400 MHz, DMSO-$d_6$): δ 10.21 (s, 1H), 7.96 (d, J=6.4 Hz, 1H), 7.65 (s, 1H), 7.60-7.54 (m, 1H), 7.40 (t, J=6.4 Hz, 1H), 5.49 (s, 1H), 3.99 (s, 3H), 3.67 (s, 3H), 3.32-3.20 (m, 1H), 2.60-2.50 (m, 2H, merged), 2.41 (s, 3H), 2.35-2.20 (m, 2H), 2.10-2.05 (m, 2H), 2.00-1.94 (m, 4H) ppm; LCMS calcd. for $C_{25}H_{26}ClF_2N_5O_3$:517.2; Found: 518.1 $[M+1]^+$.

Example 66

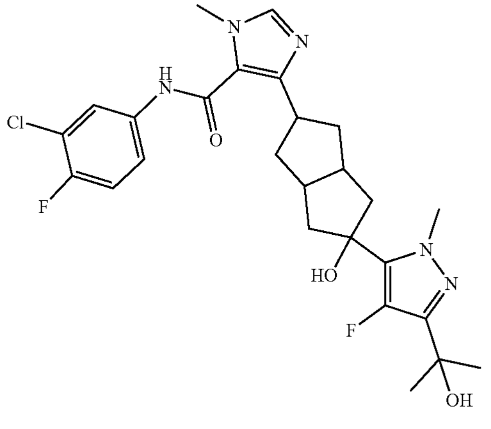 [SMILES: Cn1cnc(C2CC3CC(O)(c4c(F)c(C(C)(C)O)nn4C)CC3C2)c1C(=O)Nc1ccc(F)c(Cl)c1]

N-(3-Chloro-4-fluorophenyl)-4-(5-(4-fluoro-3-(2-hydroxypropan-2-yl)-1-methyl-1H-pyrazol-5-yl)-5-hydroxyoctahydropentalen-2-yl)-1-methyl-1H-imidazole-5-carboxamide. MeMgI (3M in diethoxy ethane, 0.32 mL, 0.96 mmol) was added slowly to a stirred solution of 4-(5-(3-acetyl-4-fluoro-1-methyl-1H-pyrazol-5-yl)-5-hydroxyoctahydropentalen-2-yl)-N-(3-chloro-4-fluorophenyl)-1-methyl-1H-imidazole-5-carboxamide (0.1 g, 0.193 mmol) in dry THF (3 mL) at 0° C. in an inert atmosphere. The reaction mixture was stirred at 50° C. for 3 h. The progress of the reaction was monitored by TLC. After completion, the reaction mixture was diluted with a sat. (aq.) solution of ammonium chloride and extracted with ethyl acetate. The organic layer was collected; washed with brine; dried over anhydrous sodium sulphate and concentrated under reduced pressure. The crude compound was purified by silica gel column chromatography to afford N-(3-chloro-4-fluorophenyl)-4-(5-(4-fluoro-3-(2-hydroxypropan-2-yl)-1-methyl-1H-pyrazol-5-yl)-5-hydroxyoctahydropentalen-2-yl)-1-methyl-1H-imidazole-5-carboxamide (12 mg, 12%) as an off white solid. TLC: 5% MeOH in DCM ($R_f$: 0.2); $^1$H NMR (400 MHz, DMSO-$d_6$): δ 10.27 (s, 1H), 7.96 (d, J=6.4 Hz, 1H), 7.92-7.62 (m, 1H), 7.60-7.54 (m, 1H), 7.41 (t, J=9.2 Hz, 1H), 5.31 (s, 1H), 4.81 (br. s, 1H), 3.81 (s, 3H), 3.70 (s, 3H), 3.30-3.20 (m, 1H, merged) 2.60-2.45 (m, 2H, merged), 2.30-2.10 (m, 4H), 1.96-1.90 (m, 4H), 1.41 (s, 6H) ppm; MS calcd. for $C_{26}H_{30}ClF_2N_5O_3$: 533.2; Found: 534.1 $[M+1]^+$.

Intermediate 24

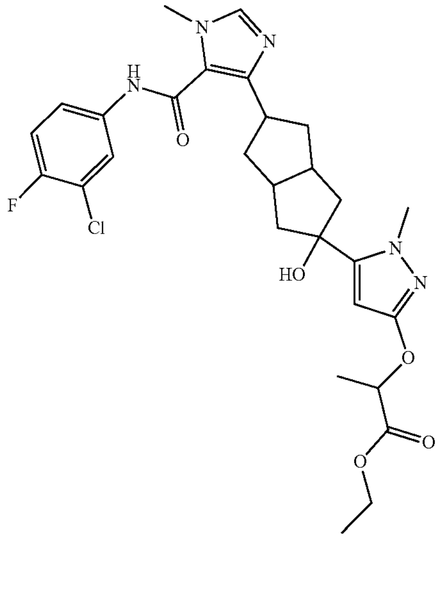 [SMILES: CCOC(=O)C(C)Oc1cc(C2(O)CC3CC(c4ncn(C)c4C(=O)Nc4ccc(F)c(Cl)c4)CC3C2)n(C)n1]

Ethyl 2-((5-(−5-(5-((3-chloro-4-fluorophenyl)carbamoyl)-1-methyl-1H-imidazol-4-yl)-2-hydroxyoctahydropentalen-2-yl)-1-methyl-1H-pyrazol-3-yl)oxy)propanoate. The title compound has been synthesized according to the general procedure for alkylation (Method B. TLC: 5% MeOH/DCM ($R_f$: 0.5); MS calcd. for $C_{28}H_{33}ClFN_5O_5$: 573.2; Found: 572.4 $[M-1]^-$.

Example 67

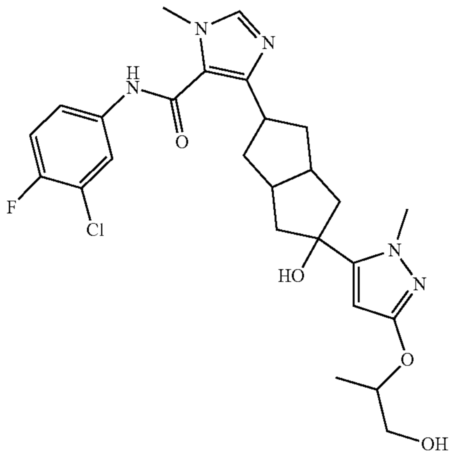 [SMILES: CC(CO)Oc1cc(C2(O)CC3CC(c4ncn(C)c4C(=O)Nc4ccc(F)c(Cl)c4)CC3C2)n(C)n1]

N-(3-Chloro-4-fluorophenyl)-4-(5-hydroxy-5-(3-((1-hydroxypropan-2-yl)oxy)-1-methyl-1H-pyrazol-5-yl)octahydropentalen-2-yl)-1-methyl-1H-imidazole-5-carboxamide. $NaBH_4$ (0.133 g, 3.49 mmol) was added to a stirred solution of ethyl 2-((5-(−5-(5-((3-chloro-4-fluorophenyl)carbamoyl)-1-methyl-1H-imidazol-4-yl)-2-hydroxyoctahydropentalen-2-yl)-1-methyl-1H-pyrazol-3-yl)oxy)propanoate (0.2 g, 0.349 mmol) in MeOH (5 mL) at 0° C. The reaction mixture was stirred at RT for 16 h. The progress of the reaction was monitored by TLC. After completion, the reaction was concentrated under reduced pressure. The residue was diluted with sat. $NH_4Cl$ and extracted with ethyl acetate. The organic layer was collected; washed with brine; dried over anhydrous sodium sulphate and concentrated under reduced pressure. The crude compound was purified by silica gel column chromatography followed by prep. HPLC to afford N-(3-chloro-4-fluorophenyl)-4-(5-hydroxy-5-(3-((1-hydroxypropan-2-yl)oxy)-1-methyl-1H-pyrazol-5-yl)octahydropentalen-2-yl)-1-methyl-H-imidazole-5-carboxamide (60 mg, 32.4%). The racemic compound was submitted for chiral prep HPLC purification to afford two diastereomers Example 68 (diastereomer 1) and Example 69 (diastereomer 2) (Table 5)

TABLE 5

| Examples 68 and 69 | |
|---|---|
| Example | $^1H$ NMR and MS |
| Example 68 | N-(3-Chloro-4-fluorophenyl)-4-(5-hydroxy-5-(3-((1-hydroxypropan-2-yl)oxy)-1-methyl-1H-pyrazol-5-yl)octahydropentalen-2-yl)-1-methyl-1H-imidazole-5-carboxamide. Single diastereomer 1 $^1H$ NMR (400 MHz, DMSO-$d_6$): δ 10.20 (s, 1H), 7.95 (d, J = 6.4 Hz, 1H), 7.65 (s, 1H), 7.60-7.54 (m, 1H), 7.40 (t, J = 9.2 Hz, 1H), 5.48 (s, 1H), 5.21 (s, 1H), 4.72 (t, J = 5.2 Hz, 1H), 4.43 (q, J = 6.0 Hz, 1H), 3.72 (s, 3H), 3.67 (s, 3H), 3.52-3.46 (m, 1H), 3.42-3.35 (m, 1H), 3.26-3.21 (m, 1H), 2.49-2.40 (m, 2H), 2.20-2.05 (m, 4H), 1.88-1.78 (m, 4H), 1.16 (d, J = 6.0 Hz, 3H). MS calcd. for $C_{26}H_{31}ClFN_5O_4$; 531.2. Found; 514.2 $[M-H_2O + 1]^+$. |

TABLE 5-continued

| Examples 68 and 69 | |
|---|---|
| Example | $^1H$ NMR and MS |
| Example 69 | N-(3-Chloro-4-fluorophenyl)-4-(5-hydroxy-5-(3-((1-hydroxypropan-2-yl)oxy)-1-methyl-1H-pyrazol-5-yl)octahydropentalen-2-yl)-1-methyl-1H-imidazole-5-carboxamide. Single diastereomer 2 $^1H$ NMR (400 MHz, DMSO-$d_6$): δ 10.20 (s, 1H), 7.95 (d, J = 6.4 Hz, 1H), 7.65 (s, 1H), 7.60-7.54 (m, 1H), 7.40 (t, J = 9.2 Hz, 1H), 5.48 (s, 1H), 5.21 (s, 1H), 4.72 (t, J = 6.0 Hz, 1H), 4.43 (q, J = 6.0 Hz, 1H), 3.72 (s, 3H), 3.67 (s, 3H), 3.52-3.46 (m, 1H), 3.40-3.36 (m, 1H), 3.30-3.20 (m, 1H), 2.49-2.40 (m, 2H), 2.20-2.05 (m, 4H), 1.90-1.78 (m, 4H), 1.16 (d, J = 6.4 Hz, 3H). MS calcd. for $C_{26}H_{31}ClFN_5O_4$; 531.2. Found; 514.2 $[M-H_2O + 1]^+$. |

Intermediate 25

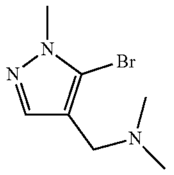

1-(5-Bromo-1-methyl-1H-pyrazol-4-yl)-N,N-dimethylmethanamine. 5-Bromo-1-methyl-1H-pyrazole-4-carbaldehyde (2.0 g, 10.59 mmol) was added to a stirred solution of dimethylamine hydrochloride (4.32 g, 52.96 mmol, 5.0 equiv), triethylamine (52.95 mmol, 7.38 mL, 5.0 equiv) and acetic acid (1.91 g, 31.78 mmol, 1.83 mL, 3.0 equiv) in 30 mL of dry DCM at RT. The resulting mixture was stirred for 20 min before sodium triacetoxyborohydride (13.47 g, 63.55 mmol, 6.0 equiv) was added in portions. The resulting suspension was left to stir overnight. After the reaction was complete, the mixture was poured into a stirring aq. $NaHCO_3$ solution. The organic phase was separated, washed with brine and concentrated under reduced pressure to give 1-(5-bromo-1-methyl-1H-pyrazol-4-yl)-N,N-dimethylmethanamine (2.2 g, 90.0% purity, 9.08 mmol, 86% yield). MS calcd. for $C_7H_{12}BrN_3$: 217.0; Found: 218.1 $[M+1]^+$.

Example 70

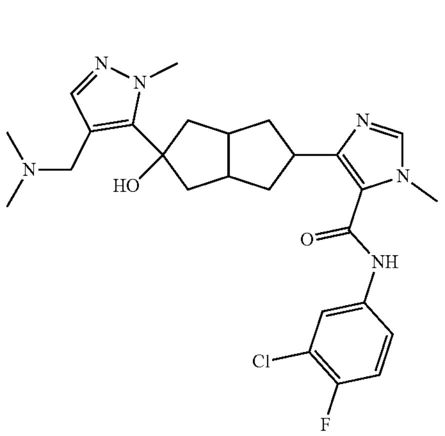

N-(3-Chloro-4-fluorophenyl)-4-(5-(4-((dimethylamino)methyl)-1-methyl-1H-pyrazol-5-yl)-5-hydroxyoctahydropentalen-2-yl)-1-methyl-1H-imidazole-5-carboxamide. n-Butyllithium (2.5M in n-hexane, 1.7 mmol, 0.68 mL, 8.0 equiv) was added dropwise to a solution of 1-(5-bromo-1-methyl-1H-pyrazol-4-yl)-N,N-dimethylmethanamine (372.65 mg, 1.71 mmol, 8.0 equiv) in anhydrous THF (10 mL) at −78° C. The resulting mixture was stirred for 30 min then warmed to −60° C. over 30 min, then cooled to −78° C. To the reaction mixture was added dropwise a solution of N-(3-chloro-4-fluorophenyl)-1-methyl-4-(5-oxooctahydropentalen-2-yl)-1H-imidazole-5-carboxamide (80 mg, 213.58 μmol) in THF (2 mL). The reaction mixture was stirred at −78° C. for 1 h, and left to warm gradually to RT. After 12 h the mixture was poured into a saturated $NH_4Cl$ solution then extracted with EtOAc (3×10 mL). The combined organic solution was dried over $Na_2SO_4$ and evaporated in vacuo to give 0.12 g of crude product. Purification with prep-HPLC gave N-(3-chloro-4-fluorophenyl)-4-(5-(4-((dimethylamino)methyl)-1-methyl-1H-pyrazol-5-yl)-5-hydroxyoctahydropentalen-2-yl)-1-methyl-1H-imidazole-5-carboxamide (26.0 mg, 50.48 μmol, 23.6% yield), as a single diastereomer. MS calcd. for C26H32ClFN6O2: 514.1; Found: 515.2 $[M+1]^+$; $^1H$ NMR (400 MHz, Chloroform-d): δ 7.78 (dd, J=6.5, 2.6 Hz, 1H), 7.51 (s, 1H), 7.48 (s, 1H), 7.42-7.35 (m, 1H), 7.22 (s, 1H), 7.16 (t, J=8.7 Hz, 1H), 3.90 (s, 3H), 3.85 (s, 3H), 3.37 (s, 2H), 3.23 (dq, J=12.1, 6.1 Hz, 1H), 2.87 (s, 2H), 2.50-2.33 (m, 4H), 2.32-2.25 (m, 2H), 2.21 (s, 6H), 2.12 (s, 1H), 2.09 (s, 1H), 2.03 (d, J=4.6 Hz, 1H) ppm.

Example 71

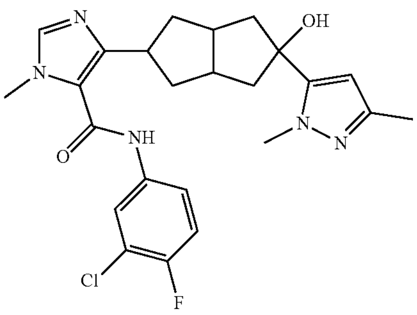

N-(3-Chloro-4-fluorophenyl)-4-(5-(1,3-dimethyl-1H-pyrazol-5-yl)-5-hydroxyoctahydropentalen-2-yl)-1-methyl-1H-imidazole-5-carboxamide. To a solution of 1,3-dimethyl-1H-pyrazole (211.0 mg, 2.2 mmol) in anhydrous THF (20 mL) was added dropwise n-butyllithium (2.5M in n-hexane, 2.2 mmol, 0.88 mL, 11.0 equiv) at −78° C. The resulting mixture was stirred for 10 min then warmed to −5° C. over 30 min. The reaction mixture was cooled to −78° C. and added dropwise a solution of N-(3-chloro-4-fluorophenyl)-1-methyl-4-(5-oxooctahydropentalen-2-yl)-1H-imidazole-5-carboxamide (75.0 mg, 199.56 μmol) in THF (2 mL). The mixture was stirred at −78° C. for 30 min, and left to warm gradually to RT. After 12 h the mixture was poured into a saturated $NH_4Cl$ solution, then extracted with EtOAc (3×20 mL). The combined organic solution was dried over $Na_2SO_4$ and evaporated in vacuo to give 0.1 g of the crude product, which was purified with prep-HPLC to give N-(3-chloro-4-fluorophenyl)-4-(5-(1,3-dimethyl-1H-pyrazol-5-yl)-5-hydroxyoctahydropentalen-2-yl)-1-methyl-1H-imidazole-5-carboxamide, as a single diastereomer (6.7 mg, 14.2 μmol, 7.1% yield). MS calcd. for $C_{24}H_{27}ClFN_5O_2$: 471.2; Found: 454.2 $[M-H_2O+1]^+$; $^1H$ NMR (400 MHz, Chloroform-d): δ 7.79 (d, J=6.8 Hz, 2H), 7.55 (s, 1H), 7.37 (s, 1H), 7.15 (t, J=8.6 Hz, 1H), 5.87 (s, 1H), 3.96 (s, 3H), 3.85 (s, 3H), 3.29 (s, 1H), 3.00 (s, 2H), 2.74 (s, 2H), 2.31 (dd, J=21.5, 13.4 Hz, 5H), 2.21 (d, J=2.1 Hz, 3H), 2.13 (d, J=13.3 Hz, 2H) ppm.

Example 72

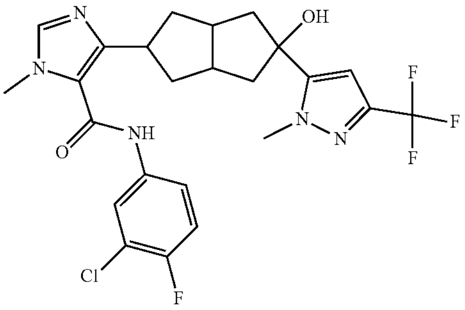 [SMILES: Cn1cnc(C2CC3CC(O)(c4cc(C(F)(F)F)nn4C)CC3C2)c1C(=O)Nc1ccc(F)c(Cl)c1]

N-(3-Chloro-4-fluorophenyl)-4-(5-hydroxy-5-(1-methyl-3-(trifluoromethyl)-1H-pyrazol-5-yl)octahydropentalen-2-yl)-1-methyl-1H-imidazole-5-carboxamide. To a solution of diisopropylamine (207.41 mg, 2.05 mmol, 290.0 μl, 11.0 equiv) in anhydrous THF (20 mL) was added n-butyllithium (2.5M in n-hexane, 2.05 mmol, 0.82 mL, 11.0 equiv) dropwise at −78° C. The resulting mixture was stirred for 10 min then warmed to −10° C. over 10 min. The mixture was cooled to −78° C. and a solution of 1-methyl-3-(trifluoromethyl)-1H-pyrazole (307.67 mg, 2.05 mmol) in THF (1 mL) was added. The reaction mixture was stirred at −70° C. for 1 h, then a solution of N-(3-chloro-4-fluorophenyl)-1-methyl-4-(5-oxooctahydropentalen-2-yl)-1H-imidazole-5-carboxamide (70.0 mg, 186.26 μmol) in THF (2 mL) was added dropwise. The mixture was stirred at −70° C. for 30 min then left to warm gradually to RT. After 12 h the mixture was poured into a saturated $NH_4Cl$ solution and extracted with EtOAc (3×20 mL). The combined organic solution was dried over $Na_2SO_4$ and evaporated in vacuo to give 0.15 g of crude product, which was purified using prep-HPLC to give N-(3-chloro-4-fluorophenyl)-4-(5-hydroxy-5-(1-methyl-3-(trifluoromethyl)-1H-pyrazol-5-yl)octahydropentalen-2-yl)-1-methyl-1H-imidazole-5-carboxamide, as a single diastereomer (20.1 mg, 38.22 μmol, 21% yield). MS calcd. for $C_{24}H_{24}ClF_4N_5O_2$: 525.2; Found: 526.2 $[M+1]^+$; $^1H$ NMR (400 MHz, Chloroform-d): δ 7.77 (dd, J=6.5, 2.5 Hz, 1H), 7.58 (s, 1H), 7.40-7.33 (m, 1H), 7.31 (s, 1H), 7.15 (td, J=8.7, 1.7 Hz, 1H), 6.34 (s, 1H), 4.10 (s, 3H), 3.81 (d, J=1.7 Hz, 3H), 3.30 (tt, J=11.8, 6.6 Hz, 1H), 2.84-2.67 (m, 3H), 2.39-2.14 (m, 8H) ppm.

Example 73

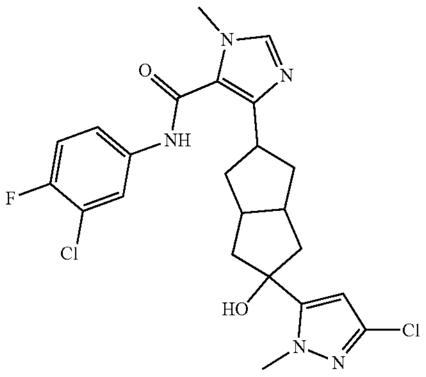 [SMILES: Cn1cnc(C2CC3CC(O)(c4cc(Cl)nn4C)CC3C2)c1C(=O)Nc1ccc(F)c(Cl)c1]

4-(5-(3-Chloro-1-methyl-1H-pyrazol-5-yl)-5-hydroxyoctahydropentalen-2-yl)-N-(3-chloro-4-fluorophenyl)-1-methyl-1H-imidazole-5-carboxamide. To a solution of 3-chloro-1-methyl-1H-pyrazole (124.04 mg, 1.06 mmol) in tetrahydrofuran (10 mL) at −78° C. was added n-butyllithium (1.06 mmol, 430.0 μl, 2.5 M in hexane, 4.0 eq.) dropwise and the resulting mixture stirred for 10 min. The temperature of the reaction was raised to −30° C. and stirred for 30 min. The reaction mixture was cooled to −78° C. and a solution of N-(3-chloro-4-fluorophenyl)-1-methyl-4-(5-oxooctahydropentalen-2-yl)-1H-imidazole-5-carboxamide (100 mg, 266.06 μmol) in tetrahydrofuran (2 mL) was added dropwise and stirring continued for 15 min. The resulting mixture was warmed to room temperature and quenched with saturated ammonium chloride. The reaction mixture was diluted with water and extracted twice with ethyl acetate. The combined organic layers were washed with brine, dried over sodium sulfate, filtered, and concentrated in vacuo to give the crude product which was purified using prep-HPLC to give 4-(5-(3-chloro-1-methyl-1H-pyrazol-5-yl)-5-hydroxyoctahydropentalen-2-yl)-N-(3-chloro-4-fluorophenyl)-1-methyl-1H-imidazole-5-carboxamide, as a single diastereomer (2.2 mg, 95.0% purity, 4.24 μmol, 1.6% yield). MS calcd. for $C_{23}H_{24}Cl_2FN_5O_2$: 491.1; Found: 493.0 $[M+2]^+$; $^1H$ NMR (400 MHz, Methanol-d4): δ 7.89 (dd, J=6.7, 2.6 Hz, 1H), 7.66 (s, 1H), 7.55-7.47 (m, 1H), 7.25 (t, J=9.0 Hz, 1H), 6.15 (s, 1H), 3.94 (s, 3H), 3.78 (s, 3H), 3.68-3.42 (m, 1H), 2.59 (s, 2H), 2.37 (dd, J=13.4, 7.2 Hz, 2H), 2.32-2.21 (m, 2H), 2.04-1.82 (m, 4H) ppm.

Example 74

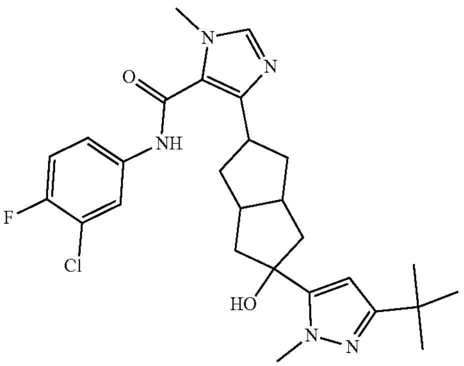 [SMILES: Cn1cnc(C2CC3CC(O)(c4cc(C(C)(C)C)nn4C)CC3C2)c1C(=O)Nc1ccc(F)c(Cl)c1]

4-(5-(3-Chloro-1-methyl-1H-pyrazol-5-yl)-5-hydroxyoctahydropentalen-2-yl)-N-(3-chloro-4-fluorophenyl)-1-methyl-1H-imidazole-5-carboxamide. To a solution of 3-tert-butyl-1-methyl-1H-pyrazole (234.46 mg, 1.7 mmol) in tetrahydrofuran (10 mL) was added n-butyllithium (109.0 mg, 1.7 mmol, 680.0 μl, 8.0 equiv) at −78° C. dropwise and the mixture stirred for 10 min. The temperature of the reaction was raised to −60° C. and stirred for 1 hour. The mixture was then cooled to −78° C. and added dropwise to a solution of 4-[-5-oxo-octahydropentalen-2-yl]-N-(3-chloro-4-fluorophenyl)-1-methyl-1H-imidazole-5-carboxamide (79.69 mg, 212.05 μmol) in tetrahydrofuran (2 mL) and the reaction stirred at −78° C. for 15 min. The resulting mixture was warmed to room temperature and quenched with saturated ammonium chloride. The reaction mixture was diluted with water and extracted twice with ethyl acetate. The combined organic layers were washed with brine, dried over sodium sulfate, filtered, and concentrated in vacuo to give the crude product, which was purified using prep-HPLC to give 4-(5-(3-chloro-1-methyl-1H-pyrazol-5-yl)-5-hydroxyoctahydropentalen-2-yl)-N-(3-chloro-4-fluorophenyl)-1-methyl-1H-imidazole-5-carboxamide, as a single diastereomer (2.8 mg, 97.8% purity, 5.33 μmol, 2.5% yield). MS calcd. for $C_{27}H_{33}ClFN_5O_2$: 513.2; Found: 512.0 $[M-H]^-$; $^1H$ NMR (400 MHz, Methanol-d4): δ 7.88 (dd, J=6.5, 2.7 Hz, 1H), 7.65 (s, 1H), 7.51 (d, J=2.4 Hz, 2H), 7.25 (t, J=8.9 Hz, 1H), 6.14 (d, J=2.4 Hz, 1H), 4.09 (s, 2H), 3.77 (s, 3H), 2.67 (s, 1H), 2.58 (s, 2H), 2.22 (d, J=8.2 Hz, 2H), 2.05 (s, 1H), 1.86 (t, J=6.6 Hz, 2H), 1.81-1.71 (m, 2H), 1.56-1.46 (m, 2H), 1.29 (d, J=2.1 Hz, 9H) ppm.

Intermediate 26

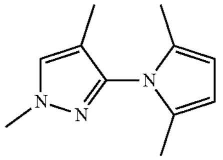

3-(2,5-Dimethyl-1H-pyrrol-1-yl)-1,4-dimethyl-1H-pyrazole. A mixture of 1,4-dimethyl-1H-pyrazol-3-amine (2.1 g, 18.9 mmol) and hexane-2,5-dione (2.22 mL, 18.9 mmol) and catalytic TsOH in toluene (100 mL) was refluxed overnight using a Dean-Stark condenser. The reaction mixture was then cooled to r.t. and cautiously decanted from the insoluble material. The resulting solution was evaporated under reduced pressure and further dried under vacuum for several hours to provide 3-(2,5-dimethyl-1H-pyrrol-1-yl)-1,4-dimethyl-1H-pyrazole.

Intermediate 27

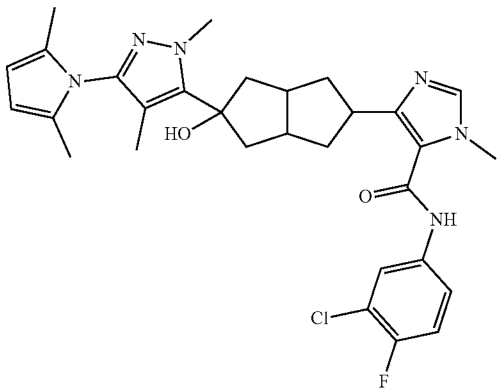 [SMILES: Cc1c(-n2c(C)ccc2C)nn(C)c1C1(O)CC2CC(c3ncn(C)c3C(=O)Nc3ccc(F)c(Cl)c3)CC2C1]

N-(3-Chloro-4-fluorophenyl)-4-(5-(3-(2,5-dimethyl-1H-pyrrol-1-yl)-1,4-dimethyl-1H-pyrazol-5-yl)-5-hydroxyoctahydropentalen-2-yl)-1-methyl-1H-imidazole-5-carboxamide. To a solution of 3-(2,5-dimethyl-1H-pyrrol-1-yl)-1,4-dimethyl-1H-pyrazole (400 mg, 2.1 mmol) in THF (8 mL) was added n-BuLi (0.85 mL, 2.5 M, 2.1 mmol) at −78° C. under argon. The mixture was stirred at −50° C. for 2.5 h. To the resulting mixture was added a solution of N-(3-chloro-4-fluorophenyl)-1-methyl-4-(5-oxooctahydropentalen-2-yl)-1H-imidazole-5-carboxamide (80 mg, 0.2 mmol) in THF (1.5 mL) at −78° C. The resulting mixture was warmed to r.t. slowly and stirred overnight. The reaction mixture was quenched with sat. $NH_4Cl$ and extracted with EtOAc (10 mL×3). The organic layer was washed with brine, dried over anhydrous $Na_2SO_4$ and concentrated to give the crude compound (420 mg), which was purified by pre-HPLC to afford N-(3-chloro-4-fluorophenyl)-4-(5-(3-(2,5-dimethyl-1H-pyrrol-1-yl)-1,4-dimethyl-1H-pyrazol-5-yl)-5-hydroxyoctahydropentalen-2-yl)-1-methyl-1H-imidazole-5-carboxamide, as a single diastereomer (11 mg, 9% yield).

Example 75

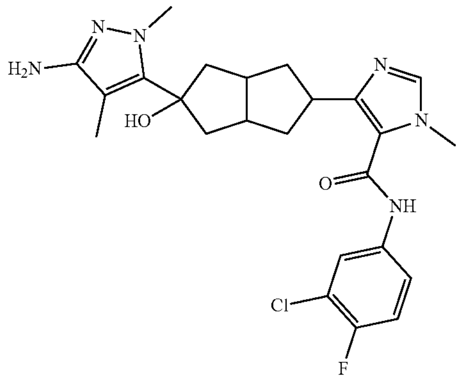 [SMILES: Cc1c(N)nn(C)c1C1(O)CC2CC(c3ncn(C)c3C(=O)Nc3ccc(F)c(Cl)c3)CC2C1]

4-(5-(3-Amino-1,4-dimethyl-1H-pyrazol-5-yl)-5-hydroxyoctahydropentalen-2-yl)-N-(3-chloro-4-fluorophenyl)-1-methyl-1H-imidazole-5-carboxamide. To a solution of N-(3-chloro-4-fluorophenyl)-4-(5-(3-(2,5-dimethyl-1H-pyrrol-1-yl)-1,4-dimethyl-1H-pyrazol-5-yl)-5-hydroxyoctahydropentalen-2-yl)-1-methyl-1H-imidazole-5-carboxamide (11 mg, 0.02 mmol) in EtOH (1 mL) was added hydroxylamine hydrochloride (270 mg, 3.9 mmol) and a solution of KOH (4.7 mL, 4.5% in EtOH:$H_2O$ 1:1, 3.8 mmol). The resulting mixture was refluxed for 2 days. After that, additional hydroxylamine hydrochloride (270 mg, 3.9 mmol) as well as triethylamine (0.528 mL, 3.85 mmol). were added and the resulting mixture was refluxed for 2 days. The last step was repeated. EtOH was evaporated from the cooled reaction mixture, and the product was extracted with EtOAc, washed with brine, dried over anhydrous $Na_2SO_4$ and concentrated to give the crude compound which was purified by pre-HPLC to afford 4-(5-(3-amino-1,4-dimethyl-1H-pyrazol-5-yl)-5-hydroxyoctahydropentalen-2-yl)-N-(3-chloro-4-fluorophenyl)-1-methyl-1H-imidazole-5-carboxamide (2.7 mg, 28% yield). MS calcd. for C24H28ClFN6O2: 486.2; Found: 485.2 $[M-1]^-$; $^1H$ NMR (600 MHz, Acetonitrile-$d_3$): δ 8.30 (s, 1H), 7.88 (dd, J=6.8, 2.6 Hz, 1H), 7.53 (ddd, J=9.0, 4.2, 2.6 Hz, 1H), 7.46 (s, 1H), 7.26 (t, J=9.0 Hz, 1H), 3.74 (d, J=14.5 Hz, 6H), 3.54 (s, 2H), 3.29 (dt, J=11.6, 5.5 Hz, 1H), 3.04 (s, 1H), 2.70 (s, 2H), 2.28 (dd, J=13.6, 8.3 Hz, 2H), 2.13 (s, 3H), 2.07 (dt, J=4.9, 2.5 Hz, 2H), 1.85 (qt, J=6.1, 3.5 Hz, 2H) ppm.

Intermediate 28

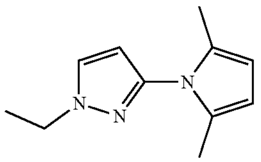

3-(2,5-Dimethyl-1H-pyrrol-1-yl)-1-ethyl-1H-pyrazole. the title compound was synthesized according to the procedure described for 3-(2,5-dimethyl-1H-pyrrol-1-yl)-1,4-dimethyl-1H-pyrazole.

Intermediate 29

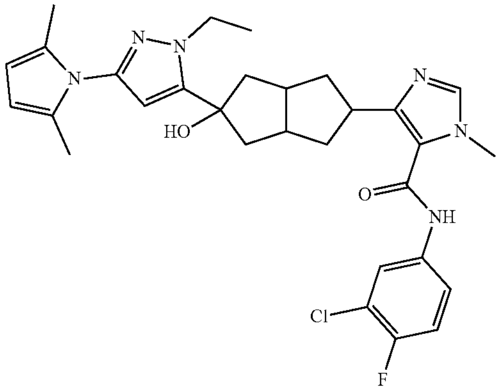 [SMILES: CCn1nc(-n2c(C)ccc2C)cc1C1(O)CC2CC(c3ncn(C)c3C(=O)Nc3ccc(F)c(Cl)c3)CC2C1]

N-(3-Chloro-4-fluorophenyl)-4-(5-(3-(2,5-dimethyl-H-pyrrol-1-yl)-1-ethyl-1H-pyrazol-5-yl)-5-hydroxyoctahydropentalen-2-yl)-1-methyl-1H-imidazole-5-carboxamide. The title compound was synthesized according to the procedure described for N-(3-chloro-4-fluorophenyl)-4-(5-(3-(2,5-dimethyl-1H-pyrrol-1-yl)-1,4-dimethyl-1H-pyrazol-5-yl)-5-hydroxyoctahydropentalen-2-yl)-1-methyl-1H-imidazole-5-carboxamide. (25 mg, 95% purity, 22% yield). MS calcd. for $C_{30}H_{34}ClFN_6O_2$: 564.2; Found: 563.1 $[M-H]^-$; $^1H$ NMR (600 MHz, DMSO-$d_6$) δ 10.20 (s, 1H), 7.94 (dd, J=6.8, 2.6 Hz, 1H), 7.64 (s, 1H), 7.55 (ddd, J=9.0, 4.3, 2.6 Hz, 1H), 7.38 (t, J=9.1 Hz, 1H), 6.08 (s, 1H), 5.70 (s, 2H), 5.43 (s, 1H), 4.29 (q, J=7.1 Hz, 2H), 3.66 (s, 3H), 3.23 (dt, J=12.2, 6.1 Hz, 1H), 2.51 (dd, 2H), 2.23 (dd, J=13.1, 7.8 Hz, 2H), 2.08 (dt, J=7.7, 6.8 Hz, 2H), 2.01 (s, 6H), 1.93-1.80 (m, 4H), 1.34 (t, J=7.1 Hz, 3H) ppm.

Example 76

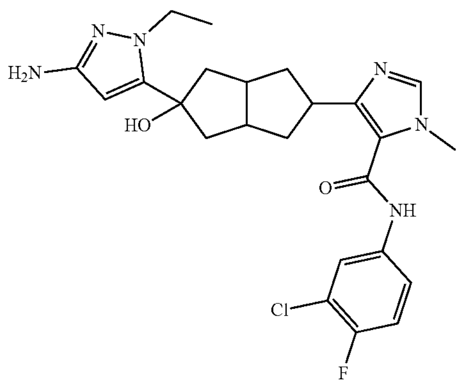 [SMILES: CCn1nc(N)cc1C1(O)CC2CC(c3ncn(C)c3C(=O)Nc3ccc(F)c(Cl)c3)CC2C1]

4-(5-(3-Amino-1,4-dimethyl-1H-pyrazol-5-yl)-5-hydroxyoctahydropentalen-2-yl)-N-(3-chloro-4-fluorophenyl)-1-methyl-1H-imidazole-5-carboxamide. The title compound was synthesized according to the procedure provided for 4-(5-(3-amino-1,4-dimethyl-1H-pyrazol-5-yl)-5-hydroxyoctahydropentalen-2-yl)-N-(3-chloro-4-fluorophenyl)-1-methyl-1H-imidazole-5-carboxamide. MS calcd. for C24H28ClFN6O2: 486.2; Found: 485.0 $[M-1]^-$; $^1H$ NMR (400 MHz, Chloroform-d): δ 7.77 (dd, J=6.5, 2.6 Hz, 1H), 7.52 (s, 1H), 7.43-7.30 (m, 2H), 7.15 (t, J=8.7 Hz, 1H), 5.42 (s, 1H), 4.22 (q, J=7.1 Hz, 2H), 3.83 (s, 3H), 3.50 (s, 1H), 3.26 (dd, J=11.7, 5.2 Hz, 1H), 2.73 (s, 3H), 2.35-2.04 (m, 8H), 1.39 (t, J=7.1 Hz, 3H) ppm.

Example 77

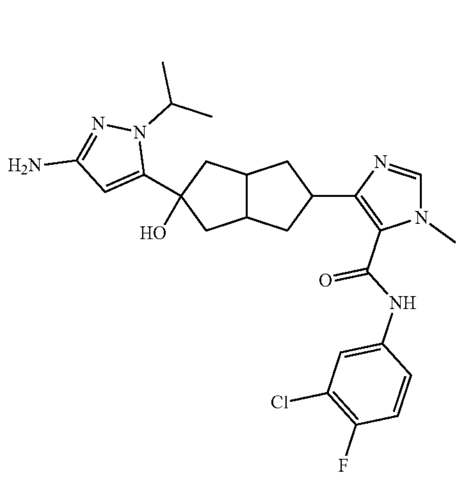 [SMILES: CC(C)n1nc(N)cc1C1(O)CC2CC(c3ncn(C)c3C(=O)Nc3ccc(F)c(Cl)c3)CC2C1]

4-(5-(3-Amino-1-Isopropyl-1H-pyrazol-5-yl)-5-hydroxyoctahydropentalen-2-yl)-N-(3-chloro-4-fluorophenyl)-1-methyl-1H-imidazole-5-carboxamide. The title compound was synthesized according to the method provided for 4-(5-(3-amino-1,4-dimethyl-1H-pyrazol-5-yl)-5-hydroxyoctahydropentalen-2-yl)-N-(3-chloro-4-fluorophenyl)-1-methyl-1H-imidazole-5-carboxamide. MS calcd. for $C_{25}H_{30}ClFN_6O_2$: 500.2; Found: 499.2 $[M-1]^-$; $^1H$ NMR (400 MHz, Chloroform-d): δ 7.78 (d, J=7.4 Hz, 1H), 7.49 (s, 2H), 7.35 (d, J=8.0 Hz, 1H), 7.16 (t, J=8.7 Hz, 1H), 5.42 (s, 1H), 5.03-4.89 (m, 1H), 3.85 (s, 3H), 3.28 (s, 1H), 2.74 (s, 2H), 2.38-2.22 (m, 7H), 2.10 (d, J=12.7 Hz, 4H), 1.42 (d, J=6.6 Hz, 6H) ppm.

Example 78

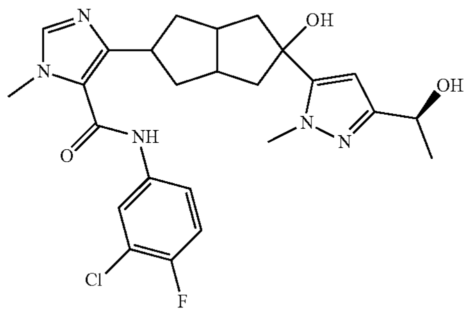 [SMILES: C[C@H](O)c1cc(C2(O)CC3CC(c4ncn(C)c4C(=O)Nc4ccc(F)c(Cl)c4)CC3C2)n(C)n1]

N-(3-Chloro-4-fluorophenyl)-4-(-5-hydroxy-5-(3-((S)-1-hydroxyethyl)-1-methyl-1H-pyrazol-5-yl)octahydropentalen-2-yl)-1-methyl-1H-imidazole-5-carboxamide. To a solution of (R)-1-(1-methyl-1H-pyrazol-3-yl)ethanol (268.91 mg, 2.13 mmol, 10.0 equiv) in anhydrous THF (10 mL) was added n-butyllithium (2.5M in n-hexane, 4.26 mmol, 1.71 mL, 20.0 equiv) dropwise at −78° C. The resulting mixture was stirred for 30 min then warmed to −30° C. over 30 min. A solution of N-(3-chloro-4-fluorophenyl)-1-methyl-4-(5-oxooctahydropentalen-2-yl)-1H-imidazole-5-carboxamide (80.0 mg, 212.87 μmol) in THF (2 mL) was added dropwise to the cooled (−78° C.) reaction mixture. The resulting mixture was stirred at −78° C. for 1 h then left to warm gradually to RT. After 12 h the mixture was poured into saturated $NH_4Cl$, and extracted with EtOAc (3×10 mL). The combined organic solution was dried over $Na_2SO_4$ and evaporated in vacuo to give 0.35 g of crude product, which was purified using prep-HPLC to give N-(3-chloro-4-fluorophenyl)-4-(-5-hydroxy-5-(3-((S)-1-hydroxyethyl)-1-methyl-1H-pyrazol-5-yl)octahydropentalen-2-yl)-1-methyl-1H-imidazole-5-carboxamide (9.4 mg, 18.73 μmol, 8.8% yield). MS calcd. for $C_{25}H_{29}ClFN_5O_3$: 501.2; Found: 484.2 $[M-18+1]^+$; $^1H$ NMR (600 MHz, Acetonitrile-d3) δ8.41 (d, J=41.1 Hz, 1H), 7.88 (dd, J=6.8, 2.6 Hz, 1H), 7.53 (ddd, J=9.0, 4.3, 2.7 Hz, 1H), 7.45 (s, 1H), 7.25 (td, J=9.0, 1.2 Hz, 1H), 6.08 (s, 1H), 4.72 (q, J=6.5 Hz, 1H), 3.90 (d, J=1.2 Hz, 3H), 3.72 (s, 3H), 3.41 (s, 1H), 3.33 (tt, J=12.0, 6.1 Hz, 1H), 3.19-2.85 (m, 2H), 2.61 (h, J=10.1, 9.3 Hz, 2H), 2.32 (ddd, J=11.8, 7.9, 2.8 Hz, 2H), 2.21 (d, J=7.0 Hz, 1H), 2.01 (d, J=4.6 Hz, 2H), 1.45-1.33 (m, 3H) ppm.

Intermediate 30

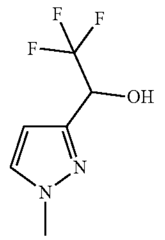

2,2,2-Trifluoro-1-(1-methyl-1H-pyrazol-3-yl)ethanol. To a solution of 1-methyl-1H-pyrazole-3-carbaldehyde (1.0 g, 9.08 mmol) and $TMSCF_3$ (1.94 g, 13.62 mmol, 1.5 equiv) in THF (20 mL) was added dropwise a solution of TBAF (1 M in THF, 908.24 μmol, 0.91 mL, 0.1 equiv) in THF at −20° C. The reaction mixture was stirred at 0° C. for 30 min then left to warm gradually to RT. After 12 h, an additional portion of TBAF (1 M in THF, 5.0 mL) was added and the mixture was poured into water and extracted with EtOAc (3×20 mL). The combined organic solution was dried over $Na_2SO_4$ and evaporated in vacuo to give 2,2,2-trifluoro-1-(1-methyl-1H-pyrazol-3-yl)ethanol as an oil (1.4 g, 95.0% purity, 7.38 mmol, 81% yield). The crude product was used directly without any further purification. MS calcd. for $C_6H_7F_3N_2O$: 180.1; Found: 181.2 $[M+1]^+$ Example 79

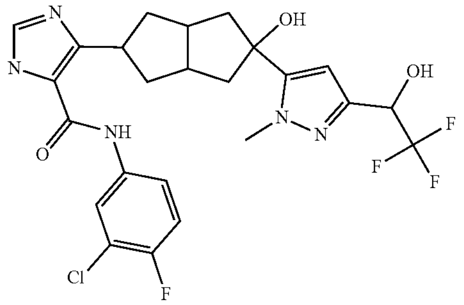

N-(3-Chloro-4-fluorophenyl)-4-(5-hydroxy-5-(1-methyl-3-(2,2,2-trifluoro-1-hydroxyethyl)-1H-pyrazol-5-yl)octahydropentalen-2-yl)-1-methyl-1H-imidazole-5-carboxamide. n-Butyllithium (2.5M in n-hexane, 3.2 mmol, 1.28 mL, 20.0 equiv) was added dropwise to a solution of 2,2,2-trifluoro-1-(1-methyl-1H-pyrazol-3-yl)ethanol (288.36 mg, 1.6 mmol, 10.0 equiv) in anhydrous THF (10 mL) at −78° C. The resulting mixture was stirred for 30 min then warmed to −20° C. over 30 min. The mixture was cooled to −78° C., and a solution of N-(3-chloro-4-fluorophenyl)-1-methyl-4-(5-oxooctahydropentalen-2-yl)-1H-imidazole-5-carboxamide (60 mg, 160.09 μmol) in THF (2 mL) was added dropwise. The reaction mixture was stirred at −78° C. for 1 h, and left to warm gradually to RT. After 12 h the mixture was poured into saturated $NH_4Cl$ solution, extracted with EtOAc (3×10 mL). The combined organic solution was dried over $Na_2SO_4$ and evaporated in vacuo to give 0.2 g of crude product, which purified with prep-HPLC to give N-(3-chloro-4-fluorophenyl)-4-(5-hydroxy-5-(1-methyl-3-(2,2,2-trifluoro-1-hydroxyethyl)-1H-pyrazol-5-yl)octahydropentalen-2-yl)-1-methyl-1H-imidazole-5-carboxamide (6.5 mg, 11.69 μmol, 7.3% yield). MS calcd. for $C_{24}H_{24}ClF_4N_5O_3$: 541.2; Found: 542.2 $[M+1]^+$; $^1H$ NMR (400 MHz, Acetonitrile-d3): δ 8.33 (s, 1H), 7.89 (dd, J=6.7, 2.7 Hz, 1H), 7.54 (ddd, J=9.0, 4.2, 2.6 Hz, 1H), 7.49 (s, 1H), 7.27 (t, J=9.0 Hz, 1H), 6.25 (s, 1H), 5.03 (q, J=7.3 Hz, 1H), 4.54 (s, 1H), 3.98 (s, 3H), 3.74 (s, 3H), 3.51 (d, J=44.4 Hz, 1H), 3.34 (dq, J=11.9, 5.9 Hz, 1H), 2.81 (s, 2H), 2.34 (dd, J=13.2, 7.7 Hz, 2H), 2.04 (dd, J=8.8, 3.6 Hz, 2H) ppm.

Example 80

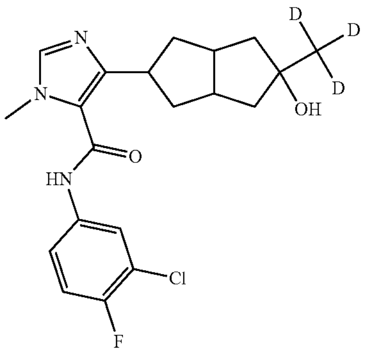 [SMILES: [2H]C([2H])([2H])C1(O)CC2CC(c3ncn(C)c3C(=O)Nc3ccc(F)c(Cl)c3)CC2C1]

N-(3-Chloro-4-fluorophenyl)-4(5-hydroxy-5-(methyl-d3)octahydropentalen-2-yl)-1-methyl-1H-imidazole-5-carboxamide. Magnesium (42.65 mg, 1.75 mmol) was stirred in dry diethyl ether (10 mL) in a three necked flask fitted with a thermometer and dropping funnel. Trideuterio methyl iodide (231.27 mg, 1.6 mmol, 100.0 μl, 10.0 equiv) in diethyl ether (2 mL) was added to the dropping funnel and a small crystal of iodine added to the magnesium suspension. The magnesium suspension was warmed briefly, and then the 1,1,1-trideuteromethyl iodide solution added dropwise to the flask. Once the addition was complete, the mixture was warmed to reflux for 30 min then cooled to −40° C. N-(3-chloro-4-fluorophenyl)-1-methyl-4-(5-oxooctahydropentalen-2-yl)-1H-imidazole-5-carboxamide (60.0 mg, 159.65 μmol) in THF (1.5 mL), was added dropwise to the reaction mixture which was allowed to reach room temperature overnight. The mixture was partitioned between aqueous ammonium chloride (20 mL) and MTBE (50 mL) and extracted with EtOAc. The combined organic solution was dried over $Na_2SO_4$ and evaporated in vacuo to give 0.075 g of the crude product, which was purified with prep-HPLC to give N-(3-chloro-4-fluorophenyl)-4-(5-hydroxy-5-(methyl-d3)octahydropentalen-2-yl)-1-methyl-1H-imidazole-5-carboxamide, as a single diastereomer (15.4 mg, 39.0 μmol, 24% yield). MS calcd. for $C_{20}H_{20}D_3ClFN_3O_2$: 394.2; Found: 395.2 $[M+1]^+$; $^1H$ NMR (400 MHz, Methanol-d4): δ 7.89 (dd, J=6.7, 2.6 Hz, 1H), 7.66 (s, 1H), 7.52 (ddd, J=9.0, 4.2, 2.6 Hz, 1H), 7.25 (t, J=8.9 Hz, 1H), 3.77 (s, 3H), 3.36 (s, 1H), 2.61-2.45 (m, 2H), 2.31-2.19 (m, 2H), 1.88 (dd, J=12.6, 8.0 Hz, 2H), 1.73 (td, J=12.3, 8.7 Hz, 2H), 1.61 (dd, J=12.6, 6.7 Hz, 2H) ppm.

Synthesis of Examples 81-113. Examples 81-113 in Table 6 were synthesized according to the procedures provided above using the corresponding starting materials.

TABLE 6

| Examples 81-113 | |
|---|---|
| Example | $^1$H NMR and MS |
| Example 81 | 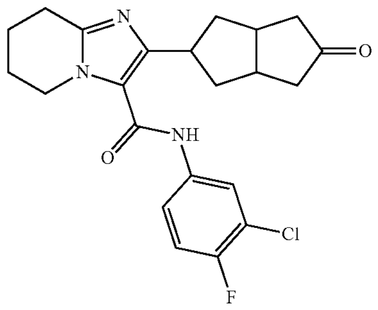 [SMILES: O=C1CC2CC(c3nc4n(c3C(=O)Nc3ccc(F)c(Cl)c3)CCCC4)CC2C1]<br>N-(3-Chloro-4-fluorophenyl)-2-(5-oxooctahydropentalen-2-yl)-5,6,7,8-tetrahydroimidazo[1,2-a]pyridine-3-carboxamide<br>$^1$H NMR (600 MHz, DMSO-$d_6$): δ 10.06 (s, 1H), 7.91 (dd, J = 6.9, 2.5 Hz, 1H), 7.54 (d, J = 9.1 Hz, 1H), 7.37 (t, J = 9.1 Hz, 1H), 3.95 (t, J = 5.9 Hz, 2H), 3.42-3.35 (m, 1H), 2.72 (t, J = 6.3 Hz, 2H), 2.69-2.61 (m, 2H), 2.39 (s, 2H), 2.19 (dt, J = 13.7, 7.1 Hz, 2H), 2.04 (dd, J = 18.8, 3.9 Hz, 2H), 1.84 (t, J = 5.8 Hz, 2H), 1.78 (p, J = 6.3 Hz, 2H), 1.55 (td, J = 12.3, 7.5 Hz, 2H) ppm; MS calcd. for $C_{22}H_{23}ClFN_3O_2$: 415.1; Found: 416.2 $[M + 1]^+$. |
| Example 82 | 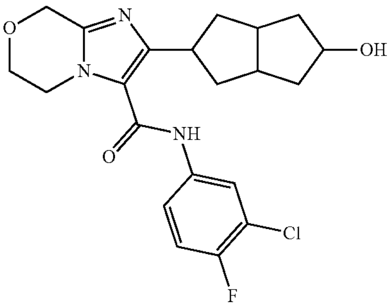 [SMILES: O=C(Nc1ccc(F)c(Cl)c1)c1c(C2CC3CC(O)CC3C2)nc2n1CCOC2]<br>N-(3-Chloro-4-fluorophenyl)-2-(5-hydroxyoctahydropentalen-2-yl)-5,6-dihydro-8H-imidazo[2,1-c][1,4]oxazine-3-carboxamide<br>$^1$H NMR (400 MHz, Acetonitrile-$d_3$): δ 8.22 (s, 1H), 7.87 (dd, J = 6.7, 2.7 Hz, 1H), 7.27 (t, J = 9.0 Hz, 1H), 4.77 (s, 2H), 4.22 (s, 1H), 4.17 (t, J = 5.2 Hz, 2H), 4.02 (t, J = 5.2 Hz, 2H), 3.45-3.25 (m, 2H), 2.51 (s, 2H), 2.17-2.13 (m, 2H), 1.84 (d, J = 13.1 Hz, 3H), 1.44 (dd, J = 12.4, 6.1 Hz, 2H) ppm; MS calcd. for $C_{21}H_{23}ClFN_3O_3$: 419.1; Found: 420.2 $[M + 1]^+$. |
| Example 83 | 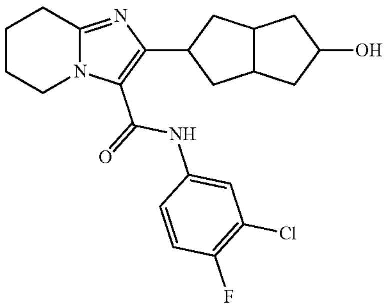 [SMILES: O=C(Nc1ccc(F)c(Cl)c1)c1c(C2CC3CC(O)CC3C2)nc2n1CCCC2]<br>N-(3-chloro-4-fluorophenyl)-2-(5-hydroxyoctahydropentalen-2-yl)-5,6,7,8-tetrahydroimidazo[1,2-a]pyridine-3-carboxamide<br>$^1$H NMR (400 MHz, DMSO-$d_6$): δ 10.04 (s, 1H), 7.93 (dd, J = 6.9, 2.4 Hz, 1H), 7.53 (s, 1H), 7.39 (t, J = 9.1 Hz, 1H), 4.50 (d, J = 4.4 Hz, 1H), 4.10-4.00 (m, 1H), 3.97 (s, 2H), 3.23 (dt, J = 12.2, 6.3 Hz, 1H), 2.76 (d, J = 6.5 Hz, 2H), 2.32 (s, 2H), 2.06 (t, J = 6.7 Hz, 2H), 1.98-1.75 (m, 6H), 1.67 (q, J = 11.0 Hz, 2H), 1.27 (dd, J = 10.3, 4.4 Hz, 2H) ppm; MS calcd. for $C_{22}H_{25}ClFN_3O_2$: 417.2; Found: 418.4 $[M + 1]^+$. |

TABLE 6-continued

| Example | $^1$H NMR and MS |
|---|---|
| | Examples 81-113 |
| Example 84 | 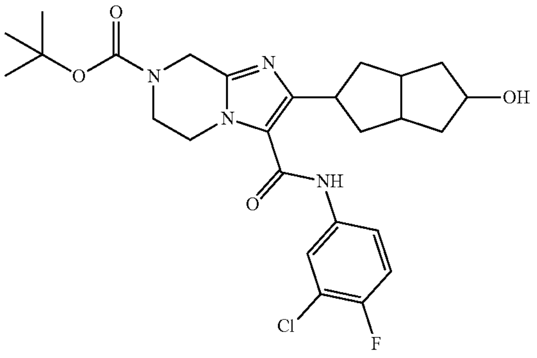 [SMILES: CC(C)(C)OC(=O)N1CCn2c(nc(C3CC4CC(O)CC4C3)c2C(=O)Nc2ccc(F)c(Cl)c2)C1]<br>tert-Butyl 3-((3-chloro-4-fluorophenyl)carbamoyl)-2-(5-hydroxy-octahydropentalen-2-yl)-5,6-dihydroimidazo[1,2-a]pyrazine-7(8H)-carboxylate<br>$^1$H NMR (400 MHz, DMSO-$d_6$): δ 10.08 (s, 1H), 7.92 (d, J = 6.4 Hz, 1H), 7.54 (s, 1H), 7.40 (t, J = 9.1 Hz, 1H), 4.57 (s, 2H), 4.50 (d, J = 4.3 Hz, 1H), 4.05 (s, 3H), 3.73 (s, 2H), 2.33 (s, 2H), 2.07 (d, J = 2.2 Hz, 3H), 1.91 (d, J = 9.1 Hz, 2H), 1.68 (d, J = 10.0 Hz, 2H), 1.44 (d, J = 2.2 Hz, 9H), 1.28 (s, 2H) ppm. MS calcd. for $C_{26}H_{32}ClFN_4O_4$: 518.2; Found: 519.2 $[M + 1]^+$. |
| Example 85 | 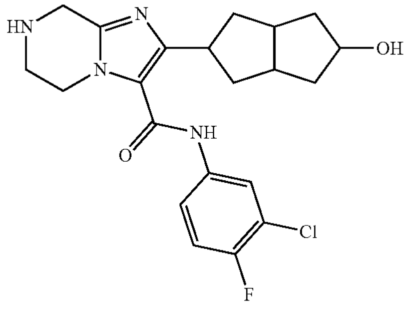 [SMILES: O=C(Nc1ccc(F)c(Cl)c1)c1c(C2CC3CC(O)CC3C2)nc2n1CCNC2]<br>N-(3-chloro-4-fluorophenyl)-2-(5-hydroxyoctahydropentalen-2-yl)-5,6,7,8-tetrahydroimidazo[1,2-a]pyrazine-3-carboxamide<br>$^1$H NMR (400 MHz, DMSO-$d_6$): δ 10.04 (s, 1H), 7.93 (dd, J = 6.7, 2.5 Hz, 1H), 7.54 (s, 1H), 7.39 (t, J = 9.1 Hz, 1H), 4.50 (d, J = 4.4 Hz, 1H), 4.04 (s, 1H), 3.92 (s, 2H), 3.85 (d, J = 5.2 Hz, 2H), 3.29-3.22 (m, 1H), 3.00 (s, 2H), 2.72 (s, 1H), 2.32 (s, 3H), 2.06 (d, J = 10.6 Hz, 2H), 1.97-1.84 (m, 2H), 1.68 (t, J = 10.3 Hz, 2H), 1.36-1.22 (m, 2H) ppm. MS calcd. for $C_{21}H_{24}ClFN_4O_2$: 418.2; Found: 419.0 $[M + 1]^+$. |
| Example 86 | 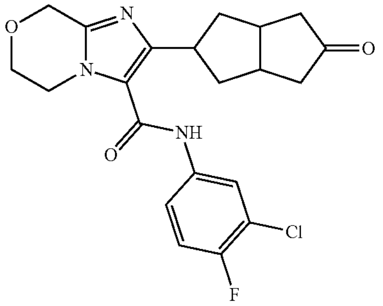 [SMILES: O=C1CC2CC(c3nc4n(c3C(=O)Nc3ccc(F)c(Cl)c3)CCOC4)CC2C1]<br>N-(3-chloro-4-fluorophenyl)-2-(5-oxooctahydropentalen-2-yl)-5,6-dihydro-8H-imidazo[2,1-c][1,4]oxazine-3-carboxamide<br>$^1$H NMR (600 MHz, DMSO-$d_6$): δ 10.09 (s, 1H), 7.91 (dt, J = 6.8, 2.5 Hz, 1H), 7.55 (dt, J = 9.5, 3.5 Hz, 1H), 7.38 (t, J = 9.1 Hz, 1H), 4.73 (s, 2H), 4.07 (t, J = 5.2 Hz, 2H), 3.94 (t, J = 5.2 Hz, 2H), 3.46 (tt, J = 10.3, 7.5 Hz, 1H), 2.75-2.63 (m, 2H), 2.46-2.40 (m, 2H), 2.27-2.15 (m, 2H), 2.03 (dd, J = 19.0, 3.7 Hz, 2H), 1.55 (td, J = 12.2, 7.5 Hz, 2H) ppm. MS calcd. for $C_{21}H_{21}ClFN_3O_3$: 417.1; Found: 418.2 $[M + 1]^+$. |

TABLE 6-continued

| Example | Examples 81-113<br>$^1$H NMR and MS |
|---|---|
| Example 87 | 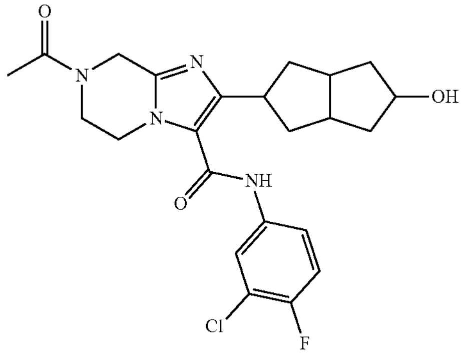 [SMILES: CC(=O)N1CCn2c(nc(C3CC4CC(O)CC4C3)c2C(=O)Nc2ccc(F)c(Cl)c2)C1]<br>7-acetyl-N-(3-chloro-4-fluorophenyl)-2-(5-hydroxyoctahydropentalen-2-yl)-5,6,7,8-tetrahydroimidazo[1,2-a]pyrazine-3-carboxamide<br>$^1$H NMR (400 MHz, Methanol-$d_4$): δ 7.87 (d, J = 6.7 Hz, 1H), 7.50 (d, J = 9.3 Hz, 1H), 7.25 (t, J = 9.1 Hz, 1H), 4.82 (d, J = 7.7 Hz, 2H), 4.24 (s, 1H), 4.16 (s, 2H), 3.99 (d, J = 14.0 Hz, 2H), 3.38 (s, 1H), 2.67 (s, 1H), 2.49 (s, 2H), 2.23 (d, J = 7.5 Hz, 5H), 2.13 (s, 2H), 1.74 (d, J = 9.3 Hz, 2H), 1.43 (s, 2H) ppm; MS calcd. for $C_{23}H_{26}ClFN_4O_3$: 460.2; Found: 461.2 $[M + 1]^+$. |
| Example 88 | 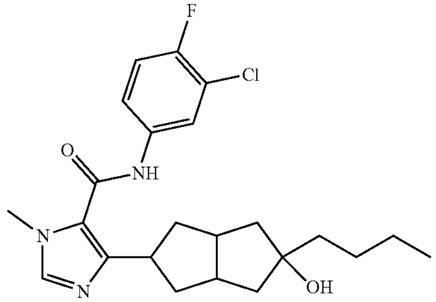 [SMILES: CCCCC1(O)CC2CC(c3ncn(C)c3C(=O)Nc3ccc(F)c(Cl)c3)CC2C1]<br>4-(5-butyl-5-hydroxyoctahydropentalen-2-yl)-N-(3-chloro-4-fluorophenyl)-1-methyl-1H-imidazole-5-carboxamide<br>$^1$H NMR (400 MHz, Chloroform-d): δ 8.95 (s, 1H), 8.07 (d, J = 24.0 Hz, 1H), 7.91 (d, J = 5.5 Hz, 1H), 7.52 (d, J = 9.2 Hz, 1H), 7.15 (t, J = 8.7 Hz, 1H), 3.91 (s, 3H), 3.28 (dd, J = 12.0, 5.8 Hz, 1H), 2.65 (d, J = 11.6 Hz, 2H), 2.32 (d, J = 11.0 Hz, 2H), 2.11 (d, J = 9.3 Hz, 2H), 1.86 (dd, J = 13.5, 7.8 Hz, 2H), 1.70 (d, J = 13.4 Hz, 2H), 1.44-1.20 (m, 4H), 0.91 (t, J = 6.9 Hz, 3H) ppm. MS calcd. for $C_{23}H_{29}ClFN_3O_2$: 433.2; Found: 434.2 $[M + 1]^+$. |
| Example 89 | 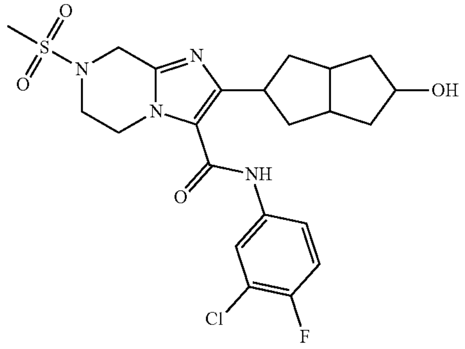 [SMILES: CS(=O)(=O)N1CCn2c(nc(C3CC4CC(O)CC4C3)c2C(=O)Nc2ccc(F)c(Cl)c2)C1]<br>N-(3-chloro-4-fluorophenyl)-2-(5-hydroxyoctahydropentalen-2-yl)-7-(methylsulfonyl)-5,6,7,8-tetrahydroimidazo[1,2-a]pyrazine-3-carboxamide<br>$^1$H NMR (400 MHz, Methanol-$d_4$): δ 7.87 (dd, J = 6.6, 2.7 Hz, 1H), 7.50 (dd, J = 9.1, 5.0 Hz, 1H), 7.25 (t, J = 9.0 Hz, 1H), 4.54 (s, 2H), 4.26 (s, 2H), 4.23-4.14 (m, 1H), 3.74 (s, 2H), 3.38 (t, J = 6.1 Hz, 1H), 3.02 (d, J = 1.8 Hz, 3H), 2.49 (s, 2H), 2.34-2.19 (m, 2H), 2.12 (dd, J = 13.3, 6.6 Hz, 2H), 1.74 (d, J = 9.4 Hz, 2H), 1.42 (d, J = 7.5 Hz, 2H) ppm; MS calcd. for $C_{22}H_{26}ClFN_4O_4S$: 496.1; Found: 497.0 $[M + 1]^+$. |

TABLE 6-continued

| Example | $^1$H NMR and MS |
|---|---|
| | Examples 81-113 |
| Example 90 | 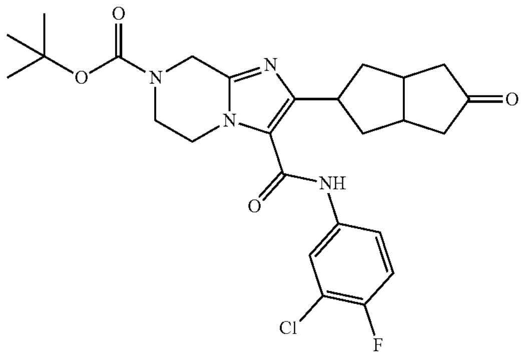 [SMILES: CC(C)(C)OC(=O)N1CCn2c(nc(C3CC4CC(=O)CC4C3)c2C(=O)Nc2ccc(F)c(Cl)c2)C1] tert-butyl 3-((3-chloro-4-fluorophenyl)carbamoyl)-2-(5-oxooctahydro-pentalen-2-yl)-5,6-dihydroimidazo[1,2-a]pyrazine-7(8H)-carboxylate $^1$H NMR (400 MHz, DMSO-$d_6$): δ 10.13 (s, 1H), 7.93 (dd, J = 6.8, 2.5 Hz, 1H), 7.57 (dt, J = 8.8, 3.2 Hz, 1H), 7.41 (t, J = 9.1 Hz, 1H), 4.57 (s, 2H), 4.07 (t, J = 5.4 Hz, 2H), 3.73 (s, 2H), 3.45 (q, J = 9.3 Hz, 1H), 2.70 (s, 2H), 2.44 (t, J = 9.1 Hz, 1H), 2.23 (dt, J = 13.4, 6.8 Hz, 2H), 2.14-2.05 (m, 2H), 2.04 (d, J = 3.6 Hz, 1H), 1.57 (q, J = 10.4 Hz, 2H), 1.44 (s, 9H) ppm; MS calcd. for $C_{26}H_{30}ClFN_4O_4$: 516.2; Found: 517.2 $[M + 1]^+$. |
| Example 91 | 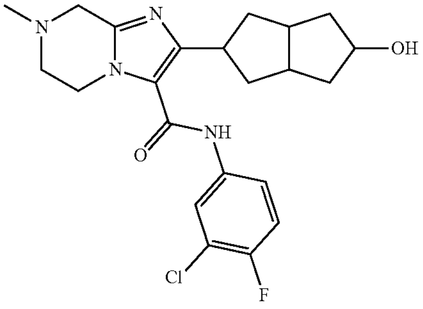 [SMILES: CN1CCn2c(nc(C3CC4CC(O)CC4C3)c2C(=O)Nc2ccc(F)c(Cl)c2)C1] N-(3-chloro-4-fluorophenyl)-2-(5-hydroxyoctahydropentalen-2-yl)-7-methyl-5,6,7,8-tetrahydroimidazo[1,2-a]pyrazine-3-carboxamide $^1$H NMR (400 MHz, DMSO-$d_6$): δ 10.04 (s, 1H), 7.92 (dd, J = 6.9, 2.6 Hz, 1H), 7.60-7.51 (m, 1H), 7.39 (t, J = 9.0 Hz, 1H), 4.50 (d, J = 4.3 Hz, 1H), 4.03 (t, J = 5.8 Hz, 3H), 3.54 (s, 2H), 3.30-3.20 (m, 1H), 2.73 (d, J = 5.6 Hz, 2H), 2.37 (s, 3H), 2.32 (s, 2H), 2.06 (dd, J = 9.5, 3.4 Hz, 2H), 1.91 (dd, J = 12.7, 6.5 Hz, 2H), 1.67 (q, J = 11.0 Hz, 2H), 1.28 (dt, J = 12.9, 6.2 Hz, 2H) ppm; MS calcd. for $C_{22}H_{26}ClFN_4O_2$: 432.2; Found: 433.2 $[M + 1]^+$. |
| Example 92 | 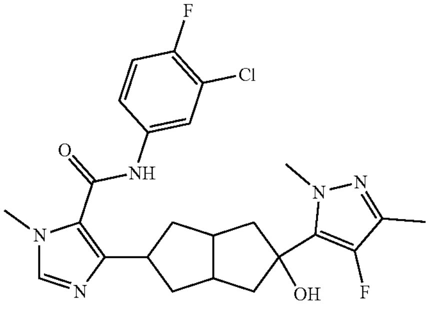 N-(3-chloro-4-fluorophenyl)-4-(5-(4-fluoro-1, 3-dimethyl-1H-pyrazol-5-yl)-5-hydroxyoctahydropentalen-2-yl)-1-methyl-1H-imidazole-5-carboxamide $^1$H NMR (400 MHz, Chloroform-d) δ 7.79 (dd, J = 6.5, 2.6 Hz, 1H), 7.68 (s, 1H), 7.50 (s, 1H), 7.37 (dt, J = 9.0, 3.4 Hz, 1H), 7.16 (t, J = 8.7 Hz, 1H), 3.92 (s, 3H), 3.84 (s, 3H), 3.28 (dt, J = 11.3, 7.0 Hz, 1H), 2.79 (d, J = 6.9 Hz, 2H), 2.44 (dd, J = 13.6, 7.4 Hz, 3H), 2.28 (q, J = 9.5, 7.7 Hz, 4H), 2.16 (d, J = 13.9 Hz, 5H) ppm. MS calcd. for $C_{24}H_{26}ClF_2N_5O_2$: 489.2; Found: 487.8 $[M - 1]^-$. |

TABLE 6-continued

| Examples 81-113 | |
|---|---|
| Example | $^1$H NMR and MS |
| Example 93 | 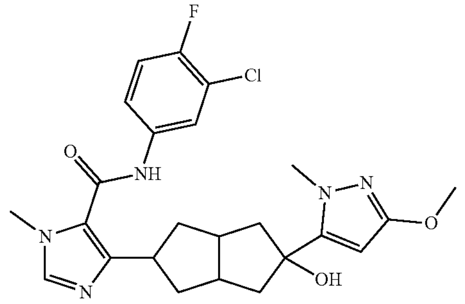 N-(3-chloro-4-fluorophenyl)-4-(5-hydroxy-5-(3-methoxy-1-methyl-1H-pyrazol-5-yl)octahydropentalen-2-yl)-1-methyl-1H-imidazole-5-carboxamide $^1$H NMR (400 MHz, Methanol-$d_4$) δ 7.89 (dd, J = 6.7, 2.7 Hz, 1H), 7.67 (s, 1H), 7.51 (ddd, J = 8.9, 4.2, 2.6 Hz, 1H), 7.24 (t, J = 9.0 Hz, 1H), 5.62 (s, 1H), 3.94-3.70 (m, 9H), 2.67 (s, 1H), 2.65-2.52 (m, 2H), 2.38 (dd, J = 13.0, 7.6 Hz, 2H), 2.26 (dt, J = 12.8, 6.8 Hz, 2H), 1.99-1.82 (m, 4H). MS calcd. for $C_{24}H_{27}ClFN_5O_3$: 487.2; Found: 486.0 $[M-1]^-$. |
| Example 94 | 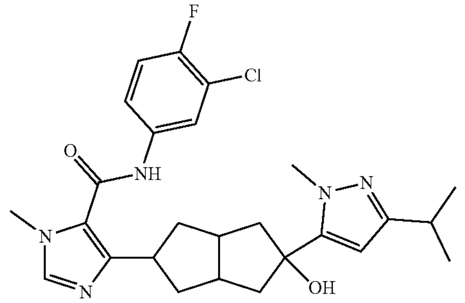 [SMILES: CC(C)c1cc(C2(O)CC3CC(c4ncn(C)c4C(=O)Nc4ccc(F)c(Cl)c4)CC3C2)n(C)n1] N-(3-chloro-4-fluorophenyl)-4-(5-hydroxy-5-(3-isopropyl-1-methyl-1H-pyrazol-5-yl)octahydropentalen-2-yl)-1-methyl-1H-imidazole-5-carboxamide $^1$H NMR (400 MHz, Chloroform-d): δ 7.78 (dd, J = 6.5, 2.6 Hz, 1H), 7.65 (s, 1H), 7.49 (s, 1H), 7.37 (dt, J = 9.0, 3.4 Hz, 1H), 7.16 (t, J = 8.7 Hz, 1H), 5.91 (s, 1H), 3.98 (s, 3H), 3.84 (s, 3H), 3.50 (s, 1H), 3.29 (tt, J = 11.7, 6.8 Hz, 1H), 2.92 (h, J = 7.0 Hz, 1H), 2.82-2.71 (m, 2H), 2.36 (dd, J = 13.7, 7.9 Hz, 2H), 2.32-2.19 (m, 5H), 2.19-2.12 (m, 2H), 1.25 (d, J = 6.9 Hz, 6H). MS calcd. for $C_{26}H_{31}ClFN_5O_2$: 499.2; Found: 498.2 $[M-1]^-$. |
| Example 95 | 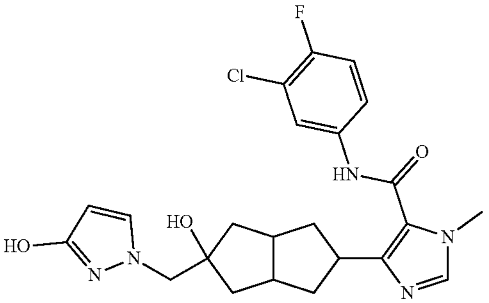 [SMILES: Cn1cnc(C2CC3CC(O)(Cn4ccc(O)n4)CC3C2)c1C(=O)Nc1ccc(F)c(Cl)c1] N-(3-chloro-4-fluorophenyl)-4-(5-hydroxy-5-((3-hydroxy-1H-pyrazol-1-yl)methyl)octahydropentalen-2-yl)-1-methyl-1H-imidazole-5-carboxamide $^1$H NMR (400 MHz, Chloroform-d): δ 7.85 (s, 1H), 7.78 (dd, J = 6.5, 2.7 Hz, 1H), 7.44 (s, 1H), 7.41-7.34 (m, 1H), 7.23-7.07 (m, 2H), 5.58 (d, J = 2.3 Hz, 1H), 3.90 (s, 2H), 3.79 (s, 3H), 3.26 (tt, J = 12.2, 6.3 Hz, 1H), 2.70-2.58 (m, 2H), 2.21 (dt, J = 13.3, 6.9 Hz, 2H), 2.08-1.99 (m, 2H), 1.86 (dd, J = 13.7, 7.4 Hz, 2H), 1.60 (dd, J = 13.6, 3.8 Hz, 2H). MS calcd. for $C_{23}H_{25}ClFN_5O_3$: 473.2; Found: 472.0 $[M-1]^-$. |

TABLE 6-continued

| Example | $^1$H NMR and MS |
|---|---|
| | Examples 81-113 |
| Example 96 | 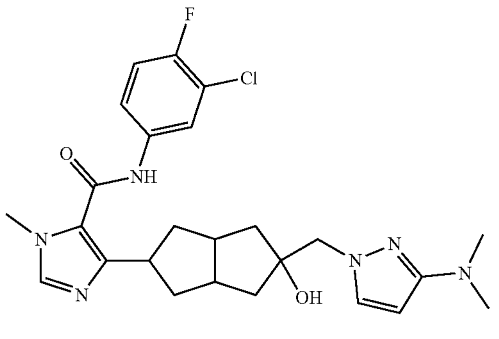 N-(3-chloro-4-fluorophenyl)-4-(5-((3-(dimethylamino)-1H-pyrazol-1-yl)methyl)-5-hydroxyoctahydropentalen-2-yl)-1-methyl-1H-imidazole-5-carboxamide $^1$H NMR (400 MHz, Chloroform-d): δ 7.76 (dd, J = 6.5, 2.7 Hz, 1H), 7.49 (d, J = 6.1 Hz, 2H), 7.39-7.33 (m, 1H), 7.22-7.11 (m, 2H), 5.59 (d, J = 2.4 Hz, 1H), 3.94 (s, 2H), 3.83 (s, 3H), 3.26 (tt, J = 12.0, 6.1 Hz, 1H), 2.85 (s, 6H), 2.58 (q, J = 10.3, 7.4 Hz, 2H), 2.23 (dt, J = 13.3, 6.8 Hz, 2H), 2.08 (q, J = 11.9 Hz, 2H), 1.81 (dd, J = 13.3, 7.7 Hz, 2H), 1.66 (dd, J = 13.4, 5.0 Hz, 2H) ppm. MS calcd. for $C_{25}H_{30}ClFN_6O_2$: 500.2; Found: 499.2 $[M-1]^-$. |
| Example 97 | 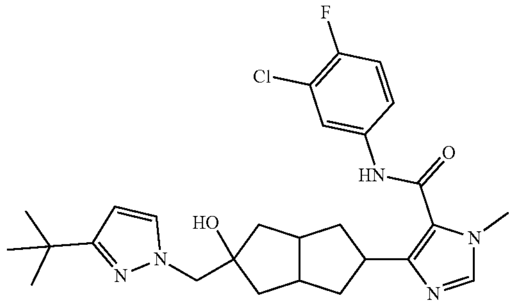 [SMILES: Cn1cnc(C2CC3CC(O)(Cn4ccc(C(C)(C)C)n4)CC3C2)c1C(=O)Nc1ccc(F)c(Cl)c1] 4-(5-((3-(tert-butyl)-1H-pyrazol-1-yl)methyl)-5-hydroxyoctahydropentalen-2-yl)-N-(3-chloro-4-fluorophenyl)-1-methyl-1H-imidazole-5-carboxamide $^1$H NMR (400 MHz, Methanol-$d_4$): δ 7.88 (dd, J = 6.4, 2.7 Hz, 1H), 7.65 (s, 1H), 7.51 (d, J = 2.4 Hz, 2H), 7.25 (t, J = 8.9 Hz, 1H), 6.14 (d, J = 2.4 Hz, 1H), 4.09 (s, 2H), 3.77 (s, 3H), 2.58 (s, 2H), 2.22 (d, J = 7.5 Hz, 2H), 2.05 (s, 1H), 1.86 (t, J = 6.7 Hz, 2H), 1.75 (t, J = 10.7 Hz, 2H), 1.56-1.46 (m, 2H), 1.29 (d, J = 1.9 Hz, 9H). MS calcd. for $C_{27}H_{33}ClFN_5O_2$: 513.2; Found: 512.2 $[M-1]^-$. |

TABLE 6-continued

| Examples 81-113 | |
|---|---|
| Example | $^1$H NMR and MS |
| Example 98 | 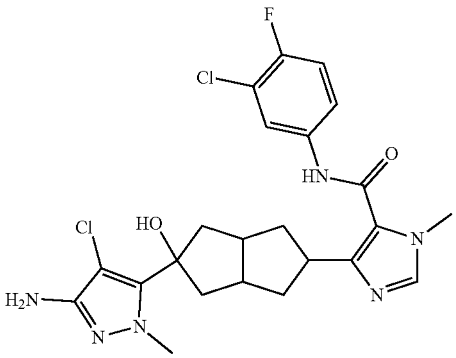 [SMILES: Cn1cnc(C2CC3CC(O)(c4c(Cl)c(N)nn4C)CC3C2)c1C(=O)Nc1ccc(F)c(Cl)c1]<br>4-(5-(3-amino-4-chloro-1-methyl-1H-pyrazol-5-yl)-5-hydroxyoctahydropentalen-2-yl)-N-(3-chloro-4-fluorophenyl)-1-methyl-1H-imidazole-5-carboxamide<br>$^1$H NMR (600 MHz, Acetonitrile-$d_3$): δ 8.32 (s, 1H), 7.88 (dd, J = 6.8, 2.7 Hz, 1H), 7.53 (ddd, J = 8.9, 4.2, 2.6 Hz, 1H), 7.48 (s, 1H), 7.26 (t, J = 9.0 Hz, 1H), 3.86 (s, 1H), 3.80 (s, 3H), 3.73 (s, 3H), 3.31 (dt, J = 11.9, 5.7 Hz, 1H), 2.73 (d, J = 7.7 Hz, 2H), 2.49 (dd, J = 13.5, 8.3 Hz, 2H), 2.13 (s, 2H), 2.10 (s, 2H), 2.09 (s, 2H), 1.89-1.79 (m, 2H). MS calcd. for $C_{23}H_{25}Cl_2FN_6O_2$: 506.1; Found: 505.0 $[M-1]^-$. |
| Example 99 | 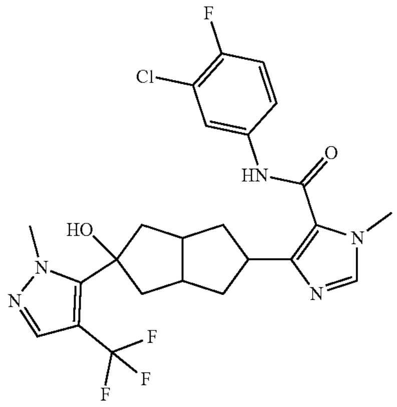 [SMILES: Cn1cnc(C2CC3CC(O)(c4c(C(F)(F)F)cnn4C)CC3C2)c1C(=O)Nc1ccc(F)c(Cl)c1]<br>N-(3-chloro-4-fluorophenyl)-4-(5-hydroxy-5-(1-methyl-4-(trifluoromethyl)-1H-pyrazol-5-yl)octahydropentalen-2-yl)-1-methyl-1H-imidazole-5-carboxamide<br>$^1$H NMR (400 MHz, Methanol-$d_4$): δ 7.91 (dd, J = 6.7, 2.6 Hz, 1H), 7.64 (s, 1H), 7.60 (s, 1H), 7.53 (ddd, J = 9.0, 4.1, 2.5 Hz, 1H), 7.26 (t, J = 8.9 Hz, 1H), 4.10 (s, 3H), 3.77 (s, 3H), 3.29-3.21 (m, 1H), 2.80 (s, 2H), 2.22 (dt, J = 19.7, 7.1 Hz, 8H) ppm. MS calcd. for $C_{24}H_{24}ClF_4N_5O_2$: 525.2; Found: 526.2 $[M+1]^+$. |

TABLE 6-continued

| Examples 81-113 | |
|---|---|
| Example | $^1$H NMR and MS |
| Example 100 | 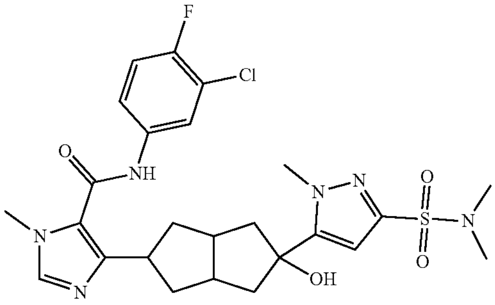<br>N-(3-chloro-4-fluorophenyl)-4-(5-(3-(N,N-dimethylsulfamoyl)-1-methyl-1H-pyrazol-5-yl)-5-hydroxyoctahydropentalen-2-yl)-1-methyl-1H-imidazole-5-carboxamide<br>$^1$H NMR (400 MHz, DMSO-$d_6$): δ 10.22 (s, 1H), 7.96 (d, J = 6.9 Hz, 1H), 7.66 (s, 1H), 7.56 (s, 1H), 7.40 (t, J = 8.9 Hz, 1H), 6.51 (s, 1H), 5.47 (s, 1H), 4.06-3.93 (m, 3H), 3.68 (s, 3H), 3.26 (s, 1H), 2.69-2.64 (m, 6H), 2.24 (s, 2H), 2.16-2.05 (m, 3H), 1.89 (t, J = 13.9 Hz, 4H). MS calcd. for $C_{25}H_{30}ClFN_6O_4S$: 564.2; Found: 563.2 $[M - 1]^-$. |
| Example 101 | 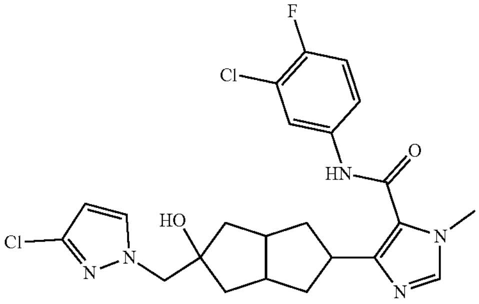 [SMILES: Cn1cnc(C2CC3CC(O)(Cn4ccc(Cl)n4)CC3C2)c1C(=O)Nc1ccc(F)c(Cl)c1]<br>4-(5-((3-Chloro-1H-pyrazol-1-yl)methyl)-5-hydroxyoctahydropentalen-2-yl)-N-(3-chloro-4-fluorophenyl)-1-methyl-1H-imidazole-5-carboxamide<br>$^1$H NMR (400 MHz, Methanol-$d_4$): δ 7.89 (dd, J = 6.6, 2.7 Hz, 1H), 7.66 (d, J = 3.1 Hz, 1H), 7.62 (d, J = 2.3 Hz, 1H), 7.53 (ddd, J = 9.1, 4.2, 2.6 Hz, 1H), 7.25 (td, J = 9.0, 3.2 Hz, 1H), 6.27-6.13 (m, 1H), 4.01 (d, J = 58.4 Hz, 2H), 3.77 (d, J = 2.7 Hz, 3H), 3.37 (dt, J = 12.2, 6.1 Hz, 1H), 2.61 (s, 2H), 2.28-2.19 (m, 2H), 1.96-1.86 (m, 2H), 1.77 (q, J = 11.5, 11.0 Hz, 2H), 1.54 (dd, J = 13.2, 5.8 Hz, 2H) ppm. MS calcd. for $C_{23}H_{24}Cl_2FN_5O_2$: 491.1; Found: 492.0 $[M + 1]^+$. |
| Example 102 | 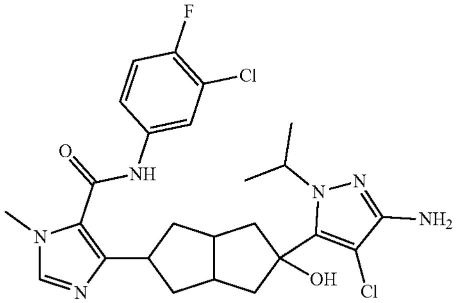 [SMILES: CC(C)n1nc(N)c(Cl)c1C1(O)CC2CC(c3ncn(C)c3C(=O)Nc3ccc(F)c(Cl)c3)CC2C1]<br>4-(5-(3-amino-4-chloro-1-isopropyl-1H-pyrazol-5-yl)-5-hydroxyoctahydropentalen-2-yl)-N-(3-chloro-4-fluorophenyl)-1-methyl-1H-imidazole-5-carboxamide<br>$^1$H NMR (400 MHz, Chloroform-d): δ 7.78 (dd, J = 6.7, 2.4 Hz, 1H), 7.46 (s, 1H), 7.43 (s, 1H), 7.35 (d, J = 8.6 Hz, 1H), 7.17 (t, J = 8.7 Hz, 1H), 5.17-5.05 (m, 1H), 3.85 (s, 3H), 3.74 (d, J = 7.4 Hz, 2H), 3.51 (s, 1H), 3.28 (s, 1H), 2.82 (s, 2H), 2.60 (t, J = 10.7 Hz, 2H), 2.31 (d, J = 15.4 Hz, 4H), 2.20 (d, J = 13.8 Hz, 2H), 1.39 (d, J = 6.5 Hz, 6H) ppm. MS calcd. for $C_{25}H_{29}Cl_2FN_6O_2$: 534.2; Found: 533.2 $[M - 1]^-$. |

TABLE 6-continued

| Examples 81-113 | |
|---|---|
| Example | $^1$H NMR and MS |
| Example 103 | 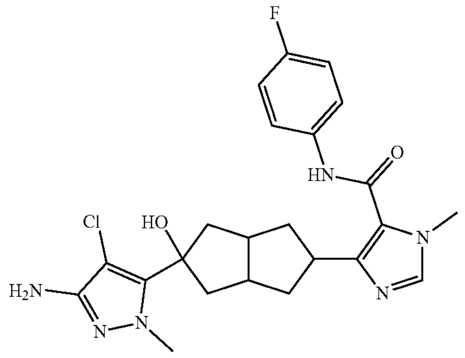 [SMILES: Cn1cnc(C2CC3CC(O)(c4c(Cl)c(N)nn4C)CC3C2)c1C(=O)Nc1ccc(F)cc1]<br>4-(5-(3-amino-4-chloro-1-methyl-1H-pyrazol-5-yl)-5-hydroxyoctahydropentalen-2-yl)-N-(4-fluorophenyl)-1-methyl-1H-imidazole-5-carboxamide<br>$^1$H NMR (400 MHz, Acetonitrile-$d_3$): δ 8.27 (s, 1H), 7.71-7.60 (m, 2H), 7.45 (s, 1H), 7.15 (dd, J = 9.9, 7.8 Hz, 2H), 3.89 (s, 2H), 3.82 (s, 3H), 3.74 (s, 3H), 3.52 (d, J = 33.6 Hz, 1H), 3.39-3.26 (m, 2H), 2.73 (d, J = 7.3 Hz, 2H), 2.58-2.42 (m, 2H), 2.17-2.06 (m, 4H). MS calcd. for $C_{23}H_{26}ClFN_6O_2$: 472.2; Found: 471.2 $[M - 1]^-$. |
| Example 104 | 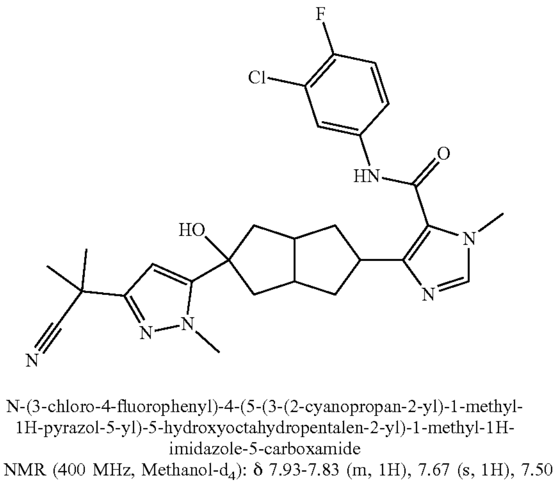<br>N-(3-chloro-4-fluorophenyl)-4-(5-(3-(2-cyanopropan-2-yl)-1-methyl-1H-pyrazol-5-yl)-5-hydroxyoctahydropentalen-2-yl)-1-methyl-1H-imidazole-5-carboxamide<br>$^1$H NMR (400 MHz, Methanol-$d_4$): δ 7.93-7.83 (m, 1H), 7.67 (s, 1H), 7.50 (s, 1H), 7.25 (t, J = 8.9 Hz, 1H), 6.22 (s, 1H), 3.98 (s, 3H), 3.78 (s, 3H), 2.60 (s, 2H), 2.47-2.34 (m, 2H), 2.27 (d, J = 6.9 Hz, 2H), 2.05 (s, 1H), 1.99 (dd, J = 13.1, 5.2 Hz, 2H), 1.90 (d, J = 9.2 Hz, 2H), 1.68 (s, 6H) ppm. MS calcd. for $C_{27}H_{30}ClFN_6O_2$: 524.2; Found: 523.0 $[M - 1]^-$. |

TABLE 6-continued

| Examples 81-113 | |
|---|---|
| Example | $^1$H NMR and MS |
| Example 105 | 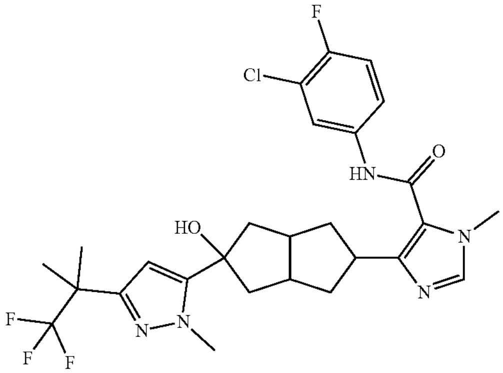 [SMILES: Cn1cnc(C2CC3CC(O)(c4cc(C(C)(C)C(F)(F)F)nn4C)CC3C2)c1C(=O)Nc1ccc(F)c(Cl)c1]<br>N-(3-chloro-4-fluorophenyl)-4-(5-hydroxy-5-(1-methyl-3-(1,1,1-trifluoro-2-methylpropan-2-yl)-1H-pyrazol-5-yl)octahydropentalen-2-yl)-1-methyl-1H-imidazole-5-carboxamide<br>$^1$H NMR (400 MHz, Methanol-$d_4$): δ 7.89 (dd, J = 6.6, 2.6 Hz, 1H), 7.67 (s, 1H), 7.52 (d, J = 9.5 Hz, 1H), 7.25 (t, J = 9.0 Hz, 1H), 6.20 (s, 1H), 3.98 (s, 3H), 3.78 (s, 3H), 3.35 (s, 1H), 2.58 (s, 2H), 2.41 (dd, J = 13.3, 6.7 Hz, 2H), 2.22 (s, 2H), 2.02-1.80 (m, 4H), 1.49 (s, 6H) ppm. MS calcd. for $C_{27}H_{30}ClF_4N_5O_2$: 567.2; Found: 566.0 $[M-1]^-$. |
| Example 106 | 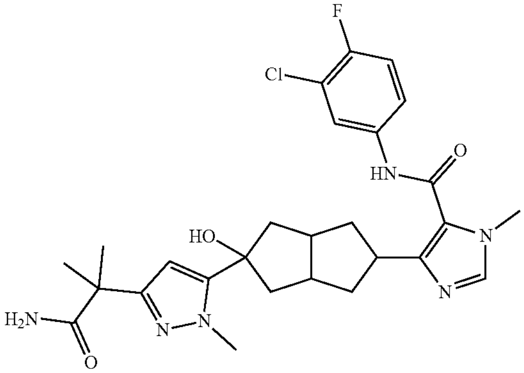 [SMILES: Cn1cnc(C2CC3CC(O)(c4cc(C(C)(C)C(N)=O)nn4C)CC3C2)c1C(=O)Nc1ccc(F)c(Cl)c1]<br>4-(5-(3-(1-amino-2-methyl-1-oxopropan-2-yl)-1-methyl-1H-pyrazol-5-yl)-5-hydroxyoctahydropentalen-2-yl)-N-(3-chloro-4-fluorophenyl)-1-methyl-1H-imidazole-5-carboxamide<br>$^1$H NMR (400 MHz, Methanol-$d_4$): δ 7.89 (dd, J = 6.7, 2.6 Hz, 1H), 7.67 (s, 1H), 7.51 (ddd, J = 8.9, 4.1, 2.6 Hz, 1H), 7.25 (td, J = 9.0, 1.2 Hz, 1H), 6.14 (d, J = 1.1 Hz, 1H), 3.97 (d, J = 1.1 Hz, 3H), 3.78 (s, 3H), 3.36 (dd, J = 12.2, 6.0 Hz, 1H), 2.58 (s, 2H), 2.42 (dd, J = 12.9, 7.6 Hz, 2H), 2.27 (dt, J = 12.6, 6.5 Hz, 2H), 2.02-1.81 (m, 4H), 1.51 (d, J = 1.2 Hz, 6H) ppm. MS calcd. for $C_{27}H_{32}ClFN_6O_3$: 542.2; Found: 541.0 $[M-1]^-$. |

TABLE 6-continued

| Examples 81-113 | |
|---|---|
| Example | $^1$H NMR and MS |
| Example 107 | 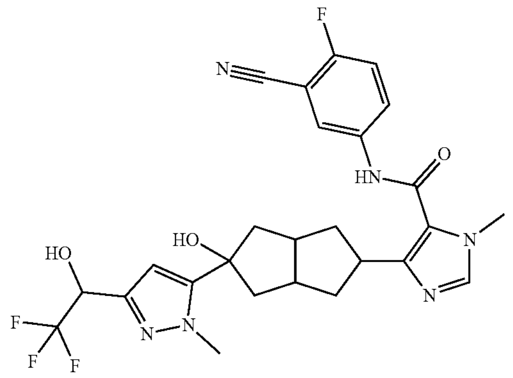 [SMILES: Cn1cnc(C2CC3CC(O)(c4cc(C(O)C(F)(F)F)nn4C)CC3C2)c1C(=O)Nc1ccc(F)c(C#N)c1] N-(3-Cyano-4-fluorophenyl)-4-(5-hydroxy-5-(1-methyl-3-(2,2,2-trifluoro-1-hydroxyethyl)-1H-pyrazol-5-yl)octahydropentalen-2-yl)-1-methyl-1H-imidazole-5-carboxamide $^1$H NMR (400 MHz, Methanol-$d_4$): δ 8.12 (dd, J = 5.7, 2.7 Hz, 1H), 7.93-7.86 (m, 1H), 7.68 (s, 1H), 7.38 (t, J = 9.0 Hz, 1H), 6.30 (s, 1H), 4.93 (d, J = 7.1 Hz, 1H), 4.00 (s, 3H), 3.79 (s, 3H), 3.43-3.34 (m, 1H), 2.63 (d, J = 33.3 Hz, 2H), 2.42 (dt, J = 15.5, 8.0 Hz, 2H), 2.33-2.18 (m, 2H), 2.08-1.79 (m, 4H) ppm. MS calcd. for $C_{26}H_{26}F_4N_6O_3$: 506.2; Found: 545.2 $[M - 1]^-$. |
| Example 108 | 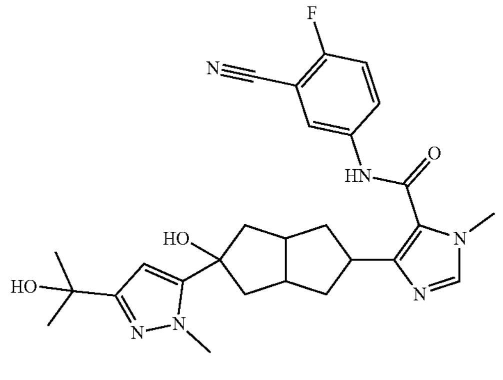 [SMILES: Cn1cnc(C2CC3CC(O)(c4cc(C(C)(C)O)nn4C)CC3C2)c1C(=O)Nc1ccc(F)c(C#N)c1] N-(3-Cyano-4-fluorophenyl)-4-(5-hydroxy-5-(3-(2-hydroxypropan-2-yl)-1-methyl-1H-pyrazol-5-yl)octahydropentalen-2-yl)-1-methyl-1H-imidazole-5-carboxamide $^1$H NMR (600 MHz, Methanol-$d_4$): δ 8.09 (dd, J = 5.6, 2.7 Hz, 1H), 7.88 (ddd, J = 9.1, 4.7, 2.7 Hz, 1H), 7.66 (s, 1H), 7.36 (t, J = 9.0 Hz, 1H), 6.15 (s, 1H), 3.93 (s, 3H), 3.77 (s, 3H), 3.35 (dt, J = 12.2, 6.1 Hz, 1H), 2.56 (t, J = 23.3 Hz, 2H), 2.40 (dd, J = 13.3, 7.4 Hz, 2H), 2.29-2.20 (m, 2H), 1.95 (dd, J = 13.0, 5.7 Hz, 2H), 1.88 (q, J = 11.8 Hz, 2H), 1.49 (s, 6H) ppm. MS calcd. for $C_{27}H_{31}FN_6O_3$: 506.2; Found: 505.0 $[M - 1]^-$. |

TABLE 6-continued

| Examples 81-113 | |
|---|---|
| Example | $^1$H NMR and MS |
| Example 109 | 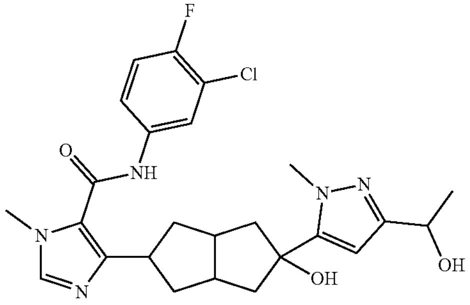 [SMILES: CC(O)c1cc(C2(O)CC3CC(c4ncn(C)c4C(=O)Nc4ccc(F)c(Cl)c4)CC3C2)n(C)n1]<br>N-(3-Chloro-4-fluorophenyl)-4-(5-hydroxy-5-(3-(1-hydroxyethyl)-1-methyl-1H-pyrazol-5-yl)octahydropentalen-2-yl)-1-methyl-1H-imidazole-5-carboxamide<br>$^1$H NMR (400 MHz, Acetonitrile-$d_3$) δ 8.31 (s, 1H), 7.89 (dd, J = 6.9, 2.7 Hz, 1H), 7.53 (d, J = 4.0 Hz, 1H), 7.50 (s, 1H), 7.27 (t, J = 9.1 Hz, 1H), 6.10 (s, 1H), 4.74 (d, J = 6.4 Hz, 1H), 3.93 (s, 3H), 3.75 (s, 3H), 3.33 (d, J = 12.3 Hz, 2H), 3.04 (s, 1H), 2.64 (s, 2H), 2.33 (d, J = 8.3 Hz, 2H), 1.86 (s, 1H), 1.84-1.77 (m, 2H), 1.41 (d, J = 6.6 Hz, 3H) ppm. MS calcd. for $C_{25}H_{29}ClFN_5O$: 501.2; Found: 500.2 $[M-1]^-$. |
| Example 110 | 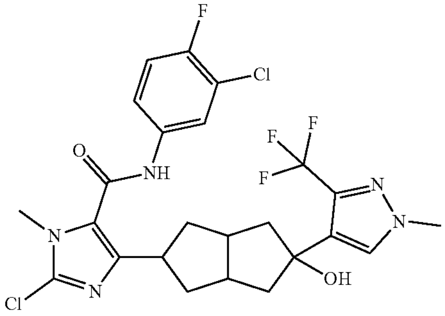<br>2-Chloro-N-(3-chloro-4-fluorophenyl)-4-(5-hydroxy-5-(1-methyl-3-(trifluoromethyl)-1H-pyrazol-4-yl)octahydropentalen-2-yl)-1-methyl-1H-imidazole-5-carboxamide.<br>$^1$H NMR (400 MHz, MeOH-$d_4$): δ 7.88 (dd, J = 6.6, 2.6 Hz, 1H), 7.66 (s, 1H), 7.57-7.48 (m, 1H), 7.26 (t, J = 8.9 Hz, 1H), 3.88 (s, 3H), 3.71 (s, 3H), 3.30-3.24 (m, 1H), 2.59 (s, 2H), 2.32 (dd, J = 13.4, 7.5 Hz, 2H), 2.27-2.16 (m, 2H), 2.06-1.78 (m, 4H) ppm. MS calcd. for $C_{24}H_{23}Cl_2F_4N_5O_2$: 559.1; Found: 558.0 $[M+1]^+$. |
| Example 111 | 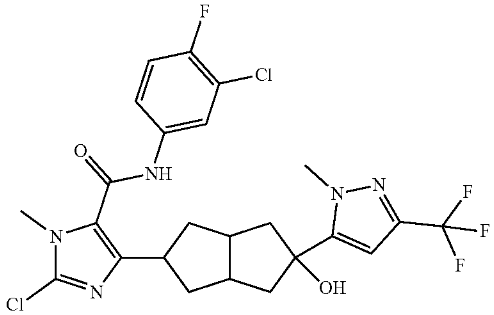 [SMILES: Cn1nc(C(F)(F)F)cc1C1(O)CC2CC(c3nc(Cl)n(C)c3C(=O)Nc3ccc(F)c(Cl)c3)CC2C1]<br>2-Chloro-N-(3-chloro-4-fluorophenyl)-4-(5-hydroxy-5-(1-methyl-3-(trifluoromethyl)-1H-pyrazol-5-yl)octahydropentalen-2-yl)-1-methyl-1H-imidazole-5-carboxamide<br>$^1$H NMR (400 MHz, MeOH-$d_4$): δ 7.90 (dd, J = 6.7, 2.7 Hz, 1H), 7.55-7.47 (m, 1H), 7.25 (t, J = 8.9 Hz, 1H), 6.50 (s, 1H), 4.06 (s, 3H), 3.71 (s, 3H), 3.28 (d, J = 7.0 Hz, 1H), 2.64 (d, J = 26.9 Hz, 2H), 2.40 (dd, J = 14.0, 6.8 Hz, 2H), 2.33-2.18 (m, 2H), 2.02 (dd, J = 13.4, 4.8 Hz, 2H), 1.97-1.83 (m, 2H) ppm. MS calcd. for $C_{24}H_{23}Cl_2F_4N_5O_2$: 559.1; Found: 558.0 $[M-1]^-$. |

TABLE 6-continued

| Examples 81-113 | |
|---|---|
| Example | $^1$H NMR and MS |
| Example 112 | 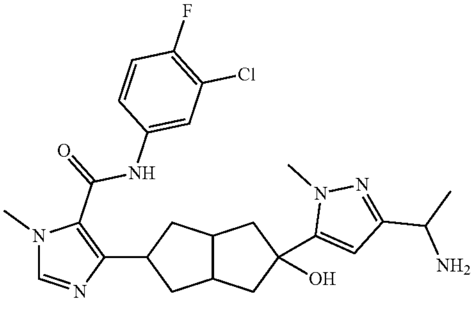 [SMILES: CC(N)c1cc(C2(O)CC3CC(c4ncn(C)c4C(=O)Nc4ccc(F)c(Cl)c4)CC3C2)n(C)n1]<br>4-(5-(3-(1-Aminoethyl)-1-methyl-1H-pyrazol-5-yl)-5-hydroxyoctahydropentalen-2-yl)-N-(3-chloro-4-fluorophenyl)-1-methyl-1H-imidazole-5-carboxamide.<br>$^1$H NMR (400 MHz, MeOH-$d_4$): δ 7.88 (dd, J = 6.7, 2.6 Hz, 1H), 7.66 (s, 1H), 7.57 (s, 1H), 7.55-7.50 (m, 1H), 7.26 (t, J = 9.0 Hz, 1H), 6.26 (s, 1H), 4.10 (s, 3H), 3.77 (s, 3H), 3.41-3.34 (m, 1H), 2.64 (d, J = 28.2 Hz, 2H), 2.23 (dd, J = 11.8, 6.0 Hz, 2H), 1.90 (s, 2H), 1.83-1.70 (m, 2H), 1.53 (dd, J = 13.1, 5.5 Hz, 2H), 1.41 (d, J = 6.7 Hz, 3H) ppm. MS calcd. for $C_{25}H_{30}ClFN_6O_2$: 500.2; Found: 499.2 $[M - 1]^-$. |
| Example 113 | 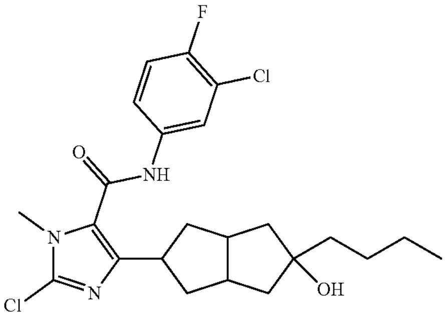 [SMILES: CCCCC1(O)CC2CC(c3nc(Cl)n(C)c3C(=O)Nc3ccc(F)c(Cl)c3)CC2C1]<br>4-(5-Butyl-5-hydroxyoctahydropentalen-2-yl)-2-chloro-N-(3-chloro-4-fluorophenyl)-1-methyl-1H-imidazole-5-carboxamide.<br>$^1$H NMR (400 MHz, Chloroform-d): δ 7.82-7.72 (m, 1H), 7.45 (s, 1H), 7.39-7.29 (m, 1H), 7.21-7.08 (m, 1H), 3.78 (d, J = 1.0 Hz, 3H), 3.19 (tt, J = 12.1, 6.2 Hz, 1H), 2.76-2.50 (m, 2H), 2.30-2.14 (m, 2H), 2.14-2.01 (m, 2H), 1.90 (dd, J = 13.3, 7.7 Hz, 2H), 1.65 (dd, J = 13.3, 3.8 Hz, 3H), 1.59-1.48 (m, 2H), 1.43-1.18 (m, 4H), 1.12-0.68 (m, 3H) ppm; MS calcd. for $C_{23}H_{28}Cl_2FN_3O_2$: 467.2; Found: 468.2 $[M + 1]^+$. |

Example 114

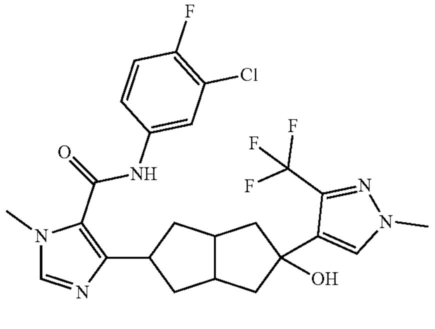

N-(3-Chloro-4-fluorophenyl)-4-(5-hydroxy-5-(1-methyl-3-(trifluoromethyl)-1H-pyrazol-4-yl)octahydropentalen-2-yl)-1-methyl-1H-imidazole-5-carboxamide: To a solution of 4-bromo-1-methyl-3-(trifluoromethyl)-1H-pyrazole (5.8 g, 25.0 mmol) in dry $Et_2O$ (65 mL) was added t-BuLi (1.3 M, 19.5 mL, 25.0 mmol) dropwise and the mixture stirred for 5 mins at −78° C. in an $N_2$ atmosphere. Then a solution of N-(3-chloro-4-fluorophenyl)-1-methyl-4-(5-oxooctahydropentalen-2-yl)-1H-imidazole-5-carboxamide (940.0 mg, 2.5 mmol) in dry THF (3 mL) was added dropwise at −78° C. The reaction mixture was stirred for 4 h at −78° C. The mixture was quenched with $NH_4Cl$ solution (3 mL) and concentrated in vacuo to give the crude product, which was purified by column chromatography to afford N-(3-chloro-4-fluorophenyl)-4-(5-hydroxy-5-(1-methyl-3-(trifluoromethyl)-1H-pyrazol-4-yl)octahydropentalen-2-yl)-1-methyl-1H-imidazole-5-carboxamide (600.0 mg, 46%), a white solid as a single diastereomer. MS calcd. for $C_{24}H_{24}ClF_4N_5O_2$: 525.2; Found: 525.9 $[M+1]^+$; $^1$H NMR (400 MHz, d6-DMSO): δ 10.23 (s, 1H), 7.96 (dd, J=6.8, 2.0 Hz, 1H), 7.77 (s, 1H), 7.65 (s, 1H), 7.61-7.54 (m, 1H), 7.41

(t, J=9.2 Hz, 1H), 4.87 (s, 1H), 3.83 (s, 3H), 3.68 (s, 3H), 3.28-3.17 (m, 1H), 2.48-2.41 (m, 2H), 2.41-2.03 (m, 4H), 1.93-1.77 (m, 4H) ppm.

Example 115

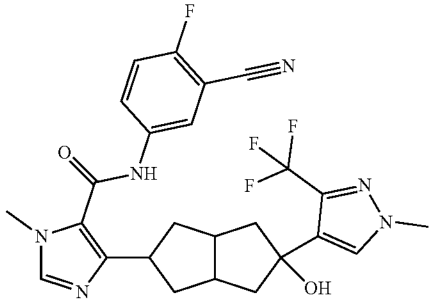

N-(3-Cyano-4-fluorophenyl)-4-(5-hydroxy-5-(1-methyl-3-(trifluoromethyl)-1H-pyrazol-4-yl)octahydropentalen-2-yl)-1-methyl-1H-imidazole-5-carboxamide. To a solution of N-(3-chloro-4-fluorophenyl)-4-(5-hydroxy-5-(1-methyl-3-(trifluoromethyl)-1H-pyrazol-4-yl)octahydropentalen-2-yl)-1-methyl-1H-imidazole-5-carboxamide (740.0 mg, 1.4 mmol) in dioxane/H2O (45 mL, v/v=2:1) was added $Zn(CN)_2$ (1.7 g, 14.0 mmol), t-BuXPhos (300.0 mg, 0.7 mmol) and 3rd generation t-BuXPhos precatalyst (560.0 mg, 0.7 mmol). The reaction was stirred at 60° C. for 4 hours. The reaction was cooled to room temperature, filtered through a pad of celite, washed with methanol, concentrated to give the crude, which was purified by column chromatography and reverse phase chromatography to afford N-(3-cyano-4-fluorophenyl)-4-(5-hydroxy-5-(1-methyl-3-(trifluoromethyl)-1H-pyrazol-4-yl)octahydropentalen-2-yl)-1-methyl-1H-imidazole-5-carboxamide (270.0 mg, 37.3%) as a white solid. TLC: 7% MeOH/DCM (Rf: 0.3); MS calcd. for $C_{25}H_{24}F_4N6O_2$: 516.2; Found: 517.0 $[M+1]^+$, 499.0 $[M-18+1]^+$; 1H NMR (400 MHz, $CD_3OD$): δ 8.09 (dd, J=5.6, 2.8 Hz, 1H), 7.91-7.81 (m, 1H), 7.66 (s, 1H), 7.65 (s, 1H), 7.37 (t, J=9.2 Hz, 1H), 3.86 (s, 3H), 3.77 (s, 3H), 3.37-3.33 (m, 1H), 2.60-2.54 (m, 2H), 2.34-2.29 (m, 2H), 2.27-2.20 (m, 2H), 1.94-1.89 (m, 4H) ppm.

Intermediate 31

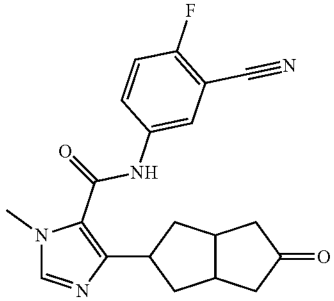 [SMILES: Cn1cnc(C2CC3CC(=O)CC3C2)c1C(=O)Nc1ccc(F)c(C#N)c1]

N-(3-Cyano-4-fluorophenyl)-1-methyl-4-(5-oxooctahydropentalen-2-yl)-1H-imidazole-5-carboxamide. tBuXPhos-Pd-G3 (6.3 g, 8 mmol) and t-BuXPhos (3.4 g, 8 mmol) were added to a solution of $Zn(CN)_2$ (9.4 g, 80 mmol) and N-(3-chloro-4-fluorophenyl)-1-methyl-4-(5-oxooctahydropentalen-2-yl)-1H-imidazole-5-carboxamide (6 g, 16 mmol) in dioxane (250 mL) under N2. The mixture was stirred at 85° C. overnight. It was then cooled, filtered, washed with EA and the organic layer concentrated in vacuo. The residue was purified by silica gel chromatography using 1-5% MeOH/DCM (v/v) to give N-(3-cyano-4-fluorophenyl)-1-methyl-4-(5-oxooctahydropentalen-2-yl)-1H-imidazole-5-carboxamide (4 g, 68%) as a yellow solid. TLC: 5% EtOH/DCM (Rf: 0.5); MS calcd. for $C_{20}H_{19}FN_4O_2$: 366.1; Found: 367.1 $[M+1]^+$.

Synthesis of Examples 116-222. Examples 116-222 in Table 7 were synthesized according to the procedures provided above using the corresponding starting materials.

TABLE 7

| Examples 116-222 | |
|---|---|
| Example 116 | 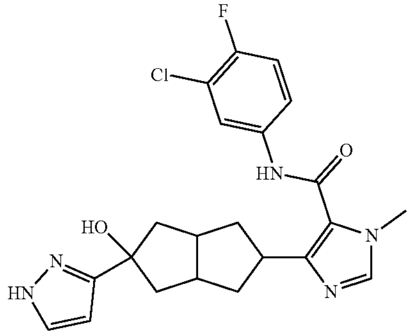 [SMILES: Cn1cnc(C2CC3CC(O)(c4cc[nH]n4)CC3C2)c1C(=O)Nc1ccc(F)c(Cl)c1] N-(3-chloro-4-fluorophenyl)-4-(5-hydroxy-5-(1H-pyrazol-3-yl)octahydropentalen-2-yl)-1-methyl-1H-imidazole-5-carboxamide. $^1H$ NMR (MeOH-d4, 400 MHz): δ 8.74 (s, 1H), 7.94 (dd, J = 6.4, 2.4 Hz, 1H), 7.53-7.53 (m, 1H), 7.50 (s, 1H), 7.26 (t, J = 8.8 Hz, 1H), 6.27 (s, 2H), 3.92 (s, 3H), 3.42-3.37 (m, 1H), 2.74-2.73 (m, 2H), 2.39-2.31 (m, 4H), 1.97-1.91 (m, 4H) ppm; MS calcd. for $C_{22}H_{23}ClFN_5O_2$: 443.2; Found: 444.3 $[M + 1]^+$. |

TABLE 7-continued

Examples 116-222

Example 117

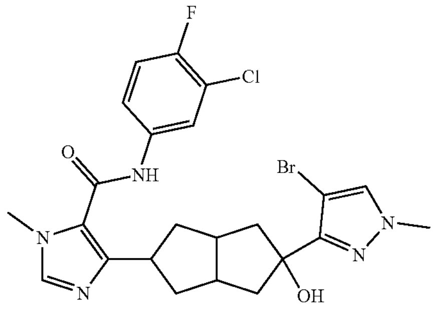

4-(5-(4-bromo-1-methyl-1H-pyrazol-3-yl)-5-hydroxyoctahydropentalen-2-yl)-N-(3-chloro-4-fluorophenyl)-1-methyl-1H-imidazole-5-carboxamide.
$^1$H NMR (MeOH-d4, 400 MHz): δ 7.88 (dd, J = 6.8, 2.4 Hz, 1H), 7.65 (s, 1H), 7.59 (s, 1H), 7.52-7.46 (m, 1H), 7.23 (t, J = 9.2 Hz, 1H), 3.80 (s, 3H), 3.76 (s, 3H), 3.28-3.25 (m, 1H), 2.73-2.64 (m, 2H), 2.58-2.47 (m, 2H), 2.28-2.17 (m, 2H), 1.92-1.81 (m, 4H) ppm. MS calcd. for $C_{23}H_{24}BrClFN_5O_2$: 535.1; Found: 536.2 $[M + 1]^+$.

Example 118

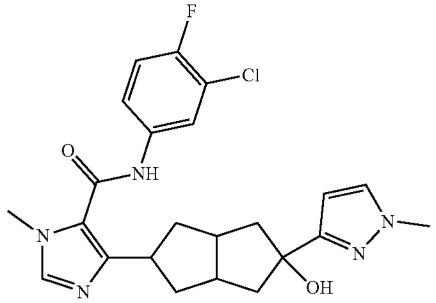

N-(3-chloro-4-fluorophenyl)-4-(5-hydroxy-5-(1-methyl-1H-pyrazol-3-yl)octahydropentalen-2-yl)-1-methyl-1H-imidazole-5-carboxamide.
$^1$H NMR (MeOH-d4, 400 MHz): δ 7.88 (dd, J = 6.8, 2.4 Hz, 1H), 7.81 (s, 1H), 7.53-7.47 (m, 1H), 7.44 (d, J = 2.4 Hz, 1H), 7.24 (t, J = 9.2 Hz, 1H), 6.26 (d, J = 2.4 Hz, 1H), 3.83 (s, 3H), 3.79 (s, 3H), 3.29-3.25 (m, 1H), 2.63-2.54 (m, 2H), 2.45-2.36 (m, 2H), 2.29-2.20 (m, 2H), 1.94-1.84 (m, 4H) ppm. MS calcd. for $C_{23}H_{25}ClFN_5O_2$: 457.2. Found: 458.3 $[M + 1]^+$.

Example 119

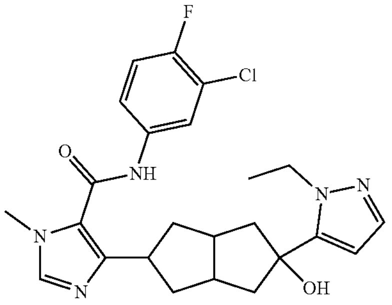 [SMILES: CCn1nccc1C1(O)CC2CC(c3ncn(C)c3C(=O)Nc3ccc(F)c(Cl)c3)CC2C1]

N-(3-chloro-4-fluorophenyl)-4-(5-(1-ethyl-1H-pyrazol-5-yl)-5-hydroxyoctahydropentalen-2-yl)-1-methyl-1H-imidazole-5-carboxamide.
$^1$H NMR (MeOH-d4, 400 MHz): δ 7.79 (dd, J = 6.8, 2.8 Hz, 1H), 7.45-7.36 (m, 1H), 7.18 (t, J = 9.2 Hz, 1H), 3.66 (s, 3H), 3.55 (s, 3H), 3.54-3.46 (m, 1H), 2.99 (d, J = 11.2 Hz, 2H), 2.72-2.60 (m, 1H), 2.56-2.46 (m, 2H), 2.40-2.26 (m, 3H), 2.24-2.08 (m, 4H), 1.93-1.84 (m, 2H), 1.78-1.67 (m, 2H), 1.62-1.52 (m, 2H), 1.36-1.21 (m, 3H) ppm. MS calcd. for $C_{24}H_{27}ClFN_5O_2$: 471.2; Found: 472.2 $[M + 1]^+$.

TABLE 7-continued

| Examples 116-222 | |
| --- | --- |
| Example 120 | 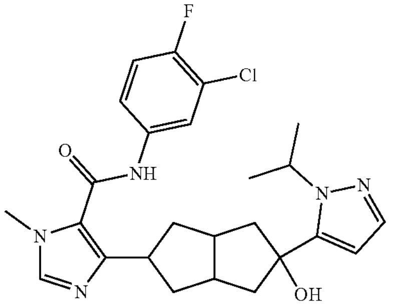 [SMILES: CC(C)n1nccc1C1(O)CC2CC(c3ncn(C)c3C(=O)Nc3ccc(F)c(Cl)c3)CC2C1]<br>N-(3-chloro-4-fluorophenyl)-4-(5-hydroxy-5-(1-isopropyl-1H-pyrazol-5-yl)octahydropentalen-2-yl)-1-methyl-1H-imidazole-5-carboxamide. $^1$H NMR (DMSO-d6, 400 MHz): δ 10.23 (s, 1H), 7.96 (dd, J = 6.8, 2.4 Hz, 1H), 7.66 (s, 1H), 7.59-7.55 (m, 1H), 7.41 (t, J = 9.2 Hz, 1H), 7.26 (d, J = 1.2 Hz, 1H), 6.00 (d, J = 1.6 Hz, 1H), 5.28 (s, 1H), 5.09-5.06 (m, 1H), 3.68 (s, 3H), 3.26-3.23 (m, 1H), 2.47-2.46 (m, 2H), 2.21-2.16 (m, 2H), 2.12-2.08 (m, 2H), 1.91-1.84 (m, 4H), 1.36-1.34 (m, 6H) ppm; MS calcd. for $C_{25}H_{29}ClFN_5O_2$: 485.2. Found: 486.3 $[M + 1]^+$. |
| Example 121 | 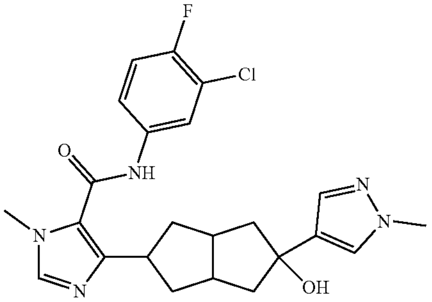<br>N-(3-chloro-4-fluorophenyl)-4-(5-hydroxy-5-(1-methyl-1H-pyrazol-4-yl)octahydropentalen-2-yl)-1-methyl-1H-imidazole-5-carboxamide. $^1$H-NMR (DMSO-d6, 400 MHz): δ 10.22 (s, 1H), 7.96 (dd, J = 6.8, 2.8 Hz, 1H), 7.65 (s, 1H), 7.60-7.54 (m, 1H), 7.50 (s, 1H), 7.41 (t, J = 9.2 Hz, 1H), 7.29 (s, 1H), 4.73 (s, 1H), 3.75 (s, 3H), 3.67 (s, 3H), 3.27-3.16 (m, 1H), 2.45-2.37 (m, 2H), 2.11-1.99 (m, 4H), 1.90-1.80 (m, 2H), 1.72 (dd, J = 12.6, 4.2 Hz, 2H) ppm. MS calcd. for $C_{23}H_{25}ClFN_5O_2$: 457.2; Found: 458.3 $[M + 1]^+$. |
| Example 122 | 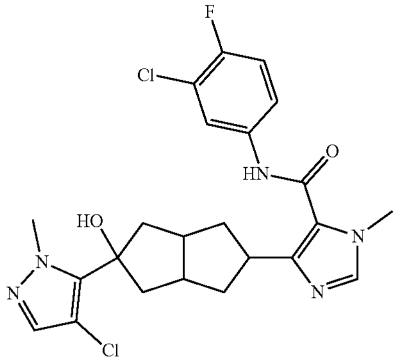 [SMILES: Cn1cnc(C2CC3CC(O)(c4c(Cl)cnn4C)CC3C2)c1C(=O)Nc1ccc(F)c(Cl)c1]<br>4-(5-(4-chloro-1-methyl-1H-pyrazol-5-yl)-5-hydroxyoctahydro-pentalen-2-yl)-N-(3-chloro-4-fluorophenyl)-1-methyl-1H-imidazole-5-carboxamide. $^1$H NMR (DMSO-d6, 400 MHz): δ 10.24 (s, 1H), 7.97 (dd, J = 6.8, 2.4 Hz, 1H), 7.65 (s, 1H), 7.61-7.55 (m, 1H), 7.41 (t, J = 9.2 Hz, 1H), 7.35 (s, 1H), 5.37 (s, 1H), 3.96 (s, 3H), 3.68 (s, 3H), 3.27-3.17 (m, 1H), 2.64-2.53 (m, 2H), 2.41-2.31 (m, 2H), 2.14-1.94 (m, 6H) ppm. MS calcd. for $C_{23}H_{24}Cl_2FN_5O_2$: 491.1; Found: 492.2 $[M + 1]^+$. |

TABLE 7-continued

| Examples 116-222 | |
|---|---|
| Example 123 | 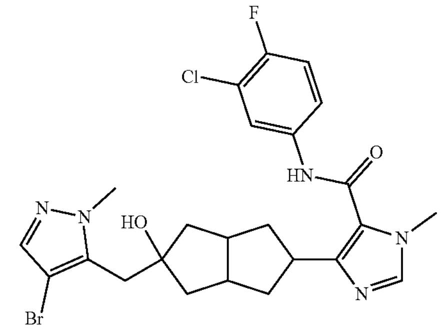 [SMILES: Cn1cnc(C2CC3CC(O)(Cc4c(Br)cnn4C)CC3C2)c1C(=O)Nc1ccc(F)c(Cl)c1] 4-(5-((4-bromo-1-methyl-1H-pyrazol-5-yl)methyl)-5-hydroxyoctahydropentalen-2-yl)-N-(3-chloro-4-fluorophenyl)-1-methyl-1H-imidazole-5-carboxamide. $^1$H NMR (DMSO-d6, 400 MHz): δ 10.24 (s, 1H), 7.97 (dd, J = 6.8, 2.4 Hz, 1H), 7.66 (s, 1H), 7.61-7.55 (m, 1H), 7.44 (s, 1H), 7.41 (t, J = 9.0 Hz, 1H), 4.78 (s, 1H), 3.84 (s, 3H), 3.68 (s, 3H), 3.31-3.20 (m, 1H), 2.77 (s, 2H), 2.62-2.52 (m, 2H), 2.15-2.05 (m, 2H), 1.94-1.85 (m, 2H), 1.80-1.68 (m, 2H), 1.48 (dd, J = 12.8, 4.8 Hz, 2H) ppm. MS calcd. for $C_{24}H_{26}BrClFN_5O_2$: 549.1. Found: 550.2 $[M + 1]^+$. |
| Example 124 | 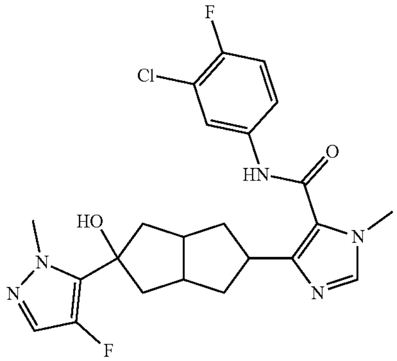 [SMILES: Cn1cnc(C2CC3CC(O)(c4c(F)cnn4C)CC3C2)c1C(=O)Nc1ccc(F)c(Cl)c1] N-(3-chloro-4-fluorophenyl)-4-(5-(4-fluoro-1-methyl-1H-pyrazol-5-yl)-5-hydroxyoctahydropentalen-2-yl)-1-methyl-1H-imidazole-5-carboxamide. $^1$H NMR (DMSO-d6, 400 MHz): δ 12.23 (s, 1H), 7.97 (dd, J = 6.4, 2.4 Hz, 1H), 7.64 (s, 1H), 7.59-7.55 (m, 1H), 7.43-7.39 (m, 1H), 7.31 (s, 1H), 5.36 (s, 1H), 3.87 (s, 3H), 3.68 (s, 3H), 3.28-3.22 (m, 1H), 2.51-2.49 (m, 2H), 2.27-2.23 (m, 2H), 2.11-2.07 (m, 2H), 1.97-1.89 (m, 4H) ppm. MS calcd. for $C_{23}H_{24}ClF_2N_5O_2$: 475.2. Found: 476.2 $[M + 1]^+$. |

TABLE 7-continued

| Examples 116-222 |
| --- |

Example 125

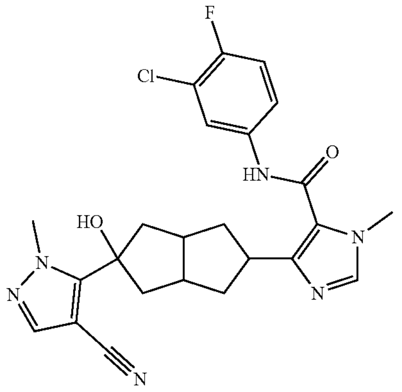 [SMILES: Cn1cnc(C2CC3CC(O)(c4c(C#N)cnn4C)CC3C2)c1C(=O)Nc1ccc(F)c(Cl)c1]

N-(3-chloro-4-fluorophenyl)-4-(5-(4-cyano-1-methyl-1H-pyrazol-5-yl)-5-hydroxyoctahydropentalen-2-yl)-1-methyl-1H-imidazole-5-carboxamide.

$^1$H NMR (DMSO-d6, 400 MHz): δ 10.24 (s, 1H), 7.97 (dd, J = 6.8, 2.4 Hz, 1H), 7.91 (s, 1H), 7.66 (s, 1H), 7.61-7.55 (m, 1H), 7.41 (t, J = 9.2 Hz, 1H), 5.65 (s, 1H), 4.00 (s, 3H), 3.68 (s, 3H), 3.28-3.18 (m, 1H), 2.66-2.56 (m, 2H), 2.38-2.29 (m, 2H), 2.16-2.05 (m, 4H), 2.04-1.94 (m, 2H) ppm. MS calcd. for $C_{24}H_{24}ClFN_6O_2$: 482.2. Found: 483.2 $[M + 1]^+$.

Example 126

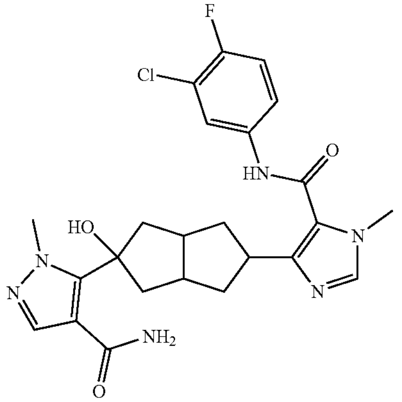 [SMILES: Cn1cnc(C2CC3CC(O)(c4c(C(N)=O)cnn4C)CC3C2)c1C(=O)Nc1ccc(F)c(Cl)c1]

5-(5-(5-((3-chloro-4-fluorophenyl)carbamoyl)-1-methyl-1H-imidazol-4-yl)-2-hydroxyoctahydropentalen-2-yl)-1-methyl-1H-pyrazole-4-carboxamide.

$^1$H NMR (DMSO-d6, 400 MHz): δ 10.24 (s, 1H), 7.97 (dd, J = 6.8, 2.4 Hz, 1H), 7.75 (s, 1H), 7.64 (s, 2H), 7.61-7.54 (m, 1H), 7.41 (t, J = 9.2 Hz, 1H), 7.30 (s, 1H), 6.36 (s, 1H), 3.94 (s, 3H), 3.67 (s, 3H), 3.24-3.12 (m, 1H), 2.65-2.55 (m, 2H), 2.34-2.24 (m, 2H), 2.13-1.96 (m, 6H) ppm. MS calcd. for $C_{24}H_{26}ClFN_6O_3$: 500.2; Found: 501.2 $[M + 1]^+$.

TABLE 7-continued

| Examples 116-222 | |
|---|---|
| Example 127 | 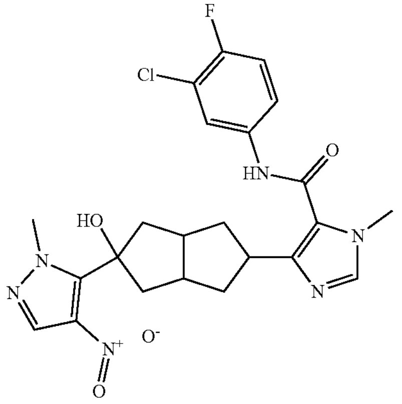<br>N-(3-chloro-4-fluorophenyl)-4-(5-hydroxy-5-(1-methyl-4-nitro-1H-pyrazol-5-yl)octahydropentalen-2-yl)-1-methyl-1H-imidazole-5-carboxamide.<br>$^1$H NMR (DMSO-d6, 400 MHz): δ 10.24 (s, 1H), 8.15 (s, 1H), 7.98 (dd, J = 6.8, 2.4 Hz, 1H), 7.65 (s, 1H), 7.60-7.58 (m, 1H), 7.44-7.39 (m, 1H), 5.56 (s, 1H), 4.10 (s, 3H), 3.69 (s, 3H), 3.22-3.17 (m, 1H), 2.74-2.66 (m, 2H), 2.44-2.39 (m, 2H), 2.12-2.07 (m, 4H), 2.00 (s, 1H), 1.96 (s, 1H) ppm. MS calcd. for $C_{23}H_{24}ClFN_6O_4$: 502.2; Found: 503.3 $[M + 1]^+$. |
| Example 128 | 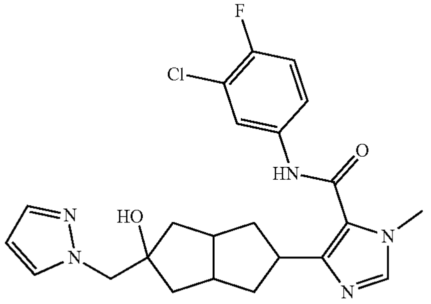 [SMILES: Cn1cnc(C2CC3CC(O)(Cn4cccn4)CC3C2)c1C(=O)Nc1ccc(F)c(Cl)c1]<br>Isomer I<br>4-(5-((1H-pyrazol-1-yl)methyl)-5-hydroxyoctahydropentalen-2-yl)-N-(3-chloro-4-fluorophenyl)-1-methyl-1H-imidazole-5-carboxamide.<br>$^1$H NMR (MeOH-d4, 400 MHz): δ 7.87 (dd, J = 6.8, 2.8 Hz, 1H), 7.64 (s, 1H), 7.62 (d, J = 2.0 Hz, 1H), 7.53-7.47 (m, 1H), 7.45 (d, J = 1.2 Hz, 1H), 7.23 (t, J = 9.2 Hz, 1H), 6.28 (t, J = 2.0 Hz, 1H), 4.25 (s, 2H), 3.75 (s, 3H), 3.45-3.34 (m, 1H), 2.83-2.70 (m, 2H), 2.27-2.16 (m, 2H), 1.87-1.75 (m, 2H), 1.61-1.49 (m, 4H) ppm; MS calcd. for $C_{23}H_{25}ClFN_5O_2$: 457.2. Found; 458.2 $[M + 1]^+$. |
| Example 129 | 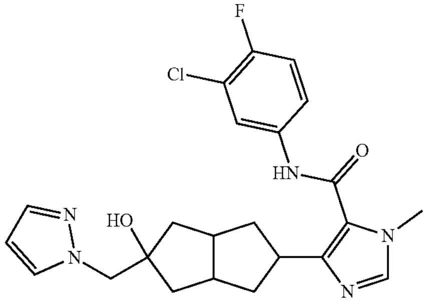 [SMILES: Cn1cnc(C2CC3CC(O)(Cn4cccn4)CC3C2)c1C(=O)Nc1ccc(F)c(Cl)c1]<br>Isomer II<br>4-(5-((1H-pyrazol-1-yl)methyl)-5-hydroxyoctahydropentalen-2-yl)-N-(3-chloro-4-fluorophenyl)-1-methyl-1H-imidazole-5-carboxamide.<br>$^1$H NMR (MeOH-d4, 400 MHz): δ 7.87 (dd, J = 6.8, 2.8 Hz, 1H), 7.66-7.62 (m, 2H), 7.54-7.48 (m, 1H), 7.47-7.44 (m, 1H), 7.24 (t, J = 9.2 Hz, 1H), 6.29 (t, J = 2.4 Hz, 1H), 4.41 (s, 2H), 3.76 (s, 3H), 3.38-3.32 (m, 1H), 2.65-2.53 (m, 2H), 2.27-2.17 (m, 2H), 1.94-1.83 (m, 2H), 1.80-1.68 (m, 2H), 1.55-1.47 (m, 2H) ppm. MS calcd. for $C_{23}H_{25}ClFN_5O_2$: 457.2. Found: 458.3 $[M + 1]^+$. |

TABLE 7-continued

Examples 116-222

Example 130

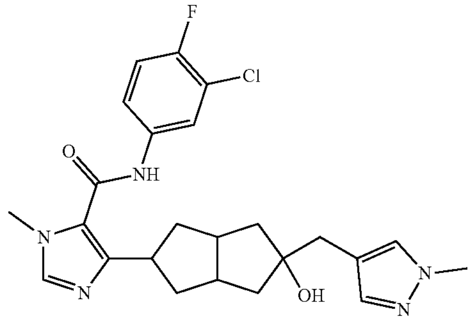

N-(3-chloro-4-fluorophenyl)-4-(5-hydroxy-5-((1-methyl-1H-pyrazol-4-yl)methyl)octahydropentalen-2-yl)-1-methyl-1H-imidazole-5-carboxamide.

$^1$H NMR (MeOH-d4, 400 MHz): δ 7.87-7.85 (dd, J = 2.4 Hz, J = 7.2 Hz, 1H), 7.64 (s, 1H), 7.52-7.50 (m, 1H), 7.41 (s, 1H), 7.26-7.21 (m, 2H), 4.05 (s, 2H), 3.75 (s, 3H), 3.29-3.32 (m, 1H), 2.59-2.56 (m, 2H), 2.22-2.11 (m, 2H), 2.06 (s, 3H), 1.89-1.83 (m, 2H), 1.75-1.72 (m, 2H), 1.52-1.47 (m, 2H) ppm. MS calcd. for $C_{24}H_{27}ClFN_5O_2$: 471.2. Found: 472.3 $[M + 1]^+$.

Example 131

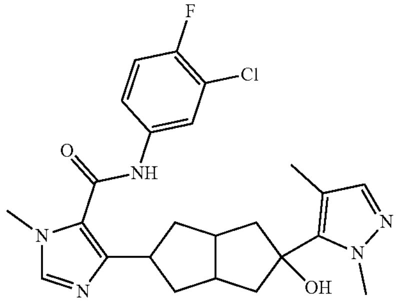 [SMILES: Cc1cnn(C)c1C1(O)CC2CC(c3ncn(C)c3C(=O)Nc3ccc(F)c(Cl)c3)CC2C1]

N-(3-chloro-4-fluorophenyl)-4-(5-(1,4-dimethyl-1H-pyrazol-5-yl)-5-hydroxyoctahydropentalen-2-yl)-1-methyl-1H-imidazole-5-carboxamide.

$^1$H NMR (MeOH-d4, 400 MHz): 7.87-7.90 (dd, J = 2.4 Hz, 7.2 Hz, 1H), 7.63 (s, 1H), 7.49-7.53 (m, 1H), 7.24 (t, J = 8.8 Hz, 1H), 7.08 (s, 1H), 3.96 (s, 3H), 3.74 (d, J = 4.8 Hz, 3H), 3.27-3.31 (m, 1H), 2.67-2.69 (m, 2H), 2.04-2.39 (m, 11H) ppm. MS calcd. for $C_{24}H_{27}ClFN_5O_2$: 471.2; Found: 472.2 $[M + 1]^+$.

Example 132

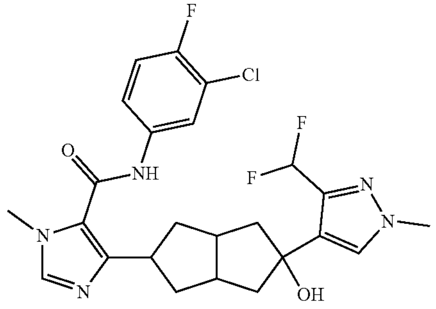

N-(3-chloro-4-fluorophenyl)-4-(5-(3-(difluoromethyl)-1-methyl-1H-pyrazol-4-yl)-5-hydroxyoctahydropentalen-2-yl)-1-methyl-1H-imidazole-5-carboxamide.

$^1$H NMR (DMSO-d6, 400 MHz): δ 10.23 (s, 1H), 7.95 (dd, J = 7.2, 2.8 Hz, 1H), 7.95-7.65 (m, 2H), 7.59-7.55 (m, 1H), 7.40 (t, J = 9.0 Hz, 1H), 7.11 (t, J = 54.6 Hz, 1H), 5.02 (s, 1H), 3.79 (s, 3H), 3.67 (s, 3H), 3.24-3.21 (m, 1H), 2.50-2.49 (m, 2H), 2.09-2.01 (m, 4H), 1.89-1.77 (m, 4H) ppm; MS calcd. for $C_{24}H_{25}ClF_3N_5O_2$: 507.2; Found: 508.2 $[M + 1]^+$.

TABLE 7-continued

Examples 116-222

Example 133

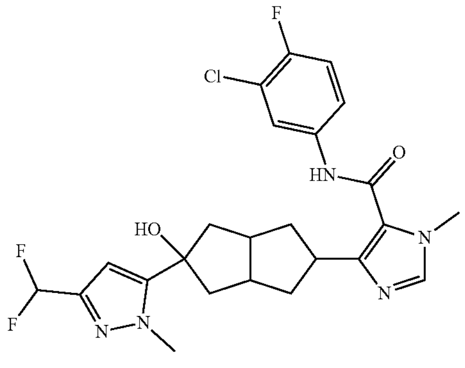 [SMILES: Cn1cnc(C2CC3CC(O)(c4cc(C(F)F)nn4C)CC3C2)c1C(=O)Nc1ccc(F)c(Cl)c1]

N-(3-chloro-4-fluorophenyl)-4-(5-(3-(difluoromethyl)-1-methyl-1H-pyrazol-5-yl)-5-hydroxyoctahydropentalen-2-yl)-1-methyl-1H-imidazole-5-carboxamide.
$^1$H NMR (DMSO-d6, 400 MHz): δ 10.23 (s, 1H), 7.96 (dd, J = 6.8, 2.4 Hz, 1H), 7.65 (m, 1H), 7.59-7.55 (m, 1H), 7.40 (t, J = 9.2 Hz, 1H), 6.86 (t, J = 56.4 Hz, 1H), 6.35 (s, 1H), 5.37 (s, 1H), 3.94 (s, 3H), 3.67 (s, 3H), 3.31-3.29 (m, 1H), 2.50-2.49 (m, 2H), 2.25-2.20 (m, 2H), 2.11-2.09 (m, 2H), 1.90-1.85 (m, 4H) ppm; MS calcd. for $C_{24}H_{25}ClF_3N_5O_2$: 507.2; Found: 508.3 $[M + 1]^+$.

Example 134

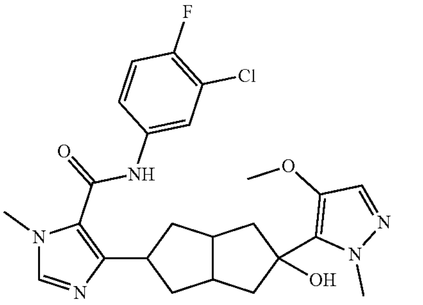 [SMILES: COc1cnn(C)c1C1(O)CC2CC(c3ncn(C)c3C(=O)Nc3ccc(F)c(Cl)c3)CC2C1]

N-(3-chloro-4-fluorophenyl)-4-(5-hydroxy-5-(4-methoxy-1-methyl-1H-pyrazol-5-yl)octahydropentalen-2-yl)-1-methyl-1H-imidazole-5-carboxamide.
$^1$H NMR (DMSO-d6, 400 MHz): δ 10.22 (s, 1H), 7.96 (dd, J = 6.8, 2.4 Hz, 1H), 7.64 (s, 1H), 7.42 (t, J = 9.2 Hz, 1H), 7.18 (s, 1H), 5.08 (s, 1H), 3.86 (s, 3H), 3.67 (s, 3H), 3.64 (s, 3H), 5.50-5.40 (m, 1H), 2.51-2.45 (m, 2H), 2.37-2.25 (m, 2H), 2.08-1.81 (m, 6H) ppm. MS calcd. for $C_{24}H_{27}ClFN_5O_3$: 487.2. Found: 487.9 $[M + 1]^+$.

Example 135

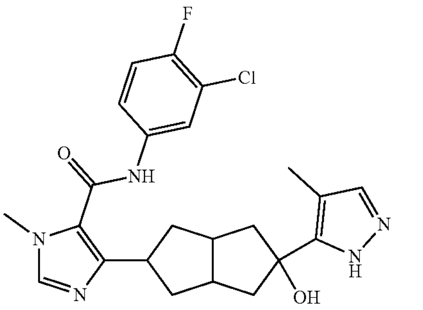 [SMILES: Cc1cn[nH]c1C1(O)CC2CC(c3ncn(C)c3C(=O)Nc3ccc(F)c(Cl)c3)CC2C1]

N-(3-chloro-4-fluorophenyl)-4-(5-hydroxy-5-(4-methyl-1H-pyrazol-5-yl)octahydropentalen-2-yl)-1-methyl-1H-imidazole-5-carboxamide.
$^1$H NMR (DMSO-d6, 400 MHz) δ 11.87 (s, 1H), 10.21 (s, 1H), 7.97 (dd, J = 6.8, 2.4 Hz, 1H), 7.65 (s, 1H), 7.61-7.53 (m, 1H), 7.40 (t, J = 9.2 Hz, 1H), 7.25 (s, 1H), 4.76 (s, 1H), 3.68 (s, 3H), 3.26-3.15 (m, 1H), 2.47-2.37 (m, 2H), 2.32-2.18 (m, 2H), 2.11-2.01 (m, 5H), 1.95-1.83 (m, 2H), 1.83-1.71 (m, 2H) ppm. MS calcd. for $C_{23}H_{25}ClFN_5O_2$: 457.2. Found: 458.2 $[M + 1]^+$.

TABLE 7-continued

| Examples 116-222 | |
|---|---|
| Example 136 | 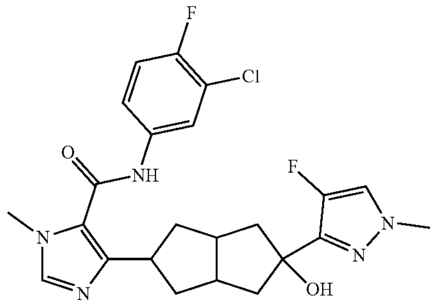<br>N-(3-chloro-4-fluorophenyl)-4-(5-(4-fluoro-1-methyl-1H-pyrazol-3-yl)-5-hydroxyoctahydropentalen-2-yl)-1-methyl-1H-imidazole-5-carboxamide.<br>$^1$H-NMR (DMSO-d6, 400 MHz): δ 10.20 (s, 1H), 7.96 (dd, J = 6.8, 2.4 Hz, 1H), 7.68 (d, J = 4.8 Hz, 1H), 7.66 (s, 1H), 7.59-7.55 (m, 1H), 7.40 (t, J = 8.8 Hz, 1H), 4.93 (s, 1H), 3.68 (s, 3H), 3.67 (s, 3H), 3.24-3.21 (m, 1H), 2.35-2.30 (m, 4H), 2.09-2.06 (m, 2H), 1.84-1.71 (m, 2H) ppm. MS calcd. for $C_{23}H_{24}ClF_2N_5O_2$: 475.2. Found; 475.9 $[M + 1]^+$. |
| Example 137 | 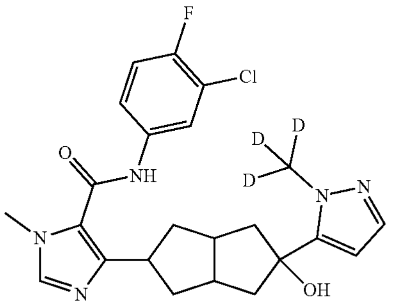 [SMILES: [2H]C([2H])([2H])n1nccc1C1(O)CC2CC(c3ncn(C)c3C(=O)Nc3ccc(F)c(Cl)c3)CC2C1]<br>N-(3-chloro-4-fluorophenyl)-4-(5-hydroxy-5-(1-(methyl-d3)-1H-pyrazol-5-yl)octahydropentalen-2-yl)-1-methyl-1H-imidazole-5-carboxamide.<br>$^1$H NMR (DMSO-d6, 400 MHz): δ 10.22 (s, 1H), 7.95 (dd, J = 6.8, 2.4 Hz, 1H), 7.66 (s, 1H), 7.58-7.55 (m, 1H), 7.41 (t, J = 9.2 Hz, 1H), 7.21 (d, J = 1.6 Hz, 1H), 6.08 (s, 1H), 5.23 (s, 1H), 3.68 (s, 3H), 3.26-3.23 (m, 1H), 2.48-2.45 (m, 2H), 2.23-2.18 (m, 2H), 2.11-2.06 (m, 2H), 1.89-1.85 (m, 4H) ppm. MS calcd. for $C_{23}H_{22}D_3ClFN5O2$: 460.2; Found: 460.9 $[M + 1]^+$. |
| Example 138 | 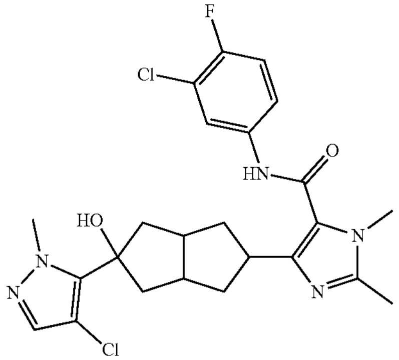 [SMILES: Cc1nc(C2CC3CC(O)(c4c(Cl)cnn4C)CC3C2)c(C(=O)Nc2ccc(F)c(Cl)c2)n1C]<br>4-(5-(4-Chloro-1-methyl-1H-pyrazol-5-yl)-5-hydroxyoctahydropentalen-2-yl)-N-(3-chloro-4-fluorophenyl)-1,2-dimethyl-1H-imidazole-5-carboxamide.<br>$^1$H NMR (DMSO-d6, 400 MHz): δ 10.14 (s, 1H), 7.96 (dd, J = 6.8, 2.4 Hz, 1H), 7.58-7.55 (m, 1H), 7.40 (t, J = 9.2 Hz, 1H), 7.35 (s, 1H), 5.37 (s, 1H), 3.96 (s, 3H), 3.55 (s, 3H), 3.20-3.17 (m, 1H), 2.57-2.54 (m, 2H), 2.39-2.33 (m, 2H), 2.31 (s, 3H), 2.07-1.98 (m, 6H) ppm. MS calcd. for $C_{24}H_{26}Cl_2FN_5O_2$: 505.1; Found; 505.9 $[M + 1]^+$. |

TABLE 7-continued

Examples 116-222

Example 139

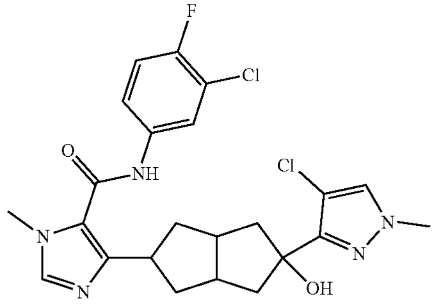

4-(5-(4-Chloro-1-methyl-1H-pyrazol-3-yl)-5-hydroxyoctahydropentalen-2-yl)-N-(3-chloro-4-fluorophenyl)-1-methyl-1H-imidazole-5-carboxamide.
$^1$H NMR (DMSO-d6, 400 MHz): δ 10.20 (s, 1H), 7.96 (dd, J = 6.8, 2.4 Hz, 1H), 7.79 (s, 1H), 7.65 (s, 1H), 7.60-7.54 (m, 1H), 7.40 (t, J = 9.2 Hz, 1H), 4.86 (s, 1H), 3.73 (s, 3H), 3.67 (s, 3H), 3.27-3.17 (m, 1H), 2.45-2.31 (m, 4H), 2.13-2.02 (m, 2H), 1.87-1.71 (m, 4H) ppm; MS calcd. for $C_{23}H_{24}Cl_2FN_5O_2$: 491.1. Found: 492.2 $[M + 1]^+$.

Example 140

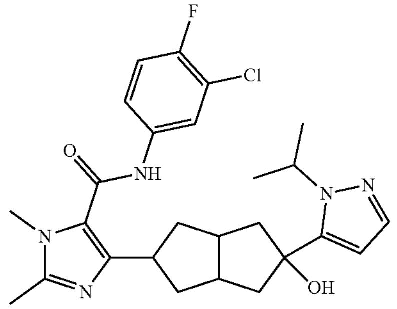 [SMILES: Cc1nc(C2CC3CC(O)(c4ccnn4C(C)C)CC3C2)c(C(=O)Nc2ccc(F)c(Cl)c2)n1C]

N-(3-Chloro-4-fluorophenyl)-4-(5-hydroxy-5-(1-isopropyl-1H-pyrazol-5-yl)octahydropentalen-2-yl)-1,2-dimethyl-1H-imidazole-5-carboxamide.
$^1$H NMR (DMSO-d6, 400 MHz): δ 10.13 (s, 1H), 7.97-7.94 (m, 1H), 7.58-7.54 (m, 1H), 7.40 (t, J = 9.2 Hz, 1H), 7.26 (d, J = 1.6 Hz, 1H), 6.00-5.99 (d, J = 1.6 Hz, 1H), 5.27 (s, 1H), 5.10-5.06 (m, 1H), 3.55 (s, 3H), 3.31-3.21 (m, 1H), 3.19-3.26 (m, 1H), 2.45-2.41 (m, 1H), 2.31 (s, 3H), 2.20-2.15 (m, 2H), 2.07-2.04 (m, 2H), 1.91-1.83 (m, 4H), 1.36-1.31 (m, 6H) ppm. MS calcd. for $C_{26}H_{31}ClFN_5O_2$: 499.2; Found; 500 $[M + 1]^+$.

Example 141

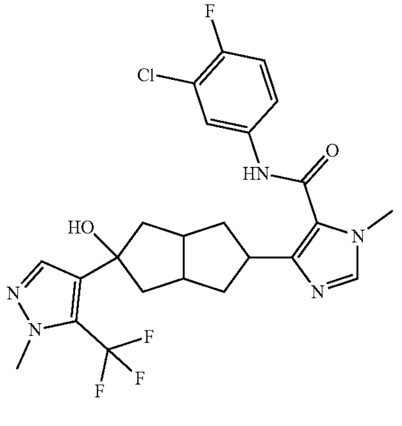 [SMILES: Cn1cnc(C2CC3CC(O)(c4cnn(C)c4C(F)(F)F)CC3C2)c1C(=O)Nc1ccc(F)c(Cl)c1]

N-(3-Chloro-4-fluorophenyl)-4-(5-hydroxy-5-(1-methyl-5-(trifluoromethyl)-1H-pyrazol-4-yl)octahydropentalen-2-yl)-1-methyl-1H-imidazole-5-carboxamide.
$^1$H NMR (DMSO-d6, 400 MHz): δ 10.22 (s, 1H), 7.96 (dd, J = 6.8, 2.4 Hz, 1H), 7.65 (s, 1H), 7.60-7.54 (m, 1H), 7.51 (s, 1H), 7.40 (t, J = 9.2 Hz, 1H), 4.97 (s, 1H), 3.93 (s, 3H), 3.67 (s, 3H), 3.28-3.18 (m, 1H), 2.46-2.38 (m, 2H), 2.20-2.04 (m, 4H), 1.92-1.78 (m, 4H) ppm; MS calcd. for $C_{24}H_{24}ClF_4N_5O_2$: 525.2; Found: 525.8 $[M + 1]^+$.

TABLE 7-continued

Examples 116-222

Example 142

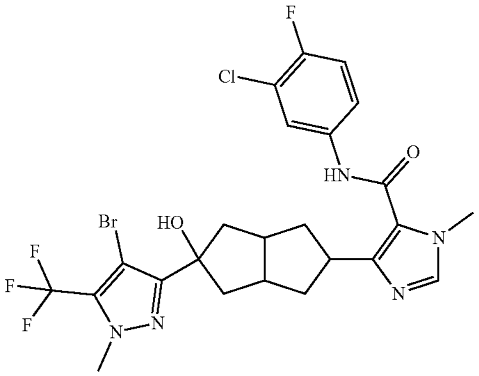 [SMILES: Cn1cnc(C2CC3CC(O)(c4nn(C)c(C(F)(F)F)c4Br)CC3C2)c1C(=O)Nc1ccc(F)c(Cl)c1]

4-(5-(4-Bromo-1-methyl-5-(trifluoromethyl)-1H-pyrazol-3-yl)-5-hydroxyoctahydropentalen-2-yl)-N-(3-chloro-4-fluorophenyl)-1-methyl-1H-imidazole-5-carboxamide.
$^1$H NMR (DMSO-d6, 400 MHz): δ 10.21 (s, 1H), 7.96 (dd, J = 6.4, 2.0 Hz, 1H), 7.66 (s, 1H), 7.60-7.53 (m, 1H), 7.40 (t, J = 8.8 Hz, 1H), 5.10 (s, 1H), 3.94 (s, 3H), 3.68 (s, 3H), 3.28-3.18 (m, 1H), 2.46-2.38 (m, 4H), 2.15-2.03 (m, 2H), 1.88-1.75 (m, 4H) ppm; MS calcd. for $C_{24}H_{23}BrClF_4N_5O_2$: 603.1; Found: 604.2 $[M + 1]^+$.

Example 143

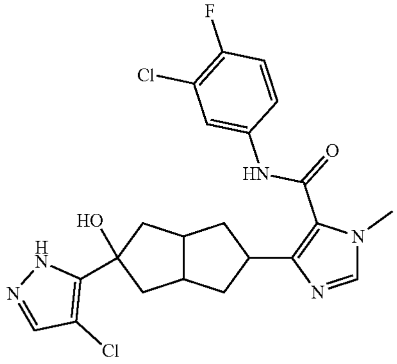

4-(5-(4-Chloro-1H-pyrazol-5-yl)-5-hydroxyoctahydropentalen-2-yl)-N-(3-chloro-4-fluorophenyl)-1-methyl-1H-imidazole-5-carboxamide.
$^1$H NMR (DMSO-d6, 400 MHz): δ 12.73 (d, J = 36.8 Hz, 1H), 10.21 (s, 1H), 7.96 (dd, J = 6.8, 2.8 Hz, 1H), 7.83 (s, 1H), 7.65 (s, 1H), 7.59-7.55 (m, 1H), 7.40 (t, J = 9.0 Hz, 1H), 5.28-8.84 (m, 1H), 3.67 (s, 3H), 3.28-3.20 (m, 1H), 2.67-2.49 (m, 1H), 2.44-2.28 (m, 3H), 2.10-1.93 (m, 3H), 1.89-1.72 (m, 3H) ppm; MS calcd. for $C_{22}H_{22}Cl_2FN_5O_2$: 477.1; Found: 478.1 $[M + 1]^+$.

Example 144

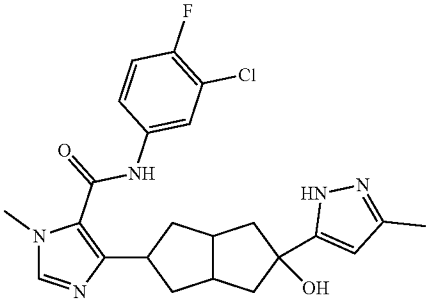

N-(3-Chloro-4-fluorophenyl)-4-(5-hydroxy-5-(3-methyl-1H-pyrazol-5-yl)octahydropentalen-2-yl)-1-methyl-1H-imidazole-5-carboxamide.
$^1$H NMR (MeOH-d4, 400 MHz): δ 7.87-7.85 (dd, J = 2.4 Hz, 7.2 Hz, 1H), 7.64 (s, 1H), 7.52-7.47 (m, 1H), 7.23 (t, J = 8.8 Hz, 1H), 6.01 (s, 1H), 3.75 (s, 3H), 3.29-3.32 (m, 1H), 2.59-2.56 (m, 2H), 2.37-2.33 (m, 2H), 2.24-2.22 (m, 5H), 1.89-1.85 (m, 4H) ppm; MS calcd. for $C_{23}H_{25}ClFN_5O_2$: 457.2. Found: 457.9 $[M + 1]^+$.

TABLE 7-continued

| Examples 116-222 |
| --- |

Example 145

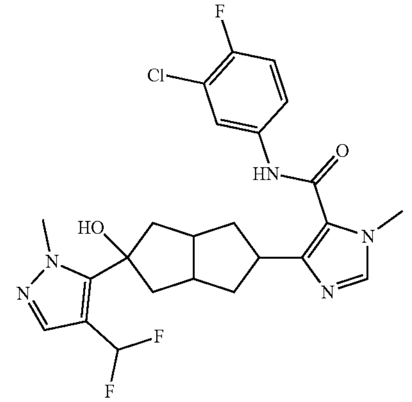 [SMILES: Cn1cnc(C2CC3CC(O)(c4c(C(F)F)cnn4C)CC3C2)c1C(=O)Nc1ccc(F)c(Cl)c1]

N-(3-Chloro-4-fluorophenyl)-4-(5-(4-(difluoromethyl)-1-methyl-1H-pyrazol-5-yl)-5-hydroxyoctahydropentalen-2-yl)-1-methyl-1H-imidazole-5-carboxamide.
$^1$H NMR (DMSO-d6, 400 MHz): δ 10.24 (s, 1H), 7.97 (dd, J = 6.8, 2.4 Hz, 1H), 7.64 (s, 1H), 7.60-7.56 (m, 1H), 7.51 (s, 1H), 7.41 (t, J = 9.0 Hz, 1H), 7.11 (t, J = 55.8 Hz, 1H), 5.32 (s, 1H), 3.95 (s, 3H), 3.67 (s, 3H), 3.22-3.17 (m, 1H), 2.67-2.62 (m, 2H), 2.10-2.04 (m, 8H) ppm; MS calcd. for $C_{24}H_{25}ClF_3N_5O_2$: 507.2. Found; 507.9 $[M + 1]^+$.

Example 146

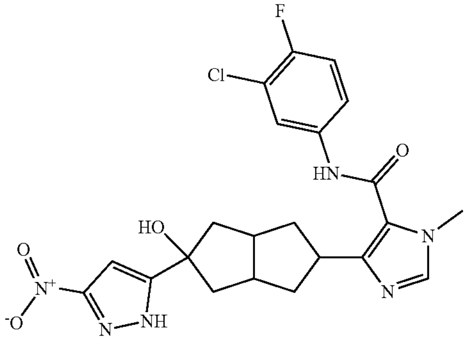

N-(3-Chloro-4-fluorophenyl)-4-(5-hydroxy-5-(3-nitro-1H-pyrazol-5-yl)octahydropentalen-2-yl)-1-methyl-1H-imidazole-5-carboxamide.
$^1$H NMR (DMSO-d6, 400 MHz): δ 13.77 (s, 1H), 10.23 (s, 1H), 7.97 (dd, J = 6.8 Hz, 2.4 Hz, 1H), 7.66 (s, 1H), 7.60-7.55 (m, 1H), 7.41 (t, J = 9.2 Hz, 1H), 6.85 (s, 1H), 5.52 (s, 1H), 3.67 (s, 3H), 3.24-3.21 (m, 1H), 2.55-2.54 (m, 2H), 2.18-2.08 (m, 4H), 1.96-1.85 (m, 4H) ppm; MS calcd. for $C_{22}H_{22}ClFN_6O_4$: 488.1; Found: 489.2 $[M + 1]^+$.

TABLE 7-continued

Examples 116-222

Example 147

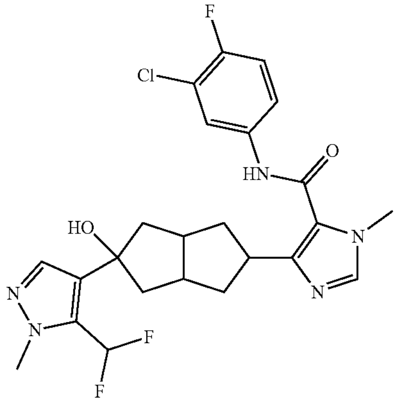 [SMILES: Cn1cnc(C2CC3CC(O)(c4cnn(C)c4C(F)F)CC3C2)c1C(=O)Nc1ccc(F)c(Cl)c1]

N-(3-Chloro-4-fluorophenyl)-4-(5-(5-(difluoromethyl)-1-methyl-1H-pyrazol-4-yl)-5-hydroxyoctahydropentalen-2-yl)-1-methyl-1H-imidazole-5-carboxamide.
$^1$H NMR (DMSO-d6, 400 MHz): δ 10.22 (s, 1H), 7.96 (dd, J = 6.8, 2.4 Hz, 1H), 7.64 (s, 1H), 7.60-7.55 (m, 1H), 7.47-7.33 (m, 3H), 5.24 (s, 1H), 3.90 (s, 3H), 3.67 (s, 3H), 3.30-3.21 (m, 1H), 2.50-2.49 (m, 2H), 2.11-2.01 (m, 4H), 1.92-1.79 (m, 4H) ppm; MS calcd. for $C_{24}H_{25}ClF_3N_5O_2$: 507.2; Found: 507.8 $[M + 1]^+$.

Example 148

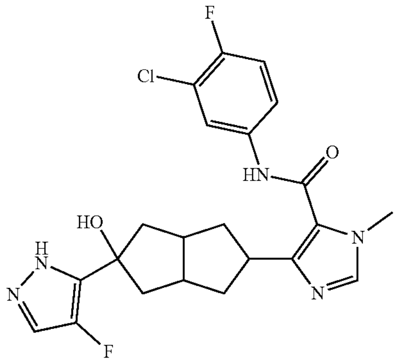

N-(3-Chloro-4-fluorophenyl)-4-(5-(4-fluoro-1H-pyrazol-5-yl)-5-hydroxyoctahydropentalen-2-yl)-1-methyl-1H-imidazole-5-carboxamide.
1H-NMR (DMSO-d6, 400 MHz): δ 12.52-12.31 (m, 1H), 10.21 (s, 1H), 7.96 (dd, J = 6.8, 3.2 Hz, 1H), 7.65 (s, 1H), 7.58-7.54 (m, 1H), 7.42-7.34 (m, 1H), 5.28-4.90 (m, 1H), 3.67 (s, 3H), 2.26-3.18 (m, 1H), 2.42-2.30 (m, 3H), 2.21-2.18 (m, 1H), 2.09-2.06 (m, 2H), 1.90-1.70 (m, 4H) ppm; MS calcd. for $C_{22}H_{22}ClF_2N_5O_2$: 461.1; Found: 462.1 $[M + 1]^+$.

TABLE 7-continued

| Examples 116-222 |
| --- |

Example 149

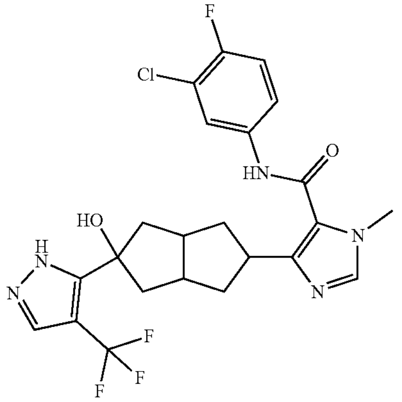 [SMILES: Cn1cnc(C2CC3CC(O)(c4[nH]ncc4C(F)(F)F)CC3C2)c1C(=O)Nc1ccc(F)c(Cl)c1]

N-(3-Chloro-4-fluorophenyl)-4-(5-hydroxy-5-(4-(trifluoromethyl)-1H-pyrazol-5-yl)octahydropentalen-2-yl)-1-methyl-1H-imidazole-5-carboxamide.

$^1$H NMR (DMSO-d6, 400 MHz): δ 13.04 (s, 1H), 10.23 (s, 1H), 8.18 (s, 1H), 7.97 (dd, J = 6.8, 2.4 Hz, 1H), 7.66 (s, 1H), 7.61-7.54 (m, 1H), 7.41 (t, J = 9.0 Hz, 1H), 4.96 (s, 1H), 3.68 (s, 3H), 3.30-3.16 (m, 1H), 2.70-2.54 (m, 1H), 2.36-2.24 (m, 1H), 2.20-2.02 (m, 4H), 2.00-1.76 (m, 4H) ppm; MS calcd. for $C_{23}H_{22}ClF_4N_5O_2$: 511.1; Found: 511.9 $[M + 1]^+$.

Example 150

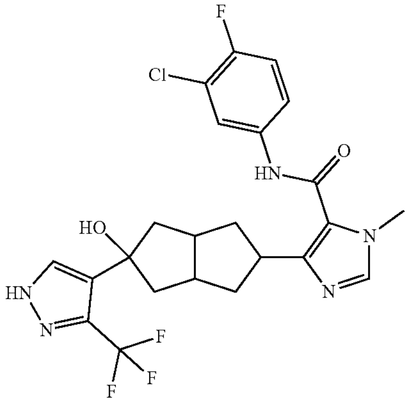 [SMILES: Cn1cnc(C2CC3CC(O)(c4c[nH]nc4C(F)(F)F)CC3C2)c1C(=O)Nc1ccc(F)c(Cl)c1]

N-(3-Chloro-4-fluorophenyl)-4-(5-hydroxy-5-(3-(trifluoromethyl)-1H-pyrazol-4-yl)octahydropentalen-2-yl)-1-methyl-1H-imidazole-5-carboxamide.

$^1$H NMR (DMSO-d6, 400 MHz): δ 13.25 (s, 1H), 10.23 (s, 1H), 7.96 (dd, J = 6.8, 2.4 Hz, 1H), 7.78 (s, 1H), 7.65 (s, 1H), 7.60-7.54 (m, 1H), 7.41 (t, J = 9.0 Hz, 1H), 4.83 (s, 1H), 3.67 (s, 3H), 3.28-3.16 (m, 1H), 2.48-2.41 (m, 2H), 2.15-2.03 (m, 4H), 1.95-1.79 (m, 4H) ppm; MS calcd. for $C_{23}H_{22}ClF_4N_5O_2$: 511.1; Found: 511.9 $[M + 1]^+$.

TABLE 7-continued

Examples 116-222

Example 151

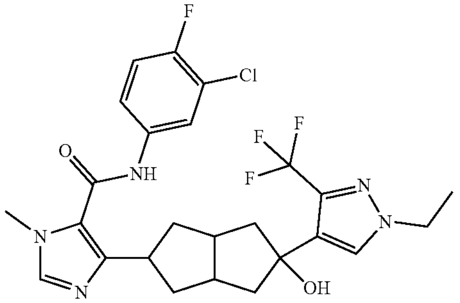 [SMILES: CCn1cc(C2(O)CC3CC(c4ncn(C)c4C(=O)Nc4ccc(F)c(Cl)c4)CC3C2)c(C(F)(F)F)n1]

N-(3-Chloro-4-fluorophenyl)-4-(5-(1-ethyl-3-(trifluoromethyl)-1H-pyrazol-4-yl)-5-hydroxyoctahydropentalen-2-yl)-1-methyl-1H-imidazole-5-carboxamide.

$^1$H NMR (MeOH-d4, 400 MHz): δ 7.77 (dd, J = 6.8, 2.8 Hz, 1H), 7.60 (d, J = 1.2 Hz, 1H), 7.55 (s, 1H), 7.43-7.38 (m, 1H), 7.14 (t, J = 9.2 Hz, 1H), 4.05 (q, J = 7.2 Hz, 2H), 3.66 (s, 3H), 3.27-3.22 (m, 1H), 2.54-2.43 (m, 2H), 2.27-2.08 (m, 4H), 1.87-1.74 (m, 4H), 1.33 (t, J = 7.6 Hz, 3H) ppm. MS calcd. for $C_{25}H_{26}ClF_4N_5O_2$: 539.2; Found: 540.2 $[M + 1]^+$.

Example 152

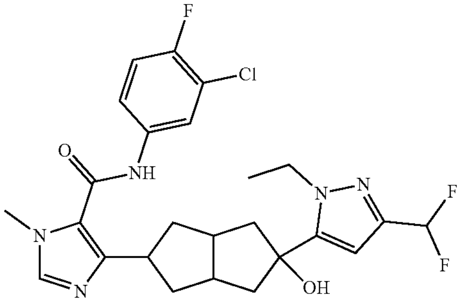 [SMILES: CCn1nc(C(F)F)cc1C1(O)CC2CC(c3ncn(C)c3C(=O)Nc3ccc(F)c(Cl)c3)CC2C1]

N-(3-Chloro-4-fluorophenyl)-4-(5-(3-(difluoromethyl)-1-ethyl-1H-pyrazol-5-yl)-5-hydroxyoctahydropentalen-2-yl)-1-methyl-1H-imidazole-5-carboxamide.

$^1$H NMR (DMSO-d6, 400 MHz): δ 10.25 (s, 1H), 7.96 (dd, J = 6.8, 2.4 Hz, 1H), 7.67 (s, 1H), 7.58-7.55 (m, 1H), 7.40 (t, J = 9.2 Hz, 1H), 6.88 (t, J = 55.0 Hz, 1H), 6.31 (s, 1H), 6.42 (s, 1H), 4.35-4.29 (m, 2H), 3.68 (s, 3H), 3.28-3.22 (m, 1H), 2.50-2.49 (m, 2H), 2.23-2.18 (m, 2H), 2.12-2.07 (m, 2H), 2.19-1.84 (m, 4H), 1.35 (t, J = 7.2 Hz, 3H) ppm; MS calcd. for $C_{25}H_{27}ClF_3N_5O_2$: 521.2; Found: 522.2 $[M + 1]^+$.

Example 153

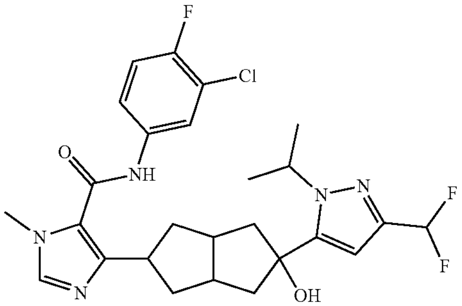 [SMILES: CC(C)n1nc(C(F)F)cc1C1(O)CC2CC(c3ncn(C)c3C(=O)Nc3ccc(F)c(Cl)c3)CC2C1]

N-(3-Chloro-4-fluorophenyl)-4-(5-(3-(difluoromethyl)-1-isopropyl-1H-pyrazol-5-yl)-5-hydroxyoctahydropentalen-2-yl)-1-methyl-1H-imidazole-5-carboxamide.

1H NMR (DMSO-d6, 400 MHz): δ 10.22 (s, 1H), 7.96 (dd, J = 6.8, 2.8 Hz, 1H), 7.65 (s, 1H), 7.59-7.55 (m, 1H), 7.40 (t, J = 9.2 Hz, 1H), 6.89 (t, J = 54.8 Hz, 1H), 6.28 (s, 1H), 5.43 ( s, 1H), 5.14-5.11 (m, 1H), 3.67 (s, 3H), 3.24-3.23 (m, 1H), 2.50-2.49 (m, 2H), 2.22-2.17 (m, 2H), 2.11-2.07 (m, 2H), 1.93-1.89 (m, 4H), 1.36 (d, J = 6.4 Hz, 6H) ppm; MS calcd. for $C_{26}H_{29}ClF_3N_5O_2$: 535.2; Found: 536.3 $[M + 1]^+$.

TABLE 7-continued

Examples 116-222

Example 154

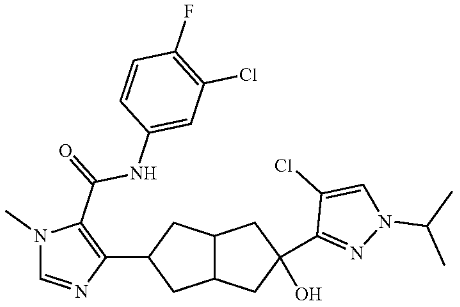 [SMILES: CC(C)n1cc(Cl)c(C2(O)CC3CC(c4ncn(C)c4C(=O)Nc4ccc(F)c(Cl)c4)CC3C2)n1]

4-(5-(4-Chloro-1-isopropyl-1H-pyrazol-3-yl)-5-hydroxyoctahydropentalen-2-yl)-N-(3-chloro-4-fluorophenyl)-1-methyl-1H-imidazole-5-carboxamide.
$^1$H NMR (DMSO-d6, 400 MHz): δ 10.19 (s, 1H), 7.95 (dd, J = 6.8, 2.8 Hz, 1H), 7.87 (s, 1H), 7.64 (s, 1H), 7.58-7.54 (m, 1H), 7.39 (t, J = 9.2 Hz, 1H), 4.86 (s, 1H), 4.36-4.33 (m, 1H), 3.67 (s, 3H), 3.23-3.20 (m, 1H), 2.46-2.32 (m, 4H), 2.08-2.05 (s, 2H), 1.85-1.74 (s, 4H), 1.35 (d, J = 6.8 Hz, 6H) ppm; MS calcd. for $C_{25}H_{28}Cl_2FN_5O_2$: 519.2. Found: 521.4 $[M + 2]^+$.

Example 155

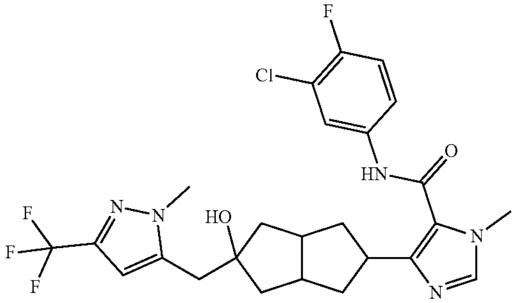 [SMILES: Cn1cnc(C2CC3CC(O)(Cc4cc(C(F)(F)F)nn4C)CC3C2)c1C(=O)Nc1ccc(F)c(Cl)c1]

N-(3-Chloro-4-fluorophenyl)-4-(5-hydroxy-5-((1-methyl-3-(trifluoromethyl)-1H-pyrazol-5-yl)methyl)octahydropentalen-2-yl)-1-methyl-1H-imidazole-5-carboxamide.
$^1$H NMR (DMSO-d6, 400 MHz): δ 10.22 (s, 1H), 7.96 (dd, J = 6.8, 2.8 Hz, 1H), 7.64 (s, 1H), 7.59-7.55 (m, 1H), 7.41 (t, J = 9.0 Hz, 1H), 6.44 (s, 1H), 4.80 (s, 1H), 4.04 (s, 2H), 3.66 (s, 3H), 3.24-3.21 (m, 1H), 2.50-2.49 (m, 2H), 2.33 (s, 3H), 2.12-2.05 (m, 2H), 1.93-1.88 (m, 2H), 1.76-1.68 (m, 2H), 1.42 (dd, J = 12.8, 4.8 Hz, 2H) ppm; MS calcd. for $C_{25}H_{26}ClF_4N_5O_2$: 539.2; Found: 540.1 $[M + 1]^+$.

Example 156

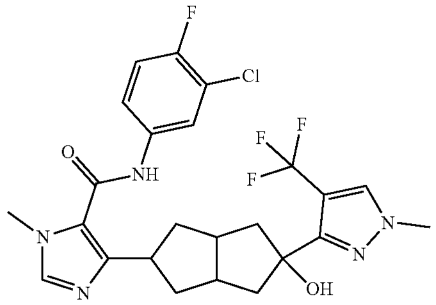

N-(3-Chloro-4-fluorophenyl)-4-(5-hydroxy-5-(1-methyl-4-(trifluoromethyl)-1H-pyrazol-3-yl)octahydropentalen-2-yl)-1-methyl-1H-imidazole-5-carboxamide.
$^1$H NMR (DMSO-d6, 400 MHz): δ 10.21 (s, 1H), 8.13 (s, 1H), 7.96 (dd, J = 6.8, 2.8 Hz, 1H), 7.65 (s, 1H), 7.60-7.54 (m, 1H), 7.41 (t, J = 9.2 Hz, 1H), 4.96 (s, 1H), 3.78 (s, 3H), 3.68 (s, 3H), 3.28-3.16 (m, 1H), 2.49-2.40 (m, 2H), 2.30-2.22 (m, 2H), 2.11-2.02 (m, 2H), 1.93-1.83 (m, 2H), 1.80 (dd, J = 13.0, 3.0 Hz, 2H) ppm; MS calcd. for $C_{24}H_{24}ClF_4N_5O_2$: 525.2; Found: 526.2 $[M + 1]^+$.

TABLE 7-continued

| Examples 116-222 | |
|---|---|
| Example 157 | 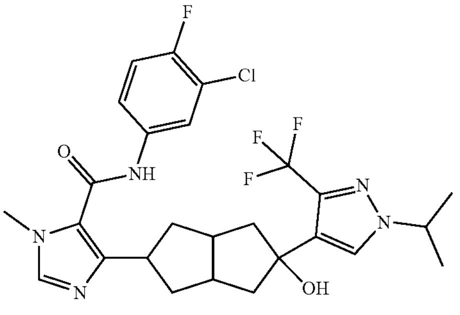 [SMILES: CC(C)n1cc(C2(O)CC3CC(c4ncn(C)c4C(=O)Nc4ccc(F)c(Cl)c4)CC3C2)c(C(F)(F)F)n1]<br>N-(3-Chloro-4-fluorophenyl)-4-(5-hydroxy-5-(1-isopropyl-3-(trifluoromethyl)-1H-pyrazol-4-yl)octahydropentalen-2-yl)-1-methyl-1H-imidazole-5-carboxamide.<br>$^1$H NMR (MeOH-d4, 400 MHz): δ 7.77 (dd, J = 6.8, 2.4 Hz, 1H), 7.60 (d, J = 0.8 Hz, 1H), 7.55 (s, 1H), 7.44-7.38 (m, 1H), 7.14 (t, J = 9.2 Hz, 1H), 4.46-4.36 (m, 1H), 3.66 (s, 3H), 3.28-3.23 (m, 1H), 2.54-2.41 (m, 2H), 2.30-2.08 (m, 4H), 1.88-1.75 (m, 4H), 1.38 (s, 3H), 1.36 (s, 3H) ppm. MS calcd. for $C_{26}H_{28}ClF_4N_5O_2$: 553.2; Found: 554.2 $[M + 1]^+$. |
| Example 158 | 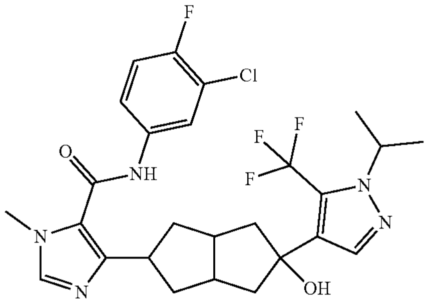 [SMILES: CC(C)n1ncc(C2(O)CC3CC(c4ncn(C)c4C(=O)Nc4ccc(F)c(Cl)c4)CC3C2)c1C(F)(F)F]<br>N-(3-Chloro-4-fluorophenyl)-4-(5-hydroxy-5-(1-isopropyl-5-(trifluoromethyl)-1H-pyrazol-4-yl)octahydropentalen-2-yl)-1-methyl-1H-imidazole-5-carboxamide.<br>$^1$H NMR (MeOH-d4, 400 MHz): δ 7.78 (dd, J = 6.8, 2.8 Hz, 1H), 7.56 (s, 1H), 7.48 (s, 1H), 7.43-7.37 (m, 1H), 7.14 (t, J = 8.8 Hz, 1H), 4.66-4.58 (m, 1H), 3.66 (s, 3H), 3.29-3.23 (m, 1H), 2.50-2.40 (m, 2H), 2.33-2.25 (m, 2H), 2.19-2.10 (m, 2H) 1.88-1.70 (m, 4H), 1.38 (s, 3H), 1.36 (s, 3H) ppm. MS calcd. for $C_{26}H_{28}ClF_4N_5O_2$: 553.2; Found: 554.2 $[M + 1]^+$. |
| Example 159 | 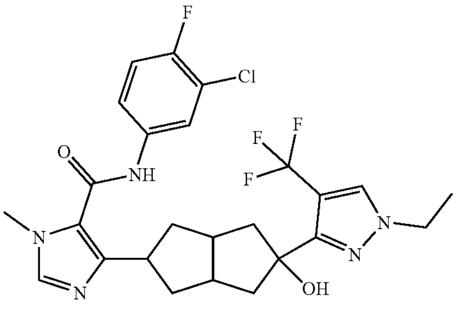 [SMILES: CCn1cc(C(F)(F)F)c(C2(O)CC3CC(c4ncn(C)c4C(=O)Nc4ccc(F)c(Cl)c4)CC3C2)n1]<br>N-(3-Chloro-4-fluorophenyl)-4-(5-(1-ethyl-4-(trifluoromethyl)-1H-pyrazol-3-yl)-5-hydroxyoctahydropentalen-2-yl)-1-methyl-1H-imidazole-5-carboxamide.<br>$^1$H NMR (DMSO-d6, 400 MHz): δ 10.22 (s, 1H), 8.18 (s, 1H), 7.96 (dd, J = 6.8, 2.4 Hz, 1H), 7.65 (s, 1H), 7.60-7.54 (m, 1H), 7.41 (t, J = 9.2 Hz, 1H), 4.97 (s, 1H), 4.07 (q, J = 7.2 Hz, 2H), 3.67 (s, 3H), 3.27-3.17 (m, 1H), 2.48-2.38 (m, 2H), 2.30-2.22 (m, 2H), 2.12-2.02 (m, 2H), 1.94-1.83 (m, 2H), 1.80 (dd, J = 12.6, 3.0 Hz, 2H), 1.34 (t, J = 7.4 Hz, 3H) ppm. MS calcd. for $C_{25}H_{26}ClF_4N_5O_2$: 539.2; Found: 540 $[M + 1]^+$. |

TABLE 7-continued

| Examples 116-222 | |
|---|---|
| Example 160 | 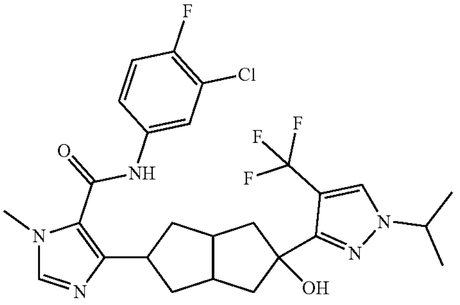 [SMILES: CC(C)n1cc(C(F)(F)F)c(C2(O)CC3CC(c4ncn(C)c4C(=O)Nc4ccc(F)c(Cl)c4)CC3C2)n1]<br>N-(3-Chloro-4-fluorophenyl)-4-(5-hydroxy-5-(1-isopropyl-4-(trifluoromethyl)-1H-pyrazol-3-yl)octahydropentalen-2-yl)-1-methyl-1H-imidazole-5-carboxamide.<br>$^1$H NMR (DMSO-d6, 400 MHz): δ 10.22 (s, 1H), 8.20 (s, 1H), 7.96 (dd, J = 6.8, 2.4 Hz, 1H), 7.65 (s, 1H), 7.60-7.54 (m, 1H), 7.41 (t, J = 9.2 Hz, 1H), 4.97 (s, 1H), 4.47-4.40 (m, 1H), 3.67 (s, 3H), 3.28-3.16 (m, 1H), 2.49-2.40 (m, 2H), 2.31-2.23 (m, 2H), 2.11-2.02 (m, 2H), 1.93-1.83 (m, 2H), 1.79 (dd, J = 12.8, 2.8 Hz, 2H), 1.38 (d, J = 6.4 Hz, 6H) ppm. MS calcd for $C_{26}H_{28}ClF_4N_5O_2$: 553.2; Found: 553.9 $[M + 1]^+$. |
| Example 161 | 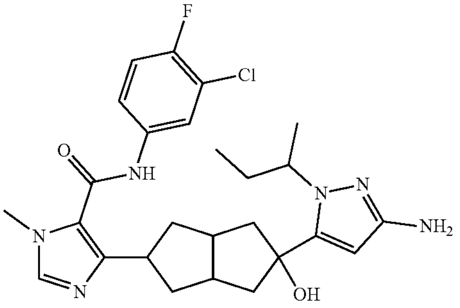 [SMILES: CCC(C)n1nc(N)cc1C1(O)CC2CC(c3ncn(C)c3C(=O)Nc3ccc(F)c(Cl)c3)CC2C1]<br>4-(5-(3-Amino-1-(sec-butyl)-1H-pyrazol-5-yl)-5-hydroxyoctahydropentalen-2-yl)-N-(3-chloro-4-fluorophenyl)-1-methyl-1H-imidazole-5-carboxamide.<br>$^1$H NMR (DMSO-d6, 400 MHz): δ 10.21 (s, 1H), 7.96 (dd, J = 6.8, 2.4 Hz, 1H), 7.65 (s, 1H), 7.58-7.55 (m, 1H), 7.41 (t, J = 9.2 Hz, 1H), 5.18 (s, 1H), 5.04 (s, 1H), 4.53 (d, J = 8.0 Hz, 1H), 4.36 (s, 2H), 3.68 (s, 3H), 3.24-3.21 (m, 1H), 2.51-2.49 (m, 2H), 2.12-2.04 (m, 4H), 1.89-1.79 (m, 5H), 1.23-1.21 (s, 1H), 1.22 (d, J = 6.4 Hz, 3H), 0.73 (t, J = 7.2 Hz, 3H) ppm. MS calcd. for $C_{26}H_{32}ClFN_6O_2$: 514.2; Found: 515.2 $[M + 1]^+$. |
| Example 162 | 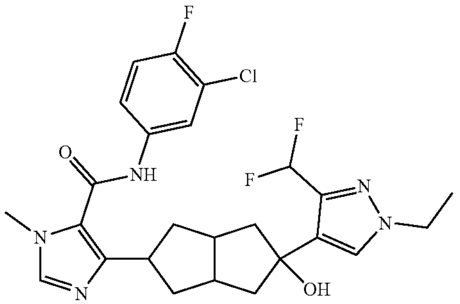 [SMILES: CCn1cc(C2(O)CC3CC(c4ncn(C)c4C(=O)Nc4ccc(F)c(Cl)c4)CC3C2)c(C(F)F)n1]<br>N-(3-Chloro-4-fluorophenyl)-4-(5-(3-(difluoromethyl)-1-ethyl-1H-pyrazol-4-yl)-5-hydroxyoctahydropentalen-2-yl)-1-methyl-1H-imidazole-5-carboxamide.<br>$^1$H NMR (DMSO-d6, 400 MHz): δ 10.23 (s, 1H), 7.96 (dd, J = 7.2, 2.8 Hz, 1H), 7.66 (d, J = 12.8 Hz, 2H), 7.59-7.55 (m, 1H), 7.41 (t, J = 9.2 Hz, 1H), 7.12 (t, J = 52.4 Hz, 1H), 5.02 (s, 1H), 4.11-4.05 (m, 2H), 3.67 (s, 3H), 3.25-3.19 (m, 1H), 2.50-2.49 (m, 2H), 2.09-2.02 (m, 4H), 1.90-1.75 (m, 4H), 1.34 (t, J = 7.2 Hz, 3H) ppm; MS calcd. for $C_{25}H_{27}ClF_3N_5O_2$: 521.2; Found: 522.2 $[M + 1]^+$. |

TABLE 7-continued

Examples 116-222

Example 163

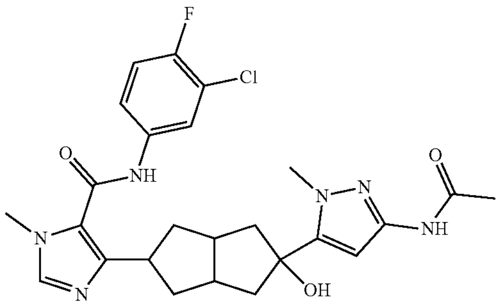 [SMILES: CC(=O)Nc1cc(C2(O)CC3CC(c4ncn(C)c4C(=O)Nc4ccc(F)c(Cl)c4)CC3C2)n(C)n1]

4-(5-(3-Acetamido-1-methyl-1H-pyrazol-5-yl)-5-hydroxyoctahydropentalen-2-yl)-N-(3-chloro-4-fluorophenyl)-1-methyl-1H-imidazole-5-carboxamide.
$^1$H NMR (DMSO-d6, 400 MHz): δ 10.28 (s, 1H), 10.21 (s, 1H), 7.97 (dd, J = 6.8, 2.4 Hz, 1H), 7.65 (s, 1H), 7.57-7.54 (m, 1H), 7.40 (t, J = 9.0 Hz, 1H), 6.27 (s, 1H), 5.29 (s, 1H), 4.20-4.15 (m, 2H), 3.67 (s, 3H), 3.30-3.24 (m, 1H), 2.51-2.49 (m, 2H), 2.18-2.08 (m, 4H), 1.94 (s, 3H), 1.90-1.85 (m, 4H), 1.30 (t, J = 9.0 Hz, 3H) ppm; MS calcd. for $C_{26}H_{30}ClFN_6O_3$: 528.2; Found: 529.3 $[M + 1]^+$.

Example 164

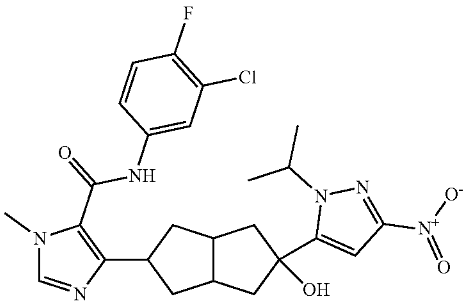 [SMILES: CC(C)n1nc([N+](=O)[O-])cc1C1(O)CC2CC(c3ncn(C)c3C(=O)Nc3ccc(F)c(Cl)c3)CC2C1]

N-(3-Chloro-4-fluorophenyl)-4-(5-hydroxy-5-(1-isopropyl-3-nitro-1H-pyrazol-5-yl)octahydropentalen-2-yl)-1-methyl-1H-imidazole-5-carboxamide.
$^1$H NMR (DMSO-d6, 400 MHz): δ 10.23 (s, 1H), 7.96 (dd, J = 6.8 Hz, 2.8 Hz, 1H), 7.66 (s, 1H), 7.59-7.55 (m, 1 H), 7.41 (t, J = 9.2 Hz, 1H), 6.89 (s, 1H), 5.68 (s, 1H), 5.27-5.20 (m, 1H), 3.68 (s, 3H), 3.31-3.22 (m, 1H), 2.49-2.42 (m, 2H), 2.27-2.22 (m, 2H), 2.13-2.07 (m, 2H), 1.95-1.85 (m, 4H), 1.42-1.40 (m, 6H) ppm; MS calcd. for $C_{25}H_{28}ClFN_6O_4$: 530.2; Found: 531.2 $[M + 1]^+$.

Example 165

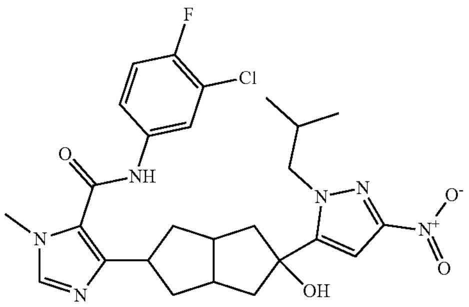 [SMILES: CC(C)Cn1nc([N+](=O)[O-])cc1C1(O)CC2CC(c3ncn(C)c3C(=O)Nc3ccc(F)c(Cl)c3)CC2C1]

N-(3-Chloro-4-fluorophenyl)-4-(5-hydroxy-5-(1-isobutyl-3-nitro-1H-pyrazol-5-yl)octahydropentalen-2-yl)-1-methyl-1H-imidazole-5-carboxamide.
$^1$H NMR (DMSO-d6, 400 MHz): δ 10.23 (s, 1H), 7.96 (dd, J = 6.8, 2.4 Hz, 1H), 7.66 (s, 1H), 7.59-7.55 (m, 1H), 7.40 (t, J = 9.0 Hz, 1H), 6.91 (s, 1H), 5.59 (s, 1H), 4.19 (d, J = 7.6 Hz, 2H), 3.67 (s, 3H), 3.31-3.23 (m, 1H), 2.50-2.49 (m, 2H), 2.37-2.32 (m, 1H), 2.27-2.22 (m, 2H), 2.13-2.07 (m, 2H), 1.93-1.83 (m, 4H), 0.90-0.85 (m, 6H) ppm. MS calcd. for $C_{26}H_{30}ClFN_6O_4$: 544.2; Found: 545.2 $[M + 1]^+$.

TABLE 7-continued

| Examples 116-222 | |
|---|---|
| Example 166 | 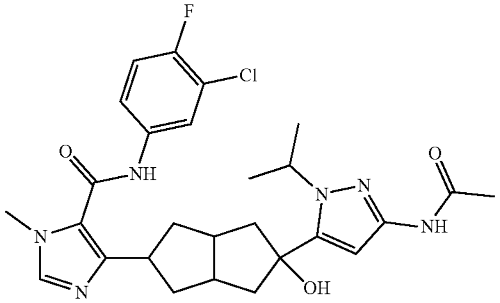 [SMILES: CC(=O)Nc1cc(C2(O)CC3CC(c4ncn(C)c4C(=O)Nc4ccc(F)c(Cl)c4)CC3C2)n(C(C)C)n1]<br>4-(5-(3-Acetamido-1-isopropyl-1H-pyrazol-5-yl)-5-hydroxyoctahydropentalen-2-yl)-N-(3-chloro-4-fluorophenyl)-1-methyl-1H-imidazole-5-carboxamide.<br>$^1$H NMR (DMSO-d6, 400 MHz): δ 10.33 (s, 1H), 10.21 (s, 1H), 7.97 (dd, J = 6.8, 2.8 Hz, 1H), 7.65 (s, 1H), 7.58-7.54 (m, 1H), 7.40 (t, J = 9.2 Hz, 1H), 6.25 (s, 1H), 5.31 (s, 1H), 5.04-4.97 (m, 1H), 3.67 (s, 3H), 3.31-3.25 (m, 1H), 2.51-2.47 (m, 2H), 2.18-2.08 (m, 4H), 1.93-1.84 (m, 7H), 1.32 (d, J = 6.4 Hz, 6H) ppm; MS calcd. for $C_{27}H_{32}ClFN_6O_3$: 542.2; Found: 543.3 $[M + 1]^+$. |
| Example 168 | 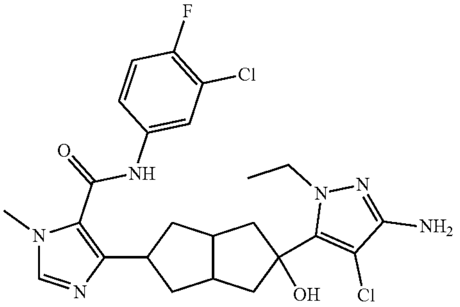 [SMILES: CCn1nc(N)c(Cl)c1C1(O)CC2CC(c3ncn(C)c3C(=O)Nc3ccc(F)c(Cl)c3)CC2C1]<br>4-(5-(3-Amino-4-chloro-1-ethyl-1H-pyrazol-5-yl)-5-hydroxyoctahydropentalen-2-yl)-N-(3-chloro-4-fluorophenyl)-1-methyl-1H-imidazole-5-carboxamide.<br>$_1$H NMR (DMSO-d6, 400 MHz): δ 10.23 (s, 1H), 7.96 (dd, J = 7.2, 2.8 Hz, 1H), 7.65 (s, 1H), 7.59-7.56 (m, 1H), 7.41 (t, J = 9.2 Hz, 1H), 5.31 (s, 1H), 4.59 (s, 2H), 4.15-4.09 (m, 2H), 3.68 (s, 3H), 3.28-3.16 (m, 1H), 2.67 (brs, 2H), 2.39-2.33 (m, 2H), 2.08-1.90 (m, 6H), 1.26-1.23 (m, 3H) ppm; MS calcd. for $C_{24}H_{27}Cl_2FN_6O_2$: 520.2; Found: 521.2 $[M + 1]^+$. |
| Example 169 | 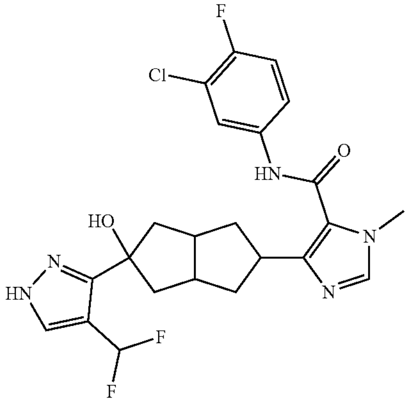 [SMILES: Cn1cnc(C2CC3CC(O)(c4n[nH]cc4C(F)F)CC3C2)c1C(=O)Nc1ccc(F)c(Cl)c1]<br>N-(3-Chloro-4-fluorophenyl)-4-(5-(4-(difluoromethyl)-1H-pyrazol-3-yl)-5-hydroxyoctahydropentalen-2-yl)-1-methyl-1H-imidazole-5-carboxamide.<br>$^1$H NMR (MeOH-d4, 400 MHz): δ 7.78 (dd, J = 6.4, 2.4 Hz, 1H), 7.66 (s, 1H), 7.56 (s, 1H), 7.44-7.38 (m, 1H), 7.17-6.86 (m, 2H), 3.67 (s, 3H), 3.23-3.18 (m, 1H), 2.60-2.50 (m, 2H), 2.30-2.25 (m, 2H), 2.16-2.12 (m, 2H), 1.95-1.75 (m, 4H) ppm. MS calcd. for $C_{23}H_{23}ClF_3N_5O_2$: 493.1; Found: 493.9 $[M + 1]^+$. |

TABLE 7-continued

Examples 116-222

Example 170

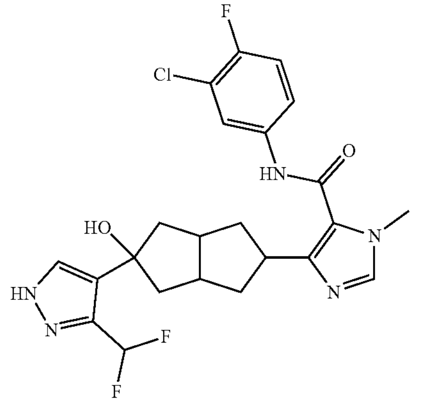 [SMILES: Cn1cnc(C2CC3CC(O)(c4c[nH]nc4C(F)F)CC3C2)c1C(=O)Nc1ccc(F)c(Cl)c1]

N-(3-Chloro-4-fluorophenyl)-4-(5-(3-(difluoromethyl)-1H-pyrazol-4-yl)-5-hydroxyoctahydropentalen-2-yl)-1-methyl-1H-imidazole-5-carboxamide.
$^1$H NMR (MeOH-d4, 400 MHz): δ 7.78 (dd, J = 6.4, 2.4 Hz, 1H), 7.60-7.45 (m, 2H), 7.45-7.35 (m, 1H), 7.17-6.98 (m, 2H), 3.67 (s, 3H), 3.23-3.18 (m, 1H), 2.55-2.45 (m, 2H), 2.25-2.10 (m, 4H), 1.90-1.74 (m, 4H) ppm. MS calcd. for $C_{23}H_{23}ClF_3N_5O_2$: 493.1; Found: 493.9 $[M + 1]^+$.

Example 171

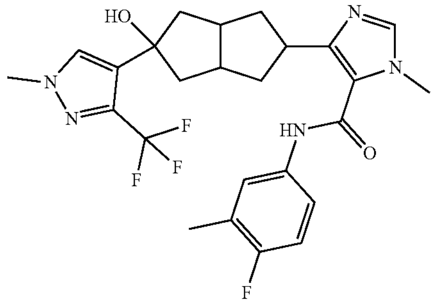

N-(4-Fluoro-3-methylphenyl)-4-(5-hydroxy-5-(1-methyl-3-(trifluoromethyl)-1H-pyrazol-4-yl)octahydropentalen-2-yl)-1-methyl-1H-imidazole-5-carboxamide.
$^1$H NMR (MeOH-d4, 400 MHz): δ 7.55-7.53 (m, 2H), 7.39-7.32 (m, 2H), 6.91 (t, J = 9.2 Hz, 1H), 3.75 (s, 3H), 3.65 (s, 3H), 3.25-3.23 (m, 1H), 2.48-2.45 (m, 2H), 2.25-2.13 (m, 7H), 1.84-1.77 (m, 4H) ppm. MS calcd. for C25H27F4N5O2: 505.2; Found: 506.2 $[M + 1]^+$.

Example 172

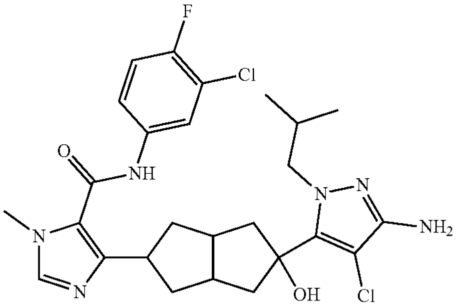 [SMILES: CC(C)Cn1nc(N)c(Cl)c1C1(O)CC2CC(c3ncn(C)c3C(=O)Nc3ccc(F)c(Cl)c3)CC2C1]

4-(5-(3-Amino-4-chloro-1-isobutyl-1H-pyrazol-5-yl)-5-hydroxyoctahydropentalen-2-yl)-N-(3-Chloro-4-fluorophenyl)-1-methyl-1H-imidazole-5-carboxamide.
$^1$H NMR (DMSO-d6, 400 MHz): δ 10.21 (s, 1H), 7.96 (dd, J = 6.8, 2.4 Hz, 1H), 7.64 (s, 1H), 7.59-7.55 (m, 1H), 7.40 (t, J = 9.2 Hz, 1H), 5.22 (s, 1H), 4.54 (s, 2H), 3.90 (m, 2H), 3.67 (s, 3H), 3.29-3.18 (s, 1H), 2.56-2.50 (m, 2H), 2.40-2.32 (m, 2H), 2.27-2.21 (m, 1H), 2.10-2.03 (m, 2H), 2.02-1.91 (m, 4H), 0.83 (d, J = 7.2 Hz, 6H) ppm; MS calcd. for $C_{26}H_{31}Cl_2FN_6O_2$: 548.2. Found; 549.2 $[M + 1]^+$.

TABLE 7-continued

Examples 116-222

Example 173

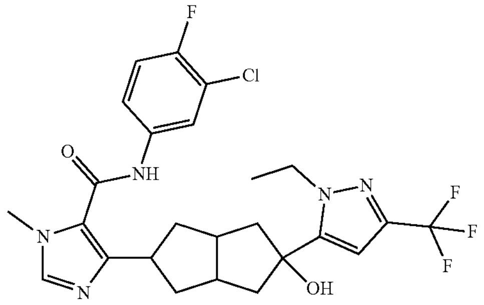 [SMILES: CCn1nc(C(F)(F)F)cc1C1(O)CC2CC(c3ncn(C)c3C(=O)Nc3ccc(F)c(Cl)c3)CC2C1]

N-(3-Chloro-4-fluorophenyl)-4-(5-(1-ethyl-3-(trifluoromethyl)-1H-pyrazol-5-yl)-5-hydroxyoctahydropentalen-2-yl)-1-methyl-1H-imidazole-5-carboxamide.
$^1$H NMR (MeOH-d4, 400 MHz): δ 7.79 (dd, J = 6.8, 2.8 Hz, 1H), 7.56 (s, 1H), 7.43-7.37 (m, 1H), 7.14 (t, J = 9.2 Hz, 1H), 6.34 (s, 1H) 4.32 (q, J = 7.2 Hz, 2H), 3.67 (s, 3H), 3.29-3.24 (m, 1H), 2.55-2.45 (m, 2H), 2.32-2.24 (m, 2H), 2.20-2.12 (m, 2H), 1.95-1.76 (m, 4H), 1.34 (t, J = 7.2 Hz, 3H). MS calcd for $C_{25}H_{26}ClF_4N_5O_2$: 539.2. Found; 540.2 $[M + 1]^+$.

Example 174

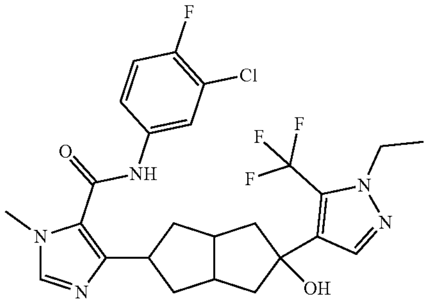 [SMILES: CCn1ncc(C2(O)CC3CC(c4ncn(C)c4C(=O)Nc4ccc(F)c(Cl)c4)CC3C2)c1C(F)(F)F]

N-(3-Chloro-4-fluorophenyl)-4-(5-(1-ethyl-5-(trifluoromethyl)-1H-pyrazol-4-yl)-5-hydroxyoctahydropentalen-2-yl)-1-methyl-1H-imidazole-5-carboxamide.
$^1$H NMR (MeOH-d4, 400 MHz): δ 7.78 (dd, J = 6.8, 2.8 Hz, 1H), 7.55 (s, 1H), 7.45 (s, 1H), 7.43-7.37 (m, 1H), 7.13 (t, J = 8.8 Hz, 1H), 4.30 (q, J = 7.2 Hz, 2H), 3.66 (s, 3H), 3.28-3.24 (m, 1H), 2.52-2.40 (m, 2H), 2.32-2.23 (m, 2H), 2.20-2.10 (m, 2H), 1.88-1.73 (m, 4H), 1.31 (t, J = 7.2 Hz, 3H) ppm. MS calcd for $C_{25}H_{26}ClF_4N_5O_2$: 539.2. Found; 540.2 $[M + 1]^+$.

Example 175

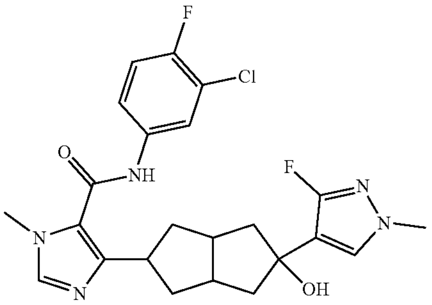

N-(3-Chloro-4-fluorophenyl)-4-(5-(3-fluoro-1-methyl-1H-pyrazol-4-yl)-5-hydroxyoctahydropentalen-2-yl)-1-methyl-1H-imidazole-5-carboxamide.
$^1$H NMR (DMSO-d6, 400 MHz): δ 10.22 (s, 1H), 7.96 (dd, J = 6.8, 2.4 Hz, 1H), 7.65 (s, 1H), 7.60-7.54 (m, 1H), 7.48 (d, J = 2.4 Hz, 1H), 7.41 (t, J = 9.2 Hz, 1H), 4.87 (s, 1H), 3.67 (s, 3H), 3.64 (s, 3H), 3.26-3.15 (m, 1H), 2.45-2.37 (m, 2H), 2.14-2.01 (m, 4H), 1.90-1.79 (m, 2H), 1.76-1.68 (m, 2H) ppm. MS calcd. for $C_{23}H_{24}ClF_2N_5O_2$: 475.2; Found: 458.2 $[M - H_2O + 1]^+$.

TABLE 7-continued

Examples 116-222

Example 176

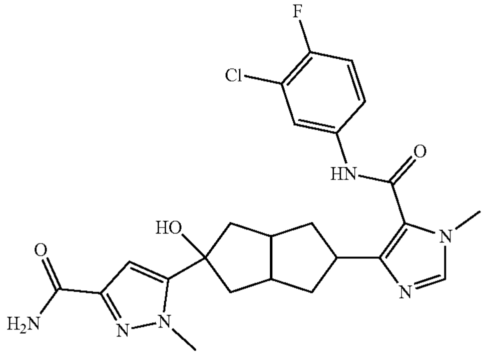 [SMILES: Cn1cnc(C2CC3CC(O)(c4cc(C(N)=O)nn4C)CC3C2)c1C(=O)Nc1ccc(F)c(Cl)c1]

5-(5-(5-((3-Chloro-4-fluorophenyl)carbamoyl)-1-methyl-1H-imidazol-4-yl)-2-hydroxyoctahydropentalen-2-yl)-1-methyl-1H-pyrazole-3-carboxamide.

$^1$H NMR (DMSO-d6, 400 MHz): δ 10.20 (s, 1H), 7.93 (dd, J = 6.8 Hz, 2.4 Hz, 1H), 7.63 (s, 1H), 7.55-7.51 (m, 1H), 7.37 (t, J = 9.2 Hz, 1H), 7.08 (s, 1H), 6.43 (s, 1H), 5.33 (s, 1H), 3.92 (s, 3H), 3.64 (s, 3H), 3.26-3.20 (m, 1H), 2.40-2.47 (m, 2H), 2.22-2.17 (m, 2H), 2.10-2.06 (m, 2H), 1.87-1.78 (m, 4H) ppm. MS calcd. for $C_{24}H_{26}ClFN_6O_3$: 500.2; Found: 501.2 $[M + 1]^+$.

Example 177

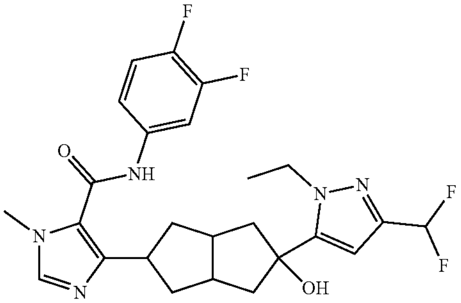 [SMILES: CCn1nc(C(F)F)cc1C1(O)CC2CC(c3ncn(C)c3C(=O)Nc3ccc(F)c(F)c3)CC2C1]

4-(5-(3-(Difluoromethyl)-1-ethyl-1H-pyrazol-5-yl)-5-hydroxyoctahydropentalen-2-yl)-N-(3,4-difluorophenyl)-1-methyl-1H-imidazole-5-carboxamide.

$^1$H NMR (MeOH-d4, 400 MHz): δ 7.78-7.71 (m, 1H), 7.65 (s, 1H), 7.33-7.17 (m, 2H), 6.63 (t, J = 54.8 Hz, 1H), 6.33 (s, 1H), 4.38 (q, J = 7.2 Hz, 2H), 3.75 (s, 3H), 3.37-3.31 (m, 1H), 2.64-2.51 (m, 2H), 2.44-2.32 (m, 2H), 2.28-2.17 (m, 2H), 2.04-1.83 (m, 4H), 1.42 (t, J = 6.8 Hz, 3H) ppm. MS calcd. for $C_{25}H_{27}F_4N_5O_2$: 505.2; Found: 506.2 $[M + 1]^+$.

Example 178

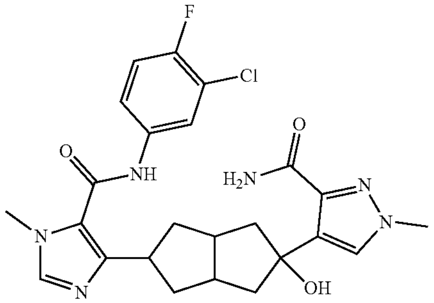

4-(5-(5-((3-Chloro-4-fluorophenyl)carbamoyl)-1-methyl-1H-imidazol-4-yl)-2-hydroxyoctahydropentalen-2-yl)-1-methyl-1H-pyrazole-3-carboxamide.

$^1$H NMR (DMSO-d6, 400 MHz): δ 10.21 (s, 1H), 7.92 (dd, J = 6.8 Hz, 2.8 Hz, 1H), 7.79 (s, 1H), 7.64-7.52 (m, 4H), 7.38 (t, J = 9.0 Hz, 1H), 6.61 (s, 1H), 3.78 (s, 3H), 3.64 (s, 3H), 3.23-3.17 (m, 1H), 2.39 (s, 2H), 2.07-1.99 (m, 4H), 1.84-1.70 (m, 4H) ppm. MS calcd. for $C_{24}H_{26}ClFN_6O_3$: 500.2; Found: 501.2 $[M + 1]^+$.

TABLE 7-continued

Examples 116-222

Example 179

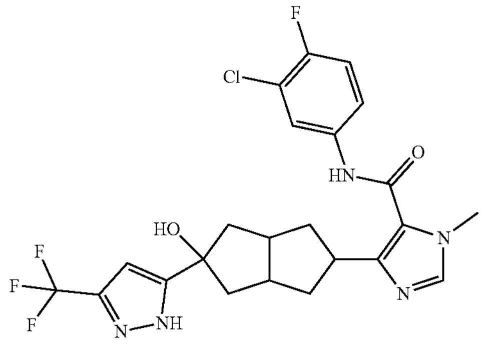 [SMILES: Cn1cnc(C2CC3CC(O)(c4cc(C(F)(F)F)n[nH]4)CC3C2)c1C(=O)Nc1ccc(F)c(Cl)c1]

N-(3-Chloro-4-fluorophenyl)-4-(5-hydroxy-5-(3-(trifluoromethyl)-1H-pyrazol-5-yl)octahydropentalen-2-yl)-1-methyl-1H-imidazole-5-carboxamide.

$^1$H NMR (MeOH-d4, 400 MHz): δ = 7.79 (dd, J = 6.8, 2.8 Hz, 1H), 7.56 (s, 1H), 7.42-7.38 (m, 1H), 7.14 (t, J = 8.8 Hz, 1H), 6.39 (s, 1H), 3.67 (s, 3H), 3.27-3.24 (m, 1H), 2.57-2.56 (m, 2H), 2.22-2.13 (m, 4H), 1.93-1.75 (m, 4H) ppm. MS calcd. for $C_{23}H_{22}ClF_4N_5O_2$: 511.1; Found: 511.9 $[M + 1]^+$.

Example 180

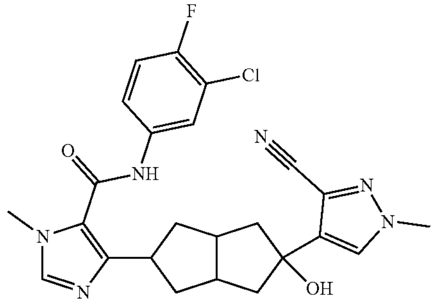

N-(3-Chloro-4-fluorophenyl)-4-(5-(3-cyano-1-methyl-1H-pyrazol-4-yl)-5-hydroxyoctahydropentalen-2-yl)-1-methyl-1H-imidazole-5-carboxamide.

$^1$H NMR (DMSO-d6, 400 MHz): δ 10.21 (s, 1H), 7.93 (dd, J = 6.8, 2.4 Hz, 1H), 7.82 (s, 1H), 7.62 (s, 1H), 7.56-7.52 (m, 1 H), 7.38 (t, J = 9.2 Hz, 1H), 5.17 (s, 1H), 3.82 (s, 3H), 3.64 (s, 3H), 3.20-3.17 (m, 1H), 2.49-2.46 (m, 2H), 2.09-2.02 (m, 4H), 1.89-1.78 (m, 4H) ppm; MS calcd. for $C_{24}H_{24}ClFN_6O_2$: 482.2; Found: 483.2 $[M + 1]^+$.

Example 181

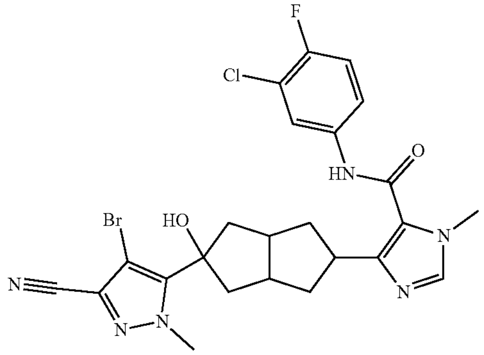 [SMILES: Cn1cnc(C2CC3CC(O)(c4c(Br)c(C#N)nn4C)CC3C2)c1C(=O)Nc1ccc(F)c(Cl)c1]

4-(5-(4-Bromo-3-cyano-1-methyl-1H-pyrazol-5-yl)-5-hydroxyoctahydropentalen-2-yl)-N-(3-chloro-4-fluorophenyl)-1-methyl-1H-imidazole-5-carboxamide.

$^1$H NMR (DMSO-d6, 400 MHz): δ 10.22 (s, 1H), 7.94 (dd, J = 6.8, 2.4 Hz, 1H), 7.62 (s, 1H), 7.57-7.53 (m, 1H), 7.39 (t, J = 9.2 Hz, 1H), 5.59 (s, 1H), 4.08 (s, 3H), 3.65 (s, 3H), 3.29-3.17 (m, 1H), 2.59-2.56 (m, 2H), 2.40-2.33 (m, 2H), 2.07-1.96 (m, 6H) ppm. MS calcd. for $C_{24}H_{23}BrClFN_6O_2$: 560.1; Found: 561.2 $[M + 1]^+$.

TABLE 7-continued

| Examples 116-222 | |
|---|---|
| Example 182 | 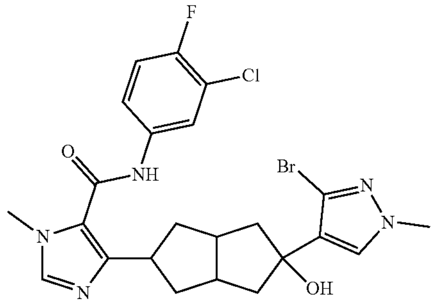<br>4-(5-(3-Bromo-1-methyl-1H-pyrazol-4-yl)-5-hydroxyoctahydropentalen-2-yl)-N-(3-chloro-4-fluorophenyl)-1-methyl-1H-imidazole-5-carboxamide.<br>$^1$H NMR (DMSO-d6, 400 MHz): δ 10.20 (s, 1H), 7.93 (dd, J = 6.8 Hz, 2.4 Hz, 1H), 7.62 (s, 1H), 7.55-7.51 (m, 1H), 7.38 (t, J = 9.2 Hz, 1H), 4.75 (s, 1H), 3.71 (s, 3H), 3.64 (s, 3H), 3.25-3.13 (m, 1H), 2.43-2.41 (m, 2H), 2.24-2.19 (m, 2H), 2.05-2.02 (m, 2H), 1.92-1.85 (m, 2H), 1.72-1.65 (m, 2H) ppm. MS calcd. for $C_{23}H_{24}BrClFN_5O_2$: 535.1; Found: 518.9 $[M - H_2O + 1]^+$. |
| Example 183 | 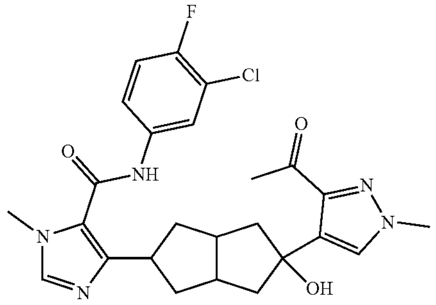<br>4-(5-(3-Acetyl-1-methyl-1H-pyrazol-4-yl)-5-hydroxyoctahydropentalen-2-yl)-N-(3-chloro-4-fluorophenyl)-1-methyl-1H-imidazole-5-carboxamide.<br>$^1$H NMR (DMSO-d6, 400 MHz): δ 10.22 (s, 1H), 7.93 (dd, J = 6.8, 2.4 Hz, 1H), 7.72 (s, 1H), 7.62 (s, 1H), 7.56-7.52 (m, 1H), 7.38 (t, 9.2 Hz, 1H), 5.30 (s, 1H), 3.85 (s, 3H), 3.64 (s, 3H), 3.29-3.17 (m, 1H), 2.51 (s, 3H), 2.48-2.41 (m, 2H), 2.10-2.03 (m, 4H), 1.84-1.71 (m, 2H), 1.70-1.67 (m, 2H) ppm; MS calcd. for $C_{25}H_{27}ClFN_5O_3$: 499.2; Found: 500 $[M + 1]^+$. |
| Example 184 | 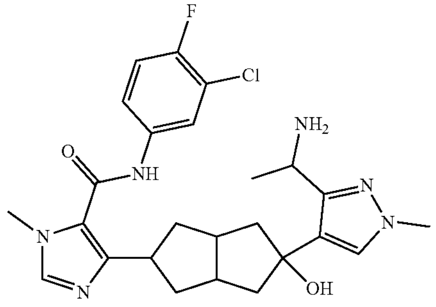<br>4-(5-(3-(1-Aminoethyl)-1-methyl-1H-pyrazol-4-yl)-5-hydroxyoctahydropentalen-2-yl)-N-(3-chloro-4-fluorophenyl)-1-methyl-1H-imidazole-5-carboxamide.<br>$^1$H NMR (DMSO-d6, 400 MHz): δ 10.21 (s, 1H), 7.93 (dd, J = 6.8, 2.4 Hz, 1H), 7.62 (s, 1H), 7.56-7.52 (m, 1 H), 7.40-7.35 (m, 2H), 4.05-4.03 (m, 1H), 3.65 (s, 6H), 3.22-3.16 (m, 1H), 2.34-2.28 (m, 2H), 2.11-1.95 (m, 4H), 1.83-1.70 (m, 4H), 1.34 (d, 6.4 Hz, 3H) ppm. MS calcd. for $C_{25}H_{30}ClFN_6O_2$: 500.2; Found: 501.2 $[M + 1]^+$. |

TABLE 7-continued

Examples 116-222

Example 185

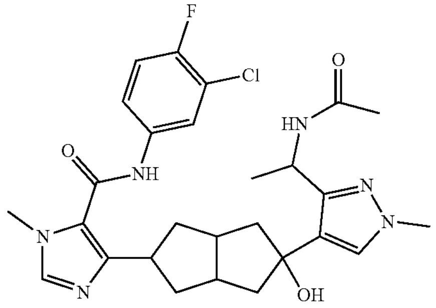

4-(5-(3-(1-Acetamidoethyl)-1-methyl-1H-pyrazol-4-yl)-5-hydroxyoctahydropentalen-2-yl)-N-(3-chloro-4-fluorophenyl)-1-methyl-1H-imidazole-5-carboxamide.
$^1$H NMR (DMSO-d6, 400 MHz): δ 10.23 (s, 1H), 8.13 (d, J = 8.0 Hz, 1H), 7.96 (dd, J = 6.8 Hz, 2.4 Hz, 1H), 7.65 (s, 1H), 7.59-7.55 (m, 1H), 7.41 (t, J = 9.2 Hz, 1H), 5.24-5.19 (m, 1H), 4.96 (s, 1H), 3.71 (s, 3H), 3.67 (s, 3H), 3.33-3.19 (m, 1H), 2.41-2.36 (m, 2H), 2.10-2.03 (m, 4H), 1.88-1.74 (m, 7H), 1.31 (d, J = 6.8 Hz, 3H) ppm. MS calcd. for $C_{27}H_{32}ClFN_6O_3$: 542.2; Found: 525.2 $[M + 1]^+$.

Example 186

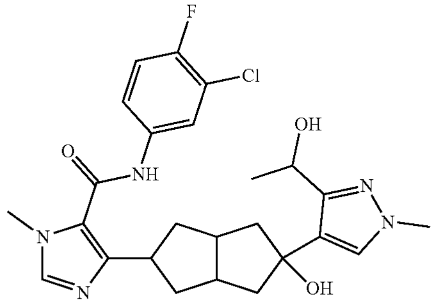

N-(3-Chloro-4-fluorophenyl)-4-(5-hydroxy-5-(3-(1-hydroxyethyl)-1-methyl-1H-pyrazol-4-yl)octahydropentalen-2-yl)-1-methyl-1H-imidazole-5-carboxamide.
$^1$H NMR (DMSO-d6, 400 MHz): δ 10.24 (s, 1H), 7.96 (dd, J = 6.8, 2.4 Hz, 1H), 7.65 (s, 1H), 7.59-7.55 (m, 1 H), 7.45 (s, 1H), 7.40 (t, 9.2 Hz, 1H), 5.41 (d, 4.4 Hz, 1H), 5.35 (s, 1H), 4.92-4.88 (m, 1H), 3.70 (s, 3H), 3.67 (s, 3H), 3.24-3.19 (m, 1H), 2.44-2.38 (m, 2H), 2.21-2.17 (m, 1H), 2.10-2.05 (m, 3H), 1.87-1.70 (m, 4H), 1.41 (d, 6.4 Hz, 3H) ppm. MS calcd. for $C_{25}H_{29}ClFN_5O_3$: 501.2; Found: 502.2 $[M + 1]^+$.

Example 187

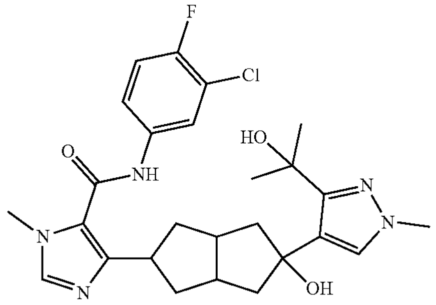

N-(3-Chloro-4-fluorophenyl)-4-(5-hydroxy-5-(3-(2-hydroxypropan-2-yl)-1-methyl-1H-pyrazol-4-yl)octahydropentalen-2-yl)-1-methyl-1H-imidazole-5-carboxamide.
$^1$H NMR (DMSO-d6, 400 MHz): δ 10.24 (s, 1H), 7.96 (dd, J = 6.8, 2.4 Hz, 1H), 7.65 (s, 1H), 7.59-7.56 (m, 1 H), 7.43-7.39 (m, 2H), 6.18 (s, 1H), 5.97 (s, 1H), 3.67 (s, 6H), 3.26-3.20 (m, 1H), 2.48-2.40 (m, 2H), 2.14-2.06 (m, 4H), 1.89-1.82 (m, 4H), 1.45 (s, 6H) ppm. MS calcd. for $C_{26}H_{31}ClFN_5O_3$: 515.2; Found: 516.2 $[M + 1]^+$.

TABLE 7-continued

Examples 116-222

Example 188

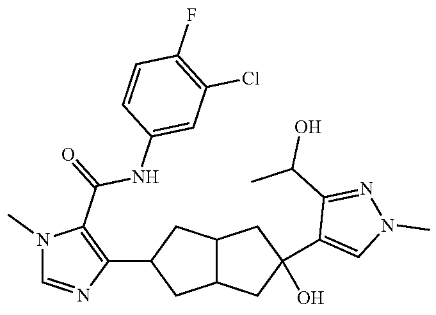

N-(3-Chloro-4-fluorophenyl)-4-(5-hydroxy-5-(3-(1-hydroxyethyl)-1-methyl-1H-pyrazol-4-yl)octahydropentalen-2-yl)-1-methyl-1H-imidazole-5-carboxamide. Single diastereomer I $^1$H NMR (DMSO-d6, 400 MHz): δ 10.24 (s, 1H), 7.96 (dd, J = 6.8, 2.4 Hz, 1H), 7.65 (s, 1H), 7.59-7.55 (m, 1 H), 7.45 (s, 1H), 7.40 (t, 9.2 Hz, 1H), 5.41 (d, 4.4 Hz, 1H), 5.35 (s, 1H), 4.92-4.88 (m, 1H), 3.70 (s, 3H), 3.67 (s, 3H), 3.24-3.19 (m, 1H), 2.44-2.38 (m, 2H), 2.21-2.17 (m, 1H), 2.10-2.05 (m, 3H), 1.87-1.70 (m, 4H), 1.41 (d, 6.4 Hz, 3H) ppm; MS calcd. for C25H29ClFN5O3: 501.2; Found: 502.2 $[M + 1]^+$.

Example 189

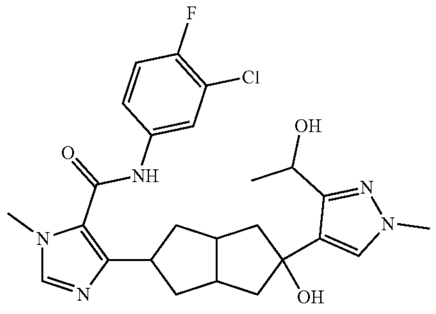

N-(3-Chloro-4-fluorophenyl)-4-(5-hydroxy-5-(3-(1-hydroxyethyl)-1-methyl-1H-pyrazol-4-yl)octahydropentalen-2-yl)-1-methyl-1H-imidazole-5-carboxamide. Single diastereomer II $^1$H NMR (DMSO-d6, 400 MHz): δ 10.24 (s, 1H), 7.96 (dd, J = 6.8, 2.4 Hz, 1H), 7.65 (s, 1H), 7.59-7.55 (m, 1 H), 7.45 (s, 1H), 7.40 (t, 9.2 Hz, 1H), 5.41 (d, 4.4 Hz, 1H), 5.35 (s, 1H), 4.92-4.88 (m, 1H), 3.70 (s, 3H), 3.67 (s, 3H), 3.24-3.19 (m, 1H), 2.44-2.38 (m, 2H), 2.21-2.17 (m, 1H), 2.10-2.05 (m, 3H), 1.87-1.70 (m, 4H), 1.41 (d, 6.4 Hz, 3H) ppm; MS calcd. for $C_{25}H_{29}ClFN_5O_3$: 501.2; Found: 502.2 $[M + 1]^+$.

Example 190

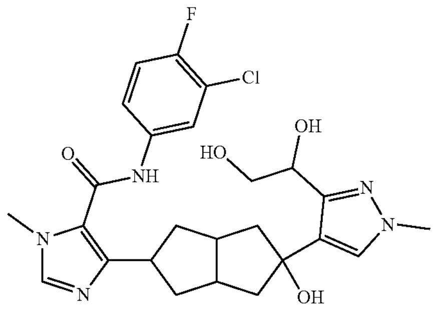

N-(3-Chloro-4-fluorophenyl)-4-(5-(3-(1,2-dihydroxyethyl)-1-methyl-1H-pyrazol-4-yl)-5-hydroxyoctahydropentalen-2-yl)-1-methyl-1H-imidazole-5-carboxamide.

$^1$H NMR (DMSO-d6, 400 MHz): δ 10.23 (s, 1H), 7.96 (dd, J = 6.8 Hz, 2.4 Hz, 1H), 7.65 (s, 1H), 7.59-7.55 (m, 1H), 7.44-7.39 (m, 2H), 5.33 (d, J = 4.8 Hz, 1H), 5.18 (s, 1H), 4.76-4.74 (m, 1H), 4.56 (t, J = 6.0 Hz, 1H), 3.70 (s, 3H), 3.67 (s, 3H), 3.64-3.60 (m, 2H), 3.24-3.21 (m, 1H), 2.49-2.44 (m, 2H), 2.14-2.06 (m, 4H), 1.85-1.77 (m, 4H) ppm. MS calcd. for $C_{25}H_{29}ClFN_5O_4$: 517.2; Found: 500.2 $[M - H_2O + 1]^+$.

TABLE 7-continued

| Examples 116-222 |
|---|

Example 191

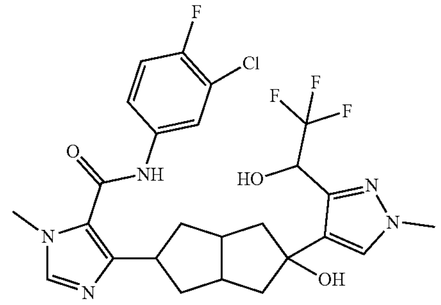

N-(3-Chloro-4-fluorophenyl)-4-(5-hydroxy-5-(1-methyl-3-(2,2,2-trifluoro-1-hydroxyethyl)-1H-pyrazol-4-yl)octahydropentalen-2-yl)-1-methyl-1H-imidazole-5-carboxamide.
$^1$H NMR (DMSO-d6, 400 MHz): δ 10.25 (S, 1H), 7.96 (dd, J = 6.8 Hz, 2.8 Hz, 1H), 7.66 (s, 1H), 7.60-7.54 (m, 2H), 7.41 (t, J = 9.2 Hz, 1H), 6.53 (d, J = 7.6 Hz, 1H), 5.49-5.45 (m, 1H), 5.14 (s, 1H), 3.75 (s, 3H), 3.68 (s, 3H), 3.34-3.22 (m, 1H), 2.44-2.39 (m, 2H), 2.12-2.07 (m, 4H), 1.88-1.75 (m, 4H) ppm. MS calcd. for $C_{25}H_{26}ClF_4N_5O_3$: 555.2; Found; 556.2 $[M + 1]^+$.

Example 192

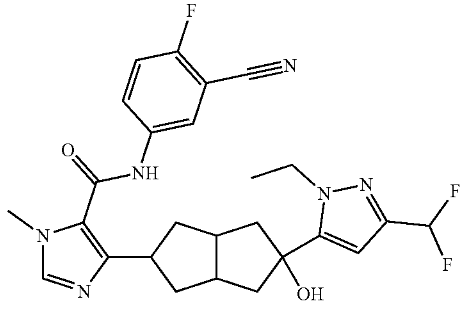 [SMILES: CCn1nc(C(F)F)cc1C1(O)CC2CC(c3ncn(C)c3C(=O)Nc3ccc(F)c(C#N)c3)CC2C1]

N-(3-Cyano-4-fluorophenyl)-4-(5-(3-(difluoromethyl)-1-ethyl-1H-pyrazol-5-yl)-5-hydroxyoctahydropentalen-2-yl)-1-methyl-1H-imidazole-5-carboxamide.
$^1$H NMR (MeOH-d4, 400 MHz): δ 7.78-7.74 (m, 1H), 7.69 (dd, J = 6.4, 2.4 Hz, 1H), 7.66 (s, 1H), 7.63 (s, 1H), 7.26 (t, J = 9.2 Hz, 1H), 6.73 (t, J = 54.8 Hz, 1H), 6.44 (s, 1H), 4.68 (q, J = 7.2 Hz, 2H), 3.76 (s, 3H), 3.53-3.49 (m, 1H), 2.84-2.76 (m, 2H), 2.55-2.48 (m, 2H), 2.39-2.32 (m, 2H), 2.23-2.17 (m, 2H), 1.74-1.66 (m, 2H), 1.45 (t, J = 7.2 Hz, 3H) ppm; MS calcd. for $C_{26}H_{27}F_3N_6O_2$; 512.2; Found: 513.2 $[M + 1]^+$.

TABLE 7-continued

Examples 116-222

Example 193

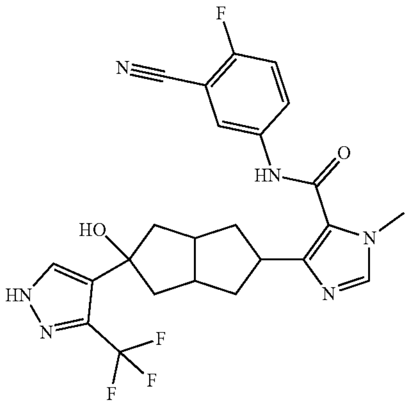 [SMILES: Cn1cnc(C2CC3CC(O)(c4c[nH]nc4C(F)(F)F)CC3C2)c1C(=O)Nc1ccc(F)c(C#N)c1]

N-(3-Cyano-4-fluorophenyl)-4-(5-hydroxy-5-(3-(trifluoromethyl)-1H-pyrazol-4-yl)octahydropentalen-2-yl)-1-methyl-1H-imidazole-5-carboxamide.

$^1$H NMR (DMSO-d6, 400 MHz): δ 13.25 (m, 1H), 10.36 (s, 1H), 8.16-8.14 (m, 1H), 7.95-7.91 (m, 1H), 7.78 (s, 1H), 7.66-7.62 (m, 1H), 7.53 (t, J = 9.0 Hz, 1H), 4.82 (s, 1H), 3.68 (s, 3H), 3.26-3.20 (m, 1H), 2.52-2.51 (m, 2H), 2.14-2.05 (m, 4H), 1.93-1.75 (m, 4H) ppm; MS calcd. for $C_{24}H_{22}F_4N_6O_2$: 502.2; Found: 503.2 $[M + 1]^+$.

Example 194

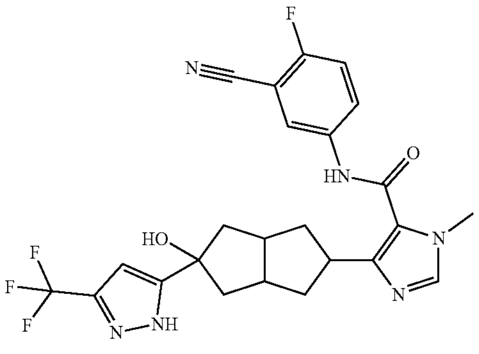 [SMILES: Cn1cnc(C2CC3CC(O)(c4cc(C(F)(F)F)n[nH]4)CC3C2)c1C(=O)Nc1ccc(F)c(C#N)c1]

N-(3-Cyano-4-fluorophenyl)-4-(5-hydroxy-5-(3-(trifluoromethyl)-1H-pyrazol-5-yl)octahydropentalen-2-yl)-1-methyl-1H-imidazole-5-carboxamide.

$^1$H NMR (DMSO-d6, 400 MHz): δ 13.37 (s, 1H), 10.36 (s, 1H), 8.16 (dd, J = 6.8, 2.4 Hz, 1H), 7.96-7.92 (m, 1H), 7.67 (s, 1H), 7.54 (t, J = 9.2 Hz, 1H), 6.51 (s, 1H), 5.38 (s, 1H), 3.68 (s, 3H), 3.25-3.22 (m, 1H), 2.51-2.50 (m, 2H), 2.17-2.06 (m, 4H), 1.96-1.91 (m, 2H), 1.87-1.80 (m, 2H) ppm; MS calcd for $C_{24}H_{22}F_4N_6O_2$: 502.2. Found: 503.2 $[M + 1]^+$.

TABLE 7-continued

| Examples 116-222 | |
|---|---|
| Example 195 | 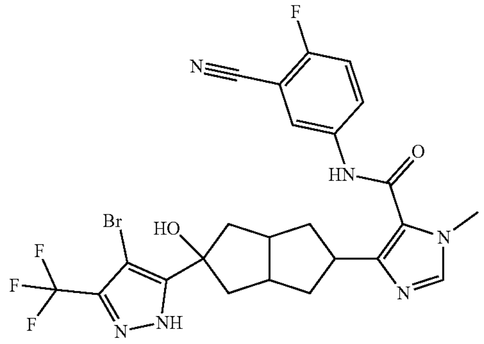 [SMILES: Cn1cnc(C2CC3CC(O)(c4[nH]nc(C(F)(F)F)c4Br)CC3C2)c1C(=O)Nc1ccc(F)c(C#N)c1]<br>4-(5-(4-Bromo-3-(trifluoromethyl)-1H-pyrazol-5-yl)-5-hydroxyoctahydropentalen-2-yl)-N-(3-cyano-4-fluorophenyl)-1-methyl-1H-imidazole-5-carboxamide.<br>$^1$H NMR (DMSO-d6, 400 MHz): δ 13.65 (s, 1H), 10.36 (s, 1H), 8.17-8.15 (m, 1H), 7.96-7.91 (m, 1H), 7.66 (s, 1H), 7.54 (t, J = 9.2 Hz, 1H), 5.51 (s, 1H), 3.68 (s, 3H), 3.30-3.20 (m, 1H), 2.67-2.58 (m, 2H), 2.42-2.30 (m, 2H), 2.09-1.99 (m, 4H), 1.91 (d, J = 5.6 Hz, 2H) ppm; MS calcd. for $C_{24}H_{21}BrF_4N_6O_2$: 580.1; Found: 581.2 $[M + 1]^+$. |
| Example 196 | 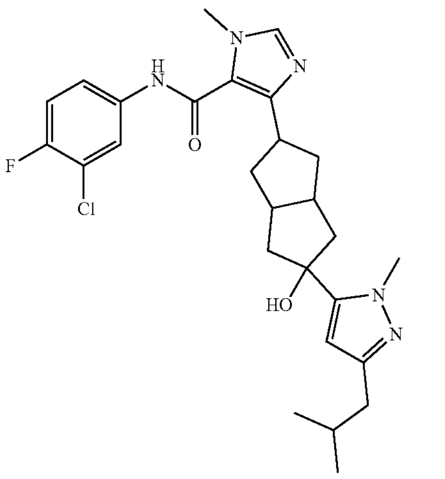 [SMILES: CC(C)Cc1cc(C2(O)CC3CC(c4ncn(C)c4C(=O)Nc4ccc(F)c(Cl)c4)CC3C2)n(C)n1]<br>N-(3-Chloro-4-fluorophenyl)-4-(5-hydroxy-5-(3-isobutyl-1-methyl-1H-pyrazol-5-yl)octahydropentalen-2-yl)-1-methyl-1H-imidazole-5-carboxamide<br>$^1$H NMR (400 MHz, DMSO-d6): δ 10.20 (s, 1H), 7.98-7.93 (m, 1H), 7.65 (s, 1H), 7.60-7.55 (m, 1H), 7.40 (t, J = 8.8 Hz, 1H), 5.84 (s, 1H), 5.16 (s, 1H), 3.81 (s, 3H), 3.67 (s, 3H), 3.29-3.19 (m, 1H), 2.48-2.38 (m, 2H), 2.31-2.02 (m, 6H), 1.90-1.74 (m, 5H), 0.86 (d, J = 6.8 Hz, 6H) ppm; TLC: 5% MeOH/DCM (Rf: 0.3); MS calcd. for $C_{27}H_{33}ClFN_5O_2$: 513.2; Observed: 514.2 $[M + 1]^+$. |

TABLE 7-continued

| Examples 116-222 | |
| --- | --- |
| Example 197 | 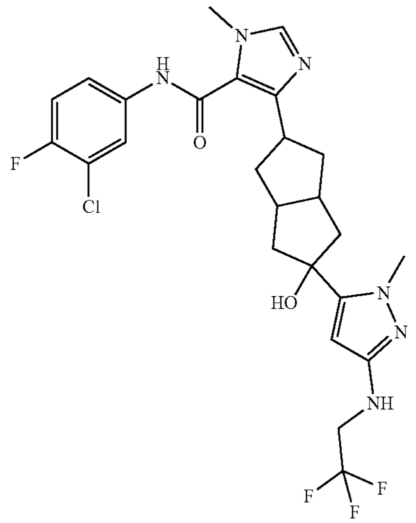 [SMILES: Cn1cnc(C2CC3CC(O)(c4cc(NCC(F)(F)F)nn4C)CC3C2)c1C(=O)Nc1ccc(F)c(Cl)c1]<br>N-(3-Chloro-4-fluorophenyl)-4-(5-hydroxy-5-(1-methyl-3-((2,2,2-trifluoroethyl)amino)-1H-pyrazol-5-yl)octahydropentalen-2-yl)-1-methyl-1H-imidazole-5-carboxamide<br>$^1$H NMR (400 MHz, DMSO-d6): δ 10.24 (br.s, 1H), 7.96 (d, J = 6.8 Hz, 1H), 7.80-7.62 (m, 1H), 7.60-7.54 (m, 1H), 7.41 (t, J = 9.2 Hz, 1H), 5.68 (t, J = 6.8 Hz, 1H), 5.38 (s, 1H), 5.16 (s, 1H), 3.78-3.72 (m, 2H), 3.68 (s, 6H), 3.26-3.22 (m, 1H), 2.50-2.43 (m, 2H), 2.17-2.10 (m, 4H), 1.90-1.78 (m, 4H) ppm; TLC: 10% MeOH/DCM (Rf: 0.4); MS calcd. for $C_{25}H_{27}ClF_4N_6O_2$: 554.2; Observed: 553.2 $[M-1]^-$. |
| Example 198 | 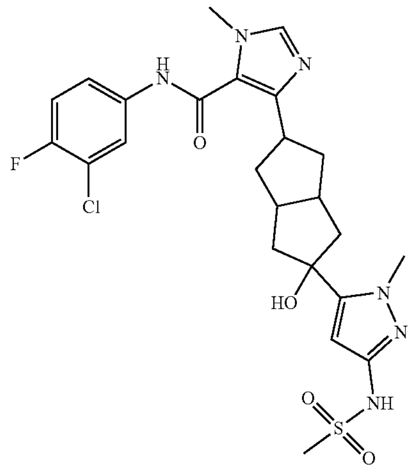 [SMILES: Cn1cnc(C2CC3CC(O)(c4cc(NS(C)(=O)=O)nn4C)CC3C2)c1C(=O)Nc1ccc(F)c(Cl)c1]<br>N-(3-Chloro-4-fluorophenyl)-4-(5-hydroxy-5-(1-methyl-3-(methylsulfonamido)-1H-pyrazol-5-yl)octahydropentalen-2-yl)-1-methyl-1H-imidazole-5-carboxamide<br>$^1$H NMR (400 MHz, DMSO-d6): δ 10.21 (s, 1H), 9.64 (s, 1H), 8.00-7.92 (m, 1H), 7.65 (s, 1H), 7.61-7.54 (m, 1H), 7.44-7.36 (m, 1H), 5.82 (s, 1H), 5.29 (s, 1H), 3.81 (s, 3H), 3.67 (s, 3H), 3.39-3.21 (m, 1H, merged), 2.99 (s, 3H), 2.57-2.41 (2H, merged), 2.22-2.04 (m, 4H), 1.92-1.80 (m, 4H) ppm; TLC: 5% MeOH/DCM (Rf: 0.3); MS calcd. for $C_{24}H_{28}ClFN_6O_4S$: 550.2; Observed: 551.2 $[M+1]^+$. |

TABLE 7-continued

Examples 116-222

Example 199

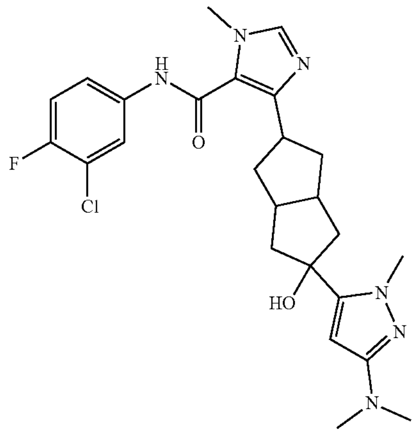 [SMILES: CN(C)c1cc(C2(O)CC3CC(c4ncn(C)c4C(=O)Nc4ccc(F)c(Cl)c4)CC3C2)n(C)n1]

N-(3-Chloro-4-fluorophenyl)-4-(5-(3-(dimethylamino)-1-methyl-1H-pyrazol-5-yl)-5-hydroxyoctahydropentalen-2-yl)-1-methyl-1H-imidazole-5-carboxamide $^1$H NMR (400 MHz, DMSO-d6): δ 10.21 (s, 1H), 8.00-7.92 (m, 1H), 7.65 (s, 1H), 7.60-7.52 (m, 1H), 7.40 (t, J = 8.8 Hz, 1H), 5.49 (s, 1H), 5.14 (s, 1H), 3.70 (s, 3H), 3.67 (s, 3H), 3.28-3.20 (m, 1H), 2.65 (s, 6H), 2.47-2.41 (m, 2H), 2.22-2.04 (m, 4H), 1.90-1.78 (m, 4H) ppm. TLC: 5% MeOH/DCM (Rf: 0.3). MS calcd. for $C_{25}H_{30}ClFN_6O_2$: 500.2; Observed: 499.2 $[M-1]^-$.

Example 200

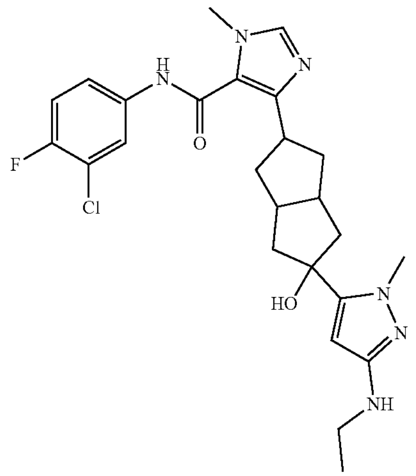 [SMILES: CCNc1cc(C2(O)CC3CC(c4ncn(C)c4C(=O)Nc4ccc(F)c(Cl)c4)CC3C2)n(C)n1]

N-(3-Chloro-4-fluorophenyl)-4-(5-(3-(ethylamino)-1-methyl-1H-pyrazol-5-yl)-5-hydroxyoctahydropentalen-2-yl)-1-methyl-1H-imidazole-5-carboxamide $^1$H NMR (400 MHz, DMSO-d6): δ 10.23 (s, 1H), 8.13 (s, 1H), 7.99-7.93 (m, 1H), 7.78-7.68 (m, 1H), 7.60-7.52 (m, 1H), 7.40 (t, J = 9.2 Hz, 1H), 5.30 (s, 1H), 5.12 (s, 1H), 3.68 (s, 3H), 3.67 (s, 3H), 3.27-3.19 (m, 1H), 2.96 (q, J = 7.6 Hz, 2H), 2.47-2.40 (m, 2H), 2.19-2.04 (m, 4H), 1.90-1.76 (m, 4H), 1.06 (t, J = 7.6 Hz, 3H) ppm. TLC: 5% MeOH/DCM (Rf: 0.3). MS calcd. for $C_{25}H_{30}ClFN_6O_2$: 500.2; Observed: 499.2 $[M-1]^-$.

TABLE 7-continued

| Examples 116-222 | |
|---|---|
| Example 201 | 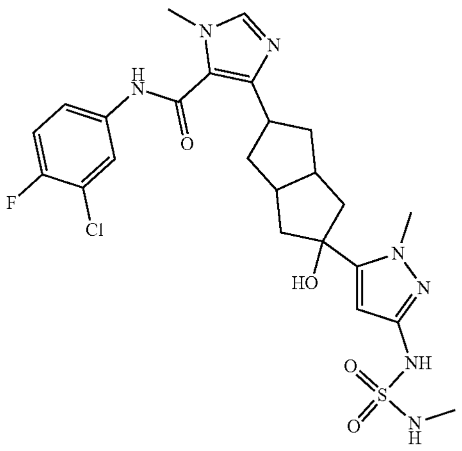 [SMILES: CNS(=O)(=O)Nc1cc(C2(O)CC3CC(c4ncn(C)c4C(=O)Nc4ccc(F)c(Cl)c4)CC3C2)n(C)n1]<br>N-(3-Chloro-4-fluorophenyl)-4-(5-hydroxy-5-(1-methyl-3-((N-methylsulfamoyl)amino)-1H-pyrazol-5-yl)octahydropentalen-2-yl)-1-methyl-1H-imidazole-5-carboxamide<br>$^1$H NMR (400 MHz, DMSO-d6): δ 10.22 (s, 1H), 9.53 (s, 1H), 7.96 (d, J = 5.2 Hz, 1H), 7.65 (s, 1H), 7.60-7.54 (m, 1H), 7.40 (t, J = 9.6 Hz, 1H), 6.92-6.88 (m, 1H), 5.84 (s, 1H), 5.26 (s, 1H), 3.78 (s, 3H), 3.67 (s, 3H), 3.30-3.20 (m, 1H), 2.48-2.45 (m, 5H), 2.10-2.06 (m, 4H), 1.90-1.85 (m, 4H) ppm. TLC: 5% MeOH/DCM (Rf: 0.2). MS calcd. for $C_{24}H_{29}ClFN_7O_4S$: 565.2; Observed: 566.6 $[M + 1]^+$. |
| Example 202 | 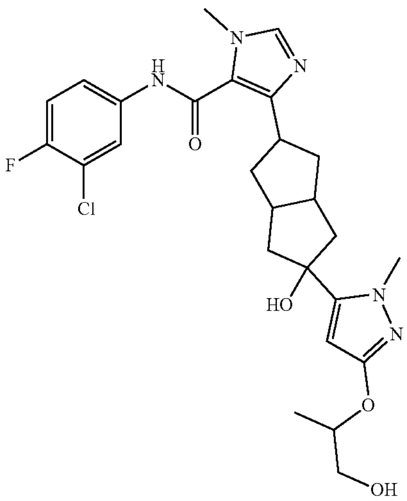 [SMILES: CC(CO)Oc1cc(C2(O)CC3CC(c4ncn(C)c4C(=O)Nc4ccc(F)c(Cl)c4)CC3C2)n(C)n1]<br>N-(3-Chloro-4-fluorophenyl)-4-(5-hydroxy-5-(3-((1-hydroxypropan-2-yl)oxy)-1-methyl-1H-pyrazol-5-yl)octahydropentalen-2-yl)-1-methyl-1H-imidazole-5-carboxamide<br>$^1$H NMR (400 MHz, DMSO-d6): δ 10.20 (s, 1H), 7.96 (d, J = 6.4 Hz, 1H), 7.65 (s, 1H), 7.60-7.54 (m, 1H), 7.40 (t, J = 8.8 Hz, 1H), 5.48 (s, 1H), 5.21 (s, 1H), 4.72 (t, J = 6.0 Hz, 1H), 4.44-4.41 (m, 1H), 3.72 (s, 3H), 3.67 (s, 3H), 3.51-3.46 (m, 1H), 3.40-3.15 (m, 2H, merged), 2.54-2.40 (m, 2H), 2.20-2.05 (m, 4H), 1.90-1.82 (m, 4H), 1.16 (d, J = 6.4 Hz, 3H) ppm. TLC: 5% MeOH/DCM (Rf: 0.4). MS calcd. for $C_{26}H_{31}ClFN_5O_4$: 531.2; Observed: 530.2 $[M - 1]^-$. |

TABLE 7-continued

Examples 116-222

Example 203

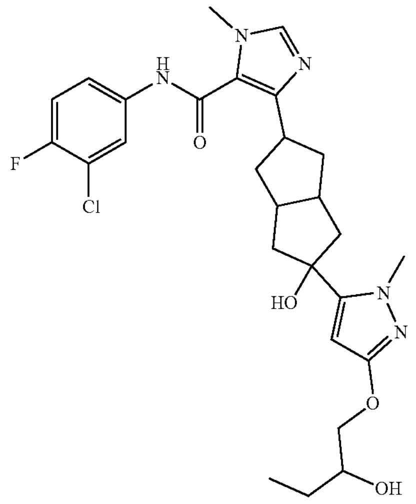 [SMILES: CCC(O)COc1cc(C2(O)CC3CC(c4ncn(C)c4C(=O)Nc4ccc(F)c(Cl)c4)CC3C2)n(C)n1]

N-(3-Chloro-4-fluorophenyl)-4-(5-hydroxy-5-(3-(2-hydroxybutoxy)-1-methyl-1H-pyrazol-5-yl)octahydropentalen-2-yl)-1-methyl-1H-imidazole-5-carboxamide $^1$H NMR (400 MHz, DMSO-d6): δ 10.20 (s, 1H), 7.95 (d, J = 6.4 Hz, 1H), 7.64 (s, 1H), 7.58-7.54 (m, 1H), 7.39 (t, J = 8.4 Hz, 1H), 5.50 (s, 1H), 5.21 (s, 1H), 4.72-4.70 (m, 1H), 3.85-3.82 (m, 2H), 3.72 (s, 3H), 3.67 (s, 3H), 3.65-3.60 (m, 1H), 3.40-3.10 (m, 1H), 2.50-2.40 (m, 2H), 2.10-2.08 (m, 4H), 1.84-1.80 (m, 4H), 1.55-1.30 (m, 2H), 0.88 (t, J = 6.8 Hz, 3H) ppm. TLC: 5% MeOH/DCM (Rf: 0.3). MS calcd. for $C_{27}H_{33}ClFN_5O_4$: 545.2; Observed: 544.2 $[M-1]^-$.

Example 204

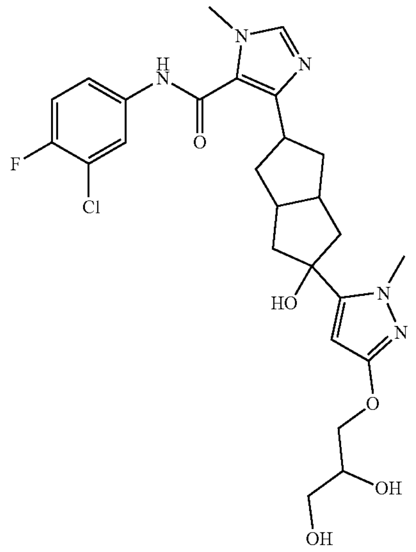 [SMILES: Cn1cnc(C2CC3CC(O)(c4cc(OCC(O)CO)nn4C)CC3C2)c1C(=O)Nc1ccc(F)c(Cl)c1]

N-(3-Chloro-4-fluorophenyl)-4-(5-(3-(2,3-dihydroxypropoxy)-1-methyl-1H-pyrazol-5-yl)-5-hydroxyoctahydropentalen-2-yl)-1-methyl-1H-imidazole-5-carboxamide $^1$H NMR (400 MHz, DMSO-d6): δ 10.21 (s, 1H), 7.98-7.94 (m, 1H), 7.65 (s, 1H), 7.60-7.52 (m, 1H), 7.40 (t, J = 9.6 Hz, 1H), 5.50 (s, 1H), 5.23 (s, 1H), 4.83 (d, J = 5.2 Hz, 1H), 4.58 (t, J = 4.8 Hz, 1H), 4.00-3.95 (m, 1H), 3.88-3.82 (m, 1H), 3.72 (s, 3H), 3.67 (s, 3H), 3.40-3.20 (m, 4H, merged), 2.49-2.42 (m, 2H), 2.20-2.07 (m, 4H), 1.90-1.80 (m, 4H) ppm. TLC: 10% MeOH/DCM (Rf: 0.3). MS calcd. for $C_{26}H_{31}ClFN_5O_5$: 547.2; Observed: 546.3 $[M-1]^-$.

TABLE 7-continued

| Examples 116-222 | |
|---|---|
| Example 205 | 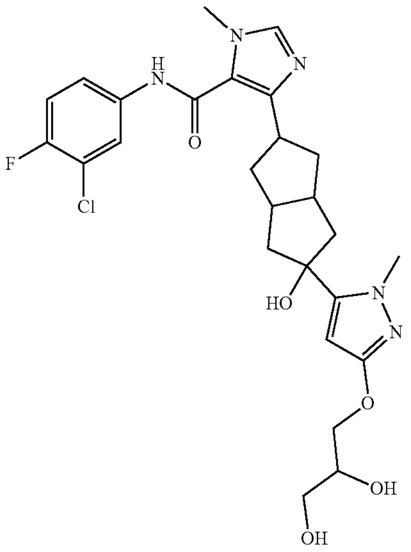 [SMILES: Cn1cnc(C2CC3CC(O)(c4cc(OCC(O)CO)nn4C)CC3C2)c1C(=O)Nc1ccc(F)c(Cl)c1] N-(3-Chloro-4-fluorophenyl)-4-(5-(3-(2,3-dihydroxypropoxy)-1-methyl-1H-pyrazol-5-yl)-5-hydroxyoctahydropentalen-2-yl)-1-methyl-1H-imidazole-5-carboxamide. Isomer I $^1$H NMR (400 MHz, DMSO-d6): δ 10.20 (s, 1H), 7.95 (dd, J = 6.8, 2.4 Hz, 1H), 7.65 (s, 1H), 7.59-7.55 (m, 1H), 7.40 (t, J = 8.8 Hz, 1H), 5.51 (s, 1H), 5.22 (s, 1H), 4.81 (d, J = 2.8 Hz, 1H), 4.57 (t, J = 7.6 Hz, 1H), 4.40-3.96 (m, 1H), 3.89-3.3.84 (m, 1H), 3.72-3.66 (m, 7H), 3.39-3.22 (m, 3H, merged), 2.50-2.48 (m, 2H, merged), 2.21-2.08 (m, 4H), 1.89-1.80 (m, 4H) ppm; TLC: 5% MeOH/DCM (Rf: 0.3); MS calcd. for $C_{26}H_{31}ClFN_5O_5$: 547.2; Observed: 546.2 $[M-1]^-$. |
| Example 206 | 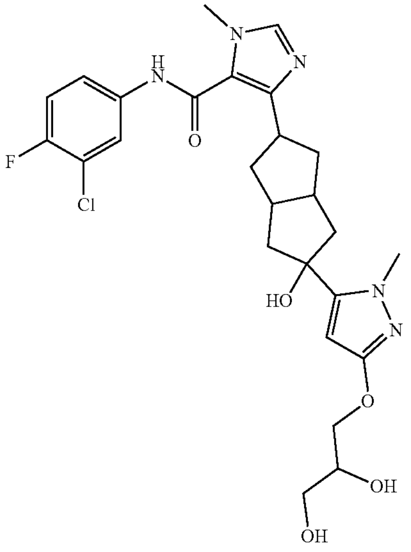 [SMILES: Cn1cnc(C2CC3CC(O)(c4cc(OCC(O)CO)nn4C)CC3C2)c1C(=O)Nc1ccc(F)c(Cl)c1] N-(3-Chloro-4-fluorophenyl)-4-(5-(3-(2,3-dihydroxypropoxy)-1-methyl-1H-pyrazol-5-yl)-5-hydroxyoctahydropentalen-2-yl)-1-methyl-1H-imidazole-5-carboxamide. Isomer II $^1$H NMR (400 MHz, DMSO-d6): δ 10.21 (s, 1H), 7.95 (dd, J = 6.8, 2.4 Hz, 1H), 7.64 (s, 1H), 7.59-7.54 (m, 1H), 7.39 (t, J = 8.4 Hz, 1H), 5.51 (s, 1H), 5.22 (s, 1H), 4.82 (d, J = 2.4 Hz, 1H), 4.59-4.57 (m, 1H), 4.02-3.97 (m, 1H), 3.89-3.3.84 (m, 1H), 3.73-3.66 (m, 7H, merged), 3.38-3.22 (m, 3H, merged), 2.50-2.48 (m, 2H, merged), 2.21-2.07 (m, 4H), 1.89-1.80 (m, 4H) ppm; TLC: 5% MeOH/DCM (Rf: 0.3). MS calcd. for $C_{26}H_{31}ClFN_5O_5$: 547.2; Observed: 546.2 $[M-1]^-$. |

TABLE 7-continued

Examples 116-222

Example 207

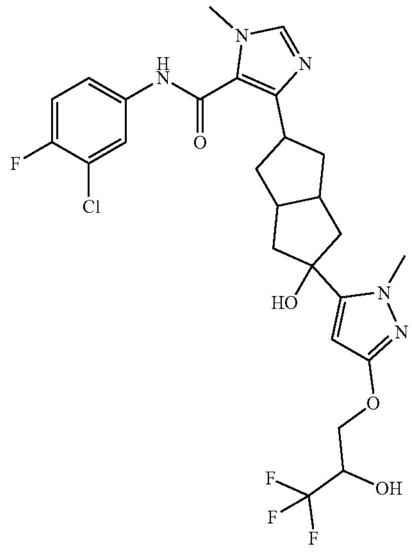 [SMILES: Cn1cnc(C2CC3CC(O)(c4cc(OCC(O)C(F)(F)F)nn4C)CC3C2)c1C(=O)Nc1ccc(F)c(Cl)c1]

N-(3-Chloro-4-fluorophenyl)-4-(5-hydroxy-5-(1-methyl-3-(3,3,3-trifluoro-2-hydroxypropoxy)-1H-pyrazol-5-yl)octahydropentalen-2-yl)-1-methyl-1H-imidazole-5-carboxamide $^1$H NMR (400 MHz, DMSO-d6): δ 10.22 (s, 1H), 7.95 (d, J = 6.4 Hz, 1H), 7.65 (s, 1H), 7.60-7.54 (m, 1H), 7.40 (t, J = 9.2 Hz, 1H), 6.55 (d, J = 6.4 Hz, 1H), 5.56 (s, 1H), 5.25 (s, 1H), 4.35-4.30 (m, 1H), 4.20-4.15 (m, 1H), 4.09-4.03 (m, 1H), 3.74 (s, 3H), 3.67 (s, 3H), 3.32-3.23 (m, 1H), 2.49-2.40 (m, 2H), 2.20-2.06 (m, 4H), 1.90-1.80 (m, 4H) ppm. TLC: 10% MeOH/DCM (Rf: 0.2). MS calcd. for $C_{26}H_{28}ClF_4N_5O_4$: 585.2; Observed: 584.3 $[M-1]^-$.

Example 208

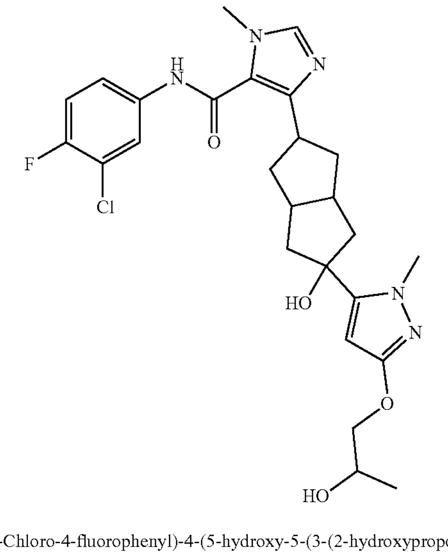

N-(3-Chloro-4-fluorophenyl)-4-(5-hydroxy-5-(3-(2-hydroxypropoxy)-1-methyl-1H-pyrazol-5-yl)octahydropentalen-2-yl)-1-methyl-1H-imidazole-5-carboxamide $^1$H NMR (400 MHz, DMSO-d6): δ 10.21 (s, 1H), 7.95 (d, J = 6.8 Hz, 1H), 7.65 (s, 1H), 7.57-7.54 (m, 1H), 7.40 (t, J = 9.2 Hz, 1H), 5.50 (s, 1H), 5.22 (s, 1H), 4.76-4.74 (m, 1H), 3.86-3.81 (m, 2H), 3.77-3.74 (m, 1H), 3.72 (s, 3H), 3.67 (s, 3H), 3.26-3.24 (m, 1H), 2.50-2.44 (m, 2H), 2.20-2.07 (m, 4H), 1.88-1.80 (m, 4H), 1.07 (d, J = 5.2 Hz, 3H) ppm. TLC: 10% MeOH/DCM (Rf: 0.4). MS calcd. for $C_{26}H_{31}ClFN_5O_4$: 531.2; Observed: 514.5 $[M-H_2O+1]^+$.

TABLE 7-continued

Examples 116-222

Example 209

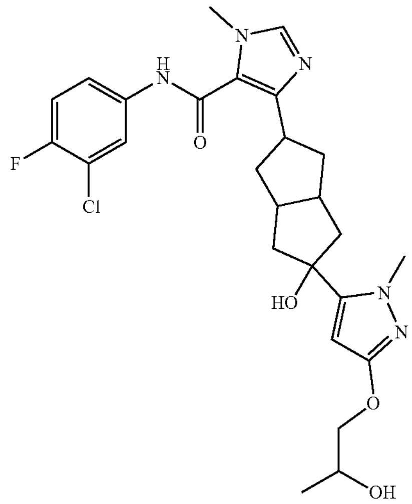

N-(3-Chloro-4-fluorophenyl)-4-(5-hydroxy-5-(3-(2-hydroxypropoxy)-1-methyl-1H-pyrazol-5-yl)octahydropentalen-2-yl)-1-methyl-1H-imidazole-5-carboxamide. Single diastereomer I $^{1}$H NMR (400 MHz, DMSO-d6): δ 10.64 (s, 1H), 7.95 (dd, J = 6.4, 2.4 Hz, 1H), 7.59-7.55 (m, 1H), 7.44 (t, J = 9.2 Hz, 1H), 5.52 (s, 1H), 5.30 (br.s, 1H), 3.89-3.27 (m, 11H), 2.50-2.48 (m, 2H, merged), 2.21-2.14 (m, 4H), 1.87-1.78 (m, 4H), 1.06 (d, J= 6.0 Hz, 3H) ppm (1H not observed); TLC: 5% MeOH/DCM (Rf: 0.3). MS calcd. for $C_{26}H_{31}ClFN_5O_4$: 531.2; Observed: 530.3 $[M - 1]^-$.

Example 210

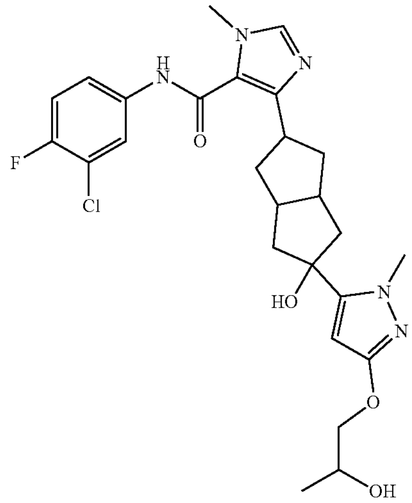 [SMILES: CC(O)COc1cc(C2(O)CC3CC(c4ncn(C)c4C(=O)Nc4ccc(F)c(Cl)c4)CC3C2)n(C)n1]

N-(3-Chloro-4-fluorophenyl)-4-(5-hydroxy-5-(3-(2-hydroxypropoxy)-1-methyl-1H-pyrazol-5-yl)octahydropentalen-2-yl)-1-methyl-1H-imidazole-5-carboxamide. Single diastereomer II $^{1}$H NMR (400 MHz, DMSO-d6): δ 10.67 (s, 1H), 7.95 (dd, J = 6.8, 2.4 Hz, 1H), 7.59-7.55 (m, 1H), 7.44 (t, J = 9.2 Hz, 1H), 5.52 (s, 1H), 5.30 (br.s, 1H), 3.89-3.27 (m, 11H), 2.50-2.48 (m, 2H, merged), 2.21-2.14 (m, 4H), 1.87-1.78 (m, 4H), 1.06 (d, J = 6.0 Hz, 3H) ppm (1H not observed); TLC: 5% MeOH/DCM (Rf: 0.3); LCMS calculated for $C_{26}H_{31}ClFN_5O_4$: 531.2; Observed: 530.2 $[M - 1]^-$.

TABLE 7-continued

| Examples 116-222 | |
|---|---|
| Example 211 | 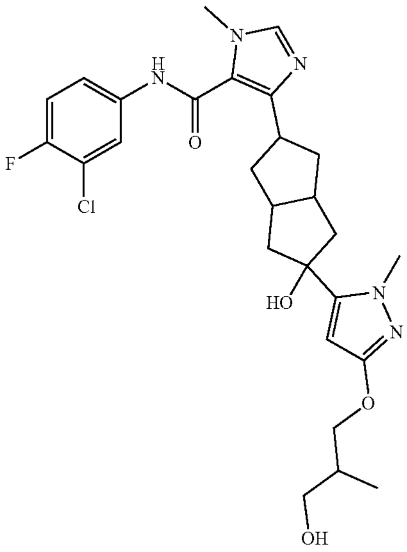 [SMILES: CC(CO)COc1cc(C2(O)CC3CC(c4ncn(C)c4C(=O)Nc4ccc(F)c(Cl)c4)CC3C2)n(C)n1]<br>N-(3-Chloro-4-fluorophenyl)-4-(5-hydroxy-5-(3-(3-hydroxy-2-methylpropoxy)-1-methyl-1H-pyrazol-5-yl)octahydropentalen-2-yl)-1-methyl-1H-imidazole-5-carboxamide<br>$^1$H NMR (400 MHz, DMSO-d6): δ 10.22 (s, 1H), 7.94 (d, J = 5.6 Hz, 1H), 7.66 (s, 1H), 7.60-7.54 (m, 1H), 7.40 (t, J = 9.6 Hz, 1H), 5.51 (s, 1H), 5.22 (s, 1H), 4.52-4.48 (m, 1H), 3.96-3.90 (m, 1H), 3.81-3.75 (m, 1H), 3.72 (s, 3H), 3.68 (s, 3H), 3.26-3.21 (m, 3H), 2.48-2.40 (m, 2H), 2.20-2.05 (m, 4H), 1.94-1.80 (m, 5H), 0.89 (d, J = 6.8 Hz, 3H) ppm. TLC: 10% MeOH/DCM (Rf: 0.2). MS calcd. for $C_{27}H_{33}ClFN_5O_4$: 545.2; Observed: 546.1 $[M + 1]^+$. |
| Example 212 | 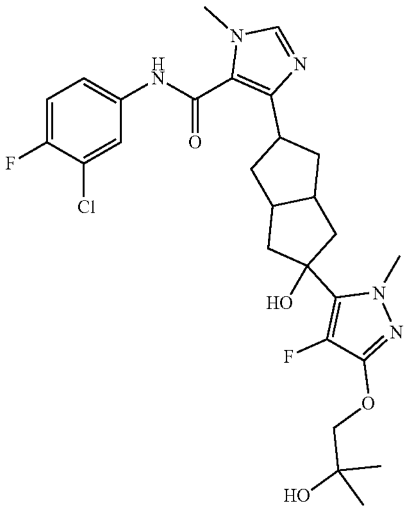 [SMILES: Cn1cnc(C2CC3CC(O)(c4c(F)c(OCC(C)(C)O)nn4C)CC3C2)c1C(=O)Nc1ccc(F)c(Cl)c1]<br>N-(3-Chloro-4-fluorophenyl)-4-(5-(4-fluoro-3-(2-hydroxy-2-methylpropoxy)-1-methyl-1H-pyrazol-5-yl)-5-hydroxyoctahydropentalen-2-yl)-1-methyl-1H-imidazole-5-carboxamide<br>$^1$H NMR (400 MHz, DMSO-d6): δ 10.22 (s, 1H), 7.96 (d, J = 5.2 Hz, 1H), 7.65 (s, 1H), 7.58-7.54 (m, 1H), 7.40 (t, J = 9.6 Hz, 1H), 5.37 (s, 1H), 4.60 (s, 1H), 3.82 (s, 2H), 3.71 (s, 3H), 3.67 (s, 3H), 3.26-3.21 (m, 1H), 2.50-2.45 (m, 2H, merged), 2.26-2.20 (m, 2H), 2.10-2.06 (m, 2H), 1.95-1.89 (m, 4H), 1.14 (s, 6H) ppm. TLC: 10% MeOH/DCM (Rf: 0.5). MS calcd. for $C_{27}H_{32}ClF_2N_5O_4$: 563.2; Observed: 546.1 $[M - 18 + 1]^+$. |

TABLE 7-continued

Examples 116-222

Example 213

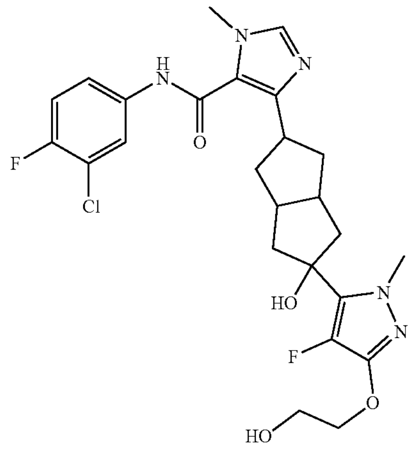 [SMILES: Cn1cnc(C2CC3CC(O)(c4c(F)c(OCCO)nn4C)CC3C2)c1C(=O)Nc1ccc(F)c(Cl)c1]

N-(3-Chloro-4-fluorophenyl)-4-(5-(4-fluoro-3-(2-hydroxyethoxy)-1-methyl-1H-pyrazol-5-yl)-5-hydroxyoctahydropentalen-2-yl)-1-methyl-1H-imidazole-5-carboxamide $^1$H NMR (400 MHz, DMSO-d6): δ 10.21 (s, 1H), 7.96 (d, J = 5.2 Hz, 1H), 7.65 (s, 1H), 7.60-7.54 (m, 1H), 7.40 (t, J = 9.2 Hz, 1H), 5.37 (s, 1H), 4.81 (t, J = 5.2 Hz, 1H), 4.08 (t, J = 5.2 Hz, 2H), 3.71 (s, 3H), 3.68-3.62 (m, 5H), 3.30-3.20 (m, 1H), 2.55-2.40 (m, 2H, merged), 2.25-2.20 (m, 2H), 2.12-2.05 (m, 2H), 1.95-1.88 (m, 4H) ppm. TLC: 10% MeOH/DCM (Rf: 0.3). MS calcd. for $C_{25}H_{28}ClF_2N_5O_4$: 535.2; Observed: 518.2 $[M - H_2O + 1]^+$.

Example 214

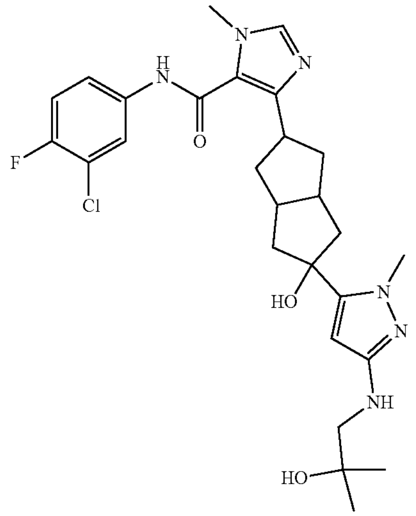 [SMILES: Cn1cnc(C2CC3CC(O)(c4cc(NCC(C)(C)O)nn4C)CC3C2)c1C(=O)Nc1ccc(F)c(Cl)c1]

N-(3-Chloro-4-fluorophenyl)-4-(5-hydroxy-5-(3-((2-hydroxy-2-methylpropyl)amino)-1-methyl-1H-pyrazol-5-yl)octahydropentalen-2-yl)-1-methyl-1H-imidazole-5-carboxamide $^1$H NMR (400 MHz, DMSO-d6): δ 10.20 (s, 1H), 7.94 (d, J = 4.8 Hz, 1H), 7.65 (s, 1H), 7.58-7.54 (m, 1H), 7.40 (t, J = 8.8 Hz, 1H), 5.33 (s, 1H), 5.12 (s, 1H), 4.63-4.60 (m, 1H), 4.47 (s, 1H), 3.67-3.63 (m, 6H), 3.30-3.20 (m, 1H), 2.88 (d, J = 5.2 Hz, 2H), 2.48-2.42 (m, 2H), 2.15-2.07 (m, 4H), 1.82-1.75 (m, 4H), 1.08 (s, 6H) ppm. TLC: 5% MeOH/DCM (Rf: 0.2). MS calcd. for $C_{27}H_{34}ClFN_6O_3$: 544.2; Observed: 545.3 $[M + 1]^+$.

TABLE 7-continued

Examples 116-222

Example 215

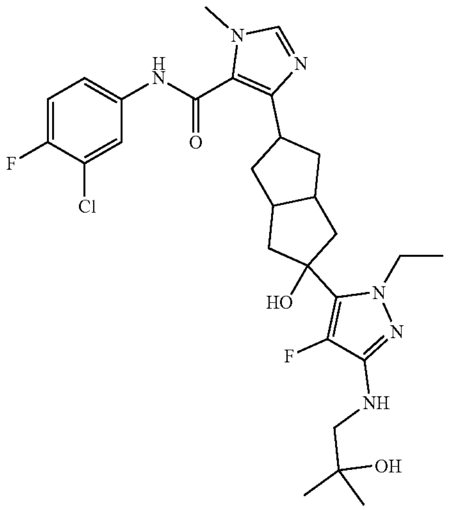 [SMILES: CCn1nc(NCC(C)(C)O)c(F)c1C1(O)CC2CC(c3ncn(C)c3C(=O)Nc3ccc(F)c(Cl)c3)CC2C1]

N-(3-Chloro-4-fluorophenyl)-4-(5-(1-ethyl-4-fluoro-3-((2-hydroxy-2-methylpropyl)amino)-1H-pyrazol-5-yl)-5-hydroxyoctahydropentalen-2-yl)-1-methyl-1H-imidazole-5-carboxamide $^1$H NMR (400 MHz, DMSO-d6): δ 10.20 (s, 1H), 7.96 (d, J = 6.8 Hz, 1H), 7.64 (s, 1H), 7.60-7.54 (m, 1H), 7.40 (t, J = 9.6 Hz, 1H), 5.29 (s, 1H), 4.57 (t, J = 5.6 Hz, 1H), 4.49 (s, 1H), 4.02 (q, J = 6.8 Hz, 2H), 3.67 (s, 3H), 3.15-3.19 (m, 1H), 2.97 (d, J = 6.4 Hz, 2H), 2.55-2.45 (m, 2H, merged), 2.25-2.20 (m, 2H), 2.10-2.06 (m, 2H), 1.98-1.86 (m, 4H), 1.22 (t, J = 6.4 Hz, 3H), 1.10 (s. 6H). TLC: 5% MeOH/DCM (Rf: 0.3). MS calcd. for $C_{28}H_{35}ClF_2N_6O_3$: 576.2; Observed: 577.2 $[M + 1]^+$.

Example 216

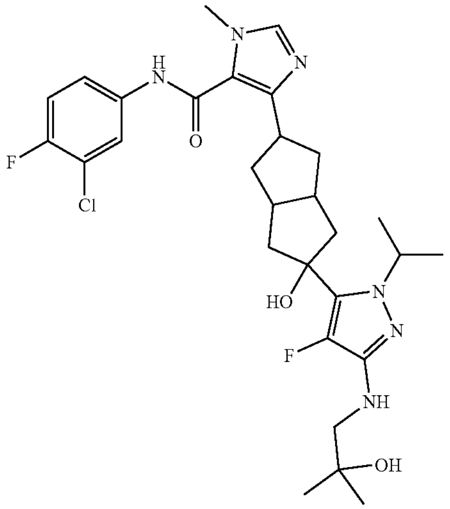 [SMILES: CC(C)n1nc(NCC(C)(C)O)c(F)c1C1(O)CC2CC(c3ncn(C)c3C(=O)Nc3ccc(F)c(Cl)c3)CC2C1]

N-(3-Chloro-4-fluorophenyl)-4-(5-(4-fluoro-3-((2-hydroxy-2-methylpropyl)amino)-1-isopropyl-1H-pyrazol-5-yl)-5-hydroxyoctahydropentalen-2-yl)-1-methyl-1H-imidazole-5-carboxamide $^1$H NMR (400 MHz, DMSO-d6): δ 10.30 (br. S, 1H), 7.98-7.94 (m, 1H), 7.60-7.54 (m, 1H), 7.42 (t, J = 9.2 Hz, 1H), 5.34 (s, 1H), 4.79 (t, J = 6.8 Hz, 1H), 4.60-4.56 (m, 1H), 3.72 (s, 3H), 3.40-3.20 (m, 1H, merged), 2.98 (s, 2H), 2.50-2.40 (m, 2H, merged), 2.25-2.12 (m, 4H), 1.92-1.87 (m, 4H), 1.25 (d, J = 6.4 Hz, 6H), 1.10 (s, 6H) ppm (OH proton not observed). TLC: 5% MeOH/DCM (Rf: 0.3). MS calcd. for $C_{29}H_{37}ClF_2N_6O_3$: 590.3; Observed: 591.2 $[M + 1]^+$.

TABLE 7-continued

| Examples 116-222 | |
|---|---|
| Example 217 | 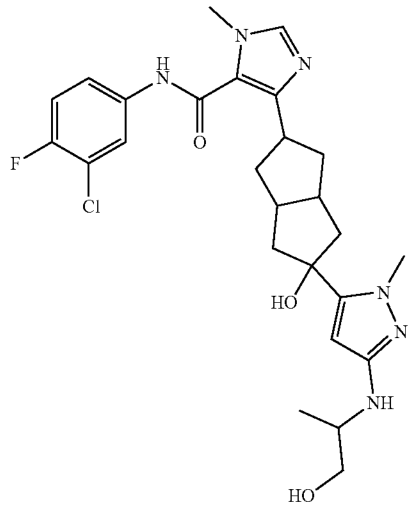 [SMILES: CC(CO)Nc1cc(C2(O)CC3CC(c4ncn(C)c4C(=O)Nc4ccc(F)c(Cl)c4)CC3C2)n(C)n1]<br>N-(3-Chloro-4-fluorophenyl)-4-(5-hydroxy-5-(3-((1-hydroxypropan-2-yl)amino)-1-methyl-1H-pyrazol-5-yl)octahydropentalen-2-yl)-1-methyl-1H-imidazole-5-carboxamide<br>$^{1}H$ NMR (400 MHz, DMSO-d6): δ 10.20 (s, 1H), 7.96 (d, J = 7.2 Hz, 1H), 7.64 (s, 1H), 7.58-7.54 (m, 1H), 7.40 (t, J = 8.8 Hz, 1H), 5.29 (s, 1H), 5.09 (s, 1H), 4.56-4.50 (m, 2H), 3.68-3.65 (m, 6H), 3.25-3.16 (m, 4H), 2.45-2.38 (m, 2H), 2.17-2.05 (m, 4H), 1.90-1.78 (m, 4H), 1.03 (d, J = 6.4 Hz, 3H) ppm. TLC: 5% MeOH/DCM (Rf: 0.2). MS calcd. for $C_{26}H_{32}ClFN_6O_3$: 530.2; Observed: 531.2 $[M + 1]^+$. |
| Example 218 | 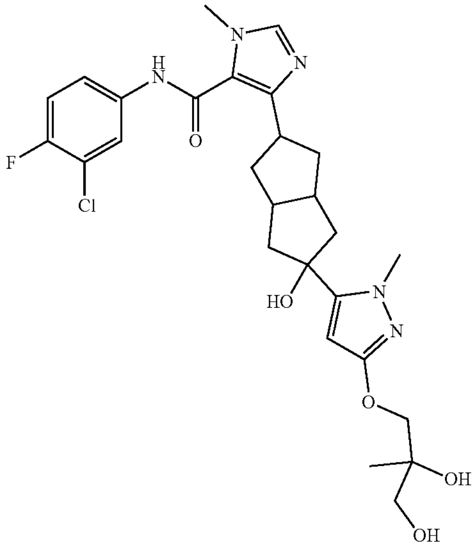 [SMILES: Cn1cnc(C2CC3CC(O)(c4cc(OCC(C)(O)CO)nn4C)CC3C2)c1C(=O)Nc1ccc(F)c(Cl)c1]<br>N-(3-Chloro-4-fluorophenyl)-4-(5-(3-(2,3-dihydroxy-2-methylpropoxy)-1-methyl-1H-pyrazol-5-yl)-5-hydroxyoctahydropentalen-2-yl)-1-methyl-1H-imidazole-5-carboxamide<br>$^{1}H$ NMR (400 MHz, DMSO-d6): δ 10.62 (br.s, 1H), 7.95 (dd, J = 6.8, 2.4 Hz, 1H), 7.69-7.55 (m, 2H), 7.44 (t, J = 8.8 Hz, 1H), 5.51 (s, 1H), 5.29 (br.s, 1H), 3.87-3.71 (m, 7H), 3.52-3.21 (m, 5H, merged), 2.50-2.48 (m, 2H, merged), 2.22-2.17 (m, 4H), 1.86-1.82 (m, 4H), 1.06 (s, 3H) ppm; TLC: 5% MeOH/DCM (Rf: 0.2). MS calcd. for $C_{27}H_{33}ClFN_5O_5$: 561.2; Observed: 562.2 $[M + 1]^+$. |

TABLE 7-continued

Examples 116-222

Example 219

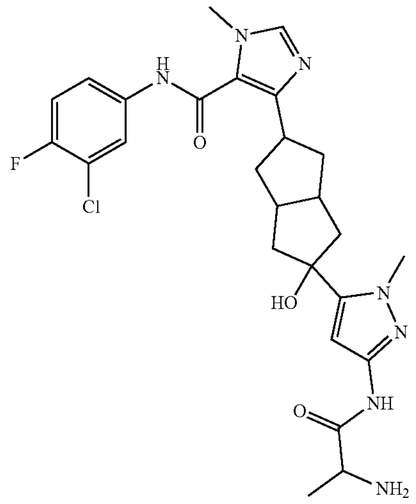 [SMILES: CC(N)C(=O)Nc1cc(C2(O)CC3CC(c4ncn(C)c4C(=O)Nc4ccc(F)c(Cl)c4)CC3C2)n(C)n1]

4-(5-(3-(2-Aminopropanamido)-1-methyl-1H-pyrazol-5-yl)-5-hydroxyoctahydropentalen-2-yl)-N-(3-chloro-4-fluorophenyl)-1-methyl-1H-imidazole-5-carboxamide 1H NMR (400 MHz, DMSO-d6): δ 10.20 (s, 1H), 8.26 (s, 1H) 7.95 (dd, J = 6.4, 2.0 Hz, 1H), 8.26 (s, 1H), 7.58-7.54 (m, 1H), 7.39 (t, J = 9.2 Hz, 1H), 6.35 (s, 1H), 5.53 (br.s, 1H), 3.80 (s, 3H), 3.67 (s, 3H), 3.52-3.42 (m, 3H), 3.30-3.20 (m, 1H), 2.50-2.45 (m, 2H, merged), 2.24-2.12 (m, 2H), 2.12-2.05 (m, 2H), 1.91-1.80 (m, 4H), 1.19 (d, J = 6.8 Hz, 3H) ppm. TLC: 5% MeOH:$NH_3$ [9:1]/DCM (Rf: 0.2). MS calcd. for $C_{26}H_{31}ClFN_7O_3$: 543.2; Observed: 544.2 $[M + 1]^+$.

Example 220

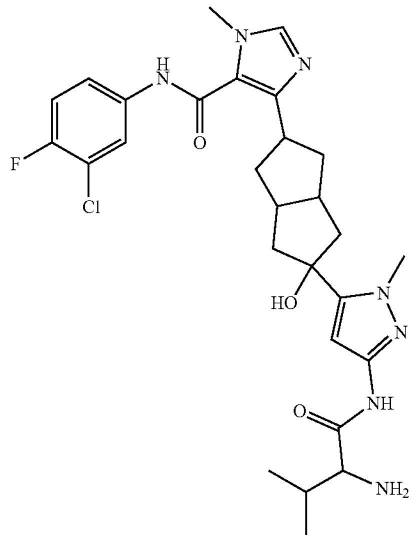 [SMILES: CC(C)C(N)C(=O)Nc1cc(C2(O)CC3CC(c4ncn(C)c4C(=O)Nc4ccc(F)c(Cl)c4)CC3C2)n(C)n1]

4-(5-(3-(2-Amino-3-methylbutanamido)-1-methyl-1H-pyrazol-5-yl)-5-hydroxyoctahydropentalen-2-yl)-N-(3-chloro-4-fluorophenyl)-1-methyl-1H-imidazole-5-carboxamide $^1$H NMR (400 MHz, DMSO-d6): δ 10.20 (s, 1H), 8.25 (br.s, 1H) 7.97 (dd, J = 6.4, 2.0 Hz, 1H), 7.66 (s, 1H) 7.60-7.54 (m, 1H), 7.41 (t, J = 9.2 Hz, 1H), 6.38 (s, 1H), 5.51 (s, 1H), 3.81 (s, 3H), 3.69 (s, 3H), 3.60-3.30 (m, 3H, merged), 3.14 (d, J = 5.16 Hz, 1H), 2.60-2.50 (m, 2H, merged), 2.28-2.18 (m, 2H), 2.17-2.08 (m, 2H), 1.95-1.82 (m, 5H), 0.90-0.80 (m, 6H) ppm. TLC: 10% MeOH:$NH_3$ [9:1]/DCM (Rf: 0.2). MS calcd. for $C_{28}H_{35}ClFN_7O_3$: 571.3; Observed: 572.3 $[M + 1]^+$.

TABLE 7-continued

Examples 116-222

Example 221

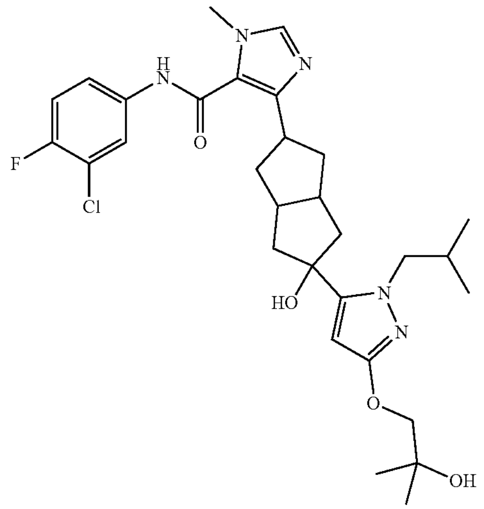 [SMILES: CC(C)Cn1nc(OCC(C)(C)O)cc1C1(O)CC2CC(c3ncn(C)c3C(=O)Nc3ccc(F)c(Cl)c3)CC2C1]

N-(3-Chloro-4-fluorophenyl)-4-(5-hydroxy-5-(3-(2-hydroxy-2-methylpropoxy)-1-isobutyl-1H-pyrazol-5-yl)octahydropentalen-2-yl)-1-methyl-1H-imidazole-5-carboxamide $^1$H NMR (400 MHz, DMSO-d6): δ 10.51 (br.s, 1H), 7.95 (dd, J = 6.8, 2.4 Hz, 1H), 7.58-7.54 (m, 1H), 7.42 (t, J = 9.2 Hz, 1H), 5.50 (s, 1H), 5.20 (s, 1H), 3.85 (t, J = 7.2 Hz, 2H), 3.78-3.72 (m, 5H), 3.30-3.28 (m, 1H, merged), 2.50-2.48 (m, 2H, merged), 2.32-2.10 (m, 5H), 1.86-1.83 (m, 4H), 1.23 (s, 6H), 0.84 (d, J = 6.8 Hz, 6H) ppm (2 protons not observed). TLC: 5% MeOH/DCM (Rf: 0.4). MS calcd. for $C_{30}H_{39}ClFN_5O_4$: 587.3; Observed: 588.3 $[M + 1]^+$.

Example 222

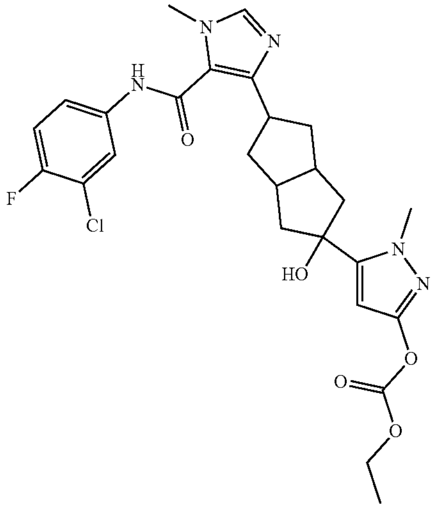 [SMILES: CCOC(=O)Oc1cc(C2(O)CC3CC(c4ncn(C)c4C(=O)Nc4ccc(F)c(Cl)c4)CC3C2)n(C)n1]

5-(5-(5-((3-Chloro-4-fluorophenyl)carbamoyl)-1-methyl-1H-imidazol-4-yl)-2-hydroxyoctahydropentalen-2-yl)-1-methyl-1H-pyrazol-3-yl ethyl carbonate $^1$H NMR (400 MHz, DMSO-d6): δ 10.21 (s, 1H), 7.97-7.93 (m, 1H), 7.65 (s, 1H), 7.58-7.56 (m, 1H), 7.39 (t, J = 8.8 Hz, 1H), 5.95 (s, 1H), 5.38 (s, 1H), 4.22 (q, J = 7.2 Hz, 2H), 3.82 (s, 3H), 3.67 (s, 3H), 3.30-3.28 (m, 1H, merged), 2.50-2.48 (m, 2H, merged), 2.18-2.07 (m, 4H), 1.88-1.84 (m, 4H), 1.26 (t, J = 7.2 Hz, 3H) ppm. TLC: 5% MeOH/DCM (Rf: 0.4). MS calcd. for $C_{26}H_{29}ClFN_5O_5$: 545.2; Observed: 546.2 $[M + 1]^+$.

TABLE 7-continued

| Examples 116-222 | |
|---|---|
| Example 223 | 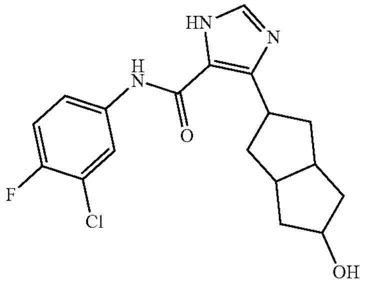 [SMILES: O=C(Nc1ccc(F)c(Cl)c1)c1[nH]cnc1C1CC2CC(O)CC2C1] N-(3-Chloro-4-fluorophenyl)-4-(5-hydroxyoctahydropentalen-2-yl)-1-methyl-1H-imidazole-5-carboxamide $^1$H NMR (400 MHz, DMSO-d6): δ 12.51 (s, 1H), 10.01 (s, 1H), 8.18 (m, 1H), 7.77 (m, 1H), 7.67 (s, 1H), 7.34 (m, 1H), 4.66 (m, 1H), 4.08 (m, 1H), 3.91 (m, 1H), 2.40 (m, 2H), 2.13 (m, 2H), 2.03 (m, 2H), 1.62 (m, 2H), 1.35 (m, 2H) ppm. MS calcd. for $C_{18}H_{19}CLFN_3O_3$: 363.1. Found: 364.2 $[M+1]^+$. |

VI. BIOLOGICAL DATA

Assay Measuring Activity of Test Compounds on Viral Production from HepAD38 Cells HepAD38 cells grown in a T-150 flask (Corning, cat #: 430825) with Growth Medium (DMEM/F12 (1:1) (Hyclone, cat #: SH30023.02), 1× Pen/Strep (Invitrogen, cat #: 15140-122), 10% FBS (Tissue Culture Biologics, cat #: 101), 250 μg/mL G418 (Alfa Aesar, cat #: J62671), 1 μg/mL Tetracycline (Teknova, cat #: T3320)) were detached with 0.25% trypsin-EDTA (Invitrogen, cat #: 25200-056). Tetracycline-free treatment medium (15 mL DMEM/F12 (1:1) 1× Pen/step, with 2% FBS, Tet-system approved (Clontech, cat #: 631106) were then added to mix, transferred into a 50 ml conical tube (Falcon, cat #: 21008-918) and spun at 1300 rpm for 5 min. Pelleted cells were then re-suspended/washed with 50 mL of 1×DPBS (Invitrogen, cat #: 14190-136) 2 times and 50 mL treatment medium twice. HepAD38 cells were then re-suspended with 10 mL of treatment medium, syringed and counted. Wells of 96-well clear bottom TC plate (Corning, cat #: 3904) were seeded at 50,000 cells/well in 180 μL of treatment medium, and 20 μL of either 10% DMSO (Sigma, cat #: D4540) as controls or a 10× solution of test compounds in 10% DMSO in treatment media was added for a final compound concentration starting at 10 μM, and plates were incubated in 5% $CO_2$ incubator at 37° C. for 5 days.

Subsequently viral load production was assayed by quantitative PCR (qPCR) of the HBV core sequence. PCR reaction mixture containing forward primers HBV-f 5'-CTGTGCCTTGGGTGGCITT-3' (IDT DNA), Reverse primers HBV-r 5'-AAGGAAAGAAGTCAGAAGGCAAAA-3' (IDT DNA), Fluorescent TaqMan™ Probes HBV-probe 5'-FAM/AGCTCCAAA/ZENMITCTITATAAGGGTCGATGTC/3IABkFQ-3' (IDT DNA), 10 μL/well of PerfeCTa® qPCR ToughMix® (Quanta Biosciences, Cat #: 95114-05K), and 6 μL/well of DEPC water (Alfa Aesar, cat #: J62087) was prepared. Four μL of supernatant was added to 16 μL of the reaction mixture in a qPCR plate (Applied Biosytems, Cat #: 4309849), sealed with a film (Applied Biosystems, Cat #: 4311971), centrifuged for a few seconds, and subsequently run on an Applied Biosystems VIIA7. The PCR mixture was incubated at 45° C. for 5 min, then 95° C. for 10 min, followed by 40 cycles of 10 seconds at 95° C. and 20 seconds at 60° C. Viral load was quantified against known HBV DNA standards by using ViiA™ 7 Software. Viral load in the supernatant from wells with treated cells were compared against viral load in supernatant from DMSO control wells (3 per plate). Cell viability assay was performed with CellTiter-Glo Luminescent Cell Viability Assay (Promega, cat #: G7573) with modification. Mixed appropriate amount of CellTiter-Glo (CTG) 1×DPBS in a 1:1 ratio, added 100 uL of the mixture to each well followed completely removal of all supernatant in each well without touching cell surface. Incubated the plate at room temperature for 10 min on an orbital shaker, and then read the plate with a plate reader (TECAN M1000 or Envision). $EC_{50}$ or $CC_{50}$ values were calculated through curve-fitting of the four-parameter non-linear-logistic-regression model (GraphPad Prism or Dotmatics). $CC_{50}$ values were all >10 μM.

Table 8 gives the viral load lowering $EC_{50}$ values for exemplified compounds of the invention grouped in the following ranges: A indicates $EC_{50}$<10 nM; B indicates $EC_{50}$ of ≥10 to <50 nM; C indicates $EC_{50}$ of ≥50 to <500 nM

TABLE 8

Viral load lowering for exemplified compounds of the invention.

| Compound | VL HepAD38 $EC_{50}$ range |
|---|---|
| Example 1 | A |
| Example 2 | A |
| Example 3 | A |
| Example 4 | A |
| Example 5 | A |
| Example 6 | A |
| Example 7 | A |
| Example 8 | A |
| Example 9 | A |
| Example 10 | A |
| Example 11 | B |
| Example 12 | A |
| Example 13 | B |
| Example 14 | A |
| Example 15 | A |
| Example 16 | A |
| Example 17 | A |
| Example 18 | B |
| Example 19 | A |

TABLE 8-continued

| Viral load lowering for exemplified compounds of the invention. | |
|---|---|
| Compound | VL HepAD38 $EC_{50}$ range |
| Example 20 | A |
| Example 21 | A |
| Example 22 | A |
| Example 23 | A |
| Example 24 | A |
| Example 25 | A |
| Example 26 | B |
| Example 27 | A |
| Example 28 | A |
| Example 29 | B |
| Example 30 | A |
| Example 31 | A |
| Example 32 | B |
| Example 33 | A |
| Example 34 | B |
| Example 35 | A |
| Example 36 | C |
| Example 37 | C |
| Example 38 | A |
| Example 39 | A |
| Example 40 | C |
| Example 41 | B |
| Example 42 | B |
| Example 43 | B |
| Example 44 | B |
| Example 45 | B |
| Example 46 | B |
| Example 47 | C |
| Example 48 | C |
| Example 49 | C |
| Example 50 | A |
| Example 51 | A |
| Example 52 | A |
| Example 53 | A |
| Example 54 | A |
| Example 55 | A |
| Example 56 | A |
| Example 57 | A |
| Example 58 | A |
| Example 59 | A |
| Example 60 | A |
| Example 61 | A |
| Example 62 | A |
| Example 63 | A |
| Example 64 | A |
| Example 65 | A |
| Example 66 | A |
| Example 67 | A |
| Example 68 | A |
| Example 69 | B |
| Example 70 | A |
| Example 71 | A |
| Example 72 | A |
| Example 73 | A |
| Example 74 | A |
| Example 75 | A |
| Example 76 | A |
| Example 77 | A |
| Example 78 | A |
| Example 79 | A |
| Example 80 | C |
| Example 81 | B |
| Example 82 | C |
| Example 84 | C |
| Example 85 | C |
| Example 87 | A |
| Example 90 | C |
| Example 91 | A |
| Example 92 | A |
| Example 93 | A |
| Example 94 | A |
| Example 95 | B |
| Example 96 | A |
| Example 97 | A |
| Example 98 | A |

TABLE 8-continued

| Viral load lowering for exemplified compounds of the invention. | |
|---|---|
| Compound | VL HepAD38 $EC_{50}$ range |
| Example 99 | A |
| Example 100 | A |
| Example 101 | A |
| Example 102 | A |
| Example 103 | A |
| Example 104 | A |
| Example 105 | A |
| Example 106 | A |
| Example 107 | A |
| Example 108 | A |
| Example 109 | A |
| Example 110 | A |
| Example 111 | B |
| Example 112 | B |
| Example 113 | A |
| Example 114 | A |
| Example 115 | A |
| Example 116 | A |
| Example 117 | A |
| Example 118 | A |
| Example 119 | A |
| Example 120 | A |
| Example 121 | A |
| Example 122 | A |
| Example 123 | A |
| Example 124 | A |
| Example 125 | A |
| Example 126 | A |
| Example 127 | B |
| Example 128 | A |
| Example 129 | B |
| Example 130 | A |
| Example 131 | A |
| Example 132 | A |
| Example 133 | A |
| Example 134 | A |
| Example 135 | A |
| Example 136 | A |
| Example 137 | A |
| Example 138 | A |
| Example 139 | A |
| Example 140 | A |
| Example 141 | A |
| Example 142 | A |
| Example 143 | A |
| Example 144 | A |
| Example 145 | A |
| Example 146 | A |
| Example 147 | A |
| Example 148 | A |
| Example 149 | A |
| Example 150 | A |
| Example 151 | A |
| Example 152 | A |
| Example 153 | A |
| Example 154 | A |
| Example 155 | A |
| Example 156 | A |
| Example 157 | A |
| Example 158 | A |
| Example 159 | A |
| Example 160 | A |
| Example 161 | A |
| Example 162 | A |
| Example 163 | A |
| Example 164 | A |
| Example 165 | A |
| Example 166 | A |
| Example 168 | B |
| Example 169 | A |
| Example 170 | A |
| Example 171 | A |
| Example 172 | A |
| Example 173 | A |
| Example 174 | A |

TABLE 8-continued

| Viral load lowering for exemplified compounds of the invention. | |
|---|---|
| Compound | VL HepAD38 $EC_{50}$ range |
| Example 175 | A |
| Example 176 | A |
| Example 177 | A |
| Example 178 | A |
| Example 179 | A |
| Example 180 | A |
| Example 181 | A |
| Example 182 | A |
| Example 183 | B |
| Example 184 | A |
| Example 185 | A |
| Example 186 | A |
| Example 187 | A |
| Example 188 | A |
| Example 189 | A |
| Example 190 | A |
| Example 191 | C |
| Example 192 | A |
| Example 193 | A |
| Example 194 | B |
| Example 195 | A |
| Example 196 | A |
| Example 197 | A |
| Example 198 | B |
| Example 199 | A |
| Example 200 | A |
| Example 201 | A |
| Example 202 | A |
| Example 203 | A |
| Example 204 | A |
| Example 205 | A |
| Example 206 | A |
| Example 207 | A |
| Example 208 | A |
| Example 209 | A |
| Example 210 | A |
| Example 211 | A |
| Example 212 | A |
| Example 213 | A |
| Example 214 | A |
| Example 215 | A |
| Example 216 | A |
| Example 217 | A |
| Example 218 | A |
| Example 219 | A |
| Example 220 | A |
| Example 221 | A |
| Example 222 | A |
| Example 223 | C |

VII. STEREOCHEMISTRY OF EXAMPLES

AIA-225

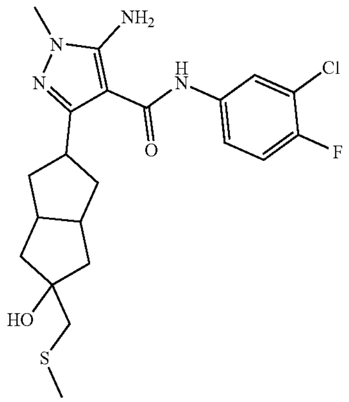

5-Amino-N-(3-chloro-4-fluorophenyl)-3-(5-hydroxy-5-(methylthiomethyl)octahydropentalen-2-yl)-1-methyl-1H-pyrazole-4-carboxamide. To a solution of 5-amino-N-(3-chloro-4-fluorophenyl)-3-(hexahydro-1'H-spiro[oxirane-2,2'-pentalene]-5'-yl)-1-methyl-1H-pyrazole-4-carboxamide (200 mg, 0.495 mmol) in THF/$H_2O$ (6 mL/2 mL) was added NaSMe (138.6 mg, 1.98 mmol). The mixture was stirred at rt overnight. The solvent was removed, and the crude product purified by silica gel column chromatography using 3:1 (v/v) petroleum ether/ethyl acetate to afford 5-amino-N-(3-chloro-4-fluorophenyl)-3-(5-hydroxy-5-(methylthiomethyl)octahydropentalen-2-yl)-1-methyl-1H-pyrazole-4-carboxamide (100 mg, 44.7%) as a yellow solid. MS (m/z): Calcd.: 452.1, Found: 452.2 $[M+1]^+$.

CP-AIA-227-1

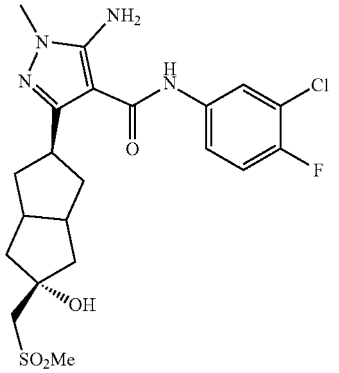

-continued

CP-AIA-227-2

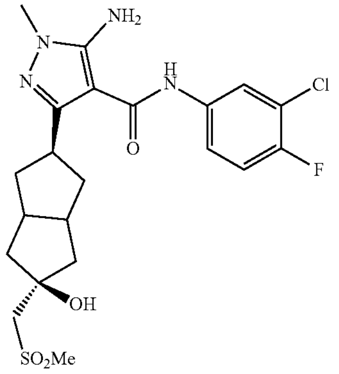

5-Amino-N-(3-chloro-4-fluorophenyl)-3-((2r,5r)-5-hydroxy-5-(methylsulfonylmethyl)octahydropentalen-2-yl)-1-methyl-1H-pyrazole-4-carboxamide (AIA-227-1) and 5-Amino-N-(3-chloro-4-fluorophenyl)-3-((2s,5s)-5-hydroxy-5-(methylsulfonylmethyl)octahydropentalen-2-yl)-1-methyl-1H-pyrazole-4-carboxamide (AIA-227-2). To a solution of 5-amino-N-(3-chloro-4-fluorophenyl)-3-(5-hydroxy-5-(methylthiomethyl)octahydropentalen-2-yl)-1-methyl-1H-pyrazole-4-carboxamide (100 mg, 0.22 mmol) in DCM (5 mL) was added m-CPBA (114.8 mg, 0.66 mmol). The mixture was stirred at rt overnight. The solvent was removed, and the crude material purified by silica gel column chromatography using 3:1 (v/v) DCM/MeOH to afford AIA-227 (40 mg, 37.3%) as a white solid. MS (m/z): Calcd.: 484.1, Found: 484.3 $[M+1]^+$. AIA-227 was separated by SFC to give AIA-227-1 (4 mg) as a white solid and AIA-227-2 (4 mg) as a white solid. AIA-227-1: $^1H$ NMR (400 MHz, DMSO-$d_6$): δ 8.95 (s, 1H), 7.91 (dd, J=6.8, 2.4 Hz, 1H), 7.54-7.50 (m, 1H), 7.35 (t, J=9.2 Hz, 1H), 5.97 (s, 2H), 4.79 (s, 1H), 3.59-3.53 (m, 1H), 3.49 (s, 3H), 3.35 (s, 2H), 2.97 (s, 3H), 2.67-2.60 (m, 2H), 2.18-2.12 (m, 2H), 2.07-2.02 (m, 2H), 1.45-1.36 (m, 4H) ppm. AIA-227-2: $^1H$ NMR (400 MHz, DMSO-$d_6$): δ 8.94 (s, 1H), 7.91 (dd, J=2.8, 2.4 Hz, 1H), 7.53-7.49 (m, 1H), 7.34 (t, J=9.2 Hz, 1H), 5.97 (s, 2H), 4.87 (s, 1H), 3.49 (s, 3H), 3.43-3.35 (m, 1H), 3.25 (s, 2H), 2.97 (s, 3H), 2.49 (s, 2H), 2.15-2.09 (m, 2H), 2.02-1.97 (m, 2H), 1.73-1.60 (m, 4H) ppm.

AIA-227-2

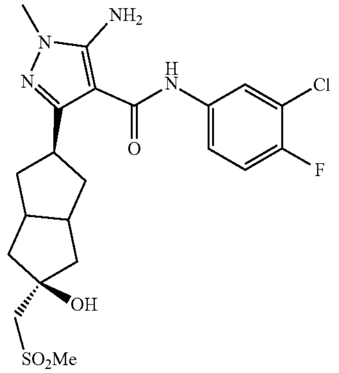

Alternative synthesis of 5-amino-N-(3-chloro-4-fluorophenyl)-3-((2s,5s)-5-hydroxy-5-(methylsulfonylmethyl)octahydropentalen-2-yl)-1-methyl-1H-pyrazole-4-carboxamide. To a solution of dimethylsulfone (77.0 g, 818.7 mmol) in THF (800 mL) was added n-BuLi (327.5 mL, 818.7 mmol, 2.5M) dropwise at −78° C. The resulting solution was allowed to warm to −20° C. and stirred for 1 hr. The reaction was cooled to −78° C., and a solution of AIA-002 (40.0 g, 102.3 mmol) in anhydrous tetrahydrofuran (1200 mL) was added over 2 hr. The mixture was warmed to RT and stirred for an additional 4 hr. The reaction mixture was quenched with saturated aqueous ammonium chloride solution (200 mL). The solvent was removed, followed by dilution with water, extraction with ethyl acetate (3×200 mL), drying over $Na_2SO_4$, filtration, and concentration to give the crude product. The crude product was purified by column chromatography using 0-5% (v/v) methanol in DCM and basic prep-HPLC to afford 5-amino-N-(3-chloro-4-fluorophenyl)-3-((2s,5s)-5-hydroxy-5-(methylsulfonylmethyl)octahydropentalen-2-yl)-1-methyl-1H-pyrazole-4-carboxamide (26.0 g, 52.4%) as a white solid. MS (m/z): Calcd.: 484.1, MS Found: 485.2 $[M+1]^+$; $^1H$ NMR (400 MHz, DMSO-$d_6$): δ 8.96 (s, 1H), 7.92 (dd, J=6.8, 2.8 Hz, 1H), 7.54-7.50 (m, 1H), 7.35 (t, J=8.8 Hz, 1H), 5.98 (s, 2H), 4.88 (s, 1H), 3.49 (s, 3H), 3.42-3.37 (m, 1H), 3.25 (s, 2H), 2.97 (s, 3H), 2.15-2.10 (m, 2H), 2.03-1.97 (m, 2H), 1.73-1.60 (m, 4H) ppm.

A crystal with size of 0.08×0.10×0.20 mm of compound AIA-227-2 was obtained from EtOH after 20 days of volatilization and was used for X-ray diffraction data collection. The data were collected on a Bruker SMART CCD area-detector diffractometer at room temperature using CuKα radiation by ω/φ scan mode. 10846 reflections were collected, of which 3754 reflections were unique (Rint=0.0507).

The crystal belongs to monoclinic crystal system, with a space group $P2_1/c$. The unit cell parameters were as follows: a=6.6143(3), b=14.0381(8), c=23.6870(14)Å, α=γ=90.0°, β=97.702(3) °, V=2179.5(2)$Å^3$, Z=4.

The structure was solved by direct methods and all of the non-H atoms were refined against $F^2$ by full-matrix least-squares methods using the SHELXTL program. All H atoms were placed in geometrically idealized positions and constrained to ride on their parent atoms. Multi-scans absorption correction method was used, and the maximum and minimum transmission parameters were 0.7531 and 0.6017, respectively. The final R, $wR_2$, GOF are 0.0457, 0.1293 and 1.024, respectively.

There is one $C_{21}H_{26}FClN_4O_4S$ molecule in the asymmetric unit and hydrogen bonds can be found between them, which play an important role for the stable packing of the crystal structure.

The ORTEP plot for compound AIA-227-2 is present in FIG. 1. The relative stereochemistry scheme of compound AIA-227-2 is shown in FIG. 2. The depictions of stereochemistry in the chemical structures of related examples are based on this assignment.

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure.

$X^1$ is $NR^{x1}$;

$X^3$ is $CR^4R^8$;

$R^a$, $R^b$ and $R^c$ are independently selected for each occurrence from the group consisting of hydrogen, $C_{1-6}$ alkyl, halo$C_{1-6}$ alkyl and $C_{3-6}$ monocycloalkyl;

$R^d$ is hydrogen, OH, $C_{1-6}$ alkyl or $C_{1-6}$ alkoxy;

$R^{x1}$ is hydrogen, $C_{1-4}$ alkyl, $C_{1-4}$ alkenyl, $C_{1-4}$ alkynyl, halo$C_{1-4}$ alkyl, or $C_{3-6}$ monocycloalkyl; or $R^{x1}$ and $R^2$

The invention claimed is:

1. A compound of Formula I

Formula I

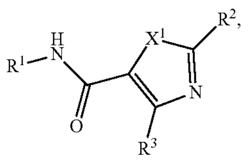

or a pharmaceutically acceptable salt thereof, wherein:

L is $C_{1-4}$alkylene or halo$C_{1-4}$alkylene;

$L^1$ is a bond, $C_{1-6}$alkylene, O, $NR^c$, C(O), C(O)O, C(O)$NR^c$, $S(O)_t$, or $S(O)_tNR^c$;

together form a $—CH_2CH_2CH_2—$, $—CH_2CH_2CH_2CH_2—$, $—CH_2CH_2O—$, $—CH_2OCH_2—$, $—CH_2CH_2CH_2O—$, $—CH_2CH_2OCH_2—$, $—CH_2CH_2—NH—$, $—CH_2NHCH_2—$, $—CH_2CH_2CH_2NH—$ or $—CH_2CH_2NHCH_2—$ group;

$R^{0a}$ is independently selected for each occurrence from the group consisting of hydrogen, halogen, OH, CN, $NO_2$, $R^aR^bN—$, $C_{1-4}$alkyl and halo$C_{1-4}$alkyl;

$R^{6a}$ are independently hydrogen or $C_{1-4}$ alkyl;

$R^0$, $R^6$ are independently selected for each occurrence from the group consisting of hydrogen, halogen, OH, CN, $NO_2$, oxo, $R^dN=$, hydrazino, formyl, azido, silyl, siloxy, HOC(O)—, $R^aR^bN—$, $R^aR^bNS(O)_t—$, $C_{1-6}$alkyl, $C_{2-6}$alkenyl, $C_{2-6}$alkynyl, halo$C_{1-6}$alkyl, hydroxy$C_{1-6}$alkyl-, $R^aR^bNC_{1-6}$alkyl-, $HOC(O)C_{1-6}$alkyl-, $R^aR^bNC_{1-6}$alkylN$R^c$—, $C_{1-6}$alkylN$R^aC_{1-6}$alkylN$R^c$—, $C_{1-6}$alkoxy, halo$C_{1-6}$alkoxy, hydroxy$C_{1-6}$alkoxy-, $R^aR^bNC_{1-6}$alkoxy-, $C_{1-6}$alkoxy$C_{1-6}$alkyl-, halo$C_{1-6}$alkoxy$C_{1-6}$alkyl-, $R^aR^bNC(O)$—, $C_{1-6}$alkylC(O)—, $C_{1-6}$alkoxyC(O)—, $C_{1-6}$alkylC(O)O—, $C_{1-6}$alkylS$(O)_q$—, $C_{1-6}$alkylS$(O)_t$N$R^c$—, $C_{1-6}$alkylS$(O)_t$$C_{1-6}$alkyl-, $C_{1-6}$alkylS$(O)_t$N$R^a$$C_{1-6}$alkyl-, $C_{3-6}$cycloalkylS$(O)_t$$C_{1-6}$alkyl-, $C_{1-6}$alkylC(O)$C_{1-6}$alkyl-, and $C_{1-6}$alkylC(O)O$C_{1-6}$alkyl-;

each $R^{11}$ independently is hydrogen, OH, CN, $NO_2$, $C_{1-6}$ alkyl, halo$C_{1-6}$alkyl, HOC(O)—, HOC(O)$C_{1-6}$alkyl, $R^aR^bN$—, $C_{2-6}$alkenyl, $C_{2-6}$alkynyl, $C_{1-6}$alkoxy, halo$C_{1-6}$alkoxy, or $C_{1-6}$alkoxy;

$R^1$ is a phenyl or 5-6 membered monocyclic heteroaryl, wherein the phenyl or 5-6 membered monocyclic heteroaryl is optionally substituted with one, two, or three independently selected $R^{11}$ groups;

$R^2$ is selected from the group consisting of hydrogen, halo, CN, OH, $R^aR^bN$, $C_{1-4}$alkyl, halo$C_{1-4}$alkyl, $C_{3-5}$monocycloalkyl, $C_{1-4}$alkoxy, and halo$C_{1-4}$alkoxy;

$R^8$ is selected from the group consisting of hydrogen, halo, CN, OH, $R^aR^bN$, $C_{1-4}$alkyl, halo$C_{1-4}$alkyl, $C_{3-5}$monocycloalkyl, $C_{1-6}$alkoxy, and halo$C_{1-4}$alkoxy;

$R^3$ is

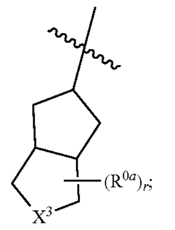

$R^4$ is $R^5$-$L^1$-, $R^6$ or $R^9$;

$R^5$ is

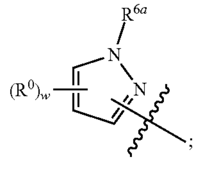

$R^9$ is $R^{14}S(O)_q$-L-, $R^{14}S(O)_q$NH-L-, or $R^{14}$C(O)NH-L-;

$R^{14}$ is $R^aR^bN$—, $C_{1-6}$alkyl, $C_{2-6}$alkenyl, $C_{2-6}$alkynyl, $C_{1-6}$haloalkyl, $C_{1-6}$alkoxy, $C_{1-6}$haloalkyl, $C_{1-6}$haloalkoxy, or $R^5$-$L^1$-;

q, r, t, and w are independently selected for each occurrence from 0, 1 and 2.

2. The compound of claim 1, or a pharmaceutically acceptable salt thereof, wherein $R^{x1}$ is hydrogen or methyl.

3. The compound of claim 2, or a pharmaceutically acceptable salt thereof, wherein $R^{x1}$ is methyl.

4. The compound according to claim 1, or a pharmaceutically acceptable salt thereof, wherein r is 0.

5. The compound according to claim 1, or a pharmaceutically acceptable salt thereof, wherein $R^2$ is hydrogen.

6. The compound according to claim 1, or a pharmaceutically acceptable salt thereof, wherein: $R^1$ is

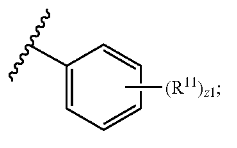

$R^{11}$ is independently selected for each occurrence from the group consisting of halogen, CN, $C_{1-6}$ alkyl and halo$C_{1-6}$ alkyl; and z1 is 0, 1,2 or 3.

7. The compound of claim 6, or a pharmaceutically acceptable salt thereof, wherein for each occurrence $R^{11}$ is independently selected from the group consisting of CN, F, Cl, Br and I.

8. The compound of claim 7, or a pharmaceutically acceptable salt thereof, wherein $R^1$ is

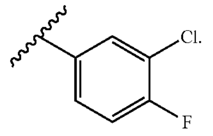 [SMILES: *c1ccc(F)c(Cl)c1]

9. The compound of claim 7, or a pharmaceutically acceptable salt thereof, wherein $R^1$ is

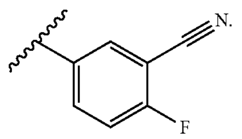 [SMILES: *c1ccc(F)c(C#N)c1]

10. The compound according to claim 1, or a pharmaceutically acceptable salt thereof, wherein $R^3$ is

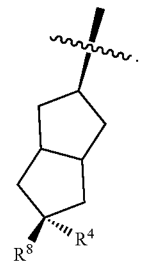

11. The compound according to claim 1, or a pharmaceutically acceptable salt thereof, wherein $R^4$ is $R^6$.

12. The compound according to claim 1, or a pharmaceutically acceptable salt thereof, wherein $R^4$ is $R^5$-$L^1$.

13. The compound of claim 12, or a pharmaceutically acceptable salt thereof, wherein $L^1$ is a bond.

14. The compound according to claim 1, or a pharmaceutically acceptable salt thereof, wherein $R^4$ is $R^9$.

15. The compound according to claim 1, or a pharmaceutically acceptable salt thereof, wherein $R^8$ is hydrogen, OH or $C_{1-6}$alkoxy.

16. The compound of claim 15, or a pharmaceutically acceptable salt thereof, wherein $R^8$ is OH.

17. A pharmaceutical composition comprising the compound according to claim 1, or a pharmaceutically acceptable salt thereof, and a pharmaceutically acceptable excipient.

18. A method of treating Hepatitis B (HBV) infection in a subject in need thereof, the method comprising: administering to the subject a therapeutically effective amount of a compound according to claim 1, or a pharmaceutically acceptable salt thereof.

19. A method of treating Hepatitis B (HBV) infection in a subject in need thereof, the method comprising: administering to the subject a therapeutically effective amount of pharmaceutical composition of claim 17.

20. A compound, or a pharmaceutically acceptable salt thereof, wherein the compound is selected from:

| Example No. | Name/Structure |
|---|---|
| Example 1 | 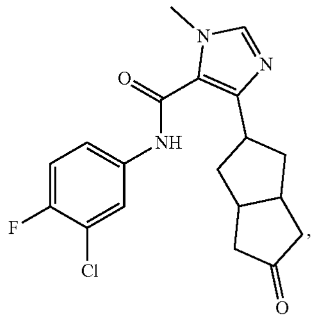 [SMILES: Cn1cnc(C2CC3CC(=O)CC3C2)c1C(=O)Nc1ccc(F)c(Cl)c1] |
| Example 2 | 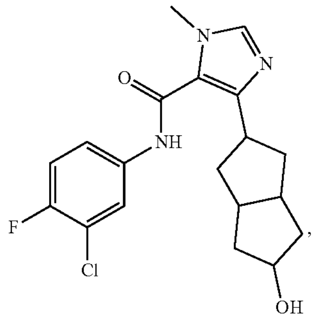 [SMILES: Cn1cnc(C2CC3CC(O)CC3C2)c1C(=O)Nc1ccc(F)c(Cl)c1] |
| Example 3 | 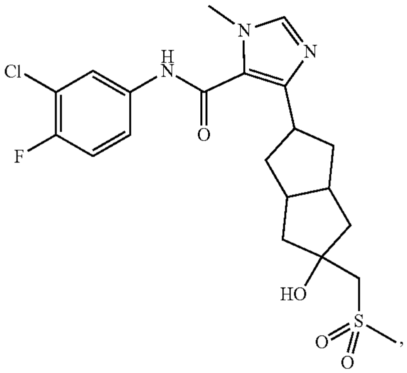 [SMILES: Cn1cnc(C2CC3CC(O)(CS(C)(=O)=O)CC3C2)c1C(=O)Nc1ccc(F)c(Cl)c1] |
| Example 4 | 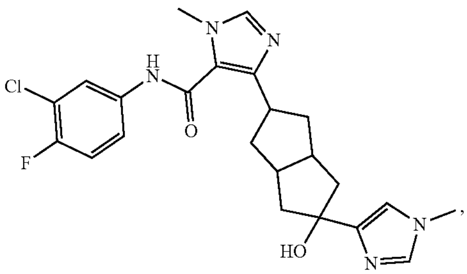 [SMILES: Cn1cnc(C2(O)CC3CC(c4ncn(C)c4C(=O)Nc4ccc(F)c(Cl)c4)CC3C2)c1] |

-continued

| Example No. | Name/Structure |
|---|---|
| Example 5 | 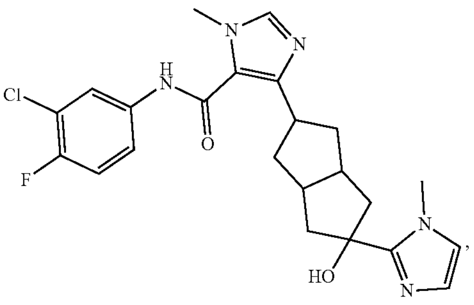 [SMILES: Cn1ccnc1C1(O)CC2CC(c3ncn(C)c3C(=O)Nc3ccc(F)c(Cl)c3)CC2C1] |
| Example 6 | 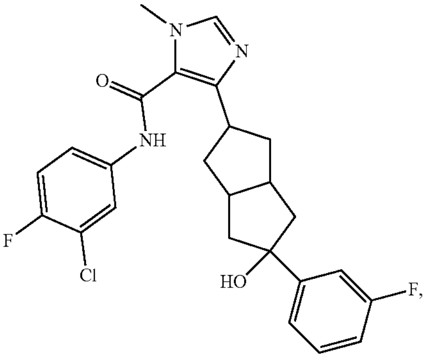 [SMILES: Cn1cnc(C2CC3CC(O)(c4cccc(F)c4)CC3C2)c1C(=O)Nc1ccc(F)c(Cl)c1] |
| Example 7 | 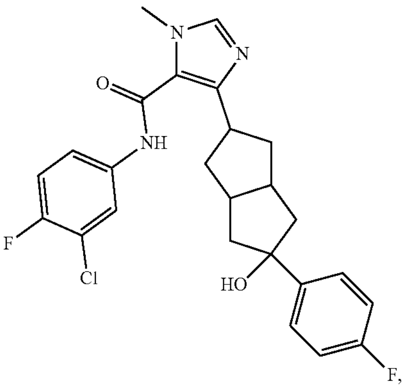 [SMILES: Cn1cnc(C2CC3CC(O)(c4ccc(F)cc4)CC3C2)c1C(=O)Nc1ccc(F)c(Cl)c1] |
| Example 8 | 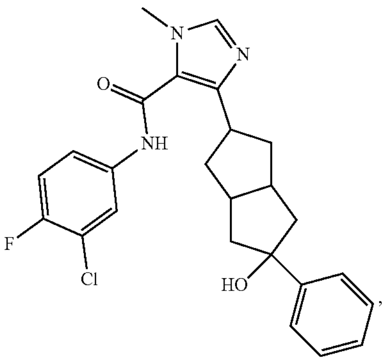 [SMILES: Cn1cnc(C2CC3CC(O)(c4ccccc4)CC3C2)c1C(=O)Nc1ccc(F)c(Cl)c1] |

-continued
| Example No. | Name/Structure |
|---|---|
| Example 9 | 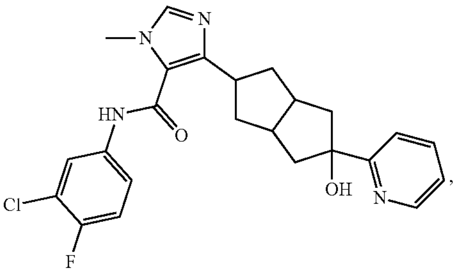 [SMILES: Cn1cnc(C2CC3CC(O)(c4ccccn4)CC3C2)c1C(=O)Nc1ccc(F)c(Cl)c1] |
| Example 10 | 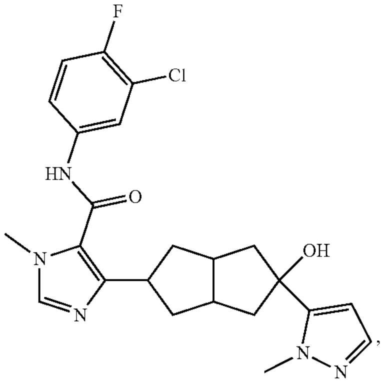 [SMILES: Cn1cnc(C2CC3CC(O)(c4ccnn4C)CC3C2)c1C(=O)Nc1ccc(F)c(Cl)c1] |
| Example 11 | 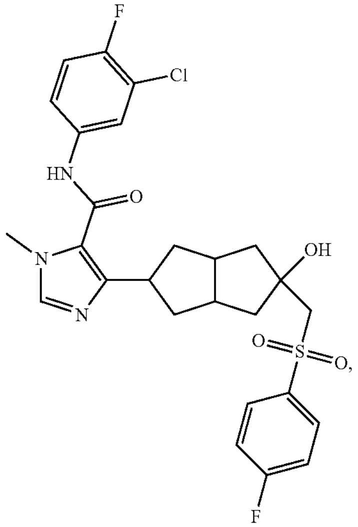 [SMILES: Cn1cnc(C2CC3CC(O)(CS(=O)(=O)c4ccc(F)cc4)CC3C2)c1C(=O)Nc1ccc(F)c(Cl)c1] |
| Example 12 | 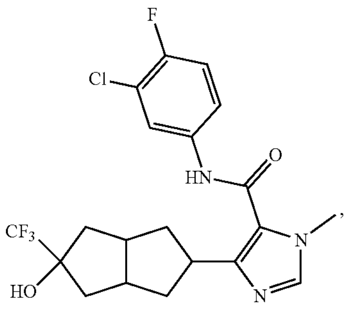 [SMILES: Cn1cnc(C2CC3CC(O)(C(F)(F)F)CC3C2)c1C(=O)Nc1ccc(F)c(Cl)c1] |
-continued
| Example No. | Name/Structure |
|---|---|
| Example 13 | 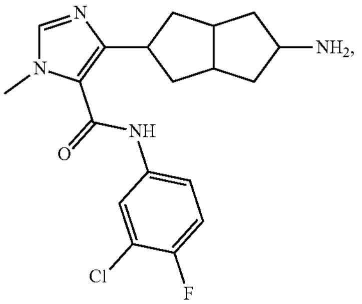 [SMILES: Cn1cnc(C2CC3CC(N)CC3C2)c1C(=O)Nc1ccc(F)c(Cl)c1] |
| Example 14 | 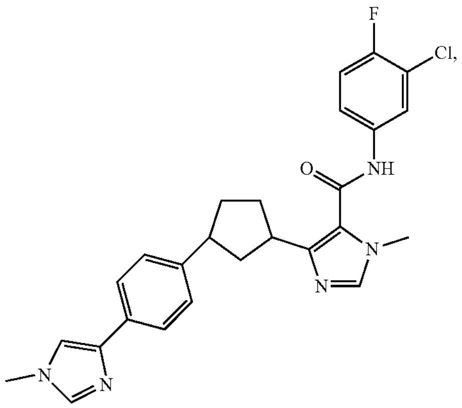 [SMILES: Cn1cnc(-c2ccc(C3CCC(c4ncn(C)c4C(=O)Nc4ccc(F)c(Cl)c4)C3)cc2)c1] |
| Example 15 | 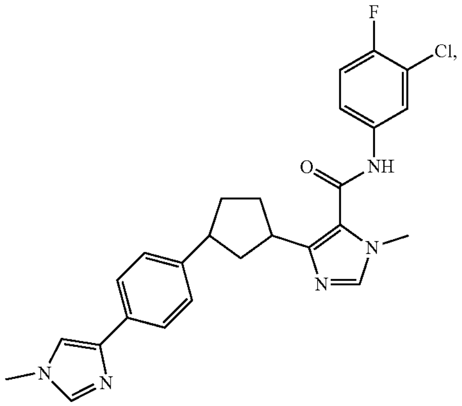 [SMILES: Cn1cnc(-c2ccc(C3CCC(c4ncn(C)c4C(=O)Nc4ccc(F)c(Cl)c4)C3)cc2)c1] |
| Example 16 | 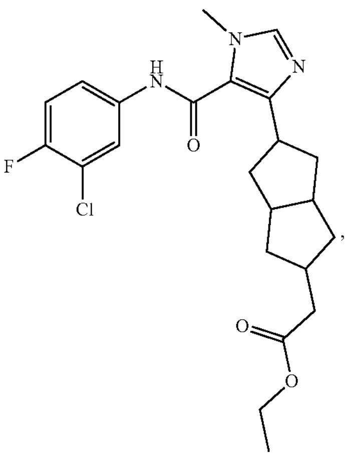 [SMILES: CCOC(=O)CC1CC2CC(c3ncn(C)c3C(=O)Nc3ccc(F)c(Cl)c3)CC2C1] |

-continued
| Example No. | Name/Structure |
|---|---|
| Example 17 | 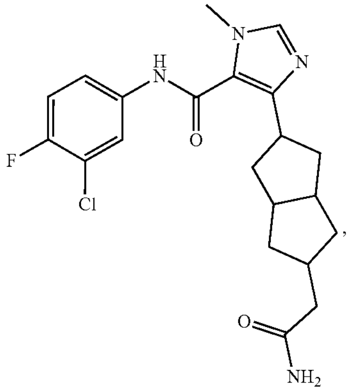 [SMILES: Cn1cnc(C2CC3CC(CC(N)=O)CC3C2)c1C(=O)Nc1ccc(F)c(Cl)c1] |
| Example 18 | 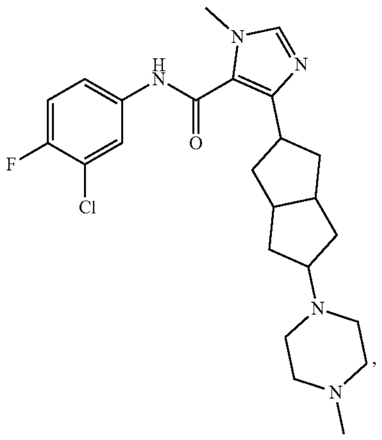 [SMILES: CN1CCN(C2CC3CC(c4ncn(C)c4C(=O)Nc4ccc(F)c(Cl)c4)CC3C2)CC1] |
| Example 19 | 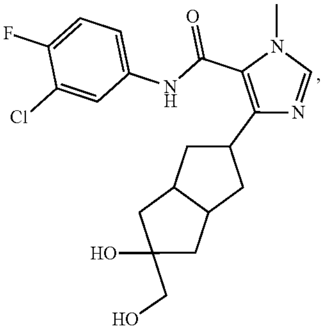 [SMILES: Cn1cnc(C2CC3CC(O)(CO)CC3C2)c1C(=O)Nc1ccc(F)c(Cl)c1] |
| Example 21 | 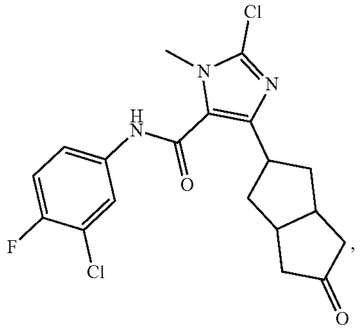 [SMILES: Cn1c(Cl)nc(C2CC3CC(=O)CC3C2)c1C(=O)Nc1ccc(F)c(Cl)c1] |
-continued
| Example No. | Name/Structure |
|---|---|
| Example 22 | 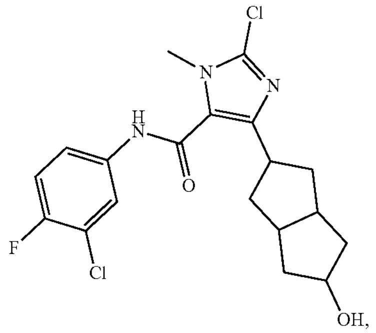 [SMILES: Cn1c(Cl)nc(C2CC3CC(O)CC3C2)c1C(=O)Nc1ccc(F)c(Cl)c1] |
| Example 23 | 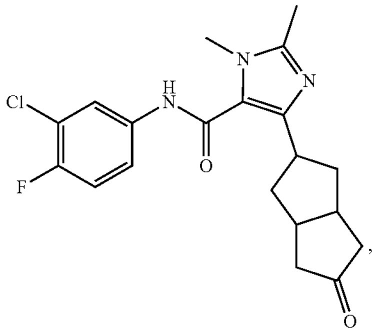 [SMILES: Cc1nc(C2CC3CC(=O)CC3C2)c(C(=O)Nc2ccc(F)c(Cl)c2)n1C] |
| Example 24 | 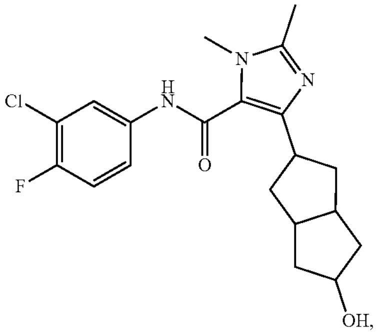 [SMILES: Cc1nc(C2CC3CC(O)CC3C2)c(C(=O)Nc2ccc(F)c(Cl)c2)n1C] |
| Example 25 | 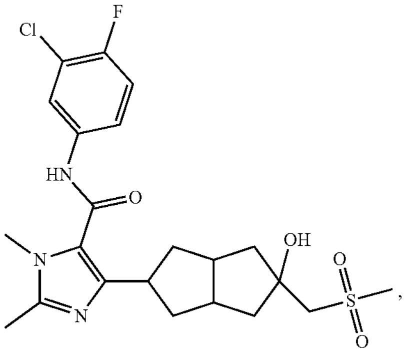 |

-continued
| Example No. | Name/Structure |
|---|---|
| Example 26 | 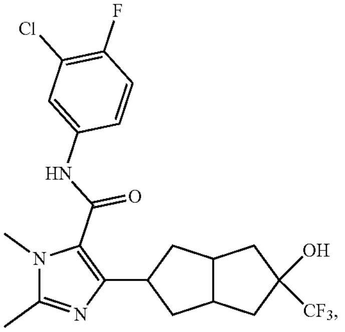 [SMILES: Cc1nc(C2CC3CC(O)(C(F)(F)F)CC3C2)c(C(=O)Nc2ccc(F)c(Cl)c2)n1C] |
| Example 27 | 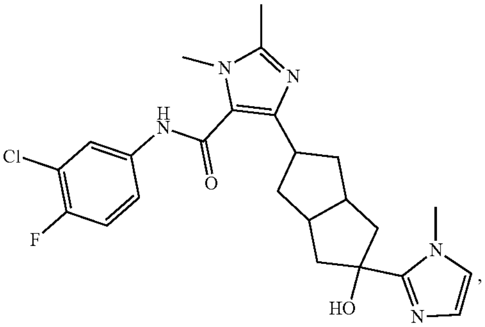 [SMILES: Cc1nc(C2CC3CC(O)(c4nccn4C)CC3C2)c(C(=O)Nc2ccc(F)c(Cl)c2)n1C] |
| Example 28 | 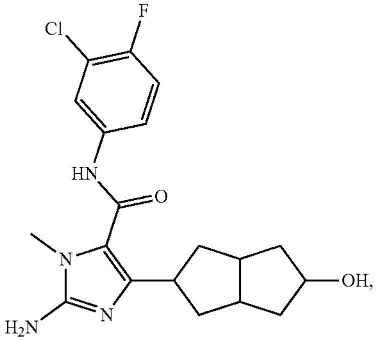 [SMILES: Cn1c(N)nc(C2CC3CC(O)CC3C2)c1C(=O)Nc1ccc(F)c(Cl)c1] |
| Example 29 | 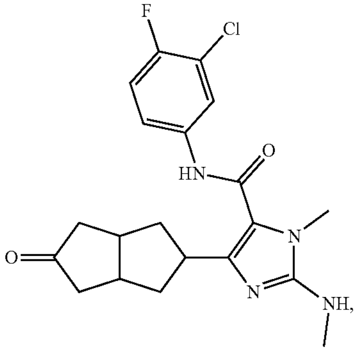 [SMILES: CNc1nc(C2CC3CC(=O)CC3C2)c(C(=O)Nc2ccc(F)c(Cl)c2)n1C] |
-continued
| Example No. | Name/Structure |
|---|---|
| Example 30 | 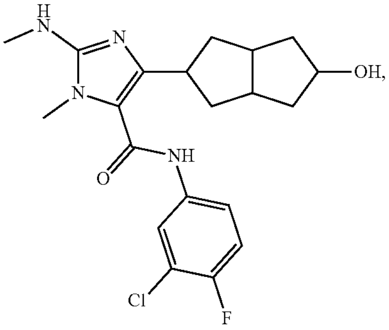 [SMILES: CNc1nc(C2CC3CC(O)CC3C2)c(C(=O)Nc2ccc(F)c(Cl)c2)n1C] |
| Example 31 | 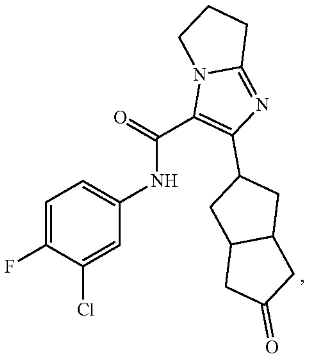 [SMILES: O=C1CC2CC(c3nc4n(c3C(=O)Nc3ccc(F)c(Cl)c3)CCC4)CC2C1] |
| Example 32 | 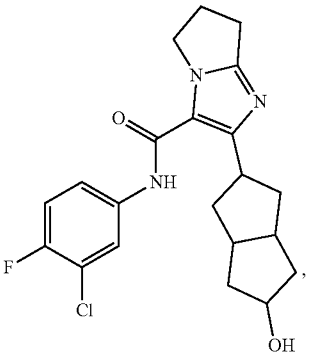 [SMILES: O=C(Nc1ccc(F)c(Cl)c1)c1c(C2CC3CC(O)CC3C2)nc2n1CCC2] |
| Example 34 | 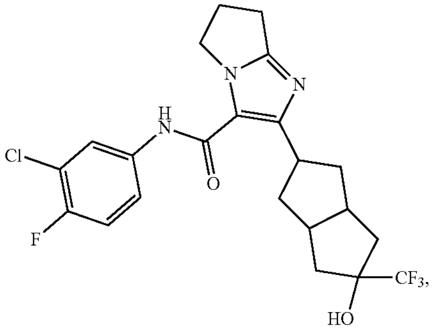 [SMILES: O=C(Nc1ccc(F)c(Cl)c1)c1c(C2CC3CC(O)(C(F)(F)F)CC3C2)nc2n1CCC2] |

-continued
| Example No. | Name/Structure |
| --- | --- |
| Example 35 | 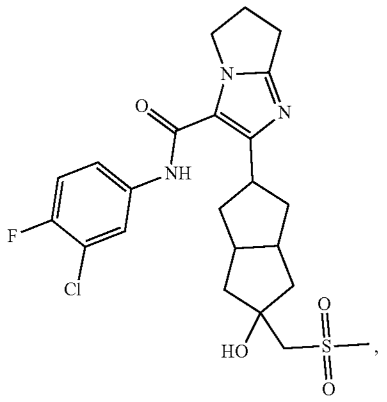 [SMILES: CS(=O)(=O)CC1(O)CC2CC(c3nc4n(c3C(=O)Nc3ccc(F)c(Cl)c3)CCC4)CC2C1] |
| Example 36 | 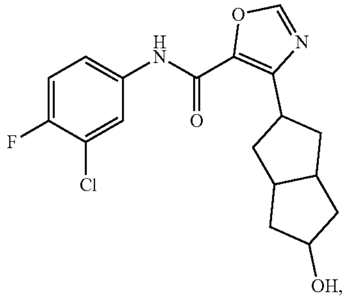 [SMILES: O=C(Nc1ccc(F)c(Cl)c1)c1ocnc1C1CC2CC(O)CC2C1] |
| Example 37 | 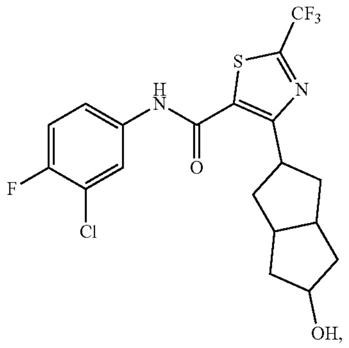 [SMILES: O=C(Nc1ccc(F)c(Cl)c1)c1sc(C(F)(F)F)nc1C1CC2CC(O)CC2C1] |
| Example 38 | 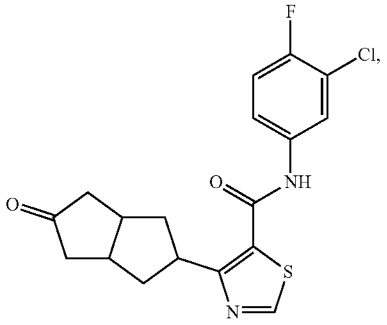 [SMILES: O=C1CC2CC(c3ncsc3C(=O)Nc3ccc(F)c(Cl)c3)CC2C1] |
-continued
| Example No. | Name/Structure |
| --- | --- |
| Example 39 | 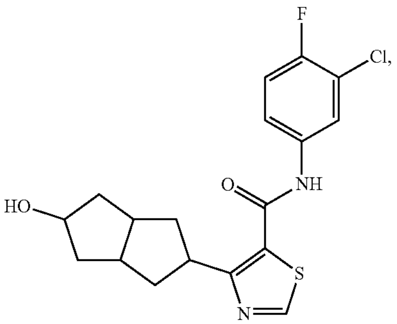 [SMILES: O=C(Nc1ccc(F)c(Cl)c1)c1scnc1C1CC2CC(O)CC2C1] |
| Example 40 | 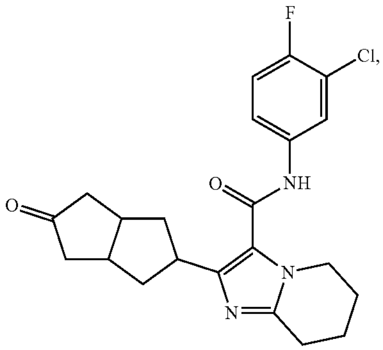 [SMILES: O=C1CC2CC(c3nc4n(c3C(=O)Nc3ccc(F)c(Cl)c3)CCCC4)CC2C1] |
| Example 41 | 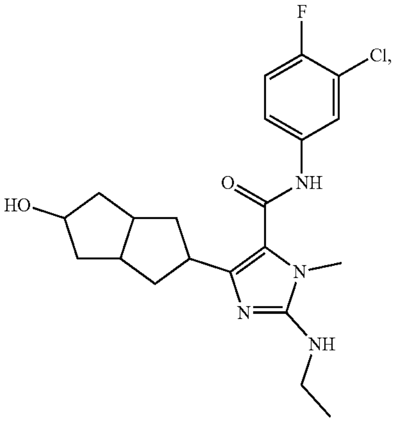 [SMILES: CCNc1nc(C2CC3CC(O)CC3C2)c(C(=O)Nc2ccc(F)c(Cl)c2)n1C] |
| Example 42 | 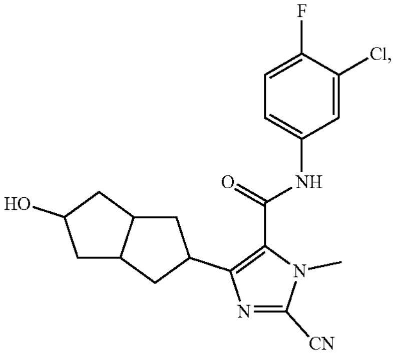 [SMILES: Cn1c(C#N)nc(C2CC3CC(O)CC3C2)c1C(=O)Nc1ccc(F)c(Cl)c1] |

-continued
| Example No. | Name/Structure |
| --- | --- |
| Example 43 | 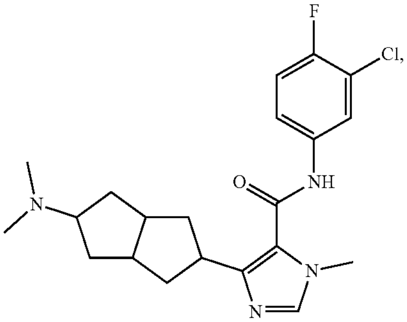 [SMILES: CN(C)C1CC2CC(c3ncn(C)c3C(=O)Nc3ccc(F)c(Cl)c3)CC2C1], |
| Example 44 | 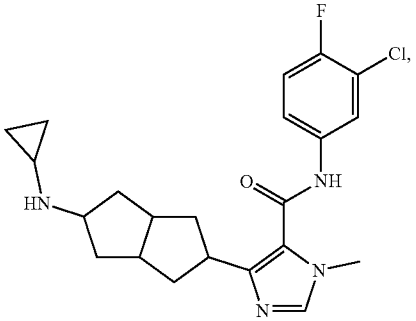 [SMILES: Cn1cnc(C2CC3CC(NC4CC4)CC3C2)c1C(=O)Nc1ccc(F)c(Cl)c1], |
| Example 46 | 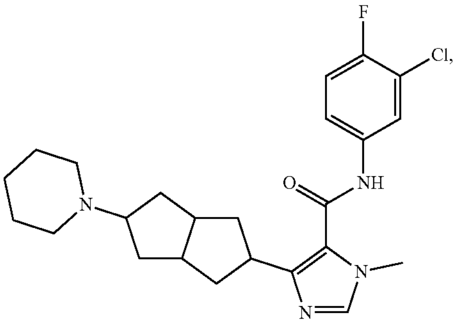 [SMILES: Cn1cnc(C2CC3CC(N4CCCCC4)CC3C2)c1C(=O)Nc1ccc(F)c(Cl)c1], |
| Example 47 | 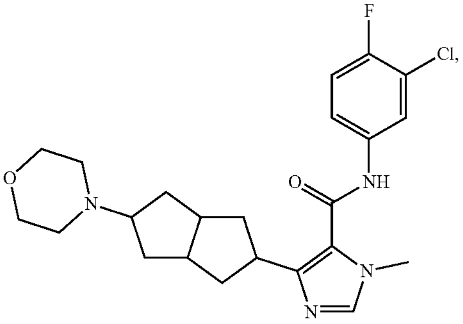 [SMILES: Cn1cnc(C2CC3CC(N4CCOCC4)CC3C2)c1C(=O)Nc1ccc(F)c(Cl)c1], |
-continued
| Example No. | Name/Structure |
| --- | --- |
| Example 48 | 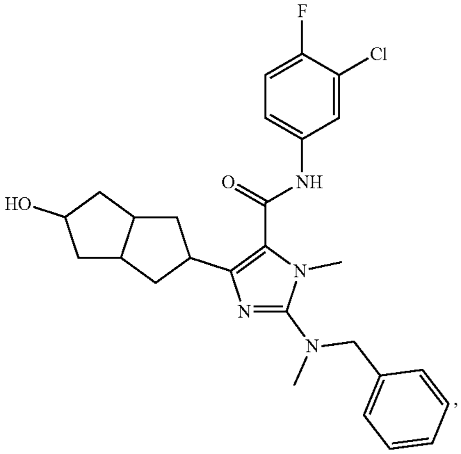 [SMILES: CN(Cc1ccccc1)c1nc(C2CC3CC(O)CC3C2)c(C(=O)Nc2ccc(F)c(Cl)c2)n1C], |
| Example 49 | 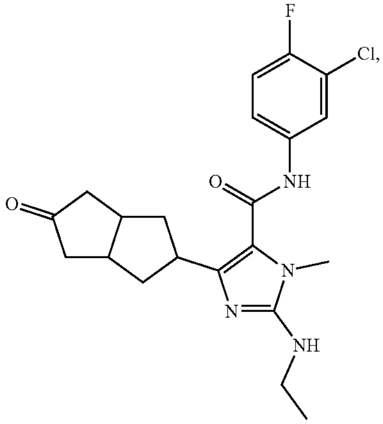 [SMILES: CCNc1nc(C2CC3CC(=O)CC3C2)c(C(=O)Nc2ccc(F)c(Cl)c2)n1C], |
| Example 50 | 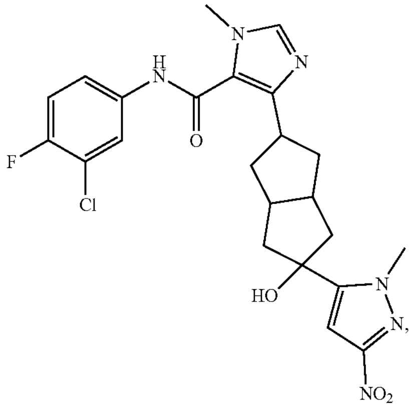 [SMILES: Cn1cnc(C2CC3CC(O)(c4cc([N+](=O)[O-])nn4C)CC3C2)c1C(=O)Nc1ccc(F)c(Cl)c1], |

-continued
| Example No. | Name/Structure |
|---|---|
| Example 51 | 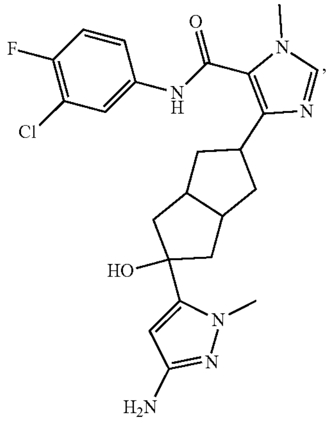 [SMILES: Cn1cnc(C2CC3CC(O)(c4cc(N)nn4C)CC3C2)c1C(=O)Nc1ccc(F)c(Cl)c1] |
| Example 52 | 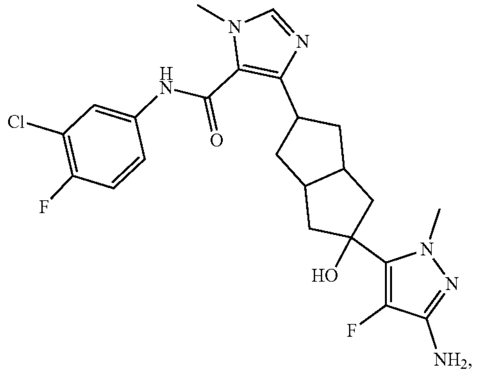 [SMILES: Cn1cnc(C2CC3CC(O)(c4c(F)c(N)nn4C)CC3C2)c1C(=O)Nc1ccc(F)c(Cl)c1] |
| Example 53 | 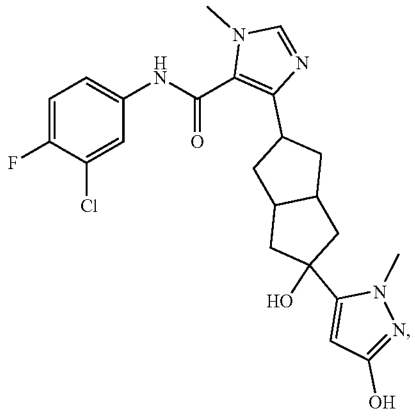 [SMILES: Cn1cnc(C2CC3CC(O)(c4cc(O)nn4C)CC3C2)c1C(=O)Nc1ccc(F)c(Cl)c1] |
-continued
| Example No. | Name/Structure |
|---|---|
| Example 54 | 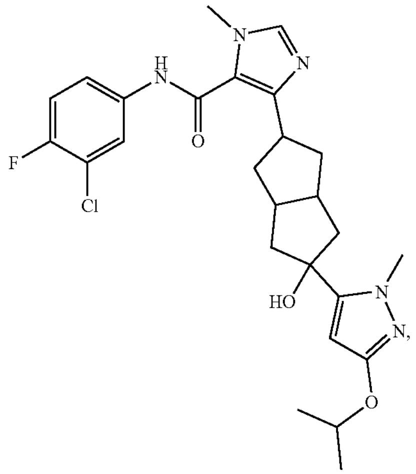 [SMILES: CC(C)Oc1cc(C2(O)CC3CC(c4ncn(C)c4C(=O)Nc4ccc(F)c(Cl)c4)CC3C2)n(C)n1] |
| Example 55 | 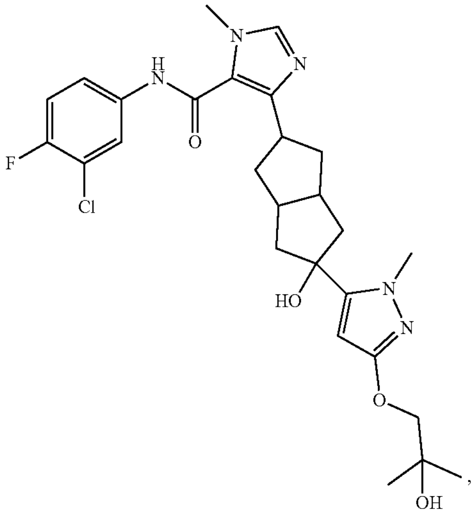 [SMILES: Cn1cnc(C2CC3CC(O)(c4cc(OCC(C)(C)O)nn4C)CC3C2)c1C(=O)Nc1ccc(F)c(Cl)c1] |
| Example 56 | 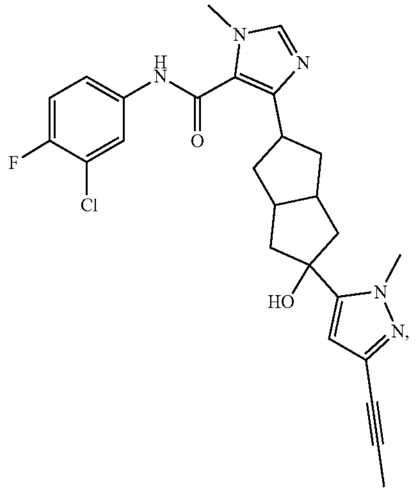 [SMILES: CC#Cc1cc(C2(O)CC3CC(c4ncn(C)c4C(=O)Nc4ccc(F)c(Cl)c4)CC3C2)n(C)n1] |

-continued
| Example No. | Name/Structure |
| --- | --- |
| Example 57 | 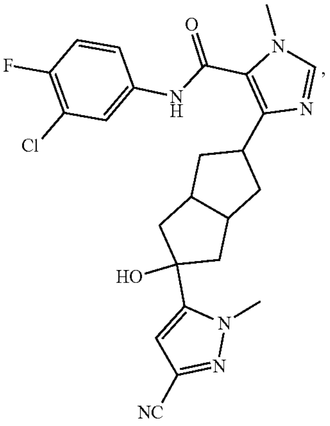 [SMILES: Cn1cnc(C2CC3CC(O)(c4cc(C#N)nn4C)CC3C2)c1C(=O)Nc1ccc(F)c(Cl)c1] |
| Example 58 | 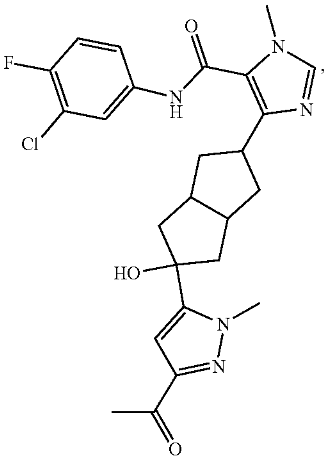 [SMILES: CC(=O)c1cc(C2(O)CC3CC(c4ncn(C)c4C(=O)Nc4ccc(F)c(Cl)c4)CC3C2)n(C)n1] |
| Example 59 | 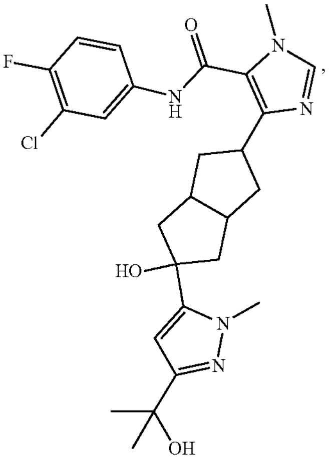 [SMILES: Cn1cnc(C2CC3CC(O)(c4cc(C(C)(C)O)nn4C)CC3C2)c1C(=O)Nc1ccc(F)c(Cl)c1] |
| Example 60 | 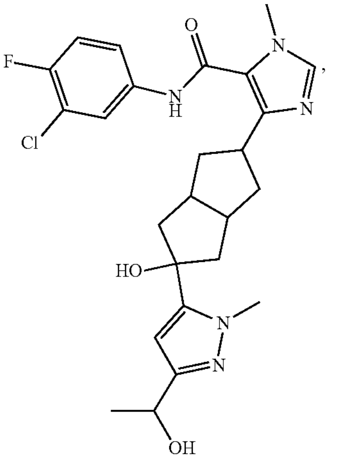 |
| Example 61 | 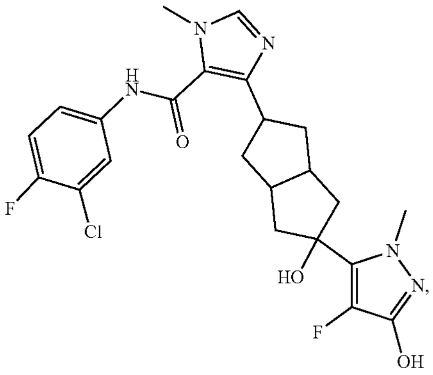 [SMILES: Cn1cnc(C2CC3CC(O)(c4c(F)c(O)nn4C)CC3C2)c1C(=O)Nc1ccc(F)c(Cl)c1] |
| Example 62 | 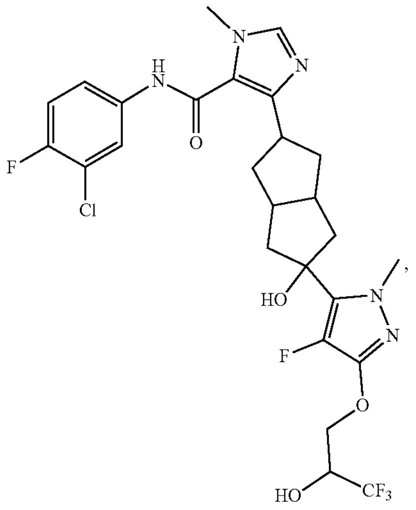 [SMILES: Cn1cnc(C2CC3CC(O)(c4c(F)c(OCC(O)C(F)(F)F)nn4C)CC3C2)c1C(=O)Nc1ccc(F)c(Cl)c1] |

-continued
| Example No. | Name/Structure |
| --- | --- |
| Example 63 | 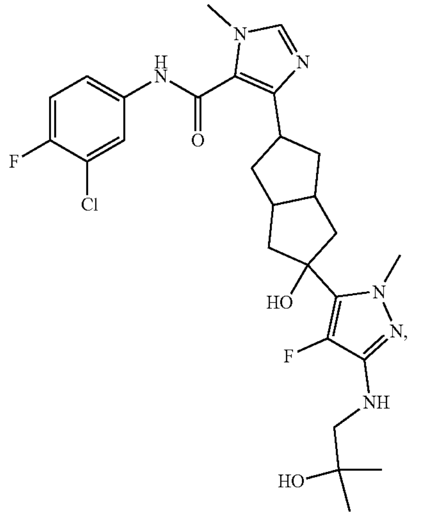 [SMILES: Cn1cnc(C2CC3CC(O)(c4c(F)c(NCC(C)(C)O)nn4C)CC3C2)c1C(=O)Nc1ccc(F)c(Cl)c1] |
| Example 64 | 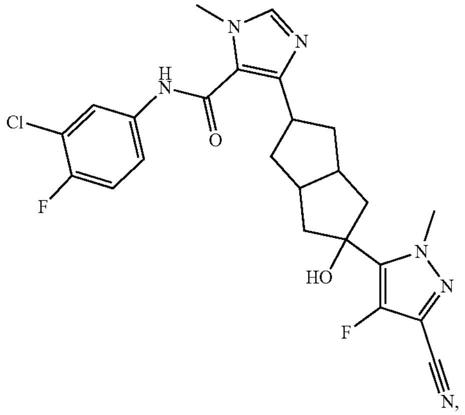 [SMILES: Cn1cnc(C2CC3CC(O)(c4c(F)c(C#N)nn4C)CC3C2)c1C(=O)Nc1ccc(F)c(Cl)c1] |
| Example 65 | 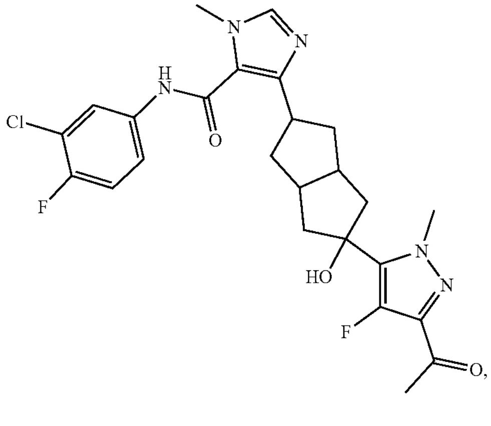 [SMILES: CC(=O)c1nn(C)c(C2(O)CC3CC(c4ncn(C)c4C(=O)Nc4ccc(F)c(Cl)c4)CC3C2)c1F] |
-continued
| Example No. | Name/Structure |
| --- | --- |
| Example 66 | 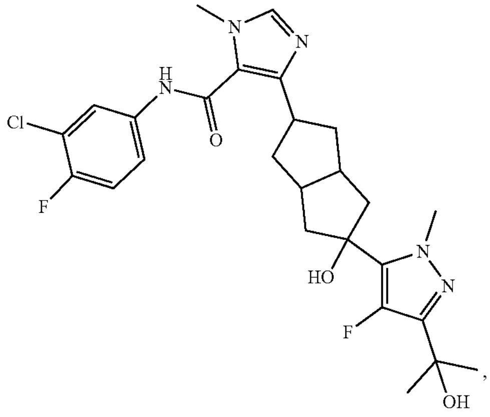 [SMILES: Cn1cnc(C2CC3CC(O)(c4c(F)c(C(C)(C)O)nn4C)CC3C2)c1C(=O)Nc1ccc(F)c(Cl)c1] |
| Example 67 | 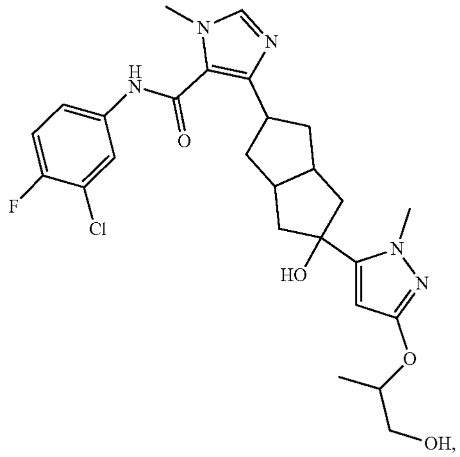 [SMILES: CC(CO)Oc1cc(C2(O)CC3CC(c4ncn(C)c4C(=O)Nc4ccc(F)c(Cl)c4)CC3C2)n(C)n1] |
| Example 68 | N-(3-Chloro-4-fluorophenyl)-4-(5-hydroxy-5-(3-((1-hydroxypropan-2-yl)oxy)-1-methyl-1H-pyrazol-5-yl)octahydropentalen-2-yl)-1-methyl-1H-imidazole-5-carboxamide, |
| Example 70 | 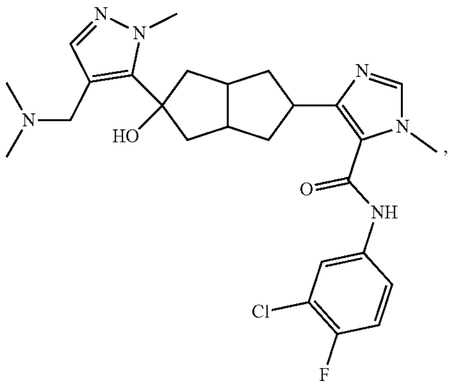 |

-continued
| Example No. | Name/Structure |
|---|---|
| Example 71 | 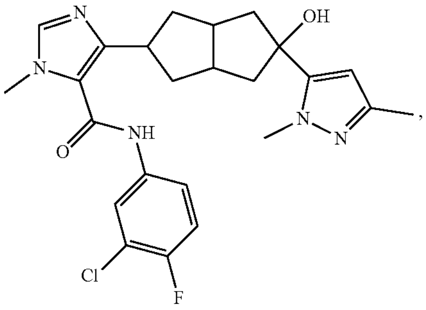 |
| Example 72 | 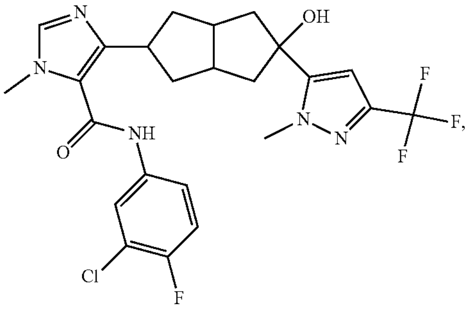 [SMILES: Cn1cnc(C2CC3CC(O)(c4cc(C(F)(F)F)nn4C)CC3C2)c1C(=O)Nc1ccc(F)c(Cl)c1] |
| Example 73 | 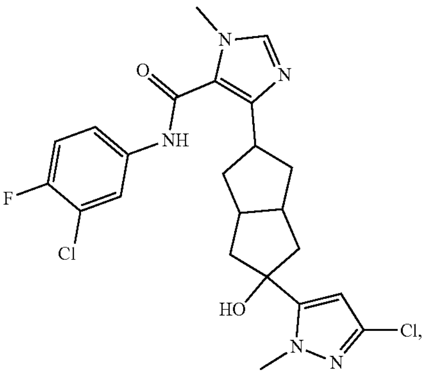 [SMILES: Cn1cnc(C2CC3CC(O)(c4cc(Cl)nn4C)CC3C2)c1C(=O)Nc1ccc(F)c(Cl)c1] |
| Example 74 | 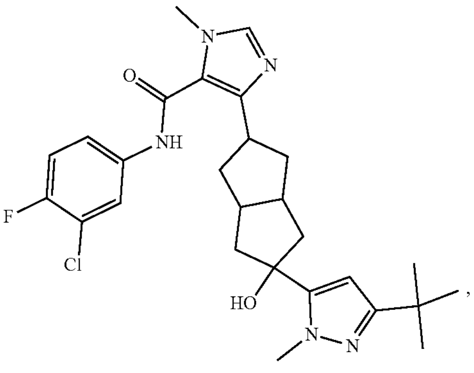 [SMILES: Cn1cnc(C2CC3CC(O)(c4cc(C(C)(C)C)nn4C)CC3C2)c1C(=O)Nc1ccc(F)c(Cl)c1] |
-continued
| Example No. | Name/Structure |
|---|---|
| Example 75 | 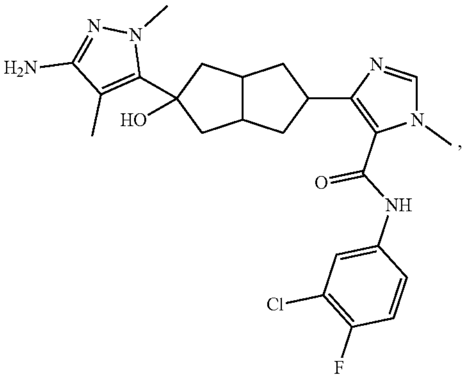 [SMILES: Cc1c(N)nn(C)c1C1(O)CC2CC(c3ncn(C)c3C(=O)Nc3ccc(F)c(Cl)c3)CC2C1] |
| Example 76 | 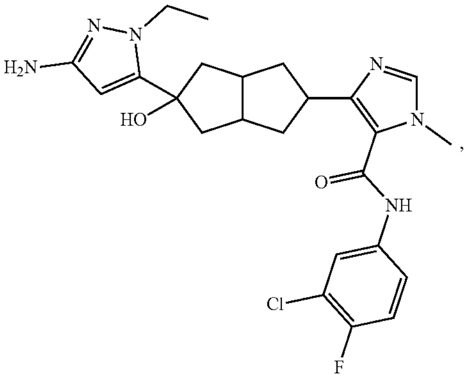 [SMILES: CCn1nc(N)cc1C1(O)CC2CC(c3ncn(C)c3C(=O)Nc3ccc(F)c(Cl)c3)CC2C1] |
| Example 77 | 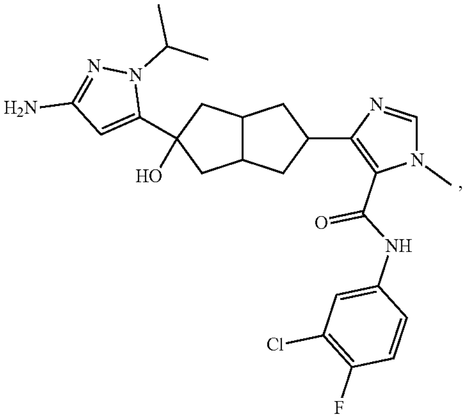 [SMILES: CC(C)n1nc(N)cc1C1(O)CC2CC(c3ncn(C)c3C(=O)Nc3ccc(F)c(Cl)c3)CC2C1] |
| Example 78 | 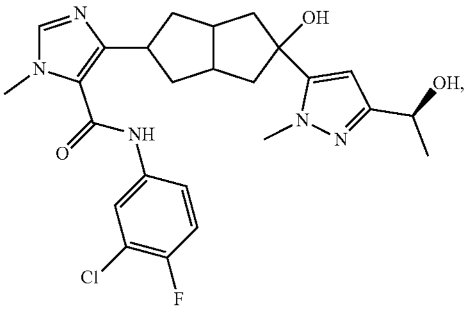 [SMILES: C[C@H](O)c1cc(C2(O)CC3CC(c4ncn(C)c4C(=O)Nc4ccc(F)c(Cl)c4)CC3C2)n(C)n1] |

-continued
| Example No. | Name/Structure |
|---|---|
| Example 79 | 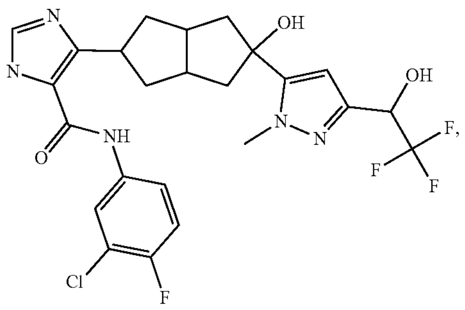 |
| Example 80 | 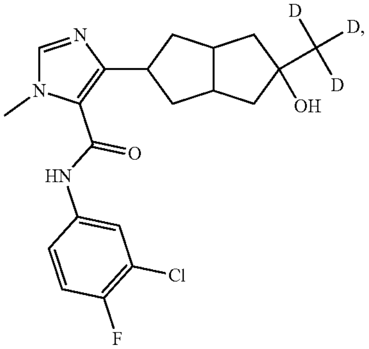 |
| Example 81 | 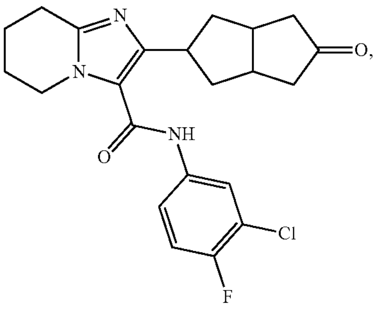 [SMILES: O=C1CC2CC(c3nc4n(c3C(=O)Nc3ccc(F)c(Cl)c3)CCCC4)CC2C1] |
| Example 82 | 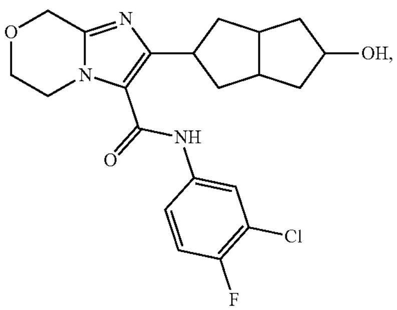 [SMILES: O=C(Nc1ccc(F)c(Cl)c1)c1c(C2CC3CC(O)CC3C2)nc2n1CCOC2] |
-continued
| Example No. | Name/Structure |
|---|---|
| Example 83 | 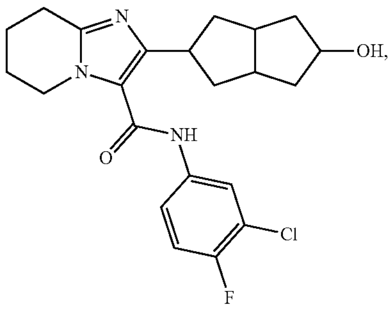 [SMILES: O=C(Nc1ccc(F)c(Cl)c1)c1c(C2CC3CC(O)CC3C2)nc2n1CCCC2] |
| Example 84 | 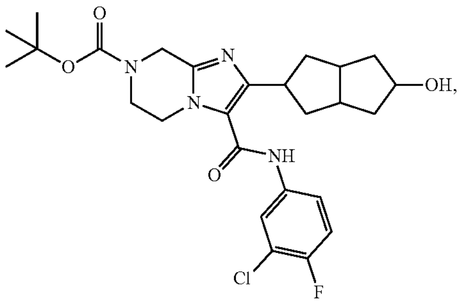 [SMILES: CC(C)(C)OC(=O)N1CCn2c(nc(C3CC4CC(O)CC4C3)c2C(=O)Nc2ccc(F)c(Cl)c2)C1] |
| Example 85 | 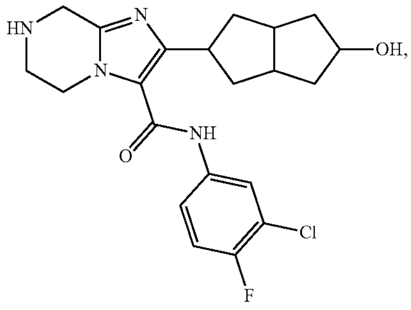 [SMILES: O=C(Nc1ccc(F)c(Cl)c1)c1c(C2CC3CC(O)CC3C2)nc2n1CCNC2] |
| Example 86 | 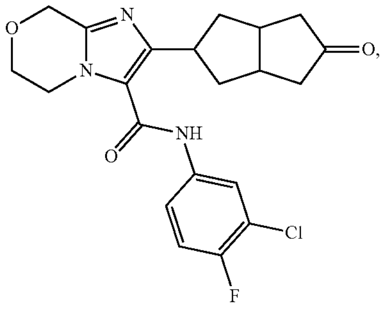 [SMILES: O=C1CC2CC(c3nc4n(c3C(=O)Nc3ccc(F)c(Cl)c3)CCOC4)CC2C1] |

-continued
| Example No. | Name/Structure |
|---|---|
| Example 87 | 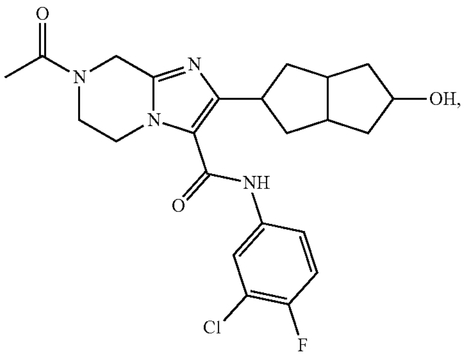 [SMILES: CC(=O)N1CCn2c(nc(C3CC4CC(O)CC4C3)c2C(=O)Nc2ccc(F)c(Cl)c2)C1] |
| Example 88 | 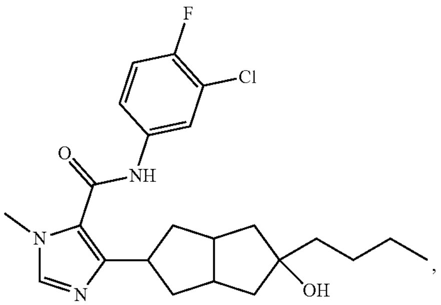 [SMILES: CCCCC1(O)CC2CC(c3ncn(C)c3C(=O)Nc3ccc(F)c(Cl)c3)CC2C1] |
| Example 89 | 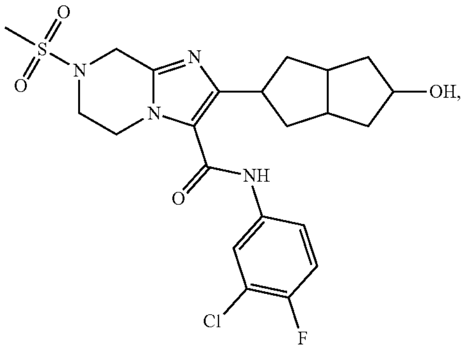 [SMILES: CS(=O)(=O)N1CCn2c(nc(C3CC4CC(O)CC4C3)c2C(=O)Nc2ccc(F)c(Cl)c2)C1] |
| Example 90 | 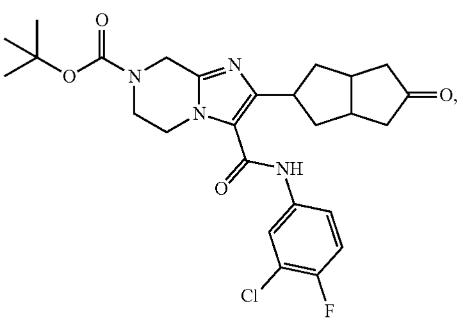 [SMILES: CC(C)(C)OC(=O)N1CCn2c(nc(C3CC4CC(=O)CC4C3)c2C(=O)Nc2ccc(F)c(Cl)c2)C1] |
| Example 91 | 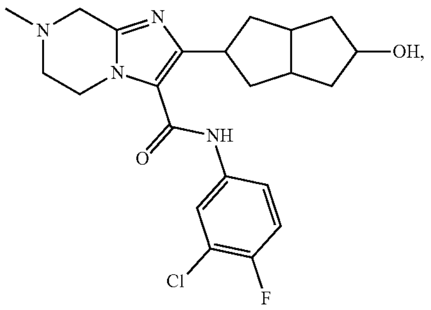 [SMILES: CN1CCn2c(nc(C3CC4CC(O)CC4C3)c2C(=O)Nc2ccc(F)c(Cl)c2)C1] |
| Example 92 | 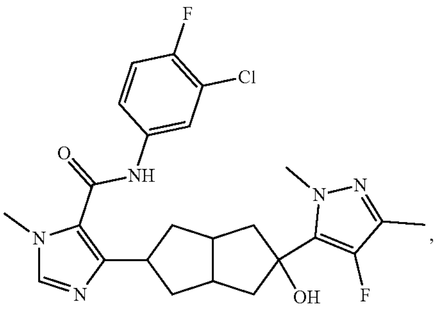 |
| Example 93 | 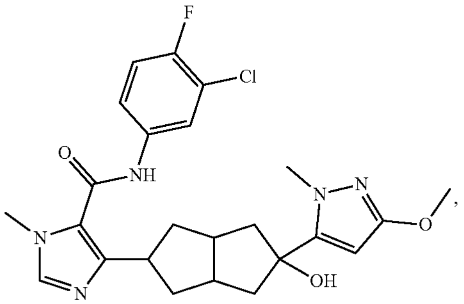 |
| Example 94 | 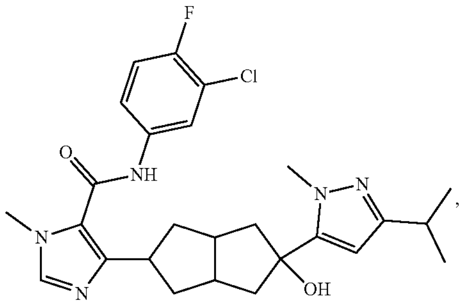 [SMILES: CC(C)c1cc(C2(O)CC3CC(c4ncn(C)c4C(=O)Nc4ccc(F)c(Cl)c4)CC3C2)n(C)n1] |
| Example 95 | 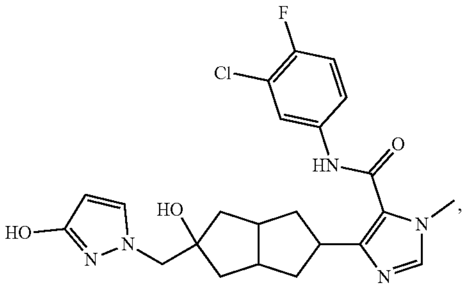 [SMILES: Cn1cnc(C2CC3CC(O)(Cn4ccc(O)n4)CC3C2)c1C(=O)Nc1ccc(F)c(Cl)c1] |

-continued
| Example No. | Name/Structure |
|---|---|
| Example 96 | 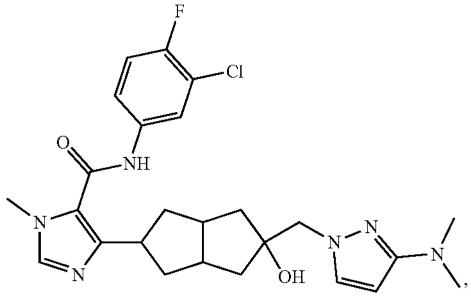, |
| Example 97 | 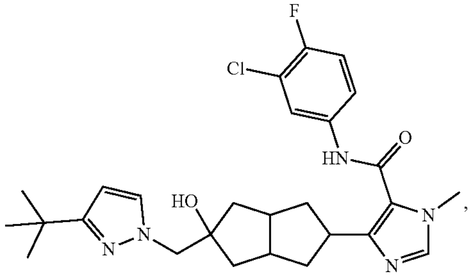 [SMILES: Cn1cnc(C2CC3CC(O)(Cn4ccc(C(C)(C)C)n4)CC3C2)c1C(=O)Nc1ccc(F)c(Cl)c1], |
| Example 98 | 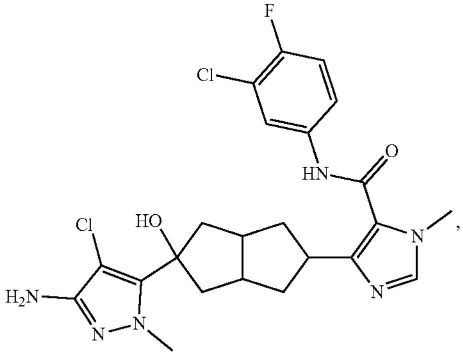 [SMILES: Cn1cnc(C2CC3CC(O)(c4c(Cl)c(N)nn4C)CC3C2)c1C(=O)Nc1ccc(F)c(Cl)c1], |
| Example 99 | 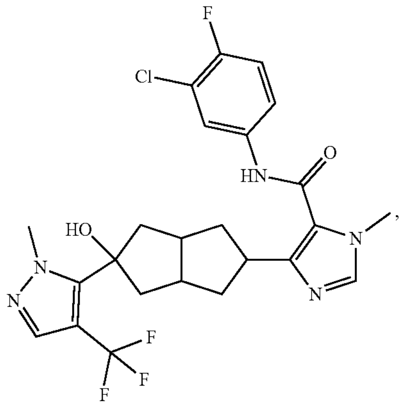 [SMILES: Cn1cnc(C2CC3CC(O)(c4c(C(F)(F)F)cnn4C)CC3C2)c1C(=O)Nc1ccc(F)c(Cl)c1], |
-continued
| Example No. | Name/Structure |
|---|---|
| Example 100 | 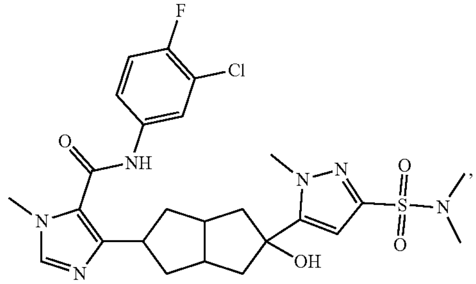, |
| Example 101 | 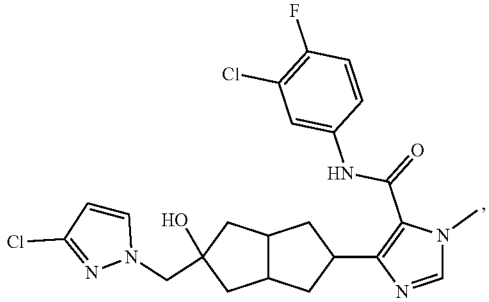 [SMILES: Cn1cnc(C2CC3CC(O)(Cn4ccc(Cl)n4)CC3C2)c1C(=O)Nc1ccc(F)c(Cl)c1], |
| Example 102 | 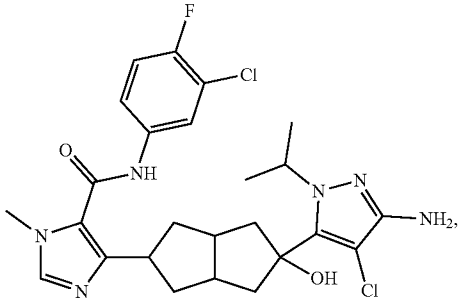 [SMILES: CC(C)n1nc(N)c(Cl)c1C1(O)CC2CC(c3ncn(C)c3C(=O)Nc3ccc(F)c(Cl)c3)CC2C1], |
| Example 103 | 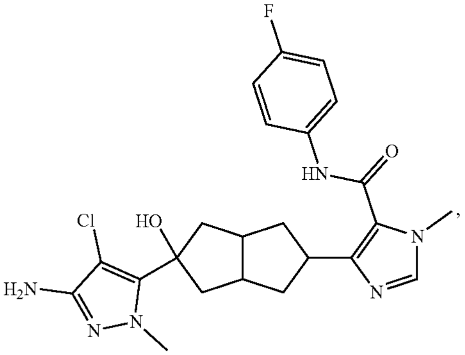 [SMILES: Cn1cnc(C2CC3CC(O)(c4c(Cl)c(N)nn4C)CC3C2)c1C(=O)Nc1ccc(F)cc1], |

-continued
| Example No. | Name/Structure |
|---|---|
| Example 104 | 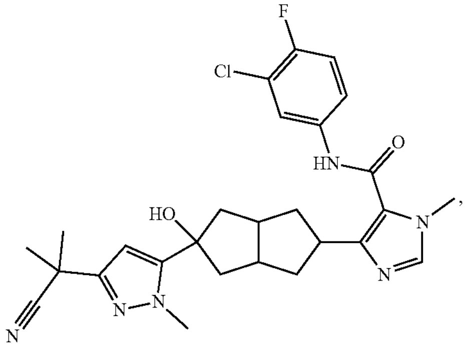 [SMILES: Cn1cnc(C2CC3CC(O)(c4cc(C(C)(C)C#N)nn4C)CC3C2)c1C(=O)Nc1ccc(F)c(Cl)c1] |
| Example 105 | 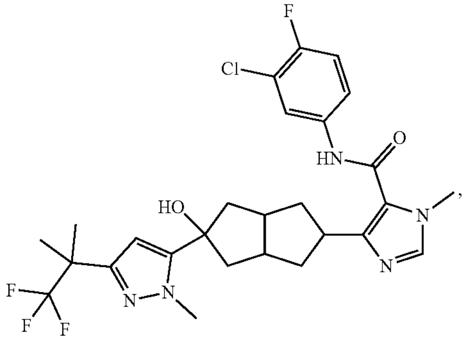 [SMILES: Cn1cnc(C2CC3CC(O)(c4cc(C(C)(C)C(F)(F)F)nn4C)CC3C2)c1C(=O)Nc1ccc(F)c(Cl)c1] |
| Example 106 | 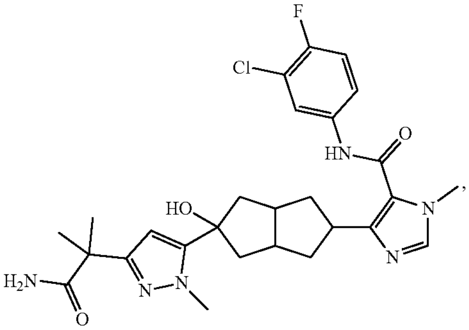 [SMILES: Cn1cnc(C2CC3CC(O)(c4cc(C(C)(C)C(N)=O)nn4C)CC3C2)c1C(=O)Nc1ccc(F)c(Cl)c1] |
| Example 107 | 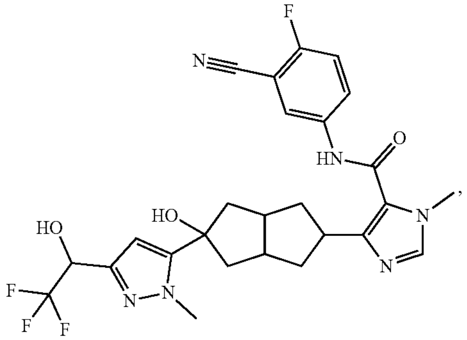 [SMILES: Cn1cnc(C2CC3CC(O)(c4cc(C(O)C(F)(F)F)nn4C)CC3C2)c1C(=O)Nc1ccc(F)c(C#N)c1] |
-continued
| Example No. | Name/Structure |
|---|---|
| Example 108 | 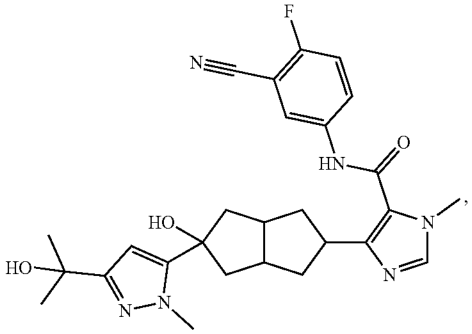 [SMILES: Cn1cnc(C2CC3CC(O)(c4cc(C(C)(C)O)nn4C)CC3C2)c1C(=O)Nc1ccc(F)c(C#N)c1] |
| Example 109 | 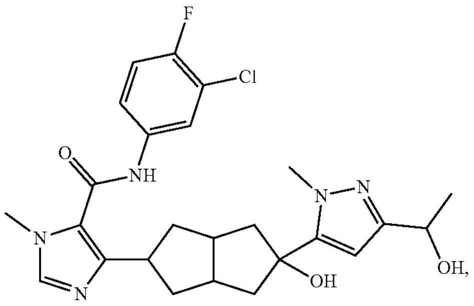 [SMILES: CC(O)c1cc(C2(O)CC3CC(c4ncn(C)c4C(=O)Nc4ccc(F)c(Cl)c4)CC3C2)n(C)n1] |
| Example 110 | 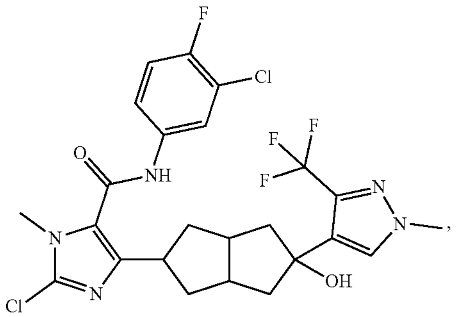 |
| Example 111 | 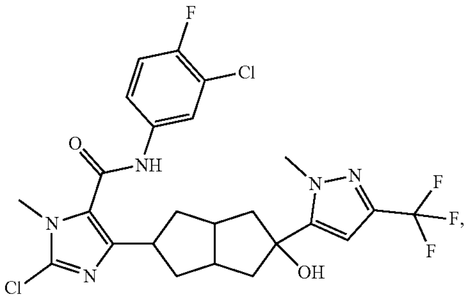 [SMILES: Cn1nc(C(F)(F)F)cc1C1(O)CC2CC(c3nc(Cl)n(C)c3C(=O)Nc3ccc(F)c(Cl)c3)CC2C1] |
| Example 112 | 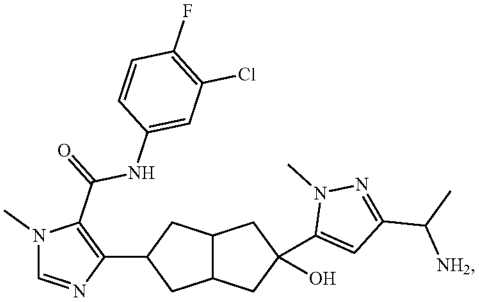 [SMILES: CC(N)c1cc(C2(O)CC3CC(c4ncn(C)c4C(=O)Nc4ccc(F)c(Cl)c4)CC3C2)n(C)n1] |

-continued
| Example No. | Name/Structure |
|---|---|
| Example 113 | 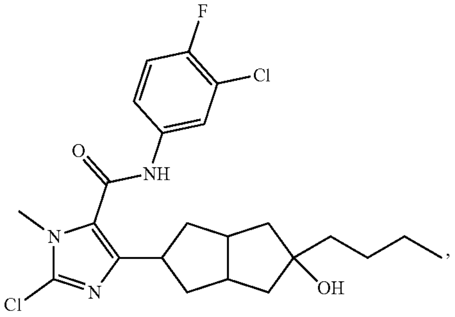 [SMILES: CCCCC1(O)CC2CC(c3nc(Cl)n(C)c3C(=O)Nc3ccc(F)c(Cl)c3)CC2C1] |
| Example 114 | 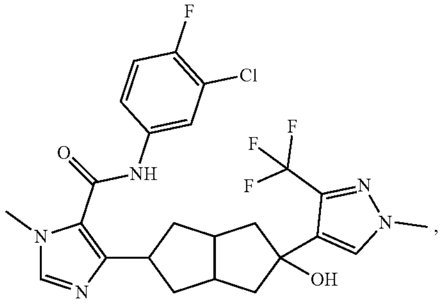 |
| Example 115 | 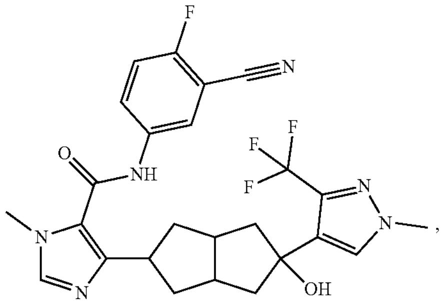 |
| Example 116 | 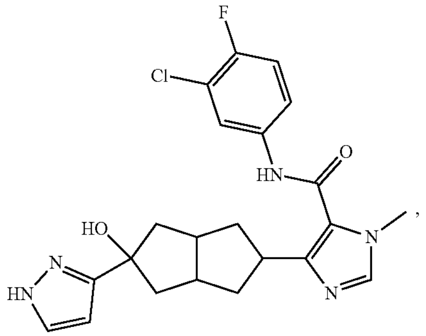 [SMILES: Cn1cnc(C2CC3CC(O)(c4cc[nH]n4)CC3C2)c1C(=O)Nc1ccc(F)c(Cl)c1] |
-continued
| Example No. | Name/Structure |
|---|---|
| Example 117 | 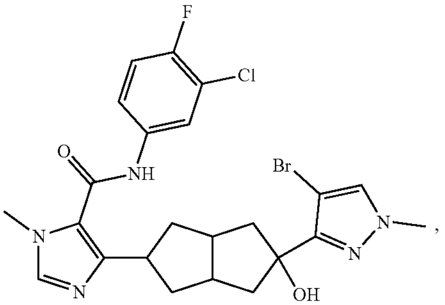 |
| Example 118 | 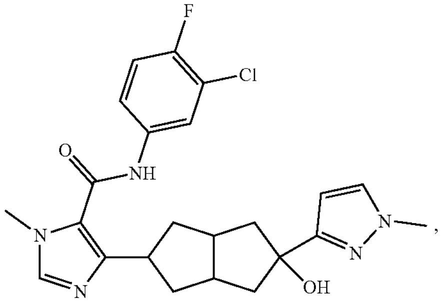 |
| Example 119 | 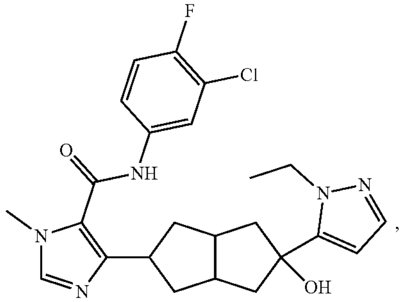 [SMILES: CCn1nccc1C1(O)CC2CC(c3ncn(C)c3C(=O)Nc3ccc(F)c(Cl)c3)CC2C1] |
| Example 120 | 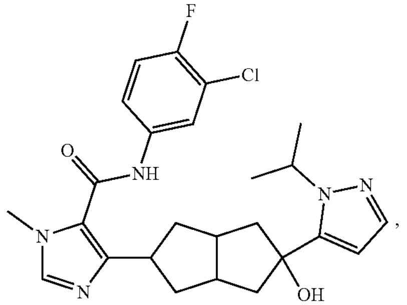 [SMILES: CC(C)n1nccc1C1(O)CC2CC(c3ncn(C)c3C(=O)Nc3ccc(F)c(Cl)c3)CC2C1] |
| Example 121 | 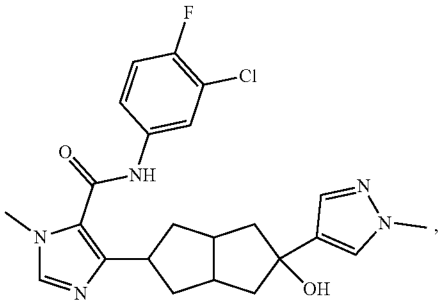 |

-continued
| Example No. | Name/Structure |
|---|---|
| Example 122 | 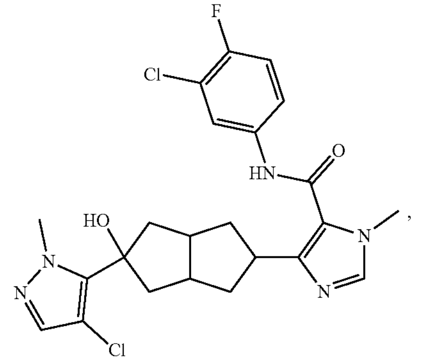 [SMILES: Cn1cnc(C2CC3CC(O)(c4c(Cl)cnn4C)CC3C2)c1C(=O)Nc1ccc(F)c(Cl)c1] |
| Example 123 | 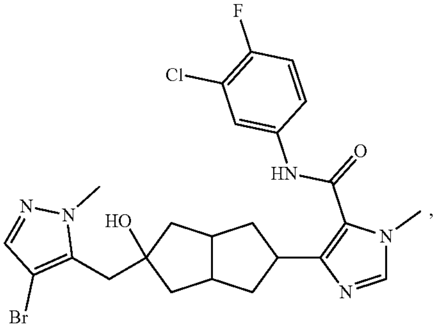 [SMILES: Cn1cnc(C2CC3CC(O)(Cc4c(Br)cnn4C)CC3C2)c1C(=O)Nc1ccc(F)c(Cl)c1] |
| Example 124 | 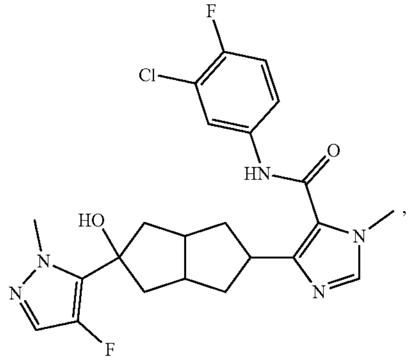 |
| Example 125 | 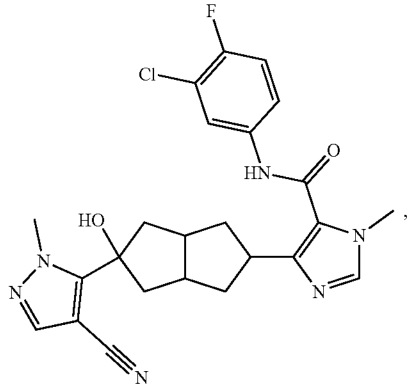 [SMILES: Cn1cnc(C2CC3CC(O)(c4c(C#N)cnn4C)CC3C2)c1C(=O)Nc1ccc(F)c(Cl)c1] |
-continued
| Example No. | Name/Structure |
|---|---|
| Example 126 | 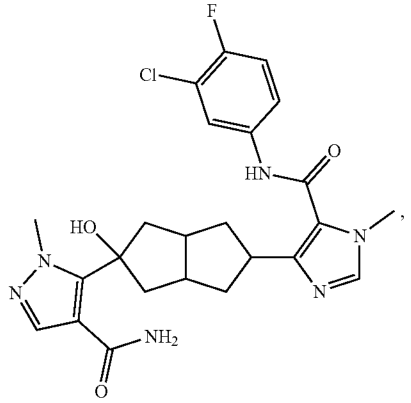 [SMILES: Cn1cnc(C2CC3CC(O)(c4c(C(N)=O)cnn4C)CC3C2)c1C(=O)Nc1ccc(F)c(Cl)c1] |
| Example 127 | 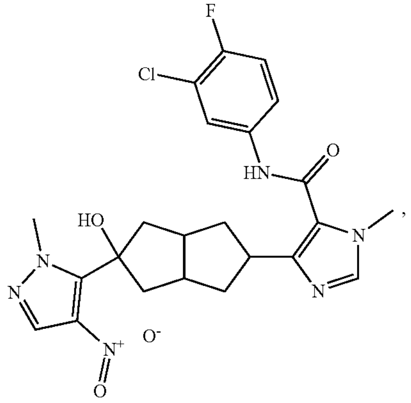 |
| Example 128 | 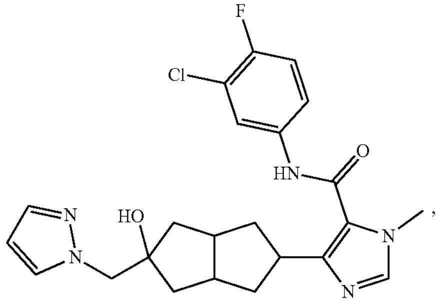 [SMILES: Cn1cnc(C2CC3CC(O)(Cn4cccn4)CC3C2)c1C(=O)Nc1ccc(F)c(Cl)c1] |
| Example 130 | 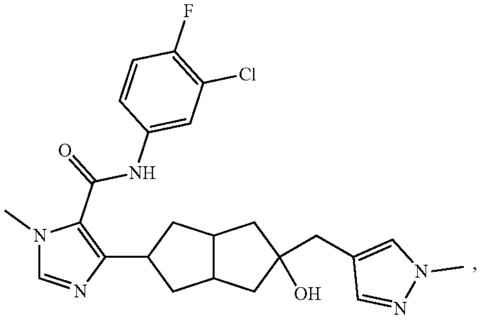 |

-continued
| Example No. | Name/Structure |
|---|---|
| Example 131 | 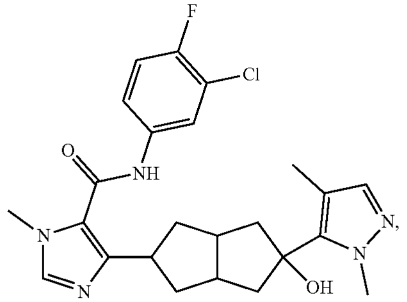 [SMILES: Cc1cnn(C)c1C1(O)CC2CC(c3ncn(C)c3C(=O)Nc3ccc(F)c(Cl)c3)CC2C1] |
| Example 132 | 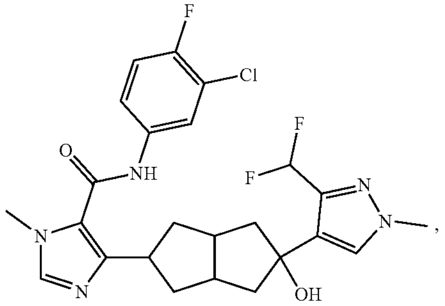 |
| Example 133 | 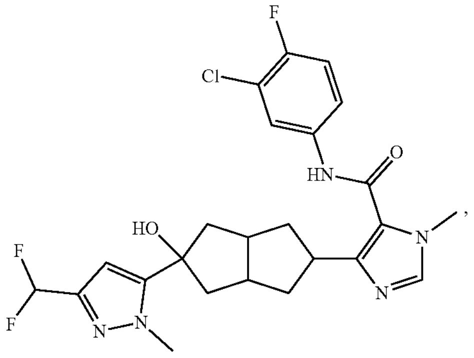 [SMILES: Cn1cnc(C2CC3CC(O)(c4cc(C(F)F)nn4C)CC3C2)c1C(=O)Nc1ccc(F)c(Cl)c1] |
| Example 134 | 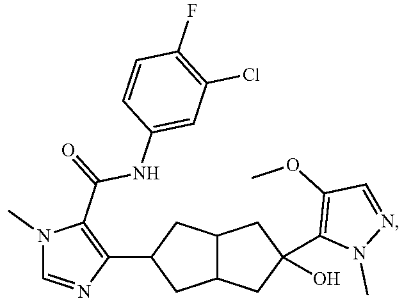 [SMILES: COc1cnn(C)c1C1(O)CC2CC(c3ncn(C)c3C(=O)Nc3ccc(F)c(Cl)c3)CC2C1] |
-continued
| Example No. | Name/Structure |
|---|---|
| Example 135 | 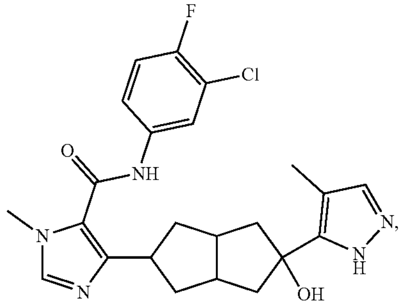 [SMILES: Cc1cn[nH]c1C1(O)CC2CC(c3ncn(C)c3C(=O)Nc3ccc(F)c(Cl)c3)CC2C1] |
| Example 136 | 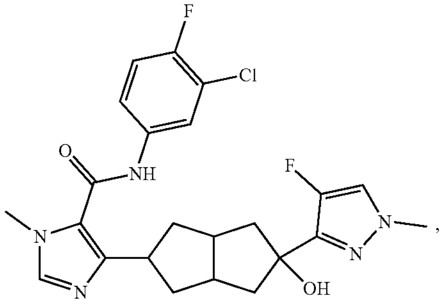 |
| Example 137 | 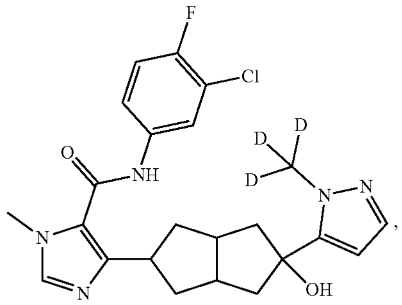 [SMILES: [2H]C([2H])([2H])n1nccc1C1(O)CC2CC(c3ncn(C)c3C(=O)Nc3ccc(F)c(Cl)c3)CC2C1] |
| Example 138 | 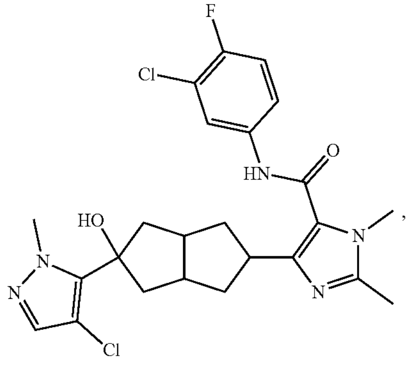 [SMILES: Cc1nc(C2CC3CC(O)(c4c(Cl)cnn4C)CC3C2)c(C(=O)Nc2ccc(F)c(Cl)c2)n1C] |

-continued
| Example No. | Name/Structure |
|---|---|
| Example 139 | 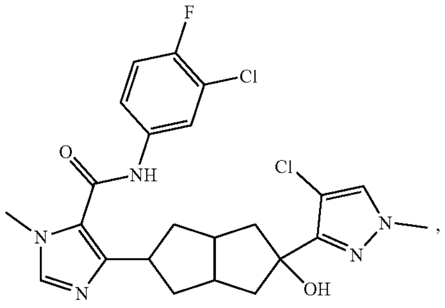 |
| Example 140 | 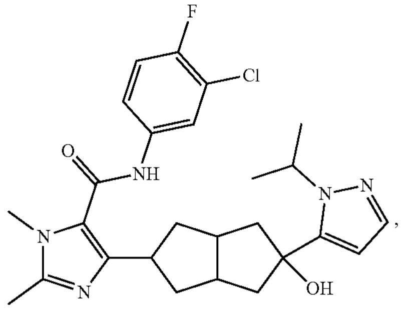 [SMILES: Cc1nc(C2CC3CC(O)(c4ccnn4C(C)C)CC3C2)c(C(=O)Nc2ccc(F)c(Cl)c2)n1C] |
| Example 141 | 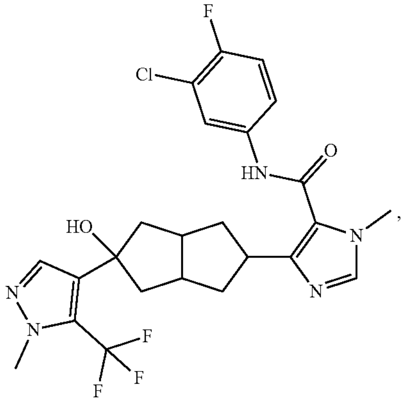 [SMILES: Cn1cnc(C2CC3CC(O)(c4cnn(C)c4C(F)(F)F)CC3C2)c1C(=O)Nc1ccc(F)c(Cl)c1] |
| Example 142 | 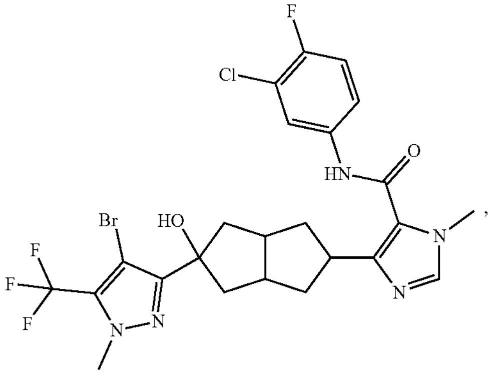 [SMILES: Cn1cnc(C2CC3CC(O)(c4nn(C)c(C(F)(F)F)c4Br)CC3C2)c1C(=O)Nc1ccc(F)c(Cl)c1] |
-continued
| Example No. | Name/Structure |
|---|---|
| Example 143 | 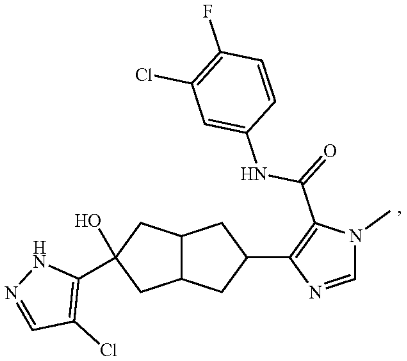 [SMILES: Cn1cnc(C2CC3CC(O)(c4[nH]ncc4Cl)CC3C2)c1C(=O)Nc1ccc(F)c(Cl)c1] |
| Example 144 | 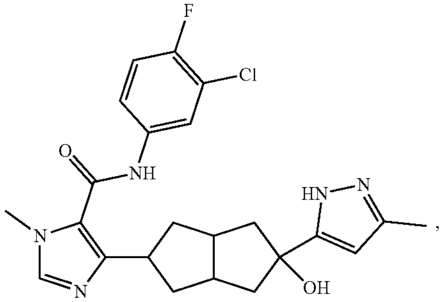 |
| Example 145 | 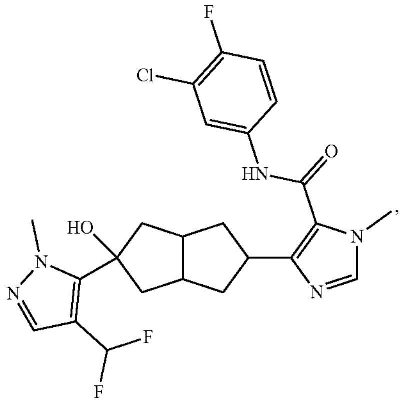 [SMILES: Cn1cnc(C2CC3CC(O)(c4c(C(F)F)cnn4C)CC3C2)c1C(=O)Nc1ccc(F)c(Cl)c1] |
| Example 146 | 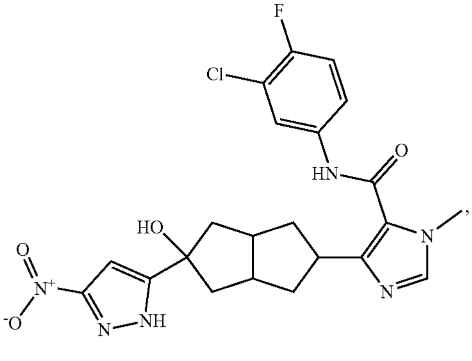 |

-continued
| Example No. | Name/Structure |
|---|---|
| Example 147 | 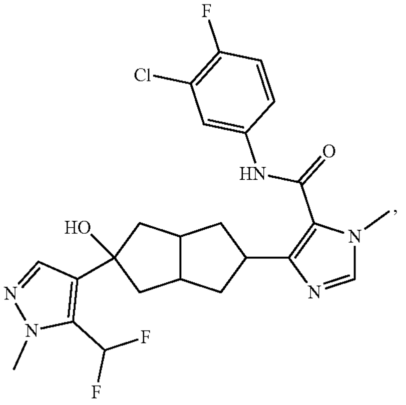 [SMILES: Cn1cnc(C2CC3CC(O)(c4cnn(C)c4C(F)F)CC3C2)c1C(=O)Nc1ccc(F)c(Cl)c1] |
| Example 148 | 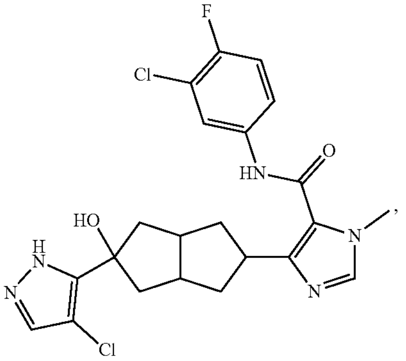 [SMILES: Cn1cnc(C2CC3CC(O)(c4[nH]ncc4Cl)CC3C2)c1C(=O)Nc1ccc(F)c(Cl)c1] |
| Example 149 | 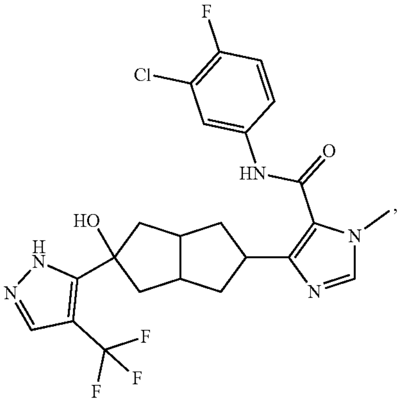 [SMILES: Cn1cnc(C2CC3CC(O)(c4[nH]ncc4C(F)(F)F)CC3C2)c1C(=O)Nc1ccc(F)c(Cl)c1] |
| Example 150 | 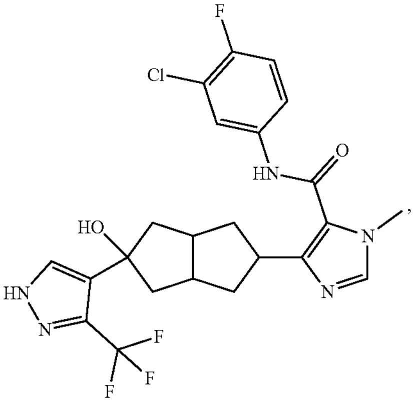 [SMILES: Cn1cnc(C2CC3CC(O)(c4c[nH]nc4C(F)(F)F)CC3C2)c1C(=O)Nc1ccc(F)c(Cl)c1] |
-continued
| Example No. | Name/Structure |
|---|---|
| Example 151 | 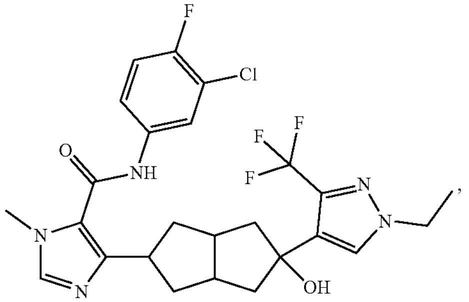 [SMILES: CCn1cc(C2(O)CC3CC(c4ncn(C)c4C(=O)Nc4ccc(F)c(Cl)c4)CC3C2)c(C(F)(F)F)n1] |
| Example 152 | 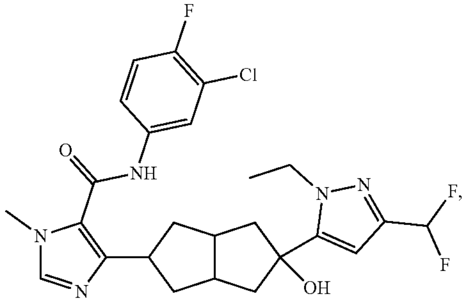 [SMILES: CCn1nc(C(F)F)cc1C1(O)CC2CC(c3ncn(C)c3C(=O)Nc3ccc(F)c(Cl)c3)CC2C1] |
| Example 153 | 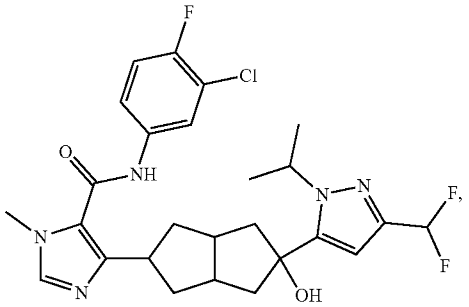 [SMILES: CC(C)n1nc(C(F)F)cc1C1(O)CC2CC(c3ncn(C)c3C(=O)Nc3ccc(F)c(Cl)c3)CC2C1] |
| Example 154 | 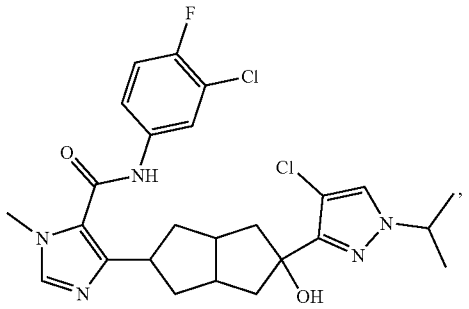 [SMILES: CC(C)n1cc(Cl)c(C2(O)CC3CC(c4ncn(C)c4C(=O)Nc4ccc(F)c(Cl)c4)CC3C2)n1] |
| Example 155 | 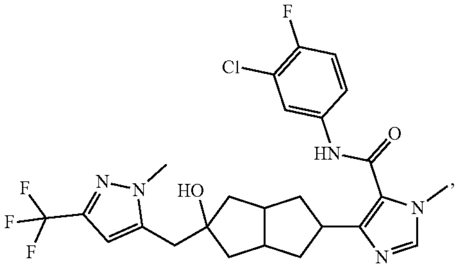 [SMILES: Cn1cnc(C2CC3CC(O)(Cc4cc(C(F)(F)F)nn4C)CC3C2)c1C(=O)Nc1ccc(F)c(Cl)c1] |

-continued
| Example No. | Name/Structure |
|---|---|
| Example 156 | 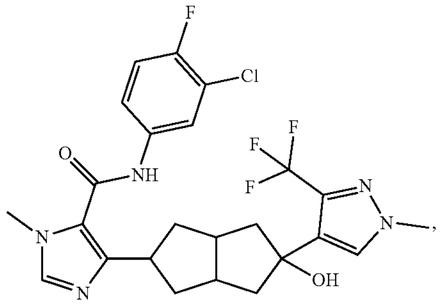 |
| Example 157 | 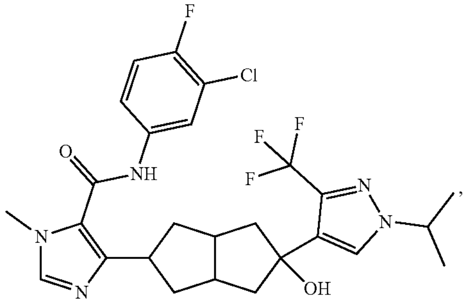 [SMILES: CC(C)n1cc(C2(O)CC3CC(c4ncn(C)c4C(=O)Nc4ccc(F)c(Cl)c4)CC3C2)c(C(F)(F)F)n1] |
| Example 158 | 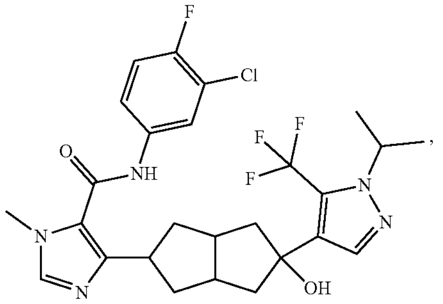 [SMILES: CC(C)n1ncc(C2(O)CC3CC(c4ncn(C)c4C(=O)Nc4ccc(F)c(Cl)c4)CC3C2)c1C(F)(F)F] |
| Example 159 | 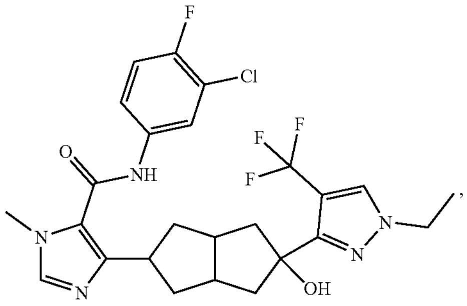 [SMILES: CCn1cc(C(F)(F)F)c(C2(O)CC3CC(c4ncn(C)c4C(=O)Nc4ccc(F)c(Cl)c4)CC3C2)n1] |
| Example 160 | 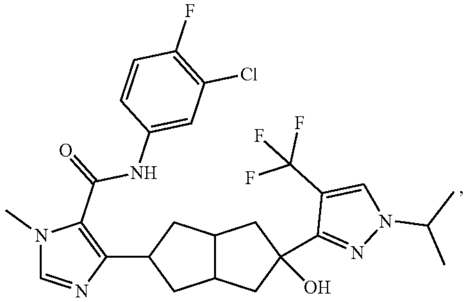 [SMILES: CC(C)n1cc(C(F)(F)F)c(C2(O)CC3CC(c4ncn(C)c4C(=O)Nc4ccc(F)c(Cl)c4)CC3C2)n1] |
-continued
| Example No. | Name/Structure |
|---|---|
| Example 161 | 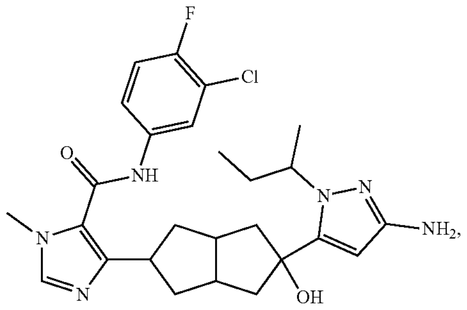 [SMILES: CCC(C)n1nc(N)cc1C1(O)CC2CC(c3ncn(C)c3C(=O)Nc3ccc(F)c(Cl)c3)CC2C1] |
| Example 162 | 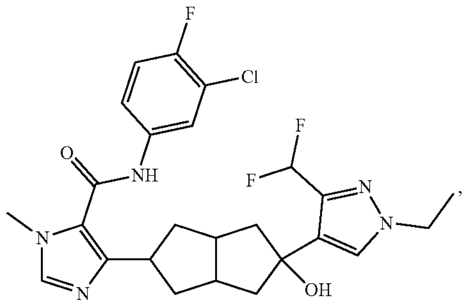 [SMILES: CCn1cc(C2(O)CC3CC(c4ncn(C)c4C(=O)Nc4ccc(F)c(Cl)c4)CC3C2)c(C(F)F)n1] |
| Example 163 | 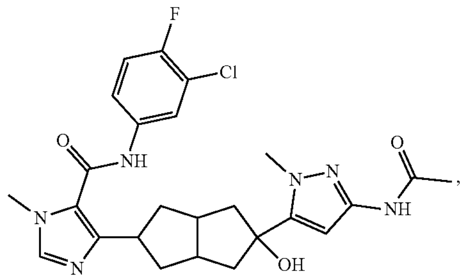 [SMILES: CC(=O)Nc1cc(C2(O)CC3CC(c4ncn(C)c4C(=O)Nc4ccc(F)c(Cl)c4)CC3C2)n(C)n1] |
| Example 164 | 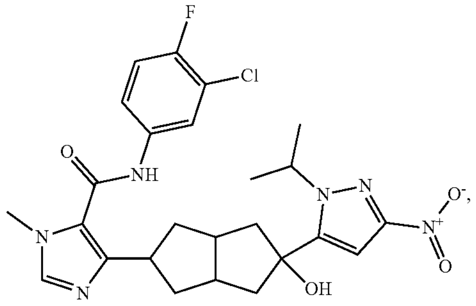 |
| Example 165 | 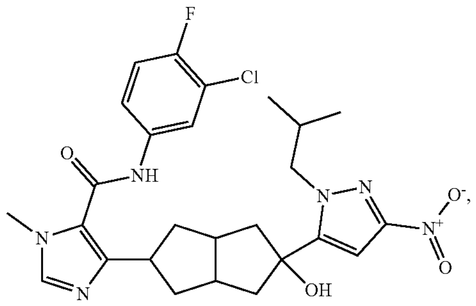 |

-continued
| Example No. | Name/Structure |
| --- | --- |
| Example 166 | 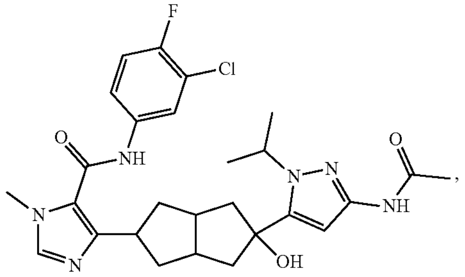 [SMILES: CC(=O)Nc1cc(C2(O)CC3CC(c4ncn(C)c4C(=O)Nc4ccc(F)c(Cl)c4)CC3C2)n(C(C)C)n1] |
| Example 168 | 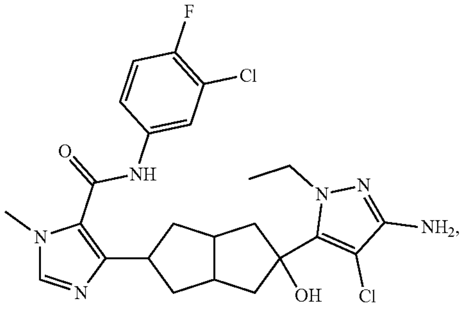 [SMILES: CCn1nc(N)c(Cl)c1C1(O)CC2CC(c3ncn(C)c3C(=O)Nc3ccc(F)c(Cl)c3)CC2C1] |
| Example 169 | 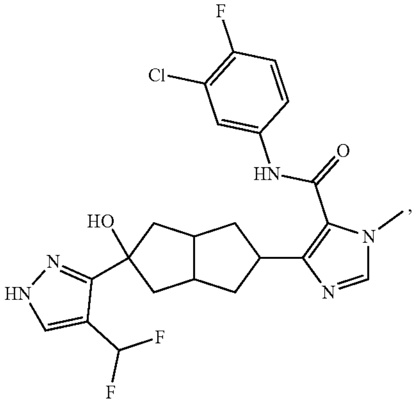 [SMILES: Cn1cnc(C2CC3CC(O)(c4n[nH]cc4C(F)F)CC3C2)c1C(=O)Nc1ccc(F)c(Cl)c1] |
| Example 170 | 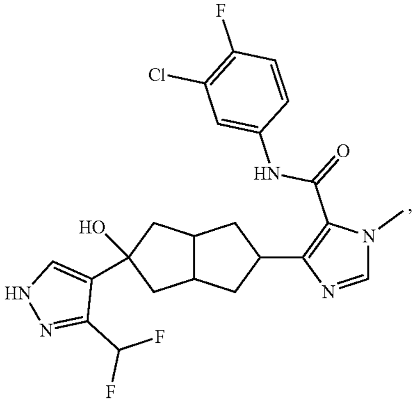 |
-continued
| Example No. | Name/Structure |
| --- | --- |
| Example 171 | 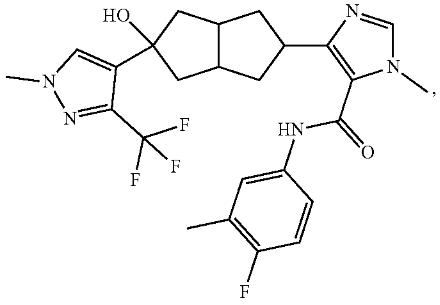 |
| Example 172 | 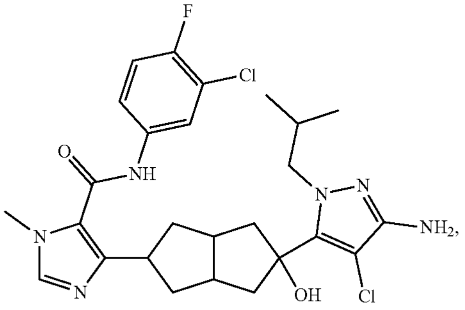 [SMILES: CC(C)Cn1nc(N)c(Cl)c1C1(O)CC2CC(c3ncn(C)c3C(=O)Nc3ccc(F)c(Cl)c3)CC2C1] |
| Example 173 | 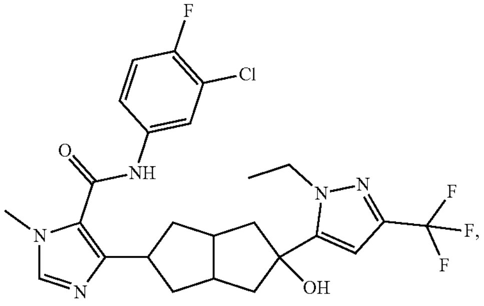 [SMILES: CCn1nc(C(F)(F)F)cc1C1(O)CC2CC(c3ncn(C)c3C(=O)Nc3ccc(F)c(Cl)c3)CC2C1] |
| Example 174 | 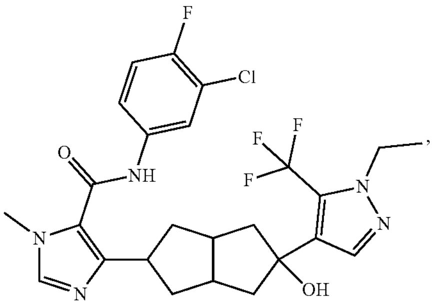 [SMILES: CCn1ncc(C2(O)CC3CC(c4ncn(C)c4C(=O)Nc4ccc(F)c(Cl)c4)CC3C2)c1C(F)(F)F] |
| Example 175 | 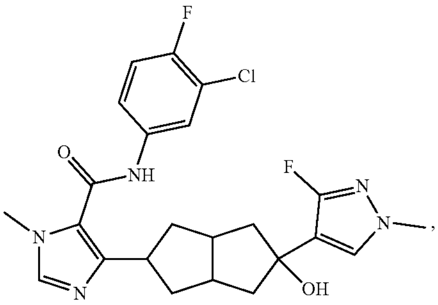 |

-continued
| Example No. | Name/Structure |
| --- | --- |
| Example 176 | 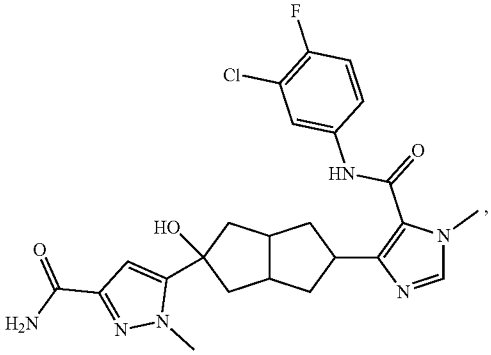 [SMILES: Cn1cnc(C2CC3CC(O)(c4cc(C(N)=O)nn4C)CC3C2)c1C(=O)Nc1ccc(F)c(Cl)c1] |
| Example 177 | 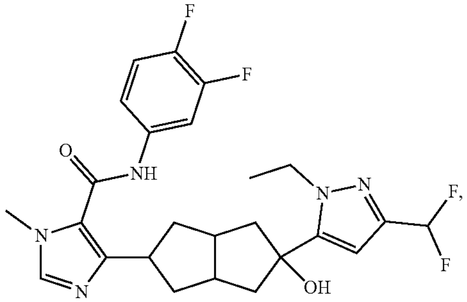 [SMILES: CCn1nc(C(F)F)cc1C1(O)CC2CC(c3ncn(C)c3C(=O)Nc3ccc(F)c(F)c3)CC2C1] |
| Example 178 | 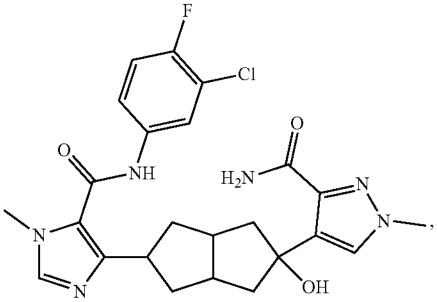 |
| Example 179 | 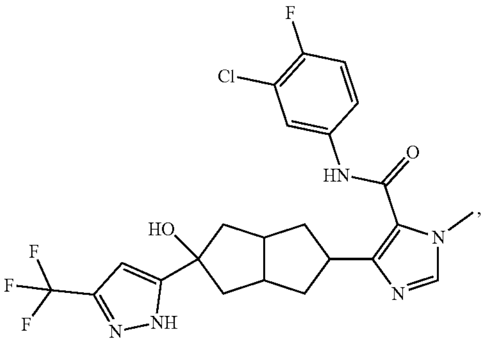 [SMILES: Cn1cnc(C2CC3CC(O)(c4cc(C(F)(F)F)n[nH]4)CC3C2)c1C(=O)Nc1ccc(F)c(Cl)c1] |
-continued
| Example No. | Name/Structure |
| --- | --- |
| Example 180 | 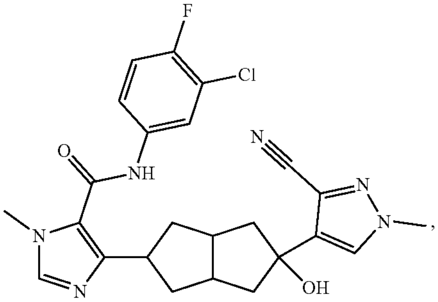 |
| Example 181 | 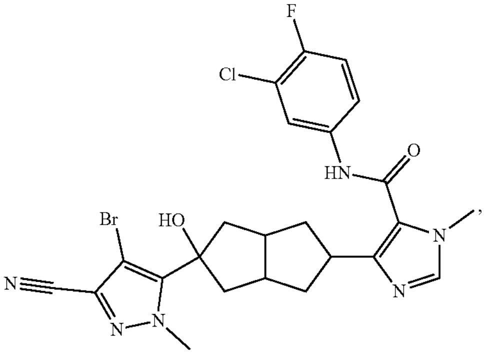 [SMILES: Cn1cnc(C2CC3CC(O)(c4c(Br)c(C#N)nn4C)CC3C2)c1C(=O)Nc1ccc(F)c(Cl)c1] |
| Example 182 | 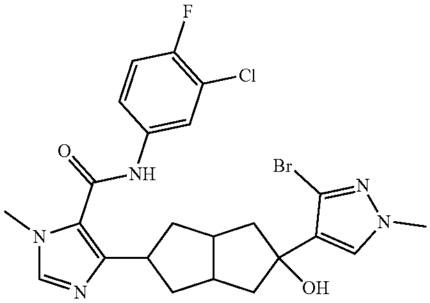 |
| Example 183 | 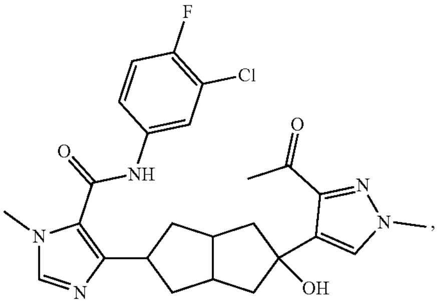 |

-continued
| Example No. | Name/Structure |
|---|---|
| Example 184 | 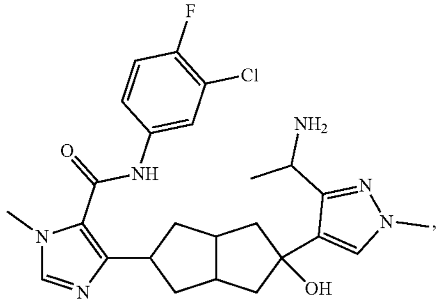 |
| Example 185 | 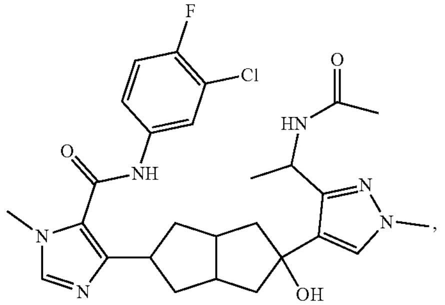 |
| Example 186 | 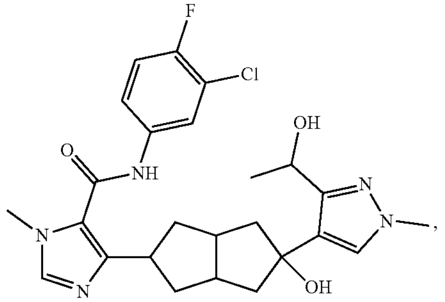 |
| Example 187 | 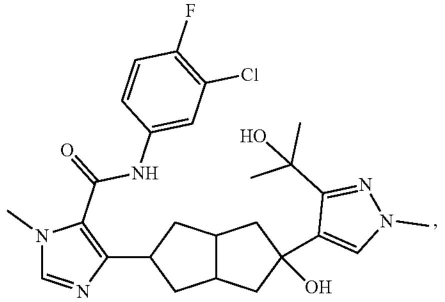 |
| Example 188 | 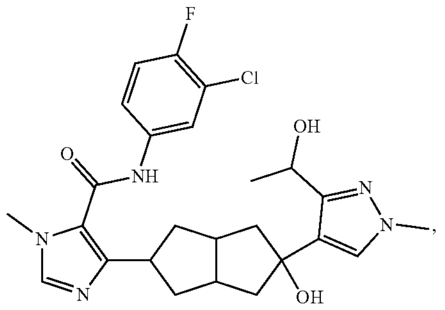 |
-continued
| Example No. | Name/Structure |
|---|---|
| Example 190 | 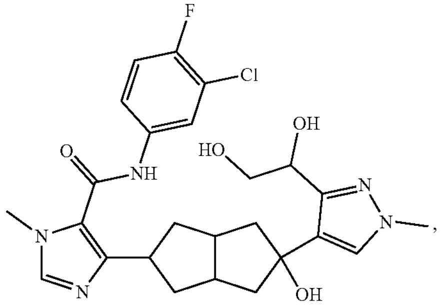 |
| Example 191 | 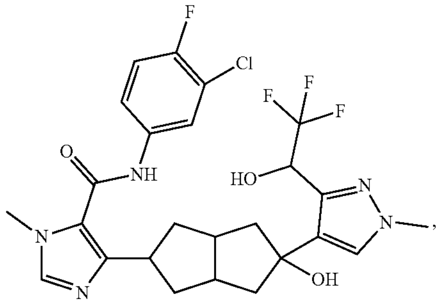 |
| Example 192 | 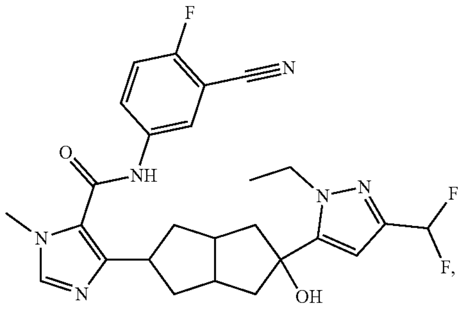 [SMILES: CCn1nc(C(F)F)cc1C1(O)CC2CC(c3ncn(C)c3C(=O)Nc3ccc(F)c(C#N)c3)CC2C1] |
| Example 193 | 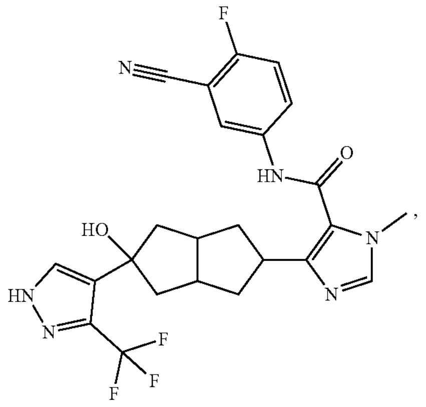 [SMILES: Cn1cnc(C2CC3CC(O)(c4c[nH]nc4C(F)(F)F)CC3C2)c1C(=O)Nc1ccc(F)c(C#N)c1] |

-continued
| Example No. | Name/Structure |
|---|---|
| Example 194 | 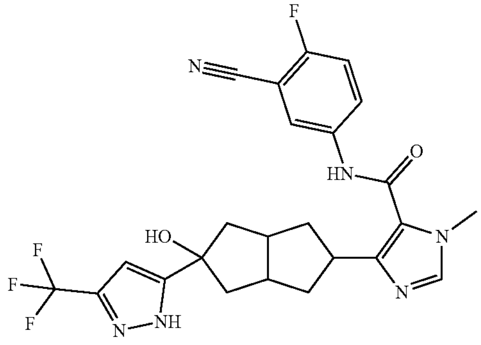 , |
| Example 195 | 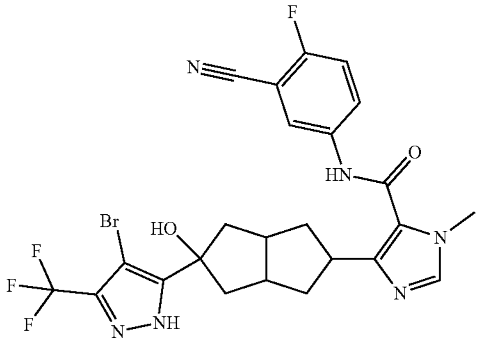 , |
| Example 196 | 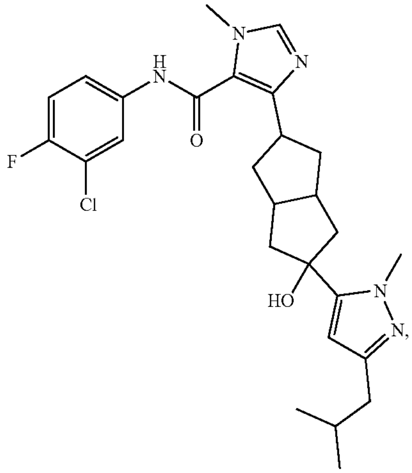 , |
-continued
| Example No. | Name/Structure |
|---|---|
| Example 197 | 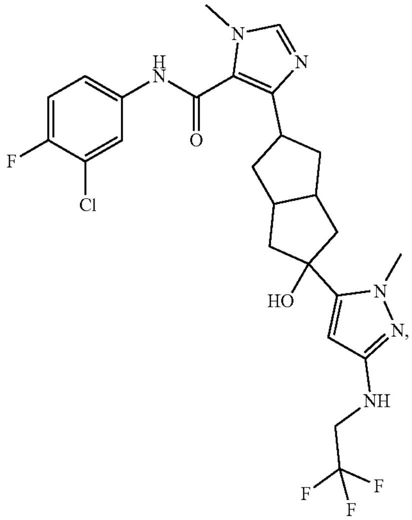 [SMILES: Cn1cnc(C2CC3CC(O)(c4cc(NCC(F)(F)F)nn4C)CC3C2)c1C(=O)Nc1ccc(F)c(Cl)c1] , |
| Example 198 | 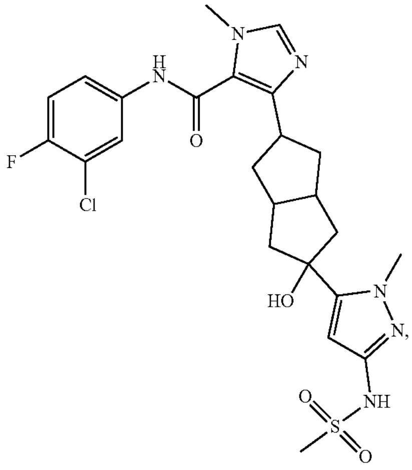 [SMILES: Cn1cnc(C2CC3CC(O)(c4cc(NS(C)(=O)=O)nn4C)CC3C2)c1C(=O)Nc1ccc(F)c(Cl)c1] , |
| Example 199 | 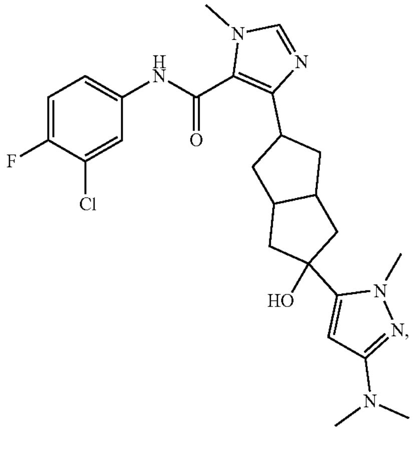 [SMILES: CN(C)c1cc(C2(O)CC3CC(c4ncn(C)c4C(=O)Nc4ccc(F)c(Cl)c4)CC3C2)n(C)n1] , |

-continued
| Example No. | Name/Structure |
| --- | --- |
| Example 200 | 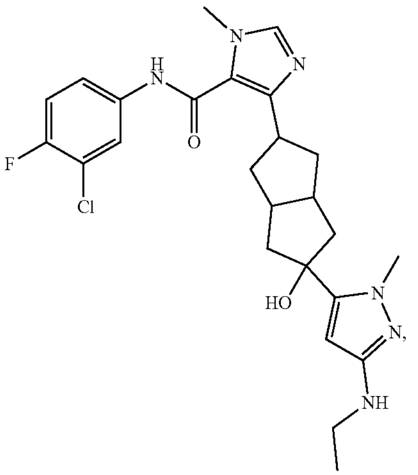 [SMILES: CCNc1cc(C2(O)CC3CC(c4ncn(C)c4C(=O)Nc4ccc(F)c(Cl)c4)CC3C2)n(C)n1] |
| Example 201 | 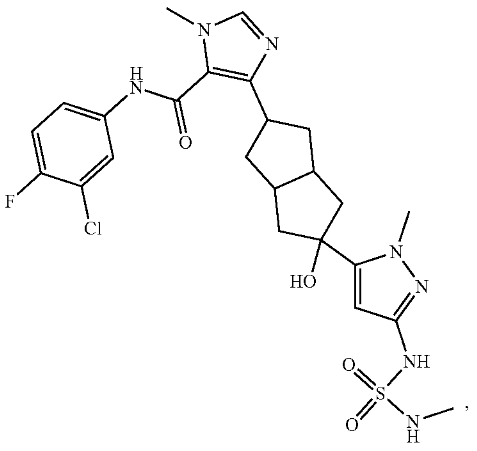 [SMILES: CNS(=O)(=O)Nc1cc(C2(O)CC3CC(c4ncn(C)c4C(=O)Nc4ccc(F)c(Cl)c4)CC3C2)n(C)n1] |
| Example 202 | 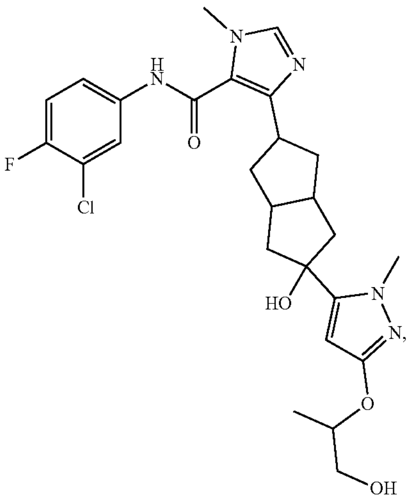 [SMILES: CC(CO)Oc1cc(C2(O)CC3CC(c4ncn(C)c4C(=O)Nc4ccc(F)c(Cl)c4)CC3C2)n(C)n1] |
| Example 203 | 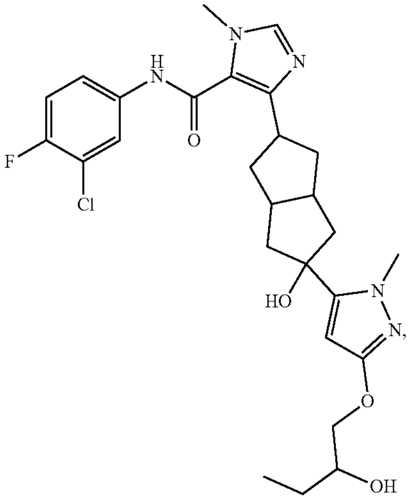 [SMILES: CCC(O)COc1cc(C2(O)CC3CC(c4ncn(C)c4C(=O)Nc4ccc(F)c(Cl)c4)CC3C2)n(C)n1] |
| Example 204 | 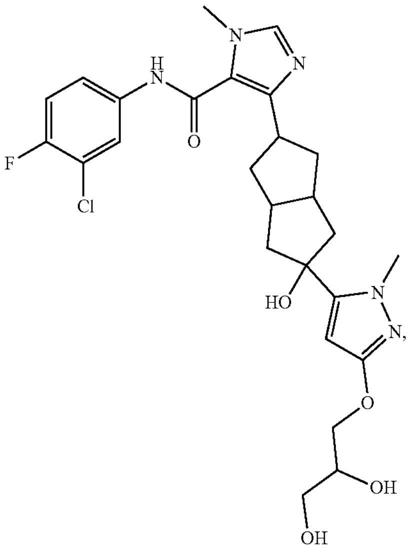 [SMILES: Cn1cnc(C2CC3CC(O)(c4cc(OCC(O)CO)nn4C)CC3C2)c1C(=O)Nc1ccc(F)c(Cl)c1] |
| Example 205 | 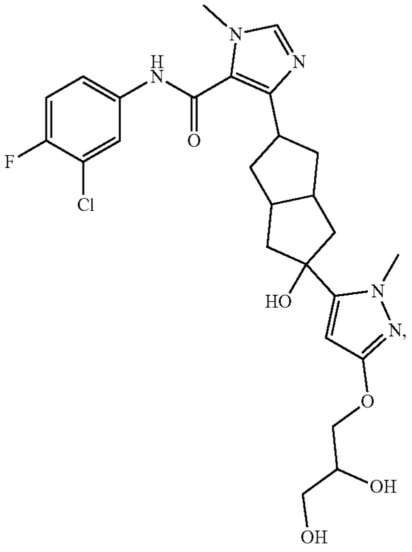 [SMILES: Cn1cnc(C2CC3CC(O)(c4cc(OCC(O)CO)nn4C)CC3C2)c1C(=O)Nc1ccc(F)c(Cl)c1] |

-continued
| Example No. | Name/Structure |
|---|---|
| Example 207 | 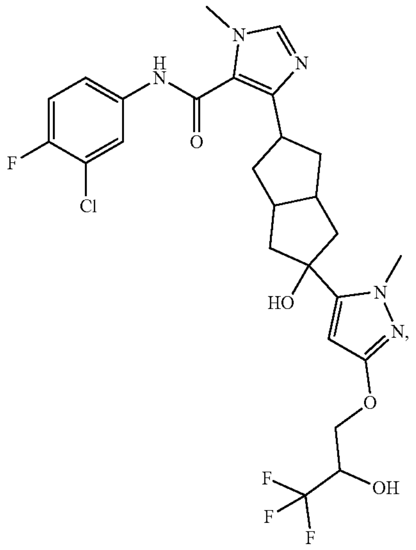 [SMILES: Cn1cnc(C2CC3CC(O)(c4cc(OCC(O)C(F)(F)F)nn4C)CC3C2)c1C(=O)Nc1ccc(F)c(Cl)c1] |
| Example 208 | 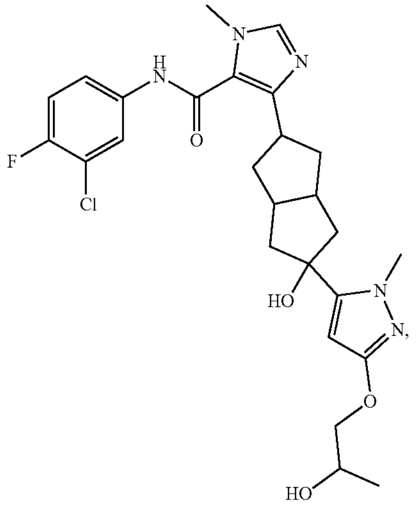 [SMILES: CC(O)COc1cc(C2(O)CC3CC(c4ncn(C)c4C(=O)Nc4ccc(F)c(Cl)c4)CC3C2)n(C)n1] |
| Example 209 | 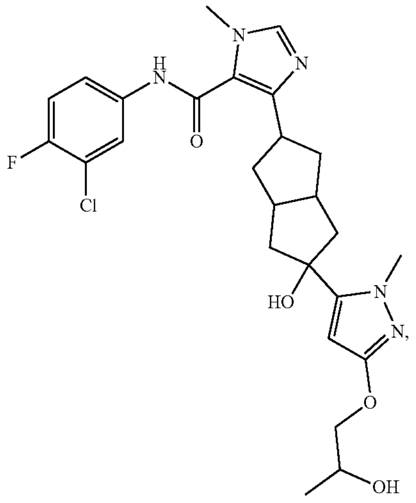 [SMILES: CC(O)COc1cc(C2(O)CC3CC(c4ncn(C)c4C(=O)Nc4ccc(F)c(Cl)c4)CC3C2)n(C)n1] |
-continued
| Example No. | Name/Structure |
|---|---|
| Example 211 | 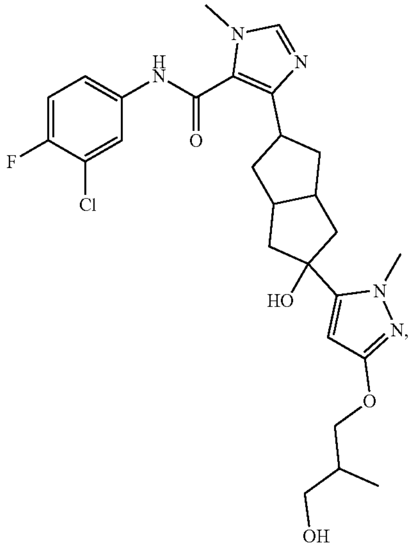 [SMILES: CC(CO)COc1cc(C2(O)CC3CC(c4ncn(C)c4C(=O)Nc4ccc(F)c(Cl)c4)CC3C2)n(C)n1] |
| Example 212 | 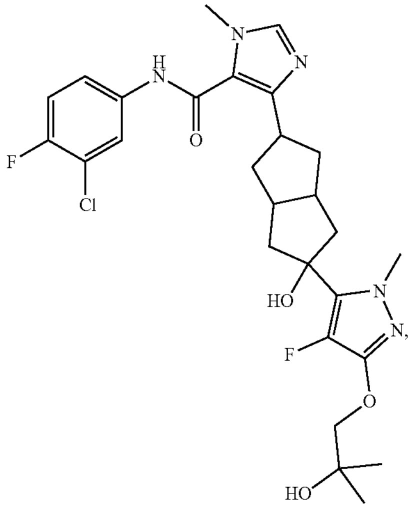 [SMILES: Cn1cnc(C2CC3CC(O)(c4c(F)c(OCC(C)(C)O)nn4C)CC3C2)c1C(=O)Nc1ccc(F)c(Cl)c1] |
| Example 213 | 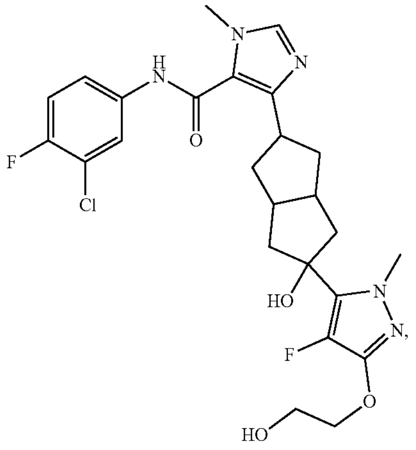 [SMILES: Cn1cnc(C2CC3CC(O)(c4c(F)c(OCCO)nn4C)CC3C2)c1C(=O)Nc1ccc(F)c(Cl)c1] |

| Example No. | Name/Structure |
|---|---|
| Example 214 | 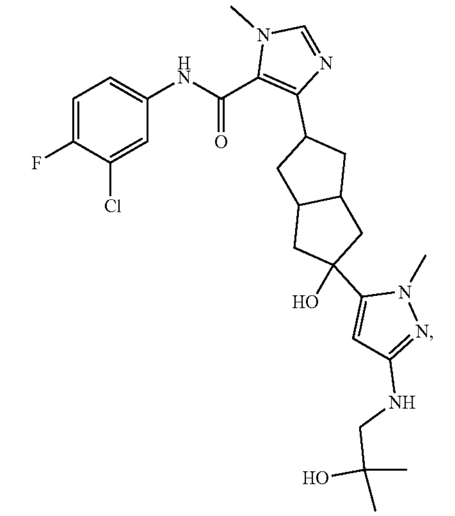 [SMILES: Cn1cnc(C2CC3CC(O)(c4cc(NCC(C)(C)O)nn4C)CC3C2)c1C(=O)Nc1ccc(F)c(Cl)c1] |
| Example 215 | 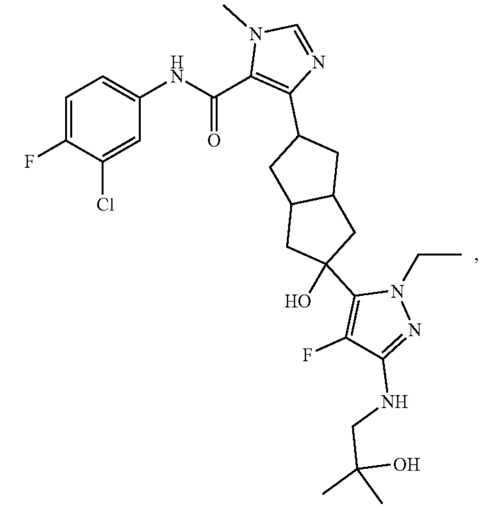 [SMILES: CCn1nc(NCC(C)(C)O)c(F)c1C1(O)CC2CC(c3ncn(C)c3C(=O)Nc3ccc(F)c(Cl)c3)CC2C1] |
| Example 216 | 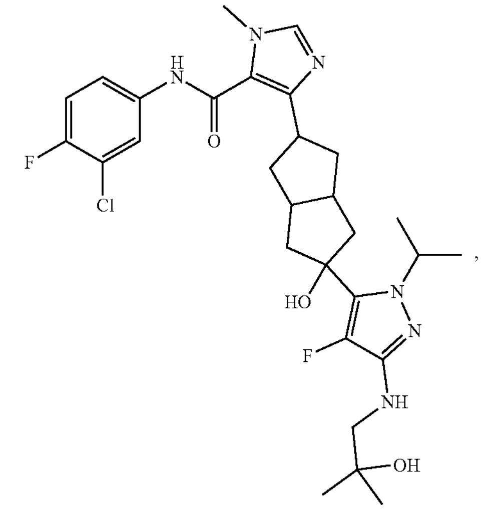 [SMILES: CC(C)n1nc(NCC(C)(C)O)c(F)c1C1(O)CC2CC(c3ncn(C)c3C(=O)Nc3ccc(F)c(Cl)c3)CC2C1] |
| Example No. | Name/Structure |
|---|---|
| Example 217 | 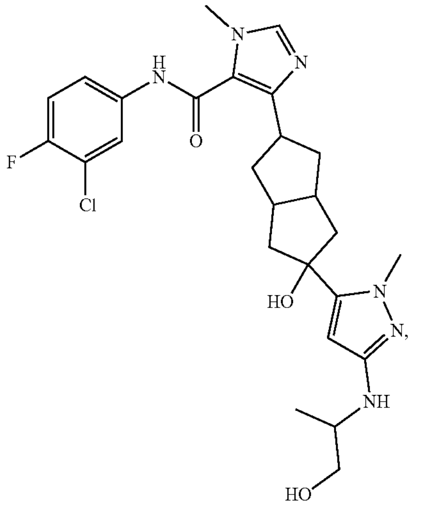 [SMILES: CC(CO)Nc1cc(C2(O)CC3CC(c4ncn(C)c4C(=O)Nc4ccc(F)c(Cl)c4)CC3C2)n(C)n1] |
| Example 218 | 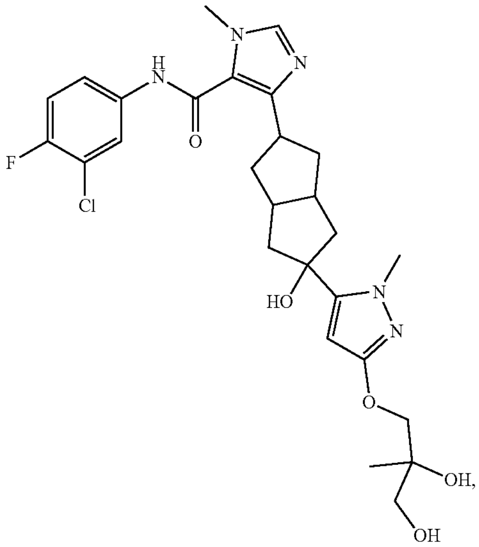 [SMILES: Cn1cnc(C2CC3CC(O)(c4cc(OCC(C)(O)CO)nn4C)CC3C2)c1C(=O)Nc1ccc(F)c(Cl)c1] |
| Example 219 | 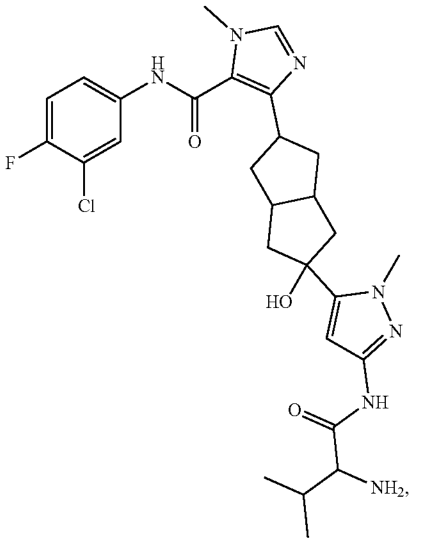 [SMILES: CC(C)C(N)C(=O)Nc1cc(C2(O)CC3CC(c4ncn(C)c4C(=O)Nc4ccc(F)c(Cl)c4)CC3C2)n(C)n1] |

-continued
| Example No. | Name/Structure |
|---|---|
| Example 220 | 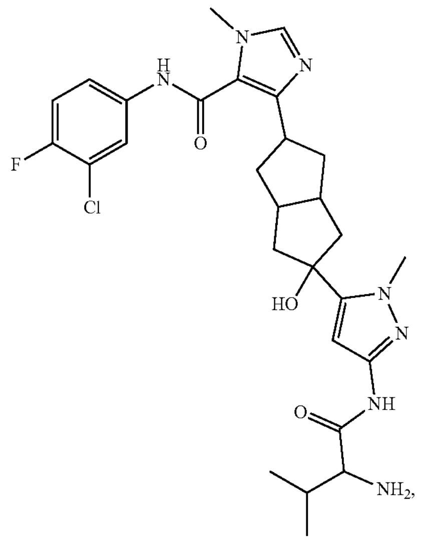 [SMILES: CC(C)C(N)C(=O)Nc1cc(C2(O)CC3CC(c4ncn(C)c4C(=O)Nc4ccc(F)c(Cl)c4)CC3C2)n(C)n1] |
| Example 221 | 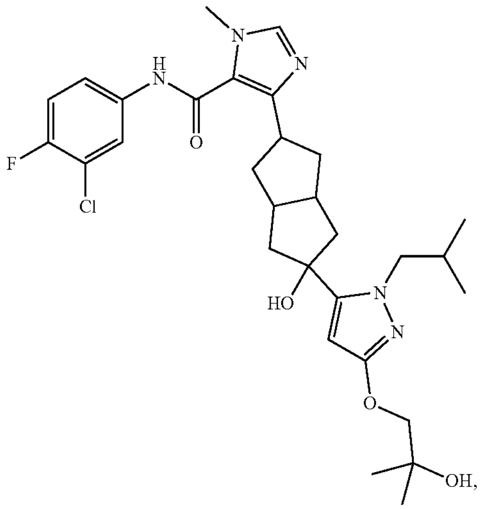 [SMILES: CC(C)Cn1nc(OCC(C)(C)O)cc1C1(O)CC2CC(c3ncn(C)c3C(=O)Nc3ccc(F)c(Cl)c3)CC2C1] |
| Example 222 | 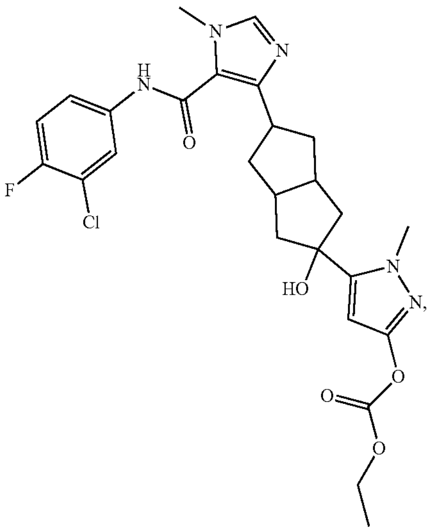 and |
| Example 223 | 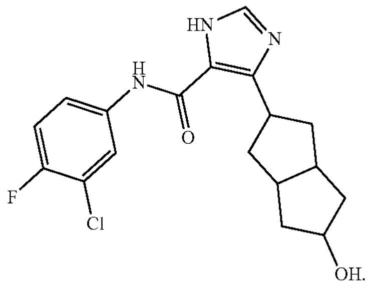 [SMILES: O=C(Nc1ccc(F)c(Cl)c1)c1[nH]cnc1C1CC2CC(O)CC2C1] |
21. A compound
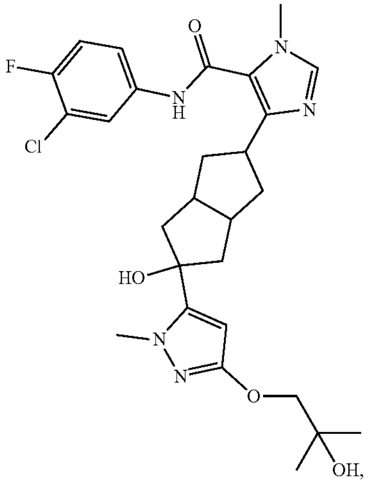 [SMILES: Cn1cnc(C2CC3CC(O)(c4cc(OCC(C)(C)O)nn4C)CC3C2)c1C(=O)Nc1ccc(F)c(Cl)c1]
or a pharmaceutically acceptable salt thereof.
22. A compound
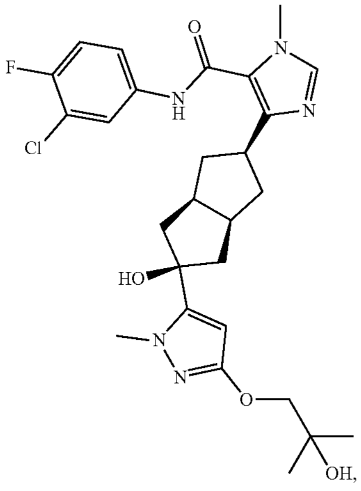 [SMILES: Cn1cnc([C@@H]2C[C@@H]3C[C@@](O)(c4cc(OCC(C)(C)O)nn4C)C[C@@H]3C2)c1C(=O)Nc1ccc(F)c(Cl)c1]
or a pharmaceutically acceptable salt thereof.

23. A diastereomer of a compound

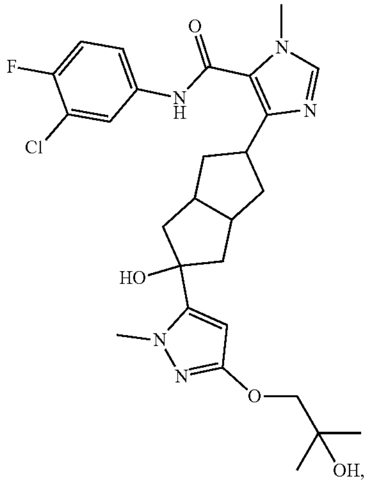 [SMILES: Cn1cnc(C2CC3CC(O)(c4cc(OCC(C)(C)O)nn4C)CC3C2)c1C(=O)Nc1ccc(F)c(Cl)c1]

or a pharmaceutically acceptable salt thereof.

24. A pharmaceutical composition comprising the compound according to claim 21, or a pharmaceutically acceptable salt thereof, and a pharmaceutically acceptable excipient.

25. A method of treating Hepatitis B (HBV) infection in a subject in need thereof, the method comprising: administering to the subject a therapeutically effective amount of a compound according to claim 21, or a pharmaceutically acceptable salt thereof.

26. A method of treating HBV infection in a subject in need thereof, the method comprising: administering to the subject a therapeutically effective amount of pharmaceutical composition of claim 24.

27. A pharmaceutical composition comprising the compound according to claim 22, or a pharmaceutically acceptable salt thereof, and a pharmaceutically acceptable excipient.

28. A method of treating HBV infection in a subject in need thereof, the method comprising: administering to the subject a therapeutically effective amount of a compound according to claim 22, or a pharmaceutically acceptable salt thereof.

29. A method of treating HBV infection in a subject in need thereof, the method comprising: administering to the subject a therapeutically effective amount of pharmaceutical composition of claim 27.

30. A pharmaceutical composition comprising the compound according to claim 23, or a pharmaceutically acceptable salt thereof, and a pharmaceutically acceptable excipient.

31. A method of treating HBV infection in a subject in need thereof, the method comprising: administering to the subject a therapeutically effective amount of a compound according to claim 23, or a pharmaceutically acceptable salt thereof.

32. A method of treating HBV infection in a subject in need thereof, the method comprising: administering to the subject a therapeutically effective amount of pharmaceutical composition of claim 30.

* * * * *